US007183075B2

(12) United States Patent
Mount et al.

(10) Patent No.: US 7,183,075 B2
(45) Date of Patent: Feb. 27, 2007

(54) PURIFIED AND ISOLATED POTASSIUM-CHLORIDE COTRANSPORTER NUCLEIC ACIDS AND POLYPEPTIDES AND THERAPEUTIC AND SCREENING METHODS USING SAME

(75) Inventors: David B. Mount, Brentwood, TN (US); Eric Delpire, Nashville, TN (US); Gerardo Gamba, Mexico City (MX); Alfred L. George, Jr., Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/835,976

(22) Filed: Apr. 16, 2001

(65) Prior Publication Data

US 2003/0027983 A1    Feb. 6, 2003

Related U.S. Application Data

(60) Provisional application No. 60/197,350, filed on Apr. 14, 2000.

(51) Int. Cl.
| C12N 15/00 | (2006.01) |
| C12N 15/85 | (2006.01) |
| C12N 15/63 | (2006.01) |
| C07H 21/04 | (2006.01) |
| C07K 14/00 | (2006.01) |
| C07K 5/00  | (2006.01) |

(52) U.S. Cl. .................. 435/69.1; 435/325; 435/320.1; 536/23.1; 536/23.5; 536/24.31; 530/350; 530/300

(58) Field of Classification Search ............... 435/69.1, 435/325; 536/23.1, 23.5; 530/350
See application file for complete search history.

(56) References Cited

U.S. PATENT DOCUMENTS

| 4,895,807 A | 1/1990 | Cherksey |
| 5,166,162 A | 11/1992 | Masreel et al. |
| 5,410,031 A | 4/1995 | Wright et al. |
| 5,441,875 A | 8/1995 | Hediger |
| 5,668,157 A | 9/1997 | Humphrey et al. |
| 5,856,338 A | 1/1999 | Brendel et al. |

FOREIGN PATENT DOCUMENTS

| CA | 2037189 | 9/1991 |
| EP | 0 560 232 A1 | 9/1993 |
| WO | WO 96/17602 | 6/1996 |
| WO | WO 96/34288 | 10/1996 |
| WO | WO 98/29431 | 7/1998 |
| WO | WO 98/37198 | 8/1998 |
| WO | WO 98/53067 | 11/1998 |

OTHER PUBLICATIONS

Oelmann, S., et al, 2001, J. Biol. Chem. 28(13): 26291-26300.*
Bisson, et al (1993, Crit Rev Biochem Mol Biol, 28:259-308.*
Liang, H., et al, 1998, Mol. Cell. Biol. 18(2): 926-935.*
Strausberg, R., 1998, Acc. No. AI313496.*
Gu, et al , 1996, Accession No. AAA99416.*
Strausberg, R., 1998, Accession No. AI313496.*
Gu, et al, 1996, Accession No. AAA9416.*
Oelmann, S., et al, 2001., J. Biol. Chem. 28(13): 26291-26300.*
Liang, H., et al, 1998, Mol. Cell. Biol. 18(2):926-935.*
Mount, et al, 1999, J. Biol. Chem., 274(23): 16355-16362.*
International Search Report for corresponding PCT International Application No. PCT/US01/12395 dated Jul. 2, 2004.
Blomqvist et al., Distal renal tubular acidosis in mice that lack the forkhead transcription factor Foxi1, The J. of Clinical Investigation 113(11):1560-1570 (Jun. 2004).
Shen et al., The KCl cotransporter isoform KCC3 can play an important role in cell growth regulation, PNAS 98(25):14714-14719 (Dec. 4, 2001).
Communication pursuant to Article 96(2) EPC in European Patent Application No. 01 928 579.0-2405 dated Sep. 22, 2005.
Examiners First Report corresponding to Australian pat. app. No. 2001255421 dated Nov. 15, 2005.
IPER corresponding to PCT International pat. app. No. PCT/US01/12395 dated Dec. 15, 2005.
Mercado et al., "NH2-Terminal Heterogeneity in the KCC3 K+-Cl-Cotransporter", Am. J. Physiol. Renal Physiol, 289: 1246-1261, 2005.
Communication pursuant to Article 96(2) EPC in European Patent Application No. 01 928 579.0-2405 dated Sep. 15, 2006.
Mount et al. Cloning and characterization of KCC3 and KCC4, new members of the cation-chloride cotransporter gene family Journal Of Biological Chemistry, American Society Of Biological Chemists, Baltimore, MD, US, vol. 274, No. 23, (1999), pp. 16355-16362.

* cited by examiner

Primary Examiner—Eileen O'Hara
Assistant Examiner—Sandra Wegert
(74) Attorney, Agent, or Firm—Jenkins, Wilson, Taylor & Hunt, P.A.

(57) ABSTRACT

KCC2, KCC3 and KCC4 potassium-chloride cotransporter proteins, and nucleic acid molecules encoding the same. Recombinant host cells, recombinant nucleic acids and recombinant proteins are also disclosed, along with methods of producing each. Isolated and purified antibodies to KCC2, KCC3 and KCC4 homologs, and methods of producing the same, are also disclosed. KCC2, KCC3 and KCC4 gene products have biological activity in potassium-chloride cotransport. Thus, therapeutic methods involving this activity are also disclosed.

13 Claims, 42 Drawing Sheets

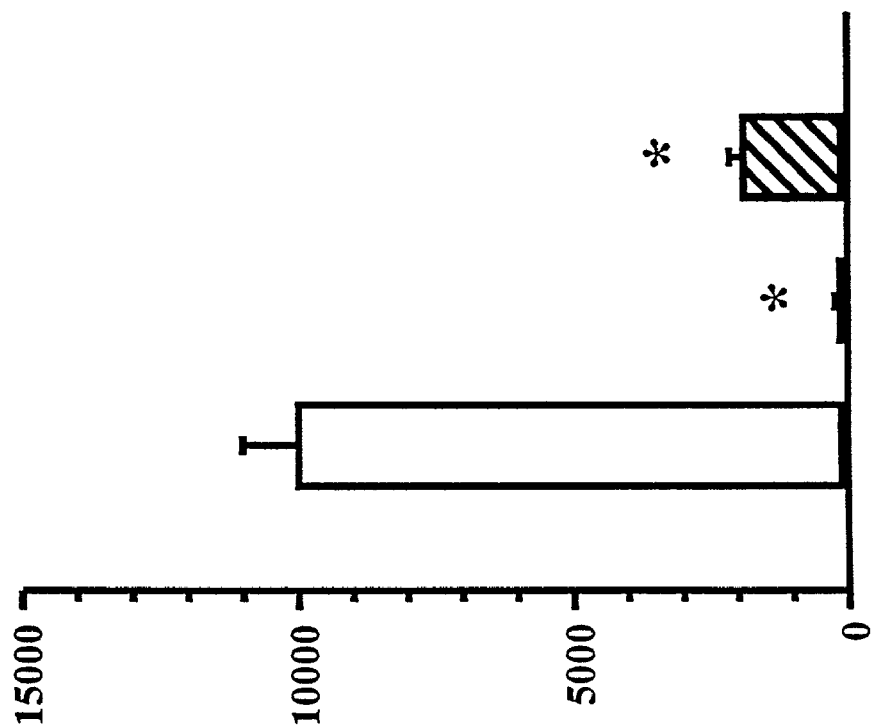
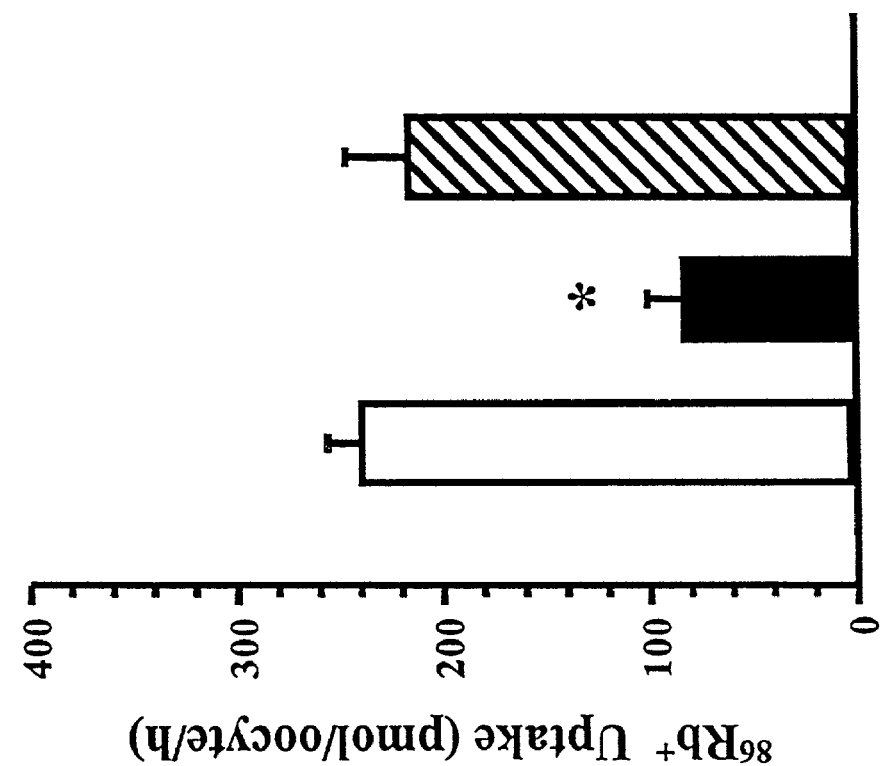
FIG. 25A
FIG. 25B

KCC3 Construct

Sequence of the hKCC2 dinucleotide repeat in several individuals:

Sample 1:
    Allele A          $(GT)_{18} (GC)_7 (AT)_1 (GT)_4 (GC)_1 (GT)_{11}$ / Total = 84

Allele B          $(GT)_{16} (GC)_5 (AT)_1 (GT)_5 (GC)_1 (GT)_9$ / Total = 74

Sample 2:
    Allele A          $(GT)_{18} (GC)_4 (AT)_2 (GT)_4 (GC)_2 (GT)_{11}$ / Total = 82

Sample 3:
    Allele A          $(GT)_{16} (GC)_6 (AT)_1 (GT)_4 (GC)_1 (GT)_{11}$ / Total = 78

Allele B          $(GT)_{14} (GC)_5 (AT)_1 (GT)_4 (GC)_1 (GT)_{11}$ / Total = 72

Sample 4:
    Allele A          $(GT)_{19} (GC)_6 (AT)_2 (GT)_4 (GC)_2 (GT)_{10}$ / Total = 86

Allele B          $(GT)_{17} (GC)_7 (AT)_2 (GT)_4 (GC)_2 (GT)_{10}$ / Total = 84

Sample 5:
    Allele A          $(GT)_{17} (GC)_6 (AT)_2 (GT)_4 (GC)_1 (GT)_{10}$ / Total = 80

Allele B          $(GT)_{16} (GC)_6 (AT)_2 (GT)_3 (GC)_2 (GT)_{10}$ / Total = 78

Sample 6:
    Allele A          $(GT)_{15} (GC)_6 (AT)_1 (GT)_4 (GC)_1 (GT)_{11}$ / Total = 76

Allele B          $(GT)_{16} (GC)_5 (GT)_1 (AT)_1 (GT)_4 (GC)_1 (GT)_{11}$ / Total = 78

Sample 7:
    Allele A          $(GT)_{16} (GC)_4 (GT)_1 (AT)_1 (GT)_5 (GC)_1 (GT)_{10}$ / Total = 76

FIG. 41

PURIFIED AND ISOLATED POTASSIUM-CHLORIDE COTRANSPORTER NUCLEIC ACIDS AND POLYPEPTIDES AND THERAPEUTIC AND SCREENING METHODS USING SAME

CROSS REFERENCE TO RELATED APPLICATIONS

This application is based on and claims priority to U.S. Provisional Application Ser. No. 60/197,350, filed Apr. 14, 2000, herein incorporated by reference in its entirety.

GRANT STATEMENT

This work was supported by National Institutes of Health grants DK02103, DK57708, and NS36758. Thus, the U.S. Government has certain rights in the invention.

REFERENCE TO SEQUENCE LISTING

The Sequence Listing associated with the instant disclosure has been submitted as an about 275 kilobyte file on compact disc (in duplicate). The enclosed compact discs are labeled to identify the applicants, the title of the invention, file name (1242-26-2.txt), creation date (Apr. 15, 2001), computer system (IBM-PC/MS-DOS/MS-Windows) used to create the Sequence Listing, and attorney docket number (1242/26/2). The Sequence Listing submitted on compact disc is hereby incorporated by reference.

TECHNICAL FIELD

The present invention relates generally to isolated and purified proteins and nucleic acids. More particularly, the present invention relates to isolated and purified potassium-chloride cotransporter polypeptides and isolated and purified nucleic acids encoding the same.

Table of Abbreviations

| | |
|---|---|
| ACCPN | peripheral neuropathy with or without agenesis of the corpus callosum |
| A-T | ataxia-telangiectasia |
| ATTC | American Tissue Type Collection |
| BSA | bovine serum albumin |
| CDR | complementarity determining region |
| CITB | California Institute of Technology BAC |
| CNPase | 2',3'-cyclic nucleotide 3'-phosphodiesterase |
| CNS | central nervous system |
| EMBL | European Molecular Biology Laboratory |
| EST | expressed sequence tag |
| HAT | cell culture media comprising hypoxanthine, aminopterin, and thymidine |
| hKCC2 | human KCC2 |
| hKCC3 | human KCC3 |
| hKCC4 | human KCC4 |
| IMAGE | integrated molecular analysis of genomes and their expression |
| KCC | potassium-chloride cotransporter; also "K$^+$-Cl$^-$ cotransporter" |
| KCC3a | KCC3 isoform a |
| KCC3b | KCC3 isoform b |
| KCC3a2m | KCC3a lacking exon 2 |
| KLH | keyhole limpet hemocyanin |
| mKCC3 | mouse KCC3 |
| mKCC4 | mouse KCC4 |
| ML-7 | myosin light chain kinase inhibitor |
| mOsm | milli-osmole |

-continued

Table of Abbreviations

| | |
|---|---|
| NCC | sodium-chloride cotransporter; also A Na$^+$-Cl$^-$ cotransporter" |
| NKCC1 | Na$^+$-K$^+$-2Cl$^-$ cotransporter |
| NKCC2 | Na$^+$-K$^+$-2Cl$^-$ cotransporter |
| NEM | N-ethylmaleimide |
| NIGMS | National Institute of General Medical Sciences |
| NKCC | sodium-potassium-chloride cotransporter; also A Na$^+$-K$^+$-2Cl$^-$ cotransporter" |
| NMDG | N-methyl-D-glucamine |
| NRSE | neuronal restricted silencing element |
| NRSF | neuronal restricted silencing factor |
| ORF | open reading frame |
| PBS | phosphate-buffered saline |
| PCR | polymerase chain reaction |
| PTZ | pentylenetetrazole |
| PKA | protein kinase A |
| PKC | protein kinase C |
| rabKCC1 | rabbit KCC1 |
| RACE | rapid amplification of cDNA ends |
| RT-PCR | reverse transcriptase polymerase chain reaction |
| STS | sequence-tagged site |
| TIGR | The Institute for Genome Research |
| TM | transmembrane domain |
| TMn | transmembrane domain n, where n is an integer |
| UTR | untranslated region |
| VNTR | variable number of tandem repeats |
| xKCC | Xenopus KCC |

BACKGROUND OF THE INVENTION

Cation-chloride cotransporters are typically categorized into one of three groups: Na$^+$—K$^+$-2 Cl$^-$ cotransporters, Na$^+$—Cl$^-$ cotransporter, and K$^+$—Cl$^-$ cotransporters. Potassium-chloride cotransporters (K$^+$—Cl$^-$ cotransporters or KCCs) were first described as a potassium efflux from erythrocytes that was induced by cell swelling. The cotransport of K$^+$ and Cl$^-$ in erythrocytes is interdependent, with a 1:1 stoichiometry and low affinity constants for both ions. KCCs belong to a gene family of electroneutral cation-chloride cotransporters; i.e., they are not influenced by membrane potential. Under most physiological conditions, they function as an efflux pathway that is involved in regulatory volume decrease. K$^+$—Cl$^-$ cotransport is sensitive to the diuretics bumetanide and furosemide, but with much lower affinities than Na$^+$—K$^+$-2Cl$^-$ cotransport.

Full-length cDNAs encoding two potassium-chloride cotransporters KCC1 and KCC2 have been reported in certain mammals. While human KCC1 has been cloned (Gillen et al. (1996) *J Biol Chem* 271(27):16237–16244; Holtzman et al. (1998) *Am J Physiol* 275(4 Pt2):F550–564), KCC2 has not been cloned from in human beings. Both proteins exhibit a level of homology to other electroneutral cation-chloride cotransporters, including the bumetanide-sensitive Na$^+$—K$^+$-2 Cl$^-$ cotransporters NKCC1 and NKCC2 (also known as BSC2 and BSC1, respectively), and the thiazide-sensitive Na$^+$—Cl$^-$ cotransporter NCC (also known as TSC). An alternatively-spliced form of human KCC3 has also been reported. See Hiki et.al. (1999) *J Biol Chem* 274: 10661–10667.

International Publication Number WO 98/29431, published Jul. 9,1998, (inventors: Lifton et al.; assignee: Yale University) discloses roles for the human thiazide-sensitive Na—Cl transporter, TSC, the human ATP-sensitive potassium channel, ROMK, and the human Na$^+$—K$^+$-2Cl cotransporter, NKCC2, in causing a series of abnormal or pathological conditions. Amino acid and nucleotide sequences of several human wild-type and variant TSC, NKCC2 and ROMK proteins are disclosed.

U.S. Pat. No. 4,895,807 issued Jan. 23, 1990 to Cherksey discloses a purified membrane channel protein that was found to be related to both $K^+$ and $Cl^-$ ion transport across cellular membranes. The channel protein is described as having a molecular weight of approximately 280 to 300 kD, as determined, for example, by SDS-polyacrylamide gel electrophoresis.

International Publication Number WO 98/53067, published Nov. 28, 1998 (inventors: Bevensee et al.; assignee Yale University) discloses the isolation and purification of polypeptides and nucleic acids pertaining to sodium bicarbonate cotransporters (NBCs).

International Publication Number WO 98/37198, published Aug. 27, 1998 (inventors: Lal et al.; assignee: Incyte Pharmaceuticals Inc.) discloses a purified and isolated human sodium-dependent phosphate cotransporter (NAPTR) and purified and isolated polynucleotides encoding the same. The polypeptides and polynucleotides pertain functionally to the homeostasis of phosphate levels in the body.

International Publication Number WO 96/34288, published Oct. 31, 1996 (inventors: Ni et al.; assignee: Eli Lilly and Company, Ltd.) discloses the isolation of a sodium-dependant inorganic phosphate cotransporter and a nucleic acid enclosing the same. The cotransporter was isolated from human brain tissue. The polypeptides and polynucleotides also pertain functionally to the homeostasis of phosphate levels in the body.

U.S. Pat. No. 5,410,031 issued Apr. 25, 1995 to Wright et al. (assignee University of California System) discloses a cDNA sequence encoding an amino acid sequence corresponding to mammalian $Na^+$/nucleoside cotransporter protein, abbreviated SNST. Thus, the encoded protein is a cotransporter that functions in conjunction with sodium ions and with nucleosides (e.g., adenosine).

U.S. Pat. No. 5,441,875 issued Aug. 15, 1995 to Hediger (assignee: Brigham and Women's Hospital) discloses the isolation and purification of a urea transporter polypeptide and to a polynucleotide encoding the same. The disclosed polypeptide thus is described as functioning in the transmembrane transport of urea.

Potassium-chloride cotransport has been described for a number of cells, tissues, and organs, including blood, skin, heart, skeletal muscle, and brain. Potassium-chloride cotransport is thought to be involved in cell volume regulation, trans-epithelial salt absorption, renal potassium secretion, and the regulation of both intra-and extra-cellular potassium and chloride ion concentrations.

Ion transporters have been implicated in a number of diseases, including hypertension, epilepsy, sickle cell anemia, Bartter's syndrome, and Meniere's disease. However, not all diseases currently thought to be associated with defective ion transport have been shown to be associated with known ion transport genes. Hence, there might be other ion transporter alleles that are defective or are affected in these diseases.

A major impediment to the study of $K^+$—$Cl^-$ cotransport has also been the lack of specific high affinity inhibitors. Thus, further characterization of the molecular heterogeneity of potassium-chloride cotransporters has implications for the physiology and pathophysiology of a number of tissues. Additionally, the characterization of additional isoforms of KCCs would be particularly useful in screening for antibodies or pharmaceutical compositions which can modulate ion transport and hence provide treatments to ameliorate the effects of these diseases or disorders. Finally, the chromosomal localization and genomic characterization of the human KCC genes will be invaluable in the investigation of their role in monogenic disease, polygenic disease, and complex traits such as hypertension. Such characterization thus represents a long-felt and continuing need in the art.

SUMMARY OF THE INVENTION

The present invention discloses isolated and purified polynucleotides encoding KCC genes, including mammalian KCC2, KCC3 and KCC4 genes, isolated and purified KCC polypeptides (including KCC2, KCC3 and KCC4 polypeptides), and the characterization of the role played by KCC polypeptides (including KCC2, KCC3 and KCC4 proteins) in modulating potassium transport. Preferably, a polypeptide of the invention is a recombinant polypeptide and comprises a mammalian KCC2, KCC3 or KCC4 polypeptide. More preferably, a polypeptide of the present invention comprises a human or mouse KCC2, KCC3 or KCC4 polypeptide. Most preferably, a polypeptide of the present invention comprises a nucleotide or amino acid sequence selected from the sequences of any of SEQ ID NOs: 1–16 or 112–113.

The present invention also provides an isolated and purified polynucleotide that encodes a KCC polypeptide (including a KCC2, KCC3 or KCC4 polypeptide) that modulates the levels of potassium and/or chloride as well as biological activities affected thereby. In a preferred embodiment, a polynucleotide of the present invention comprises a DNA molecule from a mammal. A preferred mammal is a mouse or a human. More preferably, a polynucleotide of the present invention encodes a polypeptide comprising an amino acid residue sequence of any of SEQ ID NOs:2, 4, 6, 8, 10, 12, 14, 16, and 113. Most preferably, an isolated and purified polynucleotide of the invention comprises a nucleotide sequence of any of SEQ ID NOs:1, 3, 5, 7, 9, 11, 13, 15, and 112.

In another embodiment, the present invention provides an antibody immunoreactive with a KCC polypeptide (including a KCC2, KCC3 or KCC4 polypeptide) as described above. SEQ ID NOs: 1–16 and 112–113 set forth nucleotide and amino acid sequences from exemplary mammals, mouse or human, and from a non-mammal vertebrate, *Xenopus laevis*. More preferably, the antibody of the invention is immunoreactive with a potassium-chloride cotransporter polypeptide comprising a human or mouse KCC2, KCC3 or KCC4 polypeptide. Even more preferably, an antibody of the invention is immunoreactive with a polypeptide comprising an amino acid residue sequence of any of SEQ ID NOs:2, 4, 6, 8, 10, 12, 14, 16 and 113. Also provided by the present invention are antibodies immunoreactive with homologs or biologically equivalent potassium-chloride cotransporter polynucleotides and polypeptides found in other vertebrates, and mammals. Optionally, an antibody of the invention is a monoclonal antibody.

In another aspect, the present invention provides a process of producing an antibody immunoreactive with a potassium-chloride cotransporter polypeptide as described above, the process comprising the steps of (a) transfecting a recombinant host cell with a polynucleotide that encodes a biologically active potassium-chloride cotransporter polypeptide; (b) culturing the host cell under conditions sufficient for expression of the polypeptide; (c) recovering the polypeptide; and (d) preparing the antibody to the polypeptide. SEQ ID NOs: 1–16 and 112–113 set forth nucleotide and amino acid sequences from representative mammals, human, mouse and *Xenopus*. Preferably, the host cell is transfected with a polynucleotide of SEQ ID NOs:1, 3, 5, 7, 9, 11, 13, 15, and 112. Even more preferably, the present invention provides an antibody prepared according to the process described above. Also contemplated by the present invention is the use of homologues or biologically equivalent KCC2, KCC3 and KCC4 polynucleotides and polypeptides found in other mammals to produce antibodies.

Alternatively, the present invention provides a process of detecting a potassium-chloride cotransporter polypeptide as described above, wherein the process comprises immunoreacting the polypeptide with an antibody prepared according to the process described above to form an antibody-polypeptide conjugate, and detecting the conjugate.

In yet another embodiment, the present invention provides a process of detecting a messenger RNA transcript that encodes a potassium-chloride cotransporter polypeptide as described above, wherein the process comprises hybridizing the messenger RNA transcript with a polynucleotide sequence that encodes that polypeptide to form a duplex; and detecting the duplex. Alternatively, the present invention provides a process of detecting a DNA molecule that encodes a potassium-chloride cotransporter polypeptide as described above, wherein the process comprises hybridizing DNA molecules with a polynucleotide that encodes a biologically active potassium-chloride cotransporter polypeptide to form a duplex; and detecting the duplex.

In another aspect, the present invention provides an assay or assay kit for detecting the presence of a potassium-chloride cotransporter polypeptide in a biological sample, where the kit comprises a first antibody capable of immunoreacting with a biologically active potassium-chloride cotransporter polypeptide. Preferably, the first antibody is present in an amount sufficient to perform at least one assay. Also preferably, an assay kit of the invention further comprises a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label, a fluorescent label or an enzyme.

In an alternative aspect, the present invention provides an assay or assay kit for detecting the presence, in biological samples, of a potassium-chloride cotransporter polypeptide, the kits comprising a polynucleotide identical or complementary to a segment of at least 10 contiguous nucleotide bases of a polynucleotide that encodes a potassium-chloride cotransporter polypeptide.

In another embodiment, the present invention provides an assay or assay kit for detecting the presence, in a biological sample, of an antibody immunoreactive with a potassium-chloride cotransporter polypeptide, the kit comprising a first container containing a biologically active potassium-chloride cotransporter polypeptide that immunoreacts with the antibody, with the polypeptide present in an amount sufficient to perform at least one assay.

In still a further embodiment, this invention pertains to therapeutic methods based upon the modulation of the biological activity of potassium-chloride cotransporters via polynucleotides and polypeptides as described herein. Such therapeutic methods include gene therapy approaches using an isolated and purified polynucleotide of the present invention.

In another embodiment, the present invention provides genetic assays based on the genomic sequence of the human KCC2, KCC3, and KCC4 genes. The intronic sequence flanking the individual exons encoding the three genes is employed in the design of oligonucleotide primers suitable for the mutation analysis of human genomic DNA. Thus, intronic primers are used to screen for genetic variants by a number of PCR-based techniques, including single-strand conformation polymorphism (SSCP) analysis, SSCP/heteroduplex analysis, enzyme mismatch cleavage, and direct sequence analysis of amplified exons. Similar techniques can be applied to putative 5'-regulatory regions, e.g., the putative promoters 5' of exons 1a and 1b of human KCC3. Automated methods can also be applied the large-scale characterization of single nucleotide polymorphisms within and near the human KCC genes.

Once genetic variants have been detected in specific patient populations, e.g., KCC3 mutations in patients with Andermann's syndrome, the present invention provides assays to detect the mutation by methods such as allele-specific hybridization, or restriction analysis of amplified genomic DNA containing the specific mutation. Again, these detection methods can be automated. In the case of genetic disease or human phenotypes caused by repeat expansion, the present invention provides an assay based on PCR of genomic DNA with oligonucleotide primers flanking the involved repeat.

In yet another aspect, the present invention provides a transgenic animal. In one embodiment of the present invention, the transgenic animal can comprise a mouse with targeted modification of the mouse KCC2, KCC3, and KCC4 genes and can further comprise mice strains with complete or partial functional inactivation of the KCC genes in all somatic cells. In an alternative embodiment, a transgenic animal in accordance with the present invention is prepared using anti-sense or ribozyme KCC constructs, driven by a universal or tissue-specific promoter, to reduce levels of individual KCCs in somatic cells, thus achieving a "knock-down" of individual isoforms. The present invention also provides the generation of murine strains with conditional or inducible inactivation of individual or multiple KCC genes.

The present invention also provides mice strains with specific "knocked-in" modifications in the KCC2, KCC3, or KCC4 genes. This includes mice with genetically and/or functionally relevant point mutations in the KCC genes, in addition to manipulations such as the insertion of disease-specific repeat expansions.

Thus, a key aspect of this invention pertains to the discovery of novel potassium-chloride cotransporter polypeptides and nucleic acids. Preferred nucleic acid and amino acid sequences are described in SEQ ID NOs:1–16 adn 112–113. It is thus another aspect of this invention to provide a purified and isolated potassium-chloride cotransporter polypeptide having a role in the biological activity of potassium-chloride concentration modulation.

The foregoing aspects and embodiments have broad utility given the biological significance of the potassium-chloride cotransporter proteins. By way of example, the foregoing aspects and embodiments are useful in the preparation of screening assays and assay kits that are used to identify compounds that affect or modulate potassium-chloride cotransporter biological activity, or that are used to detect the presence of the proteins and nucleic acids of this invention in biological samples.

Some of the aspects and objects of the invention having been stated herein above, other aspects and objects will become evident as the description proceeds, when taken in connection with the accompanying Drawings and Examples as best described herein below.

BRIEF DESCRIPTION OF THE DRAWINGS

FIG. 4A is an autoradiograph of an EMSA showing a retarded band in reactions where nuclear proteins were incubated with the probe, indicating an interaction between the DNA probe and a nuclear protein.

FIG. 4B is an autoradiograph of an EMSA performed using unlabeled (cold) NRSE DNA or unrelated DNA. A protein-DNA complex, evidenced by a retarded band (arrowhead labeled "complex"), was still present when excess cold DNA of unrelated sequence (unspecific oligo) was added to the reaction. By contrast, excess cold NSRE DNA can compete with the NSRE probe, indicated by the absence of the labeled protein-DNA complex.

FIG. 20A is a bar graph depicting $^{86}$Rb$^+$ uptake in mKCC4-injected oocytes in isotonic medium. Each bar represents the mean±standard error of data obtained from 20 oocytes. Open bars, $^{86}$Rb$^+$ uptake in control conditions lacking NEM; black bars, $^{86}$Rb$^+$ uptake in the absence of extracellular Cl$^-$; hatched bars $^{86}$Rb$^+$ uptake in the presence of NEM. The asterisk (*) indicates that $^{86}$Rb$^+$ uptake in NEM-treated oocytes is significantly increased relative to the control group (p<0.0001).

FIG. 20B is a bar graph depicting $^{86}$Rb$^+$ uptake in rabKCC1-injected oocytes in isotonic medium. Each bar represents the mean±standard error of data obtained from 20 oocytes. Open bars, $^{86}$Rb$^+$ uptake in control conditions lacking NEM; black bars, $^{86}$Rb$^+$ uptake in the absence of extracellular Cl$^-$; hatched bars $^{86}$Rb$^+$ uptake in the presence of NEM. The asterisk (*) indicates that $^{86}$Rb$^+$ uptake in NEM-treated oocytes is significantly increased relative to the control group (p<0.0001).

FIG. 20C is a bar graph depicting $^{86}$Rb$^+$ uptake in mKCC4-injected oocytes in hypotonic medium. Each bar represents the mean±standard error of data obtained from 20 oocytes. Open bars, $^{86}$Rb$^+$ uptake in control conditions lacking NEM; black bars, $^{86}$Rb$^+$ uptake in the absence of extracellular Cl$^-$; hatched bars $^{86}$Rb$^+$ uptake in the presence of NEM. The asterisk (*) indicates that $^{86}$Rb$^+$ uptake in NEM-treated oocytes is significantly decreased relative to the control group (p<0.0001).

FIG. 20D is a bar graph depicting $^{86}$Rb$^+$ uptake in rabKCC1-injected oocytes in hypotonic medium. Each bar represents the mean±standard error of data obtained from 20 oocytes. Open bars, $^{86}$Rb$^+$ uptake in control conditions lacking NEM; black bars, $^{86}$Rb$^+$ uptake in the absence of extracellular Cl$^-$; hatched bars $^{86}$Rb$^+$ uptake in the presence of NEM. The asterisk (*) indicates that $^{86}$Rb$^+$ uptake in NEM-treated oocytes is significantly decreased relative to the control group (p<0.0001).

FIG. 25A is a bar graph depicting the effect of the protein phosphatase inhibitor calyculin A (100 nM) on the isotonic $K^+$—$Cl^-$ cotransport mediated by hKCC2. $^{86}Rb^+$ influx was assessed in a control group (white bars), in the absence of extracellular $Cl^-$ (black bars), or in the presence 100 mM calyculin (hatched bars). Each bar represents the mean±standard error of data obtained using at least 15 oocytes. Asterisk (*) indicates that $^{86}Rb^+$ influx was significantly reduced in the absence of $Cl^-$ relative to the control group.

FIG. 25B is a bar graph depicting the effect of shows the effect of the protein phosphatase inhibitor calyculin A (100 nM) on the swelling-induced $K^+Cl^-$ cotransport mediated by hKCC2. $^{86}Rb^+$ influx was assessed in a control group (white bars), in the absence of extracellular $Cl^-$ (black bars), or in the presence 100 mM calyculin (hatched bars). Each bar represents the mean±standard error of data obtained using at least 15 oocytes. Asterisk (*) indicates that $^{86}Rb^+$ influx was significantly reduced in the absence of $Cl^-$, or in the combined absence of $Cl^-$ and presence of calyculin, relative to the control group.

FIG. 41 summarizes the distribution of KCC2 alleles that display the indicated polymorphic sequence in the region of the $(GC)_n(CG)_n(GT)_n$ dinucleotide repeat (SEQ ID NOs: 118–129). Alleles "A" and "B" arbitrarily refer to a first and second allele observed in any one of samples 1–7. Total, the number of individuals carrying each allele.

SUMMARY OF SEQUENCES IN THE SEQUENCE LISTING

Odd-numbered SEQ ID NOs:1–15 are nucleotide sequences encoding human, mouse and *xenopus* KCC polypeptides as described in Table 1.

Even-numbered SEQ ID NOs:2–16 and are human, mouse and xenopus KCC polypeptide sequences encoded by the immediately preceding nucleotide sequence, e.g., SEQ ID NO:2 is the protein encoded by the nucleotide sequence of SEQ ID NO:1, SEQ ID NO:4 is the protein encoded by the nucleotide sequence of SEQ ID NO:3, etc.

SEQ ID NOs:17–19 are mouse and human KCC3 promoter regions.

Even-numbered SEQ ID NOs:20–42 are nucleotide sequences encoding human KCC2 exons 1–24.

SEQ ID NOs:44–110 are genomic sequences encoding human KCC genes.

SEQ ID NO:111 is the nucleotide sequence of human chromosome 5 genomic clone pMS621.

SEQ ID NOs:112 and 113 are the nucleotide and polypeptide sequences, respectively, of *Xenopus* KCC.

SEQ ID NOs:114–115 are KCC2 primer sequences.

SEQ ID NO:116 is the peptide sequence of the KCC3 antigen.

SEQ ID NO:117 is the peptide sequence of the KCC4 antigen.

SEQ ID NOs:118–129 are KCC2 polymorphisms depicted in FIG. 44.

Figure 4A:
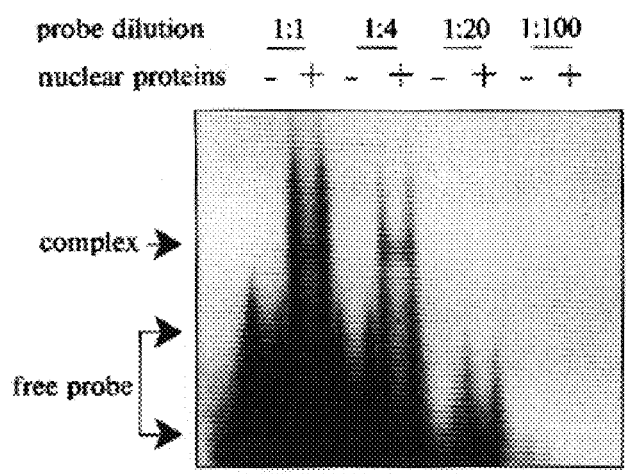
FIGS. 4A and 4B are autoradiographs of an electrophoretic mobility shift assay (EMSA) depicting the mKCC2 NSRE bound to nuclear proteins from a murine neural progenitor cell line, performed as described in the Examples.
Figure 4B:
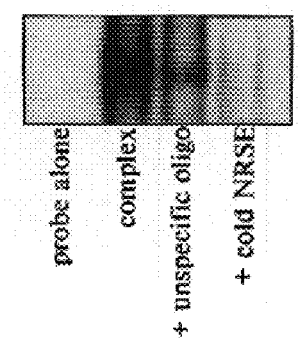

SEQ ID NO:130 is the NRSE oligonucleotide referred to for FIGS. 4A and 4B.

SEQ ID NO:131 is a mouse KCC2 promoter sequence.

TABLE 1

Summary of Sequences in the Sequence Listing

| SEQ ID NO. | description |
|---|---|
| 1–2 | human KCC4 |
| 3–4 | human KCC3a lacking exon 2 |
| 5–6 | mouse KCC3a lacking exon 2 |
| 7–8 | mouse KCC3a |
| 9–10 | mouse KCC3b |
| 11–12 | human KCC2 |
| 13–14 | mouse KCC4 |
| 15–16 | human KCC3a |
| 17 | human KCC3a promoter |
| 18 | mouse KCC3a promoter |
| 19 | mouse KCC3b promoter |
| 20–43 | coding seqeunces for human KCC2 exons 1–24 |
| 44–49 | genomic sequences for human KCC2 exons 2–7 |
| 50–55 | genomic sequences for human KCC2 exons 9–14 |
| 56–63 | genomic sequences for human KCC2 exons 17–24 |
| 64 | genomic sequence for human KCC4 exon 2 |
| 65 | genomic sequence for human KCC4 exon 3 |
| 66 | genomic sequence for human KCC4 exon 5 |
| 67–71 | genomic sequences for human KCC4 exons 6–10 |
| 72–79 | genomic sequences for human KCC4 exons 12–19 |
| 80–83 | genomic sequences for human KCC4 exons 21–24 |
| 84 | genomic sequence for human KCC3a exon 1 |
| 85 | genomic sequence for human KCC3b exon 1 |
| 86 | genomic sequence for human KCC3 exon 2 |
| 87 | genomic sequence for human KCC3 exon 3 |
| 88 | genomic sequence for human KCC3b exon 4 |
| 89 | genomic sequence for human KCC3a exon 4 |
| 90–95 | genomic sequences for human KCC3 exons 6–10 |
| 96 | genomic sequence for human KCC3b exon 12 |
| 97 | genomic sequence for human KCC3a exon 12 |
| 98–110 | genomic sequences for human KCC3 exons 13–25 |
| 111 | human chromosome 5 genomic clone pMS621 |
| 112–113 | Xenopus KCC |
| 114–155 | primers to detect KCC2 polymorphism |
| 116 | KCC3 peptide antigen |
| 117 | KCC4 peptide antigen |
| 117 | KCC4 peptide antigen |
| 118 | sample 1, KCC2 allele A |
| 119 | sample 1, KCC2 allele B |
| 120 | sample 2, KCC2 allele A |
| 121 | sample 3, KCC2 allele A |
| 122 | sample 3, KCC2 allele B |
| 123 | sample 4, KCC2 allele A |
| 124 | sample 4, KCC2 allele B |
| 125 | sample 5, KCC2 allele A |
| 126 | sample 5, KCC2 allele B |
| 127 | sample 6, KCC2 allele A |
| 128 | sample 6, KCC2 allele B |
| 129 | sample 7, KCC2 allele A |
| 130 | mKCC2 NSRE oligonucleotide |
| 131 | mKCC2 promoter sequence |

DETAILED DESCRIPTION OF THE INVENTION

The present invention teaches novel members of the KCC gene family and provides a novel human KCC2 (representative embodiments set forth in SEQ ID NOs:1–12), a novel, alternatively-spliced form of the human KCC3 gene (referred to herein as "hKCC3a", representative embodiments set forth in SEQ ID NOs:5–16) and the novel isoforms, mouse KCC3a (representative embodiments set forth in SEQ ID NOs:7–8) and mouse KCC3b (representative embodiments set forth in SEQ ID NOs:9–10), human and mouse KCC3a lacking exon 2(mKCC3a-2m and hKCC3a-2m, representative embodiments set forth in SEQ ID NOs: 3–6), human KCC4 (representative embodiments set forth in SEQ ID NOs:1–2) and mouse KCC4 (representative embodiments set forth in SEQ ID NOs: 13–14), and a Xenopus KCC gene (representative embodiments set forth as SEQ ID NOs:112–113).

The four predicted KCC proteins share 65–75% identity in primary structure. The KCC proteins also share a common predicted membrane topology with hydrophilic amino- and carboxy-terminal cytoplasmic domains flanking a central hydrophobic core of 12 highly conserved transmembrane (TM) segments. A large glycosylated extracellular loop is predicted between TM5 and TM6. The predicted cytoplasmic domains, in particular the carboxy-terminal (C-terminal) domain, contain segments of substantial homology interspersed by variable segments. The extreme C-terminus is completely identical in the four proteins, suggesting a crucial functional role. No one predicted phosphorylation site is conserved in the four KCCs, suggesting significant variation in post-transcriptional regulation. Given the known role of protein phosphorylation/dephosphorylation in cell volume regulation (Hoffmann & Dunham (1995) *Int Rev Cytol* 161:173–262), the volume-sensitivity of the four KCCs differs substantially. Although the TM segments are in general highly conserved, there is intriguing variation within TM2, a TM segment thought to influence cation affinity in the $Na^+$—$K^+$-$2Cl^-$ cotransporters. TM4 and TM7, which have been implicated in anion affinity in the $Na^+$—$K^+$-$2Cl^-$ cotransporters (Isenring et al. (1998) *J Gen Physiol* 112(5): 549–558). The kinetic characteristics of the four KCCs are heterogeneous.

The four KCCs differ in tissue distribution. KCC1 is almost ubiquitous, consistent with a "house-keeping" role in cell volume regulation. KCC2 is restricted to neuronal cells in the nervous system and retina, but can be induced in vitro by the differentiation of NT2 teratocarcinoma cells into neurons by retinoic acid (Pleasure & Lee (1993) *J Neurosci Res* 35(6):585–602). KCC4, although widely expressed, is most abundant in heart and kidney, and KCC3 is expressed in muscle, brain, lung, heart, and kidney. As shown in FIGS. 29A–29K, KCC3b predominates in kidney, whereas KCC3a predominates in brain.

Thus, the present invention pertains to isolated and purified nucleic acids encoding potassium-chloride cotransporter polypeptides, to isolated and purified potassium-chloride cotransporter polypeptides, to the characterization of the role played by the potassium-chloride cotransporter in modulating potassium and chloride levels within and outside cells, and to the characterization of downstream processes affected by such modulation.

Potassium-chloride cotransporters play important physiological roles in multiple tissues and processes, including salt transport in epithelial tissues and kidney, potassium secretion in the kidney, cell volume regulation, and the regulation of cellular chloride concentration and extracellular potassium concentration. Hence, potassium-chloride cotransporters are of major pharmacological interest, particularly for disorders such as hypertension, epilepsy, and sickle-cell anemia.

The four human KCC genes are localized on different chromosomes, as described in Examples. KCC1 is on chromosome 16q22.1, KCC2 is on 20q13, KCC3 on 15q14, and KCC4 on 5p15. KCC3 is a functional and positional candidate for a number of monogenic and polygenic diseases. The gene is located within the critical region for Andermann's syndrome (Casaubon et al. (1996) *Am J Hum Genet* 58(1):28–34). This recessive disorder comprises agenesis of the corpus callosum, a progressive peripheral neuropathy, developmental delay, and mental retardation. There is some phenotypic overlap with recessive familial spastic paraparesis, a milder disorder that also maps to 15q14 and might be allelic to Andermann's syndrome (Martinez Murillo et al. (1999) *Neurology* 53(1):50–56).

In addition to these monogenic disorders, markers flanking KCC3 are linked to juvenile myoclonic epilepsy and familial rolandic epilepsy, two subtypes of idiopathic epilepsy with a strong genetic component (Neubauer et al. (1998) *Neurology* 51(6):1608–1612; Elmslie et al. (1997) *Hum Mol Genet* 6(8):1329–1334). Patients with juvenile myoclonic epilepsy, a common subtype of idiopathic generalized epilepsy (4–10% of all epilepsy) (Callenbach & Brouwer (1997) *Clin Neurol Neurosurg* 99(3):159–171), suffer from both myoclonic and generalized tonic-clonic seizures. Many have a family history of other subtypes of epilepsy, in addition to abnormal EEGs in up to 10% of healthy family members.

Loss of heterozygosity for the genetic markers near the hKCC3 gene has been reported in metastatic brain and breast tumors (Wick et al. (1996) *Oncogene* 12(5):973–978), suggesting that this segment of chromosome 15q14 harbors a tumor suppressor. Markers near KCC3 have also been linked to inherited susceptibility to colonic malignancy (Tomlinson et al. (1999) *Gastroenterology* 116(4):789–795).

Based on its localization in renal thick ascending limb, in addition to functional evidence for $K^+$—$Cl^-$ cotransport in this nephron segment (Amlal et al. (1994) *American Journal of Physiology* 267(6 Pt 1):C1607–1615), hKCC4 is a gene candidate for the subtypes of Bartter's syndrome not due to mutations in NKCC2 (Simon et al. (1996) *Nat Genet* 13(2): 183–188), ROMK (Simon et al. (1996) *Nat Genet* 14:152–156), or CLC-NKB (Simon et al. (1997) *Nat Genet* 17:171–178). Linkage analysis implicates the genomic region containing human KCC4 in variation in bitter taste perception (Reed et al. (1999) *Am J Hum Genet* 64(5): 1478–1480). Based on synteny to human chromosome 5p15, mouse KCC4 is located on chromosome 13, in a region linked to audiogenic seizures in the "frings" mouse strain (Skradski et al. (1998) *Genomics* 49(2):188–192).

The functional and physiological data for the KCCs also implicates these transporters in human disease. Thus red cell $K^+$—$Cl^-$ cotransport is implicated in the dehydration and subsequent sickling of red cells in sickle cell anemia (Brugnara et al. (1986) *Science* 232(4748):388–390; De Franceschi et al. (1996) *Blood* 88(7):2738–2744). The expression of KCC3 and KCC4 in renal tubular cells, including proximal tubule, implicates $K^+$—$Cl^-$ cotransport in renal salt handling and hence in hypertension. In addition, KCC4 is expressed in macula densa cells, where its activity can modulate glomerular filtration and renin release.

Finally, the observation that mice genetically deficient in KCC2 have a seizure disorder (FIG. 36) implicates this transporter in epileptogenesis. The magnitude of the electrochemical gradient for $Cl^-$ modulates the response of neurons to stimuli that affect chloride conductance, such as the neurotransmitter γ-aminobutyric acid (GABA) (Misgeld et al. (1986) *Science* 232(4756):1413–1415; Miles (1999) *Nature* 397(6716):215–216). In neurons with robust inward transport of $Cl^-$, intracellular $Cl^-$ concentration ($Cl^-i$) is high and $GABA_A$ receptor stimulation is depolarizing and excitatory. In contrast, in cells with outward $Cl^-$ transport $GABA_A$ activation is hyperpolarizing and inhibitory (Miles (1999) *Nature* 397(6716):215–216).

The inward and outward transport of $Cl^-$ in neurons are encoded by the $Na^+$—$K^+$-$2Cl^-$ cotransporter NKCC1 and the KCCs, respectively. See Misgeld et al. (1986) *Science* 232(4756):1413–1415; Clayton et al. (1998) *Brain Res Dev Brain Res* 109(2):281–292. NKCC1 in the central nervous system is developmentally regulated, with high levels of expression at birth and the first few postnatal days, and decreased expression thereafter (Hubner et al. (2001) *Mech Dev* 102:267–269). In contrast, the expression of KCC2 increases dramatically during postnatal development (Lu et al. (1999) *J Neurobiology* 39:558–568; Rivera et al. (1999) *Nature* 397:251–255; Clayton et al. (1998) *Brain Res Dev Brain Res* 109(2):281–292). These developmental events correlate with a switch of the $GABA_A$ effect, from depolarizing to hyperpolarizing, during the first weeks of postnatal life.

Although other pathways can also function in neuronal $Cl^-$ homeostasis (Clayton et al. (1998) *Brain Res Dev Brain Res* 109(2):281–292), recent anti-sense experiments in cultured neurons strongly implicate KCC2 (Rivera et al. (1999) *Nature* 397:251–255), as does the phenotype of the KCC2 knockout mouse. The resulting change in the neuronal response to $GABA_A$ and other neurotransmitters is thought to have important effects on both neuronal development and neuronal remodeling (Miles (1999) *Nature* 397(6716): 215–216). Trauma to cultured neurons also has effects on neuronal $Cl^{-i}$ and response to GABA (van den Pol et al. (1996) *J Neurosci* 16(13):4283–4292). The pivotal role of KCC2 and other $K^+$—$Cl^-$ transporters in regulating neuronal $K^+$ and $Cl^-$ strongly implicates these transporters in the generation of seizure activity and epilepsy (Payne (1997) *Am J Physiol* 273:C1516-C1525). However, the KCCs can also affect epileptiform activity via effects on cell volume (Hochman et al. (1995) *Science* 270(5233):99–102).

Potassium-chloride cotransport is also envisioned to play a role in the generation of epileptiform activity in epilepsy, and in red-cell dehydration in sickle-cell anemia. The evident importance of potassium-chloride cotransport in salt absorption by the kidney also implicates potassium-chloride cotransporters in salt balance and hypertension. Immunofluorescence with isoform-specific antibodies localizes KCC3 and KCC4 to the basolateral membranes of mouse renal proximal tubule. Swelling-activated $K^+$—$Cl^-$ cotransport in this and other nephron segments is postulated to play a major role in transepithelial salt transport along the nephron (Mount et al. (1999) *J Biol Chem* 274(23):16355–16362). Moreover, the localization of KCC4 at the basolateral membrane of macula densa cells implicates this transporter in both tubuloglomerular feedback and tubular regulation of renin release, since both processes involve sensing and transport of chloride by this highly specialized nephron segment (Mount et al. (1997) *J Membr Biol* 158:177–186).

There are thus a large number of applications for drugs that target potassium-chloride cotransporters. The paucity of molecular information has hampered progress in determining the physiological and pathophysiological significance of potassium-chloride cotransport. The cloning of a human KCC2, and of KCC3 and KCC4 from various mammals is thus a major advance in this field. The development of isoform-specific antibodies to study the tissue localization of potassium-chloride cotransporters is facilitated, and is crucial for gene disruption studies of the four potassium-chloride cotransporter isoforms. The functional comparison of the four KCCs also impacts the study of their regulation and role. For example, kinetic comparisons yield important structure-function data, including ion-binding sites. Pharmacological comparison also provide for the development of isoform- and class-specific inhibitors and activators.

Summarily, the identification of the genes that encode KCC2 in humans, KCC3 in mice and humans and KCC4 in mice and humans, the cloning of the cDNAs and the expression of the proteins affords the molecular tools required for modulating potassium-chloride homeostasis, and has application in the development of pharmacological and/or therapeutic treatments for various disorders.

A. Polypeptides and Nucleic Acids

As used in the following detailed description and in the claims, the terms "KCC", "KCC2", "KCC3" and "KCC4" include nucleic acids and polypeptides encoding potassium-chloride cotransporters. The terms "KCC", "KCC2", "KCC3" and "KCC4" include invertebrate homologs; preferably, KCC, KCC2, KCC3 and KCC4 nucleic acids and polypeptides are isolated from eukaryotic sources. "KCC", "KCC2", "KCC3" and "KCC4" further include vertebrate homologs of potassium-chloride cotransporter family members, including, but not limited to, mammalian and avian homologs. Representative mammalian homologs of potassium-chloride cotransporter gene family members include, but are not limited to, murine and human homologs. The term "KCC", as used herein, can generally refer to any of the disclosed KCC nucleic acids and polypeptides, e.g. KCC2, KCC3, KCC4 or *Xenopus* KCC (xKCC).

The terms "KCC gene product", "KCC2 gene product", "KCC3 gene product", "KCC4 gene product", "KCC protein", "KCC2 protein", "KCC3 protein", "KCC4 protein", "KCC polypeptide", "KCC2 polypeptide", "KCC3 polypeptide" and "KCC4 polypeptide" refer to peptides having amino acid sequences which are substantially identical to native amino acid sequences from the organism of interest and which are biologically active in that they comprise all or a part of the amino acid sequence of a potassium-chloride cotransporter, or cross-react with antibodies raised against a KCC, KCC2, KCC3 or KCC4 polypeptide, or retain all or some of the biological activity of the native amino acid sequence or protein. Such biological activity can include immunogenicity.

The terms "KCC gene product", "KCC2 gene product", "KCC3 gene product", "KCC4 gene product", "KCC protein", "KCC2 protein", "KCC3 protein", "KCC4 protein", "KCC polypeptide", "KCC2 polypeptide", "KCC3 polypeptide" and "KCC4 polypeptide" also include analogs of potassium-chloride cotransporter molecules. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct potassium-chloride cotransporter analogs. There is no need for a "KCC gene product", "KCC2 gene product", "KCC3 gene product", "KCC4 gene product", "KCC protein", "KCC2 protein", "KCC3 protein", "KCC4 protein", "KCC polypeptide", "KCC2 polypeptide", "KCC3 polypeptide" and "KCC4 polypeptide" to comprise all or substantially all of the amino acid sequence of a native potassium-chloride cotransporter gene product. Shorter or longer sequences are anticipated to be of use in the invention; shorter sequences are herein referred to as "segments." Thus, the terms "KCC gene product", "KCC2 gene product", "KCC3 gene product", "KCC4 gene product", "KCC protein", "KCC2 protein", "KCC3 protein", "KCC4 protein", "KCC polypeptide", "KCC2 polypeptide", "KCC3 polypeptide" and "KCC4 polypeptide" also include fusion or recombinant potassium-chloride cotransporter polypeptides and proteins comprising sequences of the present invention. Methods of preparing such proteins are known in the art.

The terms "KCC gene", "KCC2 gene", "KCC3 gene", "KCC4 gene", "KCC gene sequence", "KCC2 gene sequence", "KCC3 gene sequence", "KCC4 gene sequence", "KCC gene segment", "KCC2 gene segment", "KCC3 gene segment", and "KCC4 gene segment" refer to any DNA sequence that is substantially identical to a polynucleotide sequence encoding a potassium-chloride cotransporter gene product, protein or polypeptide as defined above, and can also comprise any combination of associated control sequences. The terms also refer to RNA, or antisense sequences, complementary to such DNA sequences. As used herein, the term "DNA segment" refers to a DNA molecule that has been isolated free of total genomic DNA of a particular species. Furthermore, a DNA segment encoding a potassium-chloride cotransporter polypeptide refers to a DNA segment that contains KCC2, KCC3 or KCC4 coding sequences, yet is isolated away from, or purified free from, total genomic DNA of a source species, such as *Homo sapiens*. Included within the term "DNA segment" are DNA segments and smaller fragments of such segments, and also recombinant vectors, including, for example, plasmids, cosmids, phages, viruses, and the like.

The term "substantially identical", when used to define either a KCC, KCC2, KCC3 or KCC4 gene product or amino acid sequence, or a KCC, KCC2, KCC3 or KCC4 gene or nucleic acid sequence, means that a particular sequence varies from the sequence of a natural KCC, KCC2, KCC3 or KCC4 by one or more deletions, substitutions, or additions, the net effect of which is to retain at least some of biological activity of the natural gene, gene product, or sequence. Such sequences include "mutant" sequences, or sequences in which the biological activity is altered to some degree but retains at least some of the original biological activity.

Alternatively, DNA analog sequences are "substantially identical" to specific DNA sequences disclosed herein if: (a) the DNA analog sequence is derived from coding regions of the natural KCC, KCC2, KCC3 or KCC4 gene; or (b) the DNA analog sequence is capable of hybridization of DNA sequences of (a) under stringent conditions and which encode biologically active KCC, KCC2, KCC3 or KCC4 gene product; or (c) the DNA sequences are degenerate as a result of alternative genetic code to the DNA analog sequences defined in (a) and/or (b). Substantially identical analog proteins will be greater than about 60% identical to the corresponding sequence of the native protein. Sequences having lesser degrees of identity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids to create biologically functional equivalents.

Sequence identity or percent similarity of a DNA or peptide sequence can be determined, for example, by comparing sequence information using the GAP computer program, available from the University of Wisconsin Geneticist Computer Group. The GAP program utilizes the alignment method of Needleman et al. (1970) *J Mol Biol* 48:443, as revised by Smith et al. (1981) *Adv Appl Math* 2:482. Briefly, the GAP program defines similarity as the number of aligned symbols (i.e., nucleotides or amino acids) that are similar, divided by the total number of symbols in the shorter of the two sequences. The preferred parameters for the GAP program are the default parameters, which do not impose a penalty for end gaps. See Schwartz et al. (1979) *Nuc Acids Res* 6(2):745–755; Gribskov et al. (1986) *Nuc Acids Res* 14(1):327–334.

In certain embodiments, the invention concerns the use of KCC, KCC2, KCC3 and KCC4 genes and gene products that include within their respective sequences a sequence which is essentially that of a KCC, KCC2, KCC3 or KCC4 gene, or the corresponding protein. The term "a sequence essentially as that of a KCC, KCC2, KCC3 or KCC4 gene", means that the sequence is substantially identical or substantially similar to a portion of a KCC, KCC2, KCC3 or KCC4 gene and contain a minority of bases or amino acids (whether DNA or protein) which are not identical to those of a KCC, KCC2, KCC3 or KCC4 protein or a KCC, KCC2, KCC3 or KCC4 gene, or which are not a biologically functional equivalent. The term "biologically functional equivalent" is well understood in the art and is further defined in detail herein. Nucleotide sequences are "essentially the same" where they have between about 70% and about 80% or more preferably, between about 81% and about 90%, or even more preferably, between about 91% and about 99%; of nucleic acid residues which are identical to the nucleotide sequence of a KCC, KCC2, KCC3 or KCC4 gene. Similarly, peptide sequences which have about 35%, or 45%, or preferably from 45–55%, or more preferably 55–65%, or most preferably 65% or greater amino acids which are identical or functionally equivalent or biologically functionally equivalent to the amino acids of a KCC, KCC2, KCC3 or KCC4 polypeptide will be sequences which are "essentially the same".

KCC, KCC2, KCC3 or KCC4 gene products and KCC, KCC2-, KCC3- or KCC4-encoding nucleic acid sequences, which have functionally equivalent codons, are also covered by the invention. The term "functionally equivalent codon" is used herein to refer to codons that encode the same amino acid, such as the ACG and AGU codons for serine. Thus, when referring to the sequence examples presented in SEQ ID NOs:1, 3, 5, 7, 9, 11, 13, 15, and 112 applicants contemplate substitution of functionally equivalent codons of Table 2 into the sequence examples of SEQ ID NOs:1, 3, 5, 7, 9, 11, 13, 15, and 112. Thus, applicants are in possession of amino acid and nucleic acids sequences which include such substitutions but which are not set forth herein in their entirety for convenience.

TABLE 2

Functionally Equivalent Codons

| Amino Acids | | Codons |
|---|---|---|
| Alanine | Ala | A GCA GCC GCG GCU |
| Cysteine | Cys | C UGC UGU |
| Aspartic Acid | Asp | D GAC GAU |
| Glumatic acid | Glu | E GAA GAG |
| Phenylalanine | Phe | F UUC UUU |
| Glycine | Gly | G GGA GGC GGG GGU |
| Histidine | His | H CAC CAU |
| Isoleucine | Ile | I AUA AUC AUU |
| Lysine | Lys | K AAA AAG |
| Leucine | Leu | L UUA UUG CUA CUC CUG CUU |
| Methionine | Met | M AUG |
| Asparagine | Asn | N AAC AAU |
| Proline | Pro | P CCA CCC CCG CCU |
| Glutamine | Gln | Q CAA CAG |
| Arginine | Arg | R AGA AGG CGA CGC CGG CGU |
| Serine | Ser | S ACG AGU UCA UCC UCG UCU |
| Threonine | Thr | T ACA ACC ACG ACU |
| Valine | Val | V GUA GUC GUG GUU |

TABLE 2-continued

Functionally Equivalent Codons

| Amino Acids | | Codons |
|---|---|---|
| Tryptophan | Trp | W UGG |
| Tyrosine | Tyr | Y UAC UAU |

It will also be understood by those of skill in the art that amino acid and nucleic acid sequences can include additional residues, such as additional NB or C-terminal amino acids or 5' or 3' nucleic acid sequences, and yet still be essentially as set forth in one of the sequences disclosed herein, so long as the sequence retains biological protein activity where protein expression is concerned. The addition of terminal sequences particularly applies to nucleic acid sequences which can, for example, include various non-coding sequences flanking either of the 5' or 3' portions of the coding region or can include various internal sequences, i.e., introns, which are known to occur within genes.

The present invention also encompasses the use of nucleotide segments that are complementary to the sequences of the present invention. Nucleic acid sequences which are "complementary" are those, which are base-paired according to the standard Watson-Crick complementarity rules. As used herein, the term "complementary sequences" means nucleic acid sequences which are substantially complementary, as can be assessed by the same nucleotide comparison set forth above, or is defined as being capable of hybridizing to the nucleic acid segment in question under relatively stringent conditions such as those described herein. A particular example of a contemplated complementary nucleic acid segment is an antisense oligonucleotide.

One technique in the art for assessing complementary sequences and/or isolating complementary nucleotide sequences is hybridization. Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of about 30° C., typically in excess of about 37° C., and preferably in excess of about 45° C. Stringent salt conditions will ordinarily be less than about 1,000 mM, typically less than about 500 mM, and preferably less than about 200 mM. However, the combination of parameters is much more important than the measure of any single parameter. See e.g., Wethmur & Davidson (1968) *J Mol Biol* 31:349–370. Determining appropriate hybridization conditions to identify and/or isolate sequences containing high levels of homology is well known in the art. See e.g., Sambrook et al. (1989) *Molecular Cloning: A Laboratory Manual*, Cold Spring Harbor Laboratory Press, Cold Spring Harbor, N.Y.

For the purposes of specifying conditions of high stringency, preferred conditions are salt concentration of about 200 mM and temperature of about 45° C. One example of such stringent conditions is hybridization at 4×SSC, at 65° C., followed by a washing in 0.1×SSC at 65° C. for one hour. Another exemplary stringent hybridization scheme uses 50% formamide, 4×SSC at 42° C. As used herein, "stringent conditions" means conditions of high stringency, for example 6×SSC, 0.2% polyvinylpyrrolidone, 0.2% Ficoll, 0.2% bovine serum albumin, 0.1% sodium dodecyl sulfate, 100 µg/ml salmon sperm DNA and 15% formamide at 68°

C. Nucleic acids having sequence similarity are detected by hybridization under low stringency conditions, for example, at 50° C. and 10×SSC (0.9 M NaCl/0.09 M sodium citrate) and remain bound when subjected to washing at 55° C. in 1×SSC. Sequence identity can be determined by hybridization under stringent conditions, for example, at 50° C. or higher and 0.1×SSC (9 mM NaCl/0.9 mM sodium citrate).

Nucleic acids that are substantially identical to the provided KCC sequences, e.g., allelic variants, genetically altered versions of the gene, etc., bind to the provided KCC sequences under stringent hybridization conditions. By using probes, particularly labeled probes of DNA sequences, one can isolate homologous or related genes. The source of homologous genes can be any species, e.g., primate species, particularly human; rodents, such as rats and mice, canines, felines, bovines, ovines, equines, yeast, nematodes, etc.

Between mammalian species, e.g., human, mouse and *xenopus*, homologs have substantial sequence similarity, i.e. at least 75% sequence identity between nucleotide sequences. Sequence similarity is calculated based on a reference sequence, which can be a subset of a larger sequence, such as a conserved motif, coding region, flanking region, etc. A reference sequence will usually be at least about 18 nucleotides long, more usually at least about 30 nucleotides long, and can extend to the complete sequence that is being compared. Algorithms for sequence analysis are known in the art, such as BLAST, described in Altschul et al. (1990) *J Mol Biol* 215:403–410. The sequences provided herein are essential for recognizing KCC related and homologous proteins in database searches.

At a biological level, identity is just that, i.e. the same amino acid at the same relative position in a given family member of a gene family. Homology and similarity are generally viewed as broader terms. For example, biochemically similar amino acids, for example leucine and isoleucine or glutamate/aspartate, can be present at the same position—these are not identical per se, but are biochemically "similar". As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine.

The KCCs disclosed herein are thus homologous proteins, but when percentages are referred to herein, it is meant to refer to percent identity. The percent identities referenced herein were generated by alignments with the program GeneWorks (Oxford Molecular, Inc. of Campbell, Calif.) and/or the BLAST program at NCBI (ncbi.nlm.nih.gov/BLAST/). Another commonly used alignment program is entitled CLUSTAL W and is described in Thompson et al. (1994) *Nucleic Acids Res* 22(22):4673–4680, among other places.

Probe sequences can also hybridize specifically to duplex DNA under certain conditions to form triplex or other higher order DNA complexes. The preparation of such probes and suitable hybridization conditions are disclosed herein and are known in the art.

The term "gene" is used for simplicity to refer to a functional protein, polypeptide or peptide encoding unit. As will be understood by those in the art, this functional term includes both genomic sequences and cDNA sequences. Preferred embodiments of genomic and cDNA sequences are disclosed herein.

In particular embodiments, the invention concerns isolated DNA segments and recombinant vectors incorporating DNA sequences, which encode a potassium-chloride cotransporter polypeptide that includes within its amino acid sequence an amino acid sequence of the present invention. In other particular embodiments, the invention concerns recombinant vectors incorporating DNA segments, which encode a protein comprising the amino acid sequence of a human potassium-chloride cotransporter.

A.1. Biologically Functional Equivalents

As mentioned above, modifications and changes can be made in the structure of the potassium-chloride cotransporter proteins and peptides described herein and still constitute a molecule having like or otherwise desirable characteristics. For example, certain amino acids can be substituted for other amino acids in a protein structure without appreciable loss of interactive capacity with, for example, structures in the nucleus of a cell. Since it is the interactive capacity and nature of a protein that defines that protein's biological functional activity, certain amino acid sequence substitutions can be made in a protein sequence (or the nucleic acid sequence encoding it) to obtain a protein with the same, enhanced, or antagonistic properties. Such properties can be achieved by interaction with the normal targets of the native protein, but this need not be the case, and the biological activity of the invention is not limited to a particular mechanism of action. It is thus contemplated in accordance with the present invention that various changes can be made in the sequence of the potassium-chloride cotransporter proteins and peptides or underlying nucleic acid sequence without appreciable loss of their biological utility or activity.

Biologically functional equivalent peptides, as used herein, are peptides in which certain, but not most or all, of the amino acids can be substituted. Thus, when referring to the sequence examples presented in SEQ ID NOs:1, 3, 5, 7, 9, 11, 13, 15, and/or 112, applicants contemplate substitution of codons that encode biologically equivalent amino acids as described herein into the sequence examples of SEQ ID NOs:1, 3, 5, 7, 9, 11, 13, 15, and/or 112. Thus, applicants are in possession of amino acid and nucleic acids sequences which include such substitutions but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged, e.g., substitution of Ile for Leu at amino acids 53, 86 and/or 1028 for hKCC4 in SEQ ID NOs:1–2; substitution of Ile for Leu at amino acids 35, 472 and/or 1075 for hKCC3a2m in SEQ ID NOs:3–4; substitution of Ile for Leu at amino acids 102, 631 and/or 1113 for mKCC3a2m in SEQ ID NOs:5–6; substitution of Ile for Leu at amino acids 35, 308 and/or 848 for mKCC3a in SEQ ID NOs:7–8; substitution of Ile for Leu at amino acids 66, 537 and/or 974 for mKCC3b in SEQ ID NOs:9–10; substitution of Ile for Leu at amino acids 120, 358 and/or 916 for hKCC2 in SEQ ID NOs:11–12; substitution of Ile for Leu at amino acids 71, 467 and/or 639 for mKCC4 in SEQ ID NOs:13–14; and substitution of Ile for Leu at amino acids 35, 346 and/or 789 for hKCC3a in SEQ ID NOs: 15–16. Changes designed by man can be introduced through the application of site-directed mutagenesis techniques, e.g., to introduce improvements to the antigenicity of the protein or to test KCC mutants in order to examine KCC transport activity, or other activity at the molecular level.

Amino acid substitutions, such as those which might be employed in modifying the potassium-chloride cotransporter proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all of similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. Other biologically functionally equivalent changes will be appreciated by those of skill in the art.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al. (1982) *J Mol Biol* 157:105, herein incorporated herein by reference). It is known that certain amino acids can be substituted for other amino acids having a similar hydropathic index or score and still retain a similar biological activity. In making changes based upon the hydropathic index, the substitution of amino acids whose hydropathic indices are within±2 of the original value is preferred, those, which are within ±1 of the original value, are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those, which are within ±1 of the original value, are particularly preferred, and those within ±0.5 of the original value are even more particularly preferred.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

Thus, it will also be understood that this invention is not limited to the particular nucleic acid and amino acid sequences of SEQ ID NOs:1–16 and 112–113. Recombinant vectors and isolated DNA segments can therefore variously include the potassium-chloride cotransporter polypeptide-encoding region itself, include coding regions bearing selected alterations or modifications in the basic coding region, or include larger polypeptides which nevertheless comprise potassium-chloride cotransporter polypeptide-encoding regions or can encode biologically functional equivalent proteins or peptides which have variant amino acid sequences. Biological activity of a potassium chloride cotransporter can be determined, for example, measuring the amount of $^{86}Rb^+$ uptake following transformation of the DNA of interest into *Xenopus laevis* oocytes, as disclosed herein.

In particular embodiments, the invention concerns gene therapy methods that use isolated DNA segments and recombinant vectors incorporating DNA sequences which encode a protein comprising an amino acid sequence of any of SEQ ID NOs:2, 4, 6, 8, 10, 12, 14, 16 and 113. In other particular embodiments, the invention concerns isolated DNA sequences and recombinant DNA vectors incorporating DNA sequences which encode a protein comprising the amino acid sequence of the potassium-chloride cotransporter protein from human or mouse tissue. In certain other embodiments, the invention concerns isolated DNA segments and recombinant vectors that comprise a nucleic acid sequence essentially as set forth in any of SEQ ID NOs:1, 3, 5, 7, 9, 11, 13, 15and/or112.

The nucleic acid segments of the present invention, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. For example, nucleic acid fragments can be prepared which include a short stretch complementary to a nucleic acid sequence set forth in any of SEQ ID NOs:1, 3, 5, 7, 9, 11, 13, 15 and/or 112, such as about 10 nucleotides, and which are up to 10,000 or 5,000 base pairs in length, with segments of 3,000 being preferred in certain cases. DNA segments with total lengths of about 4,000, 3,000, 2,000, 1,000, 500, 200, 100, and about 50 base pairs in length are also contemplated to be useful.

The DNA segments of the present invention encompass biologically functional equivalent potassium-chloride cotransporter proteins and peptides. Such sequences can rise as a consequence of codon redundancy and functional equivalency that are known to occur naturally within nucleic acid sequences and the proteins thus encoded. Alternatively, functionally equivalent proteins or peptides can be created via the application of recombinant DNA technology, in which changes in the protein structure can be engineered, based on considerations of the properties of the amino acids being exchanged. Changes can be introduced through the application of site-directed mutagenesis techniques, e.g., to introduce improvements to the antigenicity of the protein or to test potassium-chloride cotransporter mutants in order to examine activity in the modulation of potassium-chloride cotransporter, or other activity at the molecular level. Site-directed mutagenesis techniques are known to those of skill in the art and are disclosed herein.

The invention further encompasses fusion proteins and peptides wherein the potassium-chloride cotransporter coding region is aligned within the same expression unit with other proteins or peptides having desired functions, such as for purification or immunodetection purposes.

Recombinant vectors form important further aspects of the present invention. Particularly useful vectors are those in which the coding portion of the DNA segment is positioned under the control of a promoter. The promoter can be that naturally associated with the potassium-chloride cotransporter gene, as can be obtained by isolating the 5' noncoding sequences located upstream of the coding segment or exon, for example, using recombinant cloning and/or PCR technology and/or other methods known in the art, in conjunction with the compositions disclosed herein.

In other embodiments, it is contemplated that certain advantages will be gained by positioning the coding DNA segment under the control of a recombinant, or heterologous, promoter. As used herein, a recombinant or heterologous promoter is a promoter that is not normally associated with a potassium-chloride cotransporter gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology (See, e.g., Sambrook et al., eds. (1989) *Molecular Cloning: A Laboratory Manual*, Cold Spring Harbor Laboratory Press, Cold Spring Harbor, N.Y.). The promoters employed can be constitutive or inducible and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the vaccinia virus promoter and the baculovirus promoter.

In an alternative embodiment, the present invention provides an expression vector comprising a polynucleotide that encodes a biologically active potassium-chloride cotransporter polypeptide in accordance with the present invention. Also preferably, an expression vector of the present invention comprises a polynucleotide that encodes human or mouse potassium-chloride cotransporter gene product. More preferably, an expression vector of the present invention comprises a polynucleotide that encodes a polypeptide comprising an amino acid residue sequence of any of SEQ ID NOs:2, 4, 6, 8, 10, 12, 14, 16, adn 113. More preferably, an expression vector of the present invention comprises a polynucleotide comprising the nucleotide sequence of any of SEQ ID NOs:1, 3, 5, 7, 9, 11, 13, 15, and 112. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a biologically active potassium-chloride cotransporter polypeptide in accordance with the present invention. SEQ ID NOs:1–16 and 112–113 set forth nucleotide and amino acid sequences from exemplary vertebrates, human, mouse, and xenopus. Also contemplated by the present invention are homologous or biologically functionally equivalent polynucleotides and potassium-chloride cotransporter polypeptides found in other vertebrates, including particularly rat and bovine homologs. Preferably, a recombinant host cell of the present invention is transfected with the polynucleotide that encodes human or mouse potassium-chloride cotransporter polypeptide. More preferably, a recombinant host cell of the present invention is transfected with the polynucleotide sequence encoding or set forth in any of SEQ ID NOs:1–16 and 112–113. Most preferably, a recombinant host cell is a mammalian cell.

In another aspect, a recombinant host cell of the present invention is a prokaryotic host cell, including parasitic and bacterial cells. Preferably, a recombinant host cell of the invention is a bacterial cell, preferably a strain of *Escherichia coli*. More preferably, a recombinant host cell comprises a polynucleotide under the transcriptional control of regulatory signals functional in the recombinant host cell, wherein the regulatory signals appropriately control expression of the potassium-chloride cotransporter polypeptide in a manner to enable all necessary transcriptional and post-transcriptional modification.

In yet another embodiment, the present invention provides a process of preparing a potassium-chloride cotransporter polypeptide comprising transfecting a cell with polynucleotide that encodes a biologically active potassium-chloride cotransporter polypeptide in accordance with the present invention, to produce a transformed host cell, and maintaining the transformed host cell under biological conditions sufficient for expression of the polypeptide. The polypeptide can be isolated if desired, using any suitable technique. The host cell can be a prokaryotic or eukaryotic cell. Preferably, the prokaryotic cell is a bacterial cell of *Escherichia coli*. More preferably, a polynucleotide transfected into the transformed cell comprises the nucleotide base sequence of any of SEQ ID NOs:1, 3, 5, 7, 9, 11, 13, 15, and 112. SEQ ID NOs:1–16 and 112–113 set forth nucleotide and amino acid sequences for representative vertebrates, human, mouse and *Xenopus*. Also contemplated by the present invention are homologs or biologically equivalent potassium-chloride cotransporter polynucleotides and polypeptides found in other vertebrates, particularly warm-blooded vertebrates, more particularly mammals, and even more particularly bovine and rat homologs.

As mentioned above, in connection with expression embodiments to prepare recombinant potassium-chloride cotransporter proteins and peptides, it is contemplated that longer DNA segments will most often be used, with DNA segments encoding the entire potassium-chloride cotransporter protein, functional domains or cleavage products thereof, being most preferred. However, it will be appreciated that the use of shorter DNA segments to direct the expression of potassium-chloride cotransporter peptides or core regions, such as can be used to generate anti-potassium-chloride cotransporter antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins can have a minimum coding length on the order of about 4,000 or 5,000 nucleotides for a protein in accordance with any of SEQ ID NOs:1, 3, 5, 7, 9, 11, 13, 15, and 112. DNA segments of the present invention can contain 300, 400, 500, 1,000, 1,500, 2,000, 2,500, 3,000, 3,500, 4,000, 4,500, or up to 5,000 nucleotides. Peptides of the present invention can contain 10, 20, 50, 100, 200, 300, 400, 500, 750, 1,000, or up to 1,500 amino acids.

A.2. Sequence Modification Techniques

Modifications to the potassium-chloride cotransporter proteins and peptides described herein can be carried out using techniques known in the art, including site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants; for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is preferred, with about 5 to 10 residues on both sides of the junction of the sequence being altered.

In general, the technique of site-specific mutagenesis is well known in the art as exemplified by publications (e.g., Adelman et al. (1983) *DNA* 2:183; Sambrook et al. (1989) *Molecular Cloning: A Laboratory Manual*, Cold Spring Harbor Laboratory Press, Cold Spring Harbor, N.Y.) and can be achieved in a variety of ways generally known to those of skill in the art.

A.3. Other Structural Equivalents

The knowledge of the structure of the potassium-chloride cotransporter polypeptide of the present invention provides a means of investigating the mechanism of action of these proteins in a subject. For example, binding of these proteins to various substrate molecules can be predicted by various computer models. Upon discovering that such binding in fact takes place, knowledge of the protein structure then allows design and synthesis of small molecules, which mimic the functional binding of the potassium-chloride cotransporter polypeptide to the substrate. This is the method of "rational" drug design.

Use of the isolated and purified potassium-chloride cotransporter polypeptide of the present invention in rational drug design is thus contemplated in accordance with the present invention. Additional rational drug design techniques are described in U.S. Pat. Nos. 5,834,228 and 5,872,011, herein incorporated in their entirety.

Thus, in addition to the peptidyl compounds described herein, the inventors also contemplate that other sterically similar compounds can be formulated to mimic the key portions of the peptide structure. Such compounds can be used in the same manner as the peptides of the invention and hence are also functional equivalents. The generation of a structural functional equivalent can be achieved by the techniques of modeling and chemical design known to those of skill in the art. It will be understood that all such sterically similar constructs fall within the scope of the present invention.

B. Introduction of Gene Products

In accordance with the present invention, where a KCC gene itself is employed to introduce a KCC gene product, a convenient method of introduction will be through the use of a recombinant vector that incorporates the desired gene, together with its associated control sequences. The preparation of recombinant vectors is well known to those of skill in the art and described in many references, such as, for example, Sambrook et al., eds. (1989) *Molecular Cloning: A Laboratory Manual*, Cold Spring Harbor Laboratory Press, Cold Spring Harbor, N.Y., incorporated herein in its entirety.

B.1. Vector Construction

It is understood that the DNA coding sequences to be expressed, in this case those encoding the potassium-chloride cotransporter gene products, are positioned in a vector adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter.

One can also desire to incorporate into the transcriptional unit of the vector an appropriate polyadenylation site (e.g., 5'-AATAAA-3'), if one was not contained within the original inserted DNA. Typically, these poly-A addition sites are placed about 30 to 2000 nucleotides "downstream" of the coding sequence at a position prior to transcription termination.

While use of the control sequences of the specific gene will be preferred, other control sequences can be employed, so long as they are compatible with the genotype of the cell being treated. Thus, one can mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs upstream of (i.e., 5' to) the point at which transcription begins (i.e., a transcription start site). That region typically contains several types of DNA sequence elements that are located in similar relative positions in different genes.

Another type of discrete transcription regulatory sequence element is an enhancer. An enhancer imposes specificity of time, location and expression level on a particular coding region or gene. A major function of an enhancer is to increase the level of transcription of a coding sequence in a cell that contains one or more transcription factors that bind to that enhancer. An enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art; the precise orientation and location relative to a coding sequence of interest is dependent, inter alia, upon the specific nature of the enhancer-promoter.

An enhancer-promoter used in a vector construct of the present invention can be any enhancer-promoter that drives expression in a cell to be transfected. By employing an enhancer-promoter with well-known properties, the level and pattern of gene product expression can be optimized.

For introduction of, for example, a human potassium-chloride cotransporter gene, a vector construct that will deliver the gene to the affected cells is desired. Viral vectors can be used. These vectors will preferably be an adenoviral, a retroviral, a vaccinia viral vector, adeno-associated virus or Lentivirus; these vectors are preferred because they have been successfully used to deliver desired sequences to cells and tend to have a high infection efficiency. Suitable vector-potassium-chloride cotransporter gene constructs are adapted for administration as pharmaceutical compositions, as described herein below. Viral promoters can also be of use in vectors of the present invention, and are known in the art.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment that also contains the SV40 viral origin of replication. Smaller or larger SV40 fragments can also be used, provided there is included the approximately 250 base pair sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

The origin of replication can be provided either by construction of the vector to include an exogenous origin, such as can be derived from SV40 or other viral source, or can be provided by the host cell chromosomal replication mechanism. If the vector is integrated into the host cell chromosome, the latter is often sufficient.

Where a potassium-chloride cotransporter gene itself is employed it will be most convenient to simply use a wild type potassium-chloride cotransporter gene directly. However, it is contemplated that certain regions of a potassium-chloride cotransporter gene can be employed exclusively without employing an entire wild type potassium-chloride cotransporter gene. It is proposed that it will ultimately be preferable to employ the smallest region needed to modulate biological activity so that one is not introducing unnecessary DNA into cells which receive a potassium-chloride cotransporter gene construct. The ability of these regions to modulate cell signaling can easily be determined by the assays reported in the Examples.

B.2. Transgenic Animals

It is also contemplated to be within the scope of the present invention to prepare a transgenic non-human animal that expresses a potassium-chloride cotransporter gene of the present invention. A preferred transgenic animal is a mouse.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), the entire contents of each of which are herein incorporated by reference.

With respect to a representative method for the preparation of a transgenic mouse, cloned recombinant or synthetic DNA sequences or DNA segments encoding a potassium-chloride cotransporter gene product are injected into fertilized mouse eggs. The injected eggs are implanted in pseudo pregnant females and are grown to term to provide transgenic mice whose cells express a potassium-chloride cotransporter gene product.

For example, a transgenic animal of the present invention can comprises a mouse with targeted modification of the mouse KCC2, KCC3, and KCC4 genes. Mice strains with complete or partial functional inactivation of the KCC genes in all somatic cells are generated using standard techniques of site-specific recombination in murine embryonic stem cells. See Capecchi (1989) Science 244(4910):1288–1292; Thomas & Capecchi (1990) Nature 346(6287):847–850; Delpire et al. (1999) Nat Genet 22(2):192–195. "knockout" murine KCC2 mice have been prepared, and the resultant homozygous KCC2$^{-/-}$ mice have a seizure disorder and increased perinatal mortality. The HCC2 knockout mice thus provide evidence that KCC2 is a drug target in epilepsy and further evidence that human KCC2 is a medically relevant gene.

Alternatives include the use of anti-sense or ribozyme KCC constructs, driven by a universal or tissue-specific promoter, to reduce levels of individual KCCs in somatic cells, thus achieving a "knock-down" of individual isoforms (Luyckx et al. (1999) Proc Natl Acad Sci USA 96(21): 12174–12179). The invention also provides the generation of murine strains with conditional or inducible inactivation of individual or multiple KCC genes (Sauer (1998) Methods 14(4):381–392). For example, mice are created which lack expression of any KCCs in the renal proximal tubule, a known site of expression of KCC3 and KCC4, through the sequential mating of mice strains with lox-P-flanked KCC genes with a transgenic line expressing Cre-recombinase in the proximal tubule, using the promoter for the kidney androgen-regulated protein (Ding et al. (1997) J Biol Chem 272(44):28142–28148).

The present invention also provides mice strains with specific "knocked-in" modifications in the KCC2, KCC3, or KCC4 genes. This includes mice with genetically (Forlino et al. (1999) J Biol Chem 274(53):37923–37931) and functionally (Kissel et al. (2000) EMBO J 19(6):1312–1326) relevant point mutations in the KCC genes, in addition to manipulations such as the insertion of disease-specific repeat expansions (White et al. (1997) Nat Genet 17(4):404–410).

C. Generation of Antibodies

In still another embodiment, the present invention provides an antibody immunoreactive with a polypeptide of the present invention. Preferably, an antibody of the invention is a monoclonal antibody. Techniques for preparing and characterizing antibodies are well known in the art (See e.g., Harlow & Lane (1988) Antibodies: A Laboratory Manual, Cold Spring Harbor Laboratory Press, Cold Spring Harbor, N.Y.

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Because of the relatively large blood volume of rabbits, a rabbit is a preferred choice for production of polyclonal antibodies.

As is well known in the art, a given polypeptide or polynucleotide can vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, NCmaleimidobencoyl-N-hydroxysuccinimide ester, carbodiimide and bis-biazotized benzidine.

As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies, inter alia, upon the nature of the immunogen as well as the animal used for immunization. A variety of routes can be used to administer the immunogen, e.g., subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention provides a process of producing an antibody immunoreactive with a potassium-chloride cotransporter polypeptide, the process comprising the steps of (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Preferably, the potassium-chloride cotransporter polypeptide is capable of modulating potassium and/or chloride levels within or outside of cells in accordance with the present invention.

A monoclonal antibody of the present invention can be readily prepared through use of well-known techniques such as the hybridoma techniques exemplified in U.S. Pat. No. 4,196,265 and the phage-displayed techniques disclosed in U.S. Pat. No. 5,260,203, the contents of which are herein incorporated by reference.

A typical technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the process of boosting and titering is repeated until a suitable titer is achieved, The spleen of the mouse with the highest titer is removed and the spleen lymphocytes are obtained by homogenizing the spleen with a syringe.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus "immortal". Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, and thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

D. Detecting a Polynucleotide or a Polypeptide of the Present Invention

Alternatively, the present invention provides a process of detecting a polypeptide of the present invention, wherein the process comprises immunoreacting the polypeptides with antibodies prepared according to the process described above to form antibody-polypeptide conjugates, and detecting the conjugates.

In yet another embodiment, the present invention provides a process of detecting messenger RNA transcripts that encode a polypeptide of the present invention, wherein the process comprises hybridizing the messenger RNA transcripts with polynucleotide sequences that encode the polypeptide to form duplexes; and detecting the duplex. Alternatively, the present invention provides a process of detecting DNA molecules that encode a polypeptide of the present invention, wherein the process comprises hybridizing DNA molecules with a polynucleotide that encodes that polypeptide to form duplexes; and detecting the duplexes.

The detection and screening assays disclosed herein can optionally be used as a prognosis tool and/or diagnostic aid. KCC2-, KCC3-and/or KCC4-encoding polypeptides and nucleic acids can be readily used in clinical setting as a prognostic and/or diagnostic indicator for screening for levels of expression of potassium-chloride cotransporters, or alterations in native sequences. The nucleotide sequences of the subject invention can be used to detect differences in gene or gene product sequences between normal, carrier, or affected individuals. Such differences can consist of single-nucleotide changes or multiple changes, deletions, or additions in the native sequence which result in altered transcription, translation, or activity or biological activity or properties of the gene or gene product. These differences can be readily detected using the compositions of the present invention and techniques known in the art, including but not limited to SSCP analysis, RFLP analysis, or other PCR- or nucleotide-based analysis.

DNA segments of the invention or RNA having the sequence of, or a sequence complementary to, SEQ ID NOs:1, 3, 5, 7, 9, 11, 13, 15, or 112 can be used. Such polynucleic acids can comprise 10, 20, 40, 50, 70, 100, 250, 300, 400, 500, or 1,000 nucleotides or up to the full length of SEQ ID NOs:1, 3, 5, 7, 9, 11, 13, 15, or 112. Such polynucleic acids can, but need not, encode polypeptides which retain some or all of the biological activity of the native gene or gene product.

D.1. Screening Assays for a Polypeptide of the Present Invention

The present invention provides a process of screening a biological sample for the presence of a potassium-chloride cotransporter polypeptide. A biological sample to be screened can be a biological fluid such as extracellular or intracellular fluid, or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide. In accordance with a screening assay process, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate). Additional details of methods for such assays are known in the art. The presence of polypeptide in the sample is detected by evaluating the formation and presence of antibody-polypeptide conjugates. Techniques for detecting such antibody-antigen conjugates or complexes are well known in the art and include but are not limited to centrifugation, affinity chromatography and the like, and binding of a secondary antibody to the antibody-candidate receptor complex.

In one embodiment, detection is accomplished by detecting an indicator affixed to the antibody. Exemplary and well-known indicators include radioactive labels (e.g., $^{32}P$, $^{125}I$, $^{14}C$), a second antibody or an enzyme such as horseradish peroxidase. Techniques for affixing indicators to antibodies are known in the art.

Figure 29:
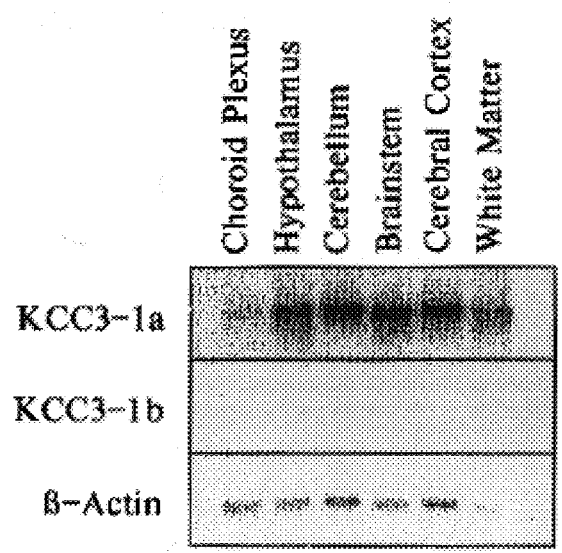
FIG. 29 is a Northern blot prepared using total RNA (10 μg/lane) isolated from different regions of mouse brain. The membrane was probed successively with KCC3 1a-specific, KCC3 1b-specific, and actin probes. KCC3b was not detected at all, but KCC3a was present in all regions of the brain examined. Densitometry of KCC3a and actin was performed, and densitometry rations of KCC3a/actin were calculated. Equivalent amounts of KCC3a transcripts were measured in all regions of the brain, with the exception of the choroid plexus, which expressed one-third of the amount of other regions.

In one embodiment, an antibody that recognizes a KCC4 polypeptide was used to detect KCC4 in mammalian tissues as described in Example 22. KCC4 is detected in a variety of tissues, including abundant expression in muscle, brain, lung, heart, and kidney. In another embodiment, an antibody that recognizes a KCC3 polypeptide was used to detect KCC3 in mammalian tissues as described in Examples 22–23. By performing this method, KCC3 isoforms KCC3a and KCC3b were distinguished by size. Further, the KCC3b isoform was shown to predominate in kidney, whereas KCC3a is predominate in the central nervous system. KCC3a is detected at the base of the choroid plexus epithelium, in large neurons, in the spinal dorsal and ventral columns, and in myelinated white matter tracts of the brain (FIGS. 29L–29M and 32). Differential expression of KCC isoforms KCC3a and KCC3b in brain and kidney, respectively, is also disclosed. KCC3a expression in brain supports a role of KCC3 in modulating neuronal communication and in controlling CNS excitability. Such a biological role is relevant to understanding, diagnosis, and treatment of epilepsy and other neural disorders, for example, Andermann's syndrome. KCC3b expression in kidney points to a role in regulating hypertension, and other disorders of osmotic imbalance.

D.2. Screening Assay for Anti-polypeptide Antibody

In another aspect, the present invention provides a process of screening a biological sample for the presence of antibodies immunoreactive with a potassium-chloride cotransporter polypeptide. Preferably the antibody so identified has activity in the modulation of potassium-chloride cotransporter biological activity in accordance with the present invention. In accordance with such a process, a biological sample is exposed to a KCC2, KCC3 and/or KCC4 polypeptide under biological conditions and for a period of time sufficient for antibody-polypeptide conjugate formation and the formed conjugates are detected.

D.3. Detection of a Polynucleotide that Encodes a KCC2, KCC3 and/or KCC4 Polypeptide of the Present Invention A DNA or RNA molecule and particularly a DNA segment or polynucleotide can be used for hybridization to a DNA or RNA source or sample suspected of encoding a KCC polypeptide of the present invention; such molecules are referred to as "probes," and such hybridization is "probing". Such probes can be made synthetically. The probing is usually accomplished by hybridizing the oligonucleotide to a DNA source suspected of possessing a KCC (e.g., KCC2, KCC3 and/or KCC4) gene. In some cases, the probes constitute only a single probe, and in others, the probes constitute a collection of probes based on a certain amino acid sequence or sequences of the polypeptide and account in their diversity for the redundancy inherent in the genetic code.

Other molecules which are neither DNA nor RNA but are capable of hybridizing in a similar manner and which are designed structurally to mimic the DNA or RNA sequence of a KCC (KCC2, KCC3 and/or KCC4) gene are also contemplated. Here, a suitable source to examine is capable of expressing a polypeptide of the present invention and can be a genomic library of a cell line of interest. Alternatively, a source of DNA or RNA can include total DNA or RNA from the cell line of interest. Once the hybridization process of the invention has identified a candidate DNA segment, a positive clone can be confirmed by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) reagents for detecting and isolating other members of the polypeptide family and related polypeptides from a DNA library potentially containing such sequences; (3) primers for hybridizing to related sequences for the purpose of amplifying those sequences; (4) primers for altering native potassium-chloride cotransporter DNA sequences; as well as (5) other techniques which rely on the similarity of the sequences of interest to those of the sequences herein disclosed.

As set forth above, in certain aspects, DNA sequence information provided by the invention allows for the preparation of probes that specifically hybridize to encoding sequences of a selected potassium-chloride cotransporter gene. In these aspects, probes of an appropriate length are prepared based on a consideration of the encoding sequence for a polypeptide of this invention. The ability of such probes to specifically hybridize to other encoding sequences lends them particular utility in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to or mimic at least a 14 to 40 or so long nucleotide stretch of a nucleic acid sequence of the present invention, such as a sequence shown in any of SEQ ID NOs:1, 3, 5, 7, 9, 11, 13, 15, and 112. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired, such as 30, 40, 50, 60, 100, 200, 300, or 500 nucleotides up to the full length of any of SEQ ID NOs:1, 3, 5, 7, 9, 11, 13, 15, and 112. Such fragments can be readily prepared by, for example, directly synthesizing the fragment by chemical synthesis, by application of nucleic acid amplification technology, such as the PCR technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M salt (e.g., NaCl), including particularly 200 mM salt, at temperatures of 50° C. to 70° C., including particularly temperatures of about 55° C., about 60° C. and about 65° C. Such conditions are particularly selective, and tolerate little, if any, mismatch between the probe and the template or target strand.

Of course, for some applications, less stringent hybridization conditions are typically needed to allow formation of the heteroduplex; one of skill in the art will know how to adjust the hybridization conditions for optimizing particular procedures. For example, it is generally appreciated that conditions can be rendered more stringent by the addition of increasing amounts of formamide, which serves to destabilize the hybrid duplex in the same manner as increased temperature. Thus, hybridization conditions can be readily manipulated by one of skill in the art using known methods to carry out the desired function or experiment, without undue experimentation.

In one embodiment, the KCC sequences disclosed herein were used to detect a KCC RNA polynucleotide as described in Examples 19. By performing this method, KCC4 was determined to be expressed in a multitude of tissues, including robust expression in muscle, brain, lung, heart, and kidney. Expression of KCC4 in kidney supports a potential role in expression in kidney points to a role in regulating hypertension, and other disorders of osmotic imbalance.

In another embodiment, KCC3 was determined to be expressed in muscle, brain, lung, heart, and kidney. Differential expression of KCC isoforms KCC3a and KCC3b in brain and kidney, respectively, is also disclosed. KCC3a expression in brain supports a role of KCC3 in modulating neuronal communication and in controlling CNS excitability. Such a biological role is relevant to understanding, diagnosis, and treatment of epilepsy and other neural disorders, for example, Andermann's syndrome. KCC3b expression in kidney points to a role in regulating hypertension, and other disorders of osmotic imbalance.

D.4. Detection Assay Kits

In another aspect, the present invention provides assay kits for detecting the presence of a polypeptide of the present invention in biological samples, where the kits comprise a first antibody capable of immunoreacting with the polypeptide. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also provides an assay kit for screening agents. Such a kit can contain a polypeptide of the present invention. The kit can additionally contain reagents for detecting an interaction between an agent and a polypeptide of the present invention.

In an alternative aspect, the present invention provides assay kits for detecting the presence, in biological samples, of a polynucleotide that encodes a polypeptide of the present invention, the kits comprising a first container that contains a second polynucleotide identical or complementary to a segment of at least 10 contiguous nucleotide bases of, as a preferred example, any of SEQ ID NOs:1, 3, 5, 7, 9, 11, 13, 15, and 112. In another embodiment, the present invention provides assay kits for detecting the presence, in a biological sample, of antibodies immunoreactive with a polypeptide of the present invention, the kits comprising a KCC (e.g., KCC2, KCC3 and/or KCC4) polypeptide that immunoreacts with the antibodies.

E. Mapping and Polynucleotide Screening

In another embodiment of the invention, the nucleic acid sequences that encode KCC2, KCC3 and/or KCC4 can also be used to generate hybridization probes which are useful for mapping naturally occurring genomic sequences and/or disease loci. The sequences can be mapped to a particular chromosome or to a specific region of the chromosome using well-known techniques. Such techniques include FISH, FACS, or artificial chromosome constructions, such as yeast artificial chromosomes, bacterial artificial chromosomes, bacterial P1 constructions or single chromosome cDNA libraries as reviewed in Price (1993) *Blood Rev* 7:127–134, and Trask (1991) *Trends Genet* 7:149–154.

FISH (as described in Verma et al. (1988) *Human Chromosomes: A Manual of Basic Techniques*, Pergamon Press, New York, N.Y.) can be correlated with other physical chromosome mapping techniques and genetic map data. Examples of genetic map data can be found in the 1994 Genome Issue of *Science* (265:1981f). Correlation between the location of the gene encoding KCC2, KCC3 and/or KCC4 on a physical chromosomal map and a specific disease, or predisposition to a specific disease, can help delimit the region of DNA associated with that genetic disease. The nucleotide sequences of the subject invention can be used to detect differences in gene sequences between normal, carrier, or affected individuals.

In situ hybridization of chromosomal preparations and physical mapping techniques such as linkage analysis using established chromosomal markers can be used for extending genetic maps. Often the placement of a gene on the chromosome of another mammalian species, such as mouse, reveals associated markers also found in other mammals such as humans even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, ataxia-telangiectasia (A-T) to 11q22–23 (Gatti et al. (1988) *Nature* 336: 577–580), any sequences mapping to that area can represent associated or regulatory genes for further investigation. The nucleotide sequences of the present invention can thus also be used to detect differences in the chromosomal location due to translocation, inversion, etc. among normal, carrier, or affected individuals.

The mapping methods of the present invention also employ genomic clones of the exons of KCC2, KCC3 and KCC4. Coding and genomic sequences for human KCC2 are set forth in SEQ ID NOs:20–63. Coding sequences from human KCC2 exons 1–24 (SEQ ID NOs:20–43) are set forth herein. Genomic sequences for human KCC2 exons 2–7 (SEQ ID NOs:44–49), exons 9–14 (SEQ ID NOs:50–55), and exons 17–24 (SEQ ID NOs:56–63) are set forth herein.

Genomic sequences for human KCC4 are set forth in SEQ ID NOs: 64–83. Genomic sequences for human KCC4 exon 2 (SEQ ID NO:64), exon 3 (SEQ ID NO:65), exon 5 (SEQ ID NO:66), exons 6–10 (SEQ ID NOs:67–71), exons 12–19 (SEQ ID NOs:72–79), and exons 21–24 (SEQ ID NOs: 80–83) are set forth herein.

Genomic sequences for human KCC3a and human KCC3b are set forth in SEQ ID NOs:84–110. Genomic sequences for human KCC3 exon 1-hKCC3a (SEQ ID NO:84), exon 1-hKCC3b (SEQ ID NO:85), exon 2 (SEQ ID NO:86), exon 3 (SEQ ID NO:87), exon 4-HKCC3b (SEQ ID NO:88), exon 4-HKCC3a (SEQ ID NO:89), exons 6–11 (SEQ ID NOs:90–95), exon 12-hKCC3b (SEQ ID NO:96), exon 12-hKCC3a (SEQ ID NO:97) and exons 13–25 (SEQ ID NOs:98–110) are set forth herein.

In another embodiment, the present invention provides genetic assays based on the genomic sequence of the human KCC2, KCC3, and KCC4 genes. The intronic sequence flanking the individual exons encoding the three genes, described as SEQ ID NOs:44–110, is employed in the design of oligonucleotide primers suitable for the mutation analysis of human genomic DNA. Thus, intronic primers can be used to screen for genetic variants by a number of PCR-based techniques, including single-strand conformation polymorphism (SSCP) analysis (Orita et al. (1989) *Proc Natl Acad Sci USA* 86(8):2766–2770), SSCP/heteroduplex analysis, enzyme mismatch cleavage, and direct sequence analysis of amplified exons (Kestila et al. (1998) *Mol Cell* 1(4), 575–582; Yuan et al. (1999) *Hum Mutat* 14(5):440–446).

Similar techniques can be applied to putative 5'-regulatory regions, e.g., the putative promoters 5' of exons 1a and 1b of human or mouse KCC3 (e.g., SEQ ID NOs:17–19). Automated methods can also be applied the large-scale characterization of single nucleotide polymorphisms (Brookes (1999) *Gene* 234(2):177–186; Wang et al. (1998) *Science* 280(5366):1077–1082) within and near the human KCC genes. Once genetic variants have been detected in specific patient populations, e.g., KCC3 mutations in patients with Andermann's syndrome, the present invention provides assays to detect the mutation by methods such as allele-specific hybridization (Stoneking et al. (1991) *Am J Hum Genet* 48(2):370–382), or restriction analysis of amplified genomic DNA containing the specific mutation. Again, these detection methods can be automated using existing technology (Wang et al. (1998) *Science* 280(5366):1077–1082). In the case of genetic disease or human phenotypes caused by repeat expansion (Lafreniere et al. (1997) *Nat Genet* 15(3):298–302; Timchenko & Caskey (1996) *FASEB J* 10(14):1589–1597), the invention provides an assay based on PCR of genomic DNA with oligonucleotide primers flanking the involved repeat.

As used herein and in the claims, the term "polymorphism" refers to the occurrence of two or more genetically determined alternative sequences or alleles in a population. A polymorphic marker is the locus at which divergence occurs. Preferred markers have at least two alleles, each occurring at frequency of greater than 1%. A polymorphic locus can be as small as one base pair.

As used herein and in the claims, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, a KCC gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

The provided nucleic acid molecules can be labeled according to any technique known in the art, such as with radiolabels, fluorescent labels, enzymatic labels, sequence tags, etc. Such molecules can be used as allele-specific oligonucleotide probes. Body samples can be tested to determine whether a KCC gene contains a polymorphism. Suitable body samples for testing include those comprising DNA, RNA or protein obtained from biopsies, including liver and intestinal tissue biopsies; or from blood, prenatal; or embryonic tissues, for example.

In one embodiment of the invention two pairs of isolated oligonucleotide primers are provided. These sets of primers are optionally derived from a KCC exon. The oligonucleotide primers are useful, for example, in detecting a polymorphism of a KCC gene. The primers direct amplification of a target polynucleotide prior to sequencing. In another embodiment of the invention isolated allele specific oligonucleotides (ASO) are provided. The allele specific oligonucleotides are also useful in detecting a polymorphism of a KCC gene.

The terms "substantially complementary to" or "substantially the sequence of" refer to sequences which hybridize to the sequences provided (e.g., SEQ ID NO:44–110) under stringent conditions as disclosed herein and/or sequences having sufficient homology with any of SEQ ID NOs: 44–110, such that the allele specific oligonucleotides of the invention hybridize to the sequence. The term "isolated" as used herein includes oligonucleotides substantially free of other nucleic acids, proteins, lipids, carbohydrates or other materials with which they can be associated, such association being either in cellular material or in a synthesis medium. A "target polynucleotide" or "target nucleic acid" refers to the nucleic acid sequence of interest e.g., a KCC-encoding polynucleotide. Other primers which can be used for primer hybridization are readily ascertainable to those of skill in the art based upon the disclosure herein.

The primers of the invention embrace oligonucleotides of sufficient length and appropriate sequence so as to provide initiation of polymerization on a significant number of nucleic acids in the polymorphic locus. Specifically, the term "primer" as used herein refers to a sequence comprising two or more deoxyribonucleotides or ribonucleotides, preferably more than three, and more preferably more than eight and most preferably at least about 20 nucleotides of a KCC exonic or intronic region as are disclosed herein. Such oligonucleotides are preferably between ten and thirty bases in length. Such oligonucleotides can optionally further comprise a detectable label.

Environmental conditions conducive to synthesis include the presence of nucleoside triphosphates and an agent for polymerization, such as DNA polymerase, and a suitable temperature and pH. The primer is preferably single stranded for maximum efficiency in amplification, but can be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it can contain fewer nucleotides.

Primers of the invention are designed to be "substantially" complementary to each strand of the genomic locus to be amplified. This means that the primers must be sufficiently complementary to hybridize with their respective strands under conditions that allow the agent for polymerization to perform. In other words, the primers should have sufficient complementarity with the 5' and 3' sequences flanking the transition to hybridize therewith and permit amplification of the genomic locus.

Oligonucleotide primers of the invention are employed in the amplification method that is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymeraseI (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention can be prepared using any suitable method, such as conventional phosphotriester and phosphodiester methods or automated embodiments thereof. In one such automated embodiment, diethylphosphoramidites are used as starting materials and can be synthesized as described by Beaucage et al. (1981) *Tetrahedron Letters* 22:1859–1862. One method for synthesizing oligonucleotides on a modified solid support is described in U.S. Pat. No. 4,458,066.

Any nucleic acid specimen, in purified or non-purified form, can be utilized as the starting nucleic acid or acids, providing it contains, or is suspected of containing, a nucleic acid sequence containing the polymorphic locus. Thus, the method can amplify, for example, DNA or RNA, including messenger RNA, wherein DNA or RNA can be single stranded or double stranded. In the event that RNA is to be used as a template, enzymes, and/or conditions optimal for reverse transcribing the template to DNA would be utilized. In addition, a DNA-RNA hybrid that contains one strand of each can be utilized. A mixture of nucleic acids can also be employed, or the nucleic acids produced in a previous amplification reaction herein, using the same or different primers can be so utilized. The specific nucleic acid sequence to be amplified, i.e., the polymorphic locus, can be a fraction of a larger molecule or can be present initially as a discrete molecule, so that the specific sequence constitutes the entire nucleic acid. It is not necessary that the sequence to be amplified is present initially in a pure form; it can be a minor fraction of a complex mixture, such as contained in whole human DNA.

DNA utilized herein can be extracted from a body sample, such as blood, tissue material (e.g., brain or kidney tissue), and the like by a variety of techniques such as that described by Maniatis et. al. (1982) in *Molecular Cloning: A Laboratory Manual*, Cold Spring Harbor Laboratory Press, New York, N.Y. If the extracted sample is impure, it can be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90–100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization can also be added together with the other reagents if it is heat stable. This synthesis (or amplification) reaction can occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization can be any compound or system that will function to accomplish the synthesis of primer extension products, including enzymes. Suitable enzymes for this purpose include, for example, E. coli DNA polymeraseI, Klenow fragment of E. coli DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described herein and this hybrid is used in subsequent steps of the method. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. See McPherson et al., eds. (1991) *PCR. A Practical Approach*, IRL Press, Oxford University Press, New York, N.Y.

The amplification products can be detected by Southern blot analysis with or without using radioactive probes. In one such method, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as dideoxy sequencing, PCR, oligomer restriction (Saiki et al. (1985) *Bio/Technology* 3:1008–1012), allele-specific oligonucleotide (ASO) probe analysis (Conner et al. (1983) *Proc Natl Acad Sci USA* 80:278), oligonucleotide ligation assays (OLAs) (Landgren et al. (1988) *Science* 241:1007), and the like. Molecular techniques for DNA analysis have been reviewed (Landgren et al. (1988) *Science* 242:229–237).

Preferably, the method of amplifying is by PCR, as described herein and in U.S. Pat. Nos. 4,683,195; 4,683,202; and 4,965,188 each of which is hereby incorporated by reference; and as is commonly used by those of ordinary skill in the art. Alternative methods of amplification have been described and can also be employed as long as a KCC locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase transcribes the RNA into cDNA and degrades the RNA, followed by reverse transcriptase polymerizing a second strand of DNA.

Another nucleic acid amplification technique is nucleic acid sequence-based amplification (NASBA™) which uses reverse transcription and T7 RNA polymerase and incorporates two primers to target its cycling scheme. NASBA™ amplification can begin with either DNA or RNA and finish with either, and amplifies to about 108 copies within 60 to 90 minutes.

Alternatively, nucleic acid can be amplified by ligation-activated transcription (LAT). LAT works from a single-stranded template with a single primer that is partially single-stranded and partially double-stranded. Amplification is initiated by ligating a cDNA to the promoter olignucleotide and within a few hours, amplification is about 108 to about 109 fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest.

Another nucleic acid amplification technique, ligase chain reaction (LCR), works by using two differently labeled halves of a sequence of interest that are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligo probe pairs, and the RCR fills and joins the gap, mimicking normal DNA repair.

Nucleic acid amplification by strand displacement activation (SDA) utilizes a short primer containing a recognition site for HincII with short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the site of the nick and begins to polymerize, displacing the initial primer strand downstream and building a new one which serves as more primer.

SDA produces greater than about a $10^7$-fold amplification in 2 hours at 37° C. Unlike PCR and LCR, SDA does not require instrumented temperature cycling. Another amplification system useful in the method of the invention is the QB Replicase System. Although PCR is the preferred method of amplification if the invention, these other methods can also be used to amplify the KCC locus as described in the method of the invention. Thus, the term "amplification technique" as used herein and in the claims is meant to encompass all the foregoing methods.

In another embodiment of the invention a method is provided for identifying a subject having a polymorphism of a KCC gene, comprising sequencing a target nucleic acid of a sample from a subject by dideoxy sequencing, preferably following amplification of the target nucleic acid.

In another embodiment of the invention a method is provided for identifying a subject having a polymorphism of a KCC gene, comprising contacting a target nucleic acid of a sample from a subject with a reagent that detects the presence of a KCC polymorphism and detecting the reagent. A number of hybridization methods are well known to those skilled in the art. Many of them are useful in carrying out the invention.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those of ordinary skill in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. See, e.g., Wethmur & Davidson (1986) *J Mol Biol* 31:349–370.

Accordingly, a nucleotide sequence of the present invention can be used for its ability to selectively form duplex molecules with complementary stretches of a KCC gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M salt at temperatures of about 50° C. to about 70° C. including particularly temperatures of about 55° C., about 60° C. and about 65° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M–0.9M salt, at temperatures ranging from about 20° C. to about 55° C., including particularly temperatures of about 25° C., about 37° C., about 45° C., and about 50° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator reagents are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a reagent visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

The materials for use in the method of the invention are ideally suited for the preparation of a screening kit. Such a kit can comprise a carrier having compartments to receive in close confinement one or more containers such as vials, tubes, and the like, each of the containers comprising one of the separate elements to be used in the method. For example, one of the containers can comprise an amplifying reagent for amplifying a KCC DNA, such as the necessary enzyme(s) and oligonucleotide primers for amplifying target DNA from the subject.

The oligonucleotide primers include primers having a sequence derived from the group including, but not limited to: SEQ ID NOs:44–110, or primer sequences substantially complementary or substantially homologous thereto. Oligonucleotide primers comprising target flanking 5' and 3' polynucleotide sequence have substantially the sequence set forth in the flanking 5' and 3' portions of any of SEQ ID NOs:1–16, 44–110, 112–113, and sequences substantially complementary or homologous thereto. Other oligonucleotide primers for amplifying a KCC will be known or readily ascertainable to those of skill in the art given the disclosure of the present invention presented herein.

A kit in accordance with the present invention can further comprise solutions, buffers or other reagents for extracting a nucleic acid sample from a biological sample obtained from a subject. Any such reagents as would be readily apparent to one of ordinary skill in the art is contemplated to fall within the scope of the present invention. By way of particular example, a suitable lysis buffer for the tissue or cells along with a suspension of glass beads for capturing the nucleic acid sample and an elution buffer for eluting the nucleic acid sample off of the glass beads comprise a reagent for extracting a nucleic acid sample from a biological sample obtained from a subject.

Other examples include commercially available extraction kits, such as the GENOMIC ISOLATION KIT A.S.A.P.™ (Boehringer Mannheim of Indianapolis, Ind.), Genomic DNA Isolation System (GIBCO BRL of Gaithersburg, Md.), ELU-QUIK™ DNA Purification Kit (Schleicher & Schuell of Keene, New Hampshire), DNA Extraction Kit (Stratagene of La Jolla, Calif.), TURBOGENT Isolation Kit (Invitrogen of San Diego, Calif.), and the like. Use of these kits according to the manufacturer's instructions is generally acceptable for purification of DNA prior to practicing the methods of the present invention.

F. Screening for Modulators of KCC Biological Activity

In yet another aspect, the present invention provides a process of screening substances for their ability to affect or modulate the biological activity of potassium-chloride cotransporter gene products, and for their ability to affect or to modulate in vivo potassium-chloride cotransporter levels. The present invention also provides a process of screening substances for their ability to affect or modulate the biological activity of KCC2, KCC3 and/or KCC4 gene products, and for their ability to affect or modulate in vivo KCC2, KCC3 and/or KCC4 levels. This modulation can affect cell growth and differentiation.

Utilizing the methods and compositions of the present invention, screening assays for the testing of candidate substances are performed. A candidate substance is a substance which potentially can promote or inhibit the biological activity of gene product by binding or other intermolecular interaction with the KCC2, KCC3 and/or KCC4 gene or gene product or control sequence.

F.1. Method of Screening for Modulators of KCC2, KCC3 and/or KCC4 Biological Activity A representative method of screening candidate substances for their ability to modulate KCC biological activity comprises: (a) establishing replicate test and control samples that comprise a biologically active KCC polypeptide; (b) administering a candidate substance to test samples; (c) measuring the biological activity of the KCC polypeptide in the test and the control samples; and (d) determining whether the candidate substance modulates KCC biological activity relative to an appropriate control. By "modulate" is intended an increase, decrease, or other alteration of any or all biological activities or properties of KCC. A candidate substance identified according to the screening assay described herein has an ability to modulate KCC biological activity. Such a candidate compound has utility in the treatment of disorders and conditions associated with the biological activity of a KCC, such as KCC2, KCC3 and/or KCC4. Candidate compounds are typically about 500–1000 daltons, and can be hydrophobic, polycyclic, or both, molecules.

In a cell-free system, the method comprises the steps of establishing a control system comprising a KCC polypeptide and a ligand to which the KCC polypeptide is capable of binding, establishing a test system comprising the KCC polypeptide, the ligand, and a candidate compound, and determining whether the candidate compound modulates KCC activity in a cell-free system. A representative ligand comprises a monoclonal antibody, and in this embodiment, the biological activity or property screened includes binding affinity.

In another embodiment of the invention, a KCC polypeptide (e.g., KCC2, KCC3 and/or KCC4) or catalytic or immunogenic fragment or oligopeptide thereof, can be used for screening libraries of compounds in any of a variety of drug screening techniques. The fragment employed in such screening can be free in solution, affixed to a solid support, borne on a cell surface, or located intracellularly. The formation of binding complexes, between the KCC polypeptide and the agent being tested, can be measured.

Another technique for drug screening that can be used provides for high throughput screening of compounds having suitable binding affinity to the protein of interest as described in published International Publication Number WO 84/03564, herein incorporated by reference. In this method, as applied to the KCC polypeptide, large numbers of different small test compounds are synthesized on a solid substrate, such as plastic pins or some other surface. The test compounds are reacted with the KCC polypeptide, or fragments thereof, and washed. Bound KCC polypeptide is then detected by methods well known in the art. Purified KCC polypeptide can also be coated directly onto plates for use in the aforementioned drug screening techniques. Alternatively, non-neutralizing antibodies can be used to capture the peptide and immobilize it on a solid support.

A screening assay of the present invention can also involve determining the ability of a candidate substance to modulate, i.e. inhibit or promote KCC biological activity and preferably, to thereby modulate the biological activity of potassium-chloride cotransporters in target cells. Target cells can be either naturally occurring cells known to contain a polypeptide of the present invention or transformed cells produced in accordance with a process of transformation set forth herein above. The test samples can further comprise a cell or cell line that expresses a KCC polypeptide; the present invention also provides a recombinant cell line suitable for use in the exemplary method. Such cell lines can be mammalian, or human, or they can from another organism, including but not limited to yeast. Exemplary assays including genetic screening assays and molecular biology screens such as a yeast two-hybrid screen that will effectively identify KCC-interacting genes important for potassium-chloride cotransport or other KCC-mediated cellular process. One version of the yeast two-hybrid system has been described (Chien et al. (1991) *Proc Natl Acad Sci USA*, 88:9578–9582) and is commercially available from Clontech (Palo Alto, Calif.).

A preferred screening system for the measurement of $K^+$—$Cl^-$ cotransport activity is the injection of cRNA (copy RNA) encoding individual KCC isoforms into *Xenopus laevis* oocytes, as described in Example 11. Indeed, the present invention provides the first disclosure of the use of oocytes for $K^+$—$Cl^-$ cotransporters. A significant advantage of *Xenopus* oocytes is the ability to express multiple different constructs in a minimum of time. The endogenous $K^+$—$Cl^-$ cotransport activity is also negligible, which facilitates the analysis of KCC constructs. A drawback is the oocyte-to-oocyte, experiment-to-experiment, and frog-to-frog variability. However, comparing multiple constructs and conditions in the same experiments can compensate for this variability. Moreover, *Xenopus* oocytes have been used successfully for the kinetic analysis of cation-chloride cotransporters (Gamba et al. (1993) *Proc Natl Acad Sci USA* 90(7):2749–2753; Gimenez et al. (1999) *FASEB J* 13:A64). A number of other volume-sensitive transporters, ion channels and related proteins have been expressed in *Xenopus* oocytes, with the appropriate physiological response (Ji et al. (1998) *Am J Physiol* 275(5 Pt 1):C1182–1190; Krapivinsky et al. (1994) *Cell* 76(3):439–448; Vandorpe et al. (1998) *J Biol Chem* 273(34): 21542–21553; and Grunder et al. (1992) *Nature* 360(6406): 759–762). Thus the $Na^+$—$K^+$-2 $Cl^-$ cotransporter BSC2/NKCC1 is activated by hypertonicity when expressed in oocytes, as they are in mammalian cells. Cell swelling also activates the major red cell $K^+$—$Cl^-$ cotransporter KCC1 (Su et al. (1999) *Am J Physiol* 277(5 Pt 1):C899–C912) and the $Ca^{2+}$-activated $K^+$ channel ISK1 (Vandorpe et al. (1998) *J Biol Chem* 273(34):21542–53) expressed in oocytes, as predicted by their behavior in red cells.

As is well known in the art, a screening assay can provide a cell under conditions suitable for testing the modulation of KCC biological activity and/or levels of potassium-chloride cotransporters. These conditions include but are not limited to pH, temperature, tonicity, the presence of relevant metabolic factors (e.g., metal ions such as for example $Ca^{++}$, growth factor, interleukins, or colony stimulating factors), and relevant modifications to the polypeptide such as glycosylation or prenylation. It is contemplated that a polypeptide of the present invention can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell. U.S. Pat. Nos. 5,837,479; 5,645,999; 5,786,152; 5,739,278; and 5,352,660 also describe exemplary screening assays, and the entire contents of each are herein incorporated by reference.

In one embodiment, a screening assay is designed to be capable of discriminating candidate substances having selective ability to interact with or modulate one or more of the genes or gene products of the present invention but which substances are without a substantially overlapping activity with another gene or gene product. For example, a substance can modulate the biological activity of KCC3 but have no effect, or a diminished effect, on KCC4. Such selective effect can consist of a 30% greater effect on one test sample versus another, or more preferably 100% or greater effect.

A method of identifying modulators of potassium-chloride cotransporters by rational drug design is contemplated in accordance with the present invention. The method comprises the steps of designing a potential modulator for a potassium-chloride cotransporter that will form non-covalent bonds with amino acids in the substrate binding site based upon the structure of a KCC (e.g., KCC2, KCC3 and/or KCC4) polypeptide; synthesizing the modulator; and determining whether the potential modulator modulates the activity of a potassium-chloride cotransporter. Modulators can be synthesized using techniques known in the art. The determination of whether the modulator modulates the biological activity of a potassium-chloride cotransporter is made in accordance with the screening methods disclosed herein, or by other screening methods known in the art.

F.2 Method of Screening for Modulators of In vivo Potassium-chloride Cotransporter Levels In accordance with the present invention there are also provided methods for screening candidate compounds for the ability to modulate in vivo potassium-chloride cotransporter levels and/or activity. Representative modulators of KCC (e.g., KCC2, KCC3 and/or KCC4) levels can comprise modulators of potassium-chloride cotransporter transcription or expression. Pharmaceuticals that increase or decrease the transcription or expression of potassium-chloride cotransporter encoding genes have important clinical application for the modulation of the biological activity of potassium-chloride cotransporters. This modulation can affect potassium-chloride homeostasis.

This invention thus includes a method for discovery of compounds that modulate the expression levels of potassium-chloride cotransporter encoding genes, including not only the KCC2, KCC3 and/or KCC4 of the present invention but also other potassium-chloride cotransporter-encoding genes, and describes the use of such compounds. The general approach is to screen compound libraries for substances which increase or decrease expression of KCC2-, KCC3-and/or KCC4-encoding genes. Exemplary techniques are described in U.S. Patent Nos. 5,846,720 and 5,580,722, the entire contents of each of which are herein incorporated by reference.

While the following terms are believed to be well understood by one of skill in the art, the following definitions are set forth to facilitate explanation of the invention.

"Transcription" means a cellular process involving the interaction of an RNA polymerase with a gene that directs the expression as RNA of the structural information present in the coding sequences of the gene. The process includes, but is not limited to the following steps: (a) the transcription initiation, (b) transcript elongation, (c) transcript splicing, (d) transcript capping, (e) transcript termination, (f) transcript polyadenylation, (g) nuclear export of the transcript, (h) transcript editing, and (i) stabilizing the transcript. "Expression" generally refers to the cellular processes by which a biologically active polypeptide is produced from RNA.

"Transcription factor" means a cytoplasmic or nuclear protein which binds to such gene, or binds to an RNA transcript of such gene, or binds to another protein which binds to such gene or such RNA transcript or another protein which in turn binds to such gene or such RNA transcript, so as to thereby modulate expression of the gene. Such modulation can additionally be achieved by other mechanisms; the essence of "transcription factor for a gene" is that the level of transcription of the gene is altered in some way.

In accordance with the present invention there is provided a method of identifying a candidate compound or molecule that is capable of modulating the transcription level of a gene encoding a potassium-chloride cotransporter and thus is capable of acting as a therapeutic agent in the modulation of potassium-chloride cotransporter effects. This modulation can affect cell growth and differentiation. Such modulation can be direct, i.e., through binding of a candidate molecule directly to the nucleotide sequence, whether DNA or RNA transcript, or such modulation can be achieved via one or more intermediaries, such as proteins other than KCC2, KCC3 and/or KCC4 which are affected by the candidate compound and ultimately modulate potassium-chloride cotransporter transcription by any mechanism, including direct binding, phosphorylation or dephosphorylation, etc.

This method comprises contacting a cell or nucleic acid sample with a candidate compound or molecule to be tested. These samples contain nucleic acids which can contain elements that modulate transcription and/or translation of the KCC2, KCC3 and/or KCC4 gene, such as a KCC2, KCC3 or KCC4 promoter or putative upstream regulatory region (representative promoters disclosed herein as SEQ ID NOs:17–19 and 131), and a DNA sequence encoding a polypeptide which can be detected in some way. Thus, the polypeptide can be described as a "reporter" or "marker." Preferably, the candidate compound directly and specifically transcriptionally modulates expression of the potassium-chloride-cotransporter-encoding gene. Such compounds are anticipated to have therapeutic or pharmaceutical uses in treating potassium-chloride-cotransporter-related diseases and/or disorders.

The DNA sequence is coupled to and under the control of the promoter, under conditions such that the candidate compound or molecule, if capable of acting as a transcriptional modulator of the gene encoding KCC2, KCC3 and/or KCC4, causes the polypeptide to be expressed and so produces a detectable signal, which can be assayed quantitatively and compared to an appropriate control. Candidate compounds or molecules of interest can include those which increase or decrease, i.e., modulate, transcription from the KCC2, KCC3 or KCC4 promoters. The reporter gene can encode a reporter known in the art, such as luciferase, or it can encode KCC2, KCC3 and/or KCC4.

In certain embodiments of the invention the polypeptide so produced is capable of complexing with an antibody or is capable of complexing with biotin. In this case the resulting complexes can be detected by methods known in the art. The detectable signal of this assay can also be provided by messenger RNA produced by transcription of said reporter gene. Exactly how the signal is produced and detected can vary and is not the subject of the present invention; rather, the present invention provides the nucleotide sequences and/or putative regulatory regions of KCC2, KCC3 and/or KCC4 for use in such an assay. The molecule to be tested in these methods can be a purified molecule, a homogenous sample, or a mixture of molecules or compounds. Further, in the method of the invention, the DNA in the cell can comprise more than one modulatable transcriptional regulatory sequence.

In accordance with the present invention there is also provided a rapid and high throughput screening method that relies on the methods described above. This screening method comprises separately contacting each of a plurality of substantially identical samples. In such a screening method the plurality of samples preferably comprises more than about $10^4$ samples, or more preferably comprises more than about $5 \times 10^4$ samples.

F.3. Animal Models

In addition, animal-based systems can be used to identify compounds capable of modulating KCC2, KCC3 and/or KCC4 biological activity. Such animal models can be used for the identification of drugs, pharmaceuticals, therapies, and interventions that can be effective in modulating potassium-chloride cotransporter biological activity. For example, animal models can be exposed to a compound that is suspected of exhibiting an ability to modulate potassium-chloride cotransporter biological activity symptoms at a sufficient concentration and for a time sufficient to elicit such modulation of potassium-chloride cotransporter biological activity symptoms in the exposed animals. The response of the animals to the exposure can be monitored by assessing in vivo potassium-chloride cotransporter expression levels and activity, or by testing biological samples from the animal. As in the methods described above, the mechanism by which a compound modulates KCC2, KCC3, KCC4, or other potassium-chloride cotransporter or ion transporter activity or achieves therapeutic effects can vary; the utility of the present invention does not depend on the precise mechanism by which an effect is achieved.

For example, an animal model of the present invention can comprises a mouse with targeted modification of the mouse KCC2, KCC3, and KCC4 genes. Mice strains with complete or partial functional inactivation of the KCC genes in all somatic cells are generated using standard techniques of site-specific recombination in murine embryonic stem cells. See Capecchi (1989) *Science* 244(4910):1288–92; Thomas & Capecchi (1990) *Nature* 346(6287):847–50; Delpire et al. (1999) *Nat Genet* 22(2):192–5. "Knockout" murine KCC2 mice have been prepared, and the resultant homozygous KCC2−/− mice have a seizure disorder and increased perinatal mortality. The HCC2 knockout mice thus provide evidence that KCC2 is a drug target in epilepsy and further evidence that human KCC2 is a medically relevant gene.

Alternatives include the use of anti-sense or ribozyme KCC constructs, driven by a universal or tissue-specific promoter, to reduce levels of individual KCCs in somatic cells, thus achieving a "knock-down" of individual isoforms (Luyckx et al. (1999) *Proc Natl Acad Sci USA* 96(21): 12174–12179). The invention also provides the generation of murine strains with conditional or inducible inactivation of individual or multiple KCC genes (Sauer (1998) *Methods* 14(4):381–392). For example, mice are created which lack expression of any KCCs in the renal proximal tubule, a known site of expression of KCC3 and KCC4, through the sequential mating of mice strains with lox-P-flanked KCC genes with a transgenic line expressing Cre-recombinase in the proximal tubule, using the promoter for the kidney androgen-regulated protein (Ding et al. (1997) *J Biol Chem* 272(44):28142–28148).

The present invention also provides mice strains with specific "knocked-in" modifications in the KCC2, KCC3, or KCC4 genes. This includes mice with genetically (Forlino et al. (1999) *J Biol Chem* 274(53):37923–37931) and functionally (Kissel et al. (2000) *EMBO J* 19(6):1312–1326) relevant point mutations in the KCC genes, in addition to manipulations such as the insertion of disease-specific repeat expansions (White et al. (1997) *Nat Genet* 17(4):404–410).

An aspect of the invention encompasses any treatments that alter any aspect of potassium-chloride-cotransporter-mediated biological activity. Such compounds should be considered as candidates for human therapeutic intervention in accordance with the methods described herein below. Dosages of test agents can be determined by deriving dose-response curves, such as those disclosed in U.S. Pat. No. 5,849,578, herein incorporated by reference.

G. Therapeutic Methods

As used herein, the terms "activity" and "biological activity" are meant to be synonymous and are meant to refer to any biological activity of, for example, a KCC2, KCC3 and/or KCC4 polypeptide. Representative biological activities of KCC3 and/or KCC4 comprise activity in the modulation of potassium-chloride cotransporter activity or other biological activity in accordance with the present invention.

With respect to the therapeutic methods of the present invention, a preferred subject is a vertebrate subject. A preferred vertebrate is warm-blooded; a preferred warm-blooded vertebrate is a mammal. A preferred mammal is a mouse or, most preferably, a human. As used herein and in the claims, the term "patient" is contemplated to include both human and animal patients. Thus, veterinary therapeutic uses are contemplated in accordance with the present invention.

Contemplated is the treatment of mammals such as humans, as well as those mammals of importance due to being endangered, such as Siberian tigers; of economical importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also contemplated is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine, ruminants, ungulates, horses, poultry, and the like.

G.1. Modulation of Potassium-chloride Cotransporter Biological Activity

In one embodiment, a therapeutic method according to the present invention comprises administering to a subject a substance that modulates, i.e., inhibits or promotes potassium-chloride cotransporter biological activity. Such a substance can be identified according to any of the screening assays set forth above, either in vitro or in vivo. The method comprises treating a vertebrate subject suffering from a disorder associated with or mediated by potassium-chloride cotransporter biological activity by administering to the subject an effective amount of a substance identified according to a screening assay described above. By the term "modulating", it is contemplated that the substance can either promote or inhibit the biological activity of potassium-chloride cotransporter polypeptides, depending on the disorder to be treated, and can affect one or several of the potassium-chloride cotransporters, including KCC2, KCC3 and/or KCC4, as well as other isoforms of potassium-chloride cotransporters, ion transporters, or other unrelated genes or gene products. Therapeutic treatment can comprise the administration of antibodies against a chosen region of potassium-chloride cotransporters, the administration of a protein that enhances activity, or the administration of a protein that inhibits the transcription of the potassium-chloride cotransporter. Such administration can provide treatment of disorders which can be caused or exacerbated by potassium-chloride-cotransporter-mediated mechanisms, including but not limited to hypertension, epilepsy, sickle cell anemia, Bartter's syndrome, and Meniere's disease.

Insofar as a modulator of potassium-chloride-cotransporter activity can take the form of a polypeptide or of an anti-potassium-chloride-cotransporter monoclonal antibody or fragment thereof, it is to be appreciated that the potency can vary, and therefore a "therapeutically effective" amount can vary. However, as shown by the present assay methods, one skilled in the art can readily assess the potency and efficacy of a candidate potassium-chloride cotransporter biological activity modulator of this invention and adjust the therapeutic regimen accordingly. A modulator of potassium-chloride-cotransporter biological activity can be evaluated by a variety of means including through the use of a responsive reporter, which drives expression of a reporter gene; interaction of potassium-chloride cotransporter polypeptides with a monoclonal antibody as described herein; and other assays known in the art and described herein.

The monoclonal antibodies or polypeptides of the invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule and are known to those of skill in the art. The compositions are formulated in an appropriate manner and administered in a manner compatible with the dosage formulation.

G.2. Monoclonal Antibodies

The present invention describes, in one embodiment, potassium-chloride cotransporter modulators in the form of monoclonal antibodies which were elicited in response to KCC2, KCC3 and/or KCC4 but which can immunoreact with any potassium-chloride cotransporter polypeptide, or with a specific isoform of a potassium-chloride cotransporter polypeptide, and bind the potassium-chloride cotransporter polypeptide to modulate biological activity. The invention also describes cell lines that produce the antibodies, methods for producing the cell lines, and methods for producing the monoclonal antibodies.

The term "antibody" or "antibody molecule" refers collectively to a population of immunoglobulin molecules and/or immunologically active portions of immunoglobulin molecules, i.e., molecules that contain a paratope. A paratope is the portion or portions of an antibody that is or are responsible for that antibody binding to an antigenic determinant, or epitope.

Representative antibodies for use in the present invention are intact immunoglobulin molecules, substantially intact immunoglobulin molecules, single chain immunoglobulins or antibodies, those portions of an immunoglobulin molecule that contain the paratope, including antibody fragments. Indeed, it is contemplated to be within the scope of the present invention that a monovalent modulator can optionally be used. Thus, the terms "modulate", "modulating", and "modulator" are intended to encompass such a mechanism.

The term "monoclonal antibody" refers to a population of antibody molecules that contain only one species of paratope and thus typically display a single binding affinity for any particular epitope with which it immunoreacts; a monoclonal antibody can have a plurality of antibody combining sites, each immunospecific for a different epitope, e.g., a bispecific monoclonal antibody. Methods of producing a monoclonal antibody, a hybridoma cell, or a hybridoma cell culture are described above.

It is also possible to determine, without undue experimentation, if a monoclonal antibody has the same or equivalent specificity or immunoreaction characteristics as a monoclonal antibody of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. "CDRs" (complementarity-determining regions) mean the three sub-regions of the light or heavy chain variable regions which have hypervariable sequences and form loop structures that are primarily responsible for making direct contact with antigen. Antibody molecules having identical, or functionally equivalent, amino acid residue sequences in their CDR regions have the same binding specificity. Methods for sequencing polypeptides are well known in the art. Further, other ways of determining whether antibodies have similar immunospecificities are known in the art and can be useful in practicing the present invention.

The immunospecificity of an antibody, its target molecule binding capacity, and the attendant affinity the antibody exhibits for the epitope are defined by the epitope with which the antibody immunoreacts. The epitope specificity is defined at least in part by the amino acid residue sequence of the variable region of the heavy chain of the immunoglobulin that comprises the antibody, and in part by the light-chain-variable-region amino acid residue sequence. Use of the terms "having the binding specificity of" or "having the binding preference of" indicates that equivalent monoclonal antibodies exhibit the same or similar immunoreaction (binding) characteristics and compete for binding to a preselected target molecule.

Humanized monoclonal antibodies offer particular advantages over monoclonal antibodies derived from other mammals, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention.

The use of a molecular cloning approach to generate antibodies, particularly monoclonal antibodies, and more particularly single chain monoclonal antibodies, is also contemplated. The production of single chain antibodies has been described in the art, see e.g., U.S. Pat. No. 5,260,203, the contents of which are herein incorporated by reference. For this approach, combinatorial immunoglobulin phagemid libraries are prepared from RNA isolated from the spleen of the immunized animal, and phagemids expressing appropriate antibodies are selected by panning on endothelial tissue. The advantages of this approach over conventional hybridoma techniques are that approximately $10^4$ times as many antibodies can be produced and screened in a single round, and that new specificities are generated by hours and L chain combination in a single chain, which further increases the chance of finding appropriate antibodies. Thus, an antibody of the present invention, or a "derivative" of an antibody of the present invention, pertains to a single polypeptide chain binding molecule which has binding specificity and affinity substantially similar to the binding specificity and affinity of the light and heavy chain aggregate variable region of an antibody described herein.

G.3. Other Modulators

Given the disclosure of the potassium-chloride cotransporter activity in tissues herein, it is also contemplated that chemical compounds (e.g., small molecule mimetics) can be used to modulate potassium-chloride cotransporter activity in tissues in accordance with the methods of the present invention. The identification of such compounds is facilitated by the description of screening assays directed to potassium-chloride cotransporter activity in tissues presented above.

For example, the initial functional data (FIGS. 24-25) indicate that agents that enhance protein phosphatase-1 can increase $K^+$—$Cl^-$ cotransport activity. Derivatives of anion transport inhibitors such as bumetanide, furosemide, DIDS, and DIOA can have significant inhibitory potential for the $K^+$—$Cl^-$ cotransporters. Finally, structure-function studies using the four KCCs, in addition to mutants and chimeras thereof, can yield important data crucial for the generation of KCC-specific and isoform-specific inhibitors.

G.4. Gene Therapy

Potassium-chloride cotransporter genes can be used for gene therapy in accordance with the present invention. Exemplary gene therapy methods, including liposomal transfection of nucleic acids into host cells, are described in U.S. Pat. Nos. 5,279,833; 5,286,634; 5,399,346; 5,646,008; 5,651,964; 5,641,484; and 5,643,567, the contents of each of which are herein incorporated by reference.

Briefly, gene therapy directed toward modulation of potassium-chloride cotransporter levels, to thereby affect or modulate the biological activity of potassium-chloride cotransporter in a target cell is described. This modulation can affect cell growth and differentiation. In one embodiment, a therapeutic method of the present invention provides a process for modulation of potassium-chloride cotransporter levels comprising the steps of: (a) delivering to the cell an effective amount of a DNA molecule comprising a polynucleotide that encodes a polypeptide that modulates the biological activity of one or more than one potassium-chloride cotransporter; and (b) maintaining the cell under conditions sufficient for expression of said polypeptide.

In a preferred embodiment, the delivered polypeptide comprises the sequence of any of SEQ ID NOs:1, 3, 5, 7, 9, 11, 13, 15, and 112. Delivery can be accomplished by injecting the DNA molecule into the cell. Where the cell is in a subject, administering comprises the steps of: (a) providing a vehicle that contains the DNA molecule; and (b) administering the vehicle to the subject.

A vehicle is preferably a cell transformed or transfected with the DNA molecule or a transfected cell derived from such a transformed or transfected cell. An exemplary and preferred transformed or transfected cell is a lymphocyte or a tumor cell from the tumor being treated. Means for transforming or transfecting a cell with a DNA molecule of the present invention are set forth above.

Alternatively, the vehicle is a virus or an antibody that specifically infects or immunoreacts with an antigen of the target tissue or tumor. An advantage of a viral infection system is that it allows for a very high level of infection into the appropriate recipient cell. Also, antibodies have been used to target and deliver DNA molecules.

It is also envisioned that this embodiment of the present invention can be practiced using alternative viral or phage vectors, including retroviral vectors and vaccinia viruses whose genome has been manipulated in alternative ways so as to render the virus non-pathogenic. Methods for creating such a viral mutation are set forth in detail in U.S. Pat. No. 4,769,331, incorporated herein by reference.

G.5. Method of Modulating in vivo Potassium-chloride Cotransporter Levels in the Treatment of Related Diseases and Disorders A method for transcriptionally modulating in a multicellular organism the expression of a gene encoding a potassium-chloride cotransporter to modulate potassium-chloride cotransporter biological activity in a warm-blooded vertebrate subject is also contemplated in accordance with the present invention. This method comprises administering to the warm-blooded vertebrate subject a compound at a concentration effective to transcriptionally modulate expression of potassium-chloride cotransporter or cotransporters.

In accordance with the present invention, the contemplated compound can optionally comprise an antibody or polypeptide prepared as described above and which transcriptionally modulates expression of potassium-chloride cotransporters. Optionally, the antibody or polypeptide directly binds to DNA or RNA, or directly binds to a protein involved in transcription.

Particularly contemplated chemical entities (e.g., small molecule mimetics) for use in accordance with the present invention do not naturally occur in any cell, whether of a multicellular or a unicellular organism. Even more particularly, the contemplated chemical entity is not a naturally occurring molecule, e.g., it is a chemically synthesized entity. Optionally, the compound can bind a modulatable transcription sequence of the gene. For example, the compound can bind a promoter region upstream of a nucleic acid sequence encoding KCC2, KCC3 and/or KCC4 as well as other potassium-chloride cotransporters.

In the methods above, modulation of transcription results in either upregulation or downregulation of expression of the gene encoding the protein of interest, depending on the identity of the molecule which contacts the cell.

G.6. Antisense Oligonucleotide Therapy

It is also contemplated according to the present invention that expression of a potassium-chloride cotransporter can be modulated in a vertebrate subject through the administration of an antisense oligonucleotide derived from a nucleic acid molecule encoding a potassium-chloride cotransporter, such as those described in any of SEQ ID NOs:1, 3, 5, 7, 9, 11, 13, 15, and 112. Therapeutic methods utilizing antisense oligonucleotides have been described in the art, for example, in U.S. Pat. Nos. 5,627,158 and 5,734,033, the contents of each of which are herein incorporated by reference.

G.7. Dosages

As used herein, an "effective" dose refers to one that is administered in doses tailored to each individual patient manifesting symptoms of $K^+$—$Cl^-$ cotransport malfunction sufficient to cause an improvement therein. After review of the disclosure herein of the present invention, one of ordinary skill in the art can tailor the dosages to an individual patient, taking into account the particular formulation and method of administration to be used with the composition as well as patient height, weight, severity of symptoms, and stage of the disorder to be treated.

An effective dose and a therapeutically effective dose are generally synonymous. However, compounds can be administered to patients having reduced symptoms or even administered to patients as a preventative measure. Hence, the composition can be effective in therapeutic treatment even in the absence of symptoms of the disorder.

A unit dose can be administered, for example, 1 to 4 times per day. Most preferably, the unit dose is administered twice a day (BID). The dose depends on the route of administration and the formulation of a composition containing the compound or compounds. Further, it will be appreciated by one of ordinary skill in the art after receiving the disclosure of the present invention that it can be necessary to make routine adjustments or variations to the dosage depending on the combination of agents employed, on the age and weight of the patient, and on the severity of the condition to be treated.

Such adjustments or variations, as well as evaluation of when and how to make such adjustments or variations, are well known to those of ordinary skill in the art of medicine. Evaluation parameters and techniques can vary with the patient and the severity of the disease. Particularly useful evaluative techniques are disclosed in the Examples.

G.7.1. Gene Therapy Vector Construct Dosing

Maximally tolerated dose (MTD) of vector construct when administered directly into the affected tissue is determined. Primary endpoints are: 1) the rate of transduction in abnormal and/or normal cells, 2) the presence and stability of this vector in the systemic circulation and in affected cells, and 3) the nature of the systemic (fever, myalgias) and local (infections, pain) toxicities induced by the vector. A secondary endpoint is the clinical efficacy of the vector construct.

For example, a 4 ml serum-free volume of viral (e.g., adenoviral, retroviral, etc.) vector construct (containing up to $5\times10^7$ viral particles in AIM V media) is administered daily per session. During each session, 1 ml of medium containing the appropriate titer of vector construct is injected into 4 regions of the affected tissue for a total of 4 ml per session in a clinical examination room. This is repeated daily for 4 days (4 sessions). This 16 ml total inoculum volume over 4 days is proportionally well below the one safely tolerated by nude mice (0.5 ml/20 g body weight).

Patient evaluation includes history and physical examination prior to initiation of therapy and daily during the 4 day period of vector construct injection. Toxicity grading is done using the ECOG Common Toxicity Criteria. CBC, SMA-20, urinalysis, and conventional studies are performed daily during this period.

G.7.2. Dose escalation and MTD

Patients are treated with $3\times10^6$ viral particles$\times4$. Once they have all recovered from all grade 2 or less toxicities (except alopecia), and as long as grade 3–4 toxicity is not encountered, a subsequent dose level is initiated in patients. As one grade 3 or 4 toxicity occurs at a given dose level, a minimum of 6 patients are enrolled at that level. As only 1 of 6 patients has grade 3 or 4 toxicity, dose escalation continues. The MTD of vector construct is defined as the dose where 2 of 6 patients experience grade 3 or 4 toxicity. If 2 of 3, or if 3 of 6 patients experience grade 3 or 4 toxicity, the MTD is defined as the immediately lower dose level.

The following escalation schema is followed: 1) level 1, $3\times10^6$ viral particles; 2) level 2, $1\times10^7$; 3) level 3, $3\times10^7$; 4) level 4, $5\times10^7$. Patients with measurable disease are evaluated for a clinical response to vector construct. Histology and local symptoms are followed. NE clearance, tyramine administration and other standard tests such as are disclosed in the Examples are employed.

G.8. Formulation of Therapeutic Compositions

The potassium-chloride-cotransporter biological activity modulating substances, gene therapy vectors, and substances that inhibit or promote expression of a potassium-chloride cotransporter encoding nucleic acid segment described above are adapted for administration as a pharmaceutical compositions as described above. Additional formulation and dose preparation techniques have been described in the art, see for example, those described in U.S. Pat. No. 5,326,902 issued to Seipp et al. on Jul. 5, 1994, U.S. Pat. No. 5,234,933 issued to Marnett et al. on Aug. 10, 1993, and International Publication Number WO 93/25521 of Johnson et al. published Dec. 23, 1993, the entire contents of each of which are herein incorporated by reference.

For the purposes described above, the identified substances can normally be administered systemically or partially, usually by oral or parenteral administration. The doses to be administered are determined depending upon age, body weight, symptom, the desired therapeutic effect, the route of administration, and the duration of the treatment, etc.; one of skill in the art of therapeutic treatment will recognize appropriate procedures and techniques for determining the appropriate dosage regimen for effective therapy. Various compositions and forms of administration are contemplated and are generally known in the art. Other compositions for administration include liquids for external use, and endermic linaments (ointment, etc.), suppositories and pessaries that comprise one or more of the active substance(s) and can be prepared by known methods.

Thus, the present invention provides pharmaceutical compositions comprising a polypeptide, polynucleotide, or molecule or compound of the present invention and a physiologically acceptable carrier. More preferably, a pharmaceutical composition comprises a compound discovered via the screening methods described herein below.

A composition of the present invention is typically administered parenterally in dosage unit formulations containing standard, well-known nontoxic physiologically acceptable carriers, adjuvants, and vehicles as desired. The term "parenteral" as used herein includes intravenous, intramuscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A transfected cell can also serve as a carrier. By way of example, a liver cell can be removed from an organism, transfected with a polynucleotide of the present invention using methods set forth above and then the transfected cell returned to the organism (e.g., injected intra-vascularly).

EXAMPLES

The following Examples have been included to illustrate modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Example 1

Cloning of mKCC4 cDNA

Figure 1:
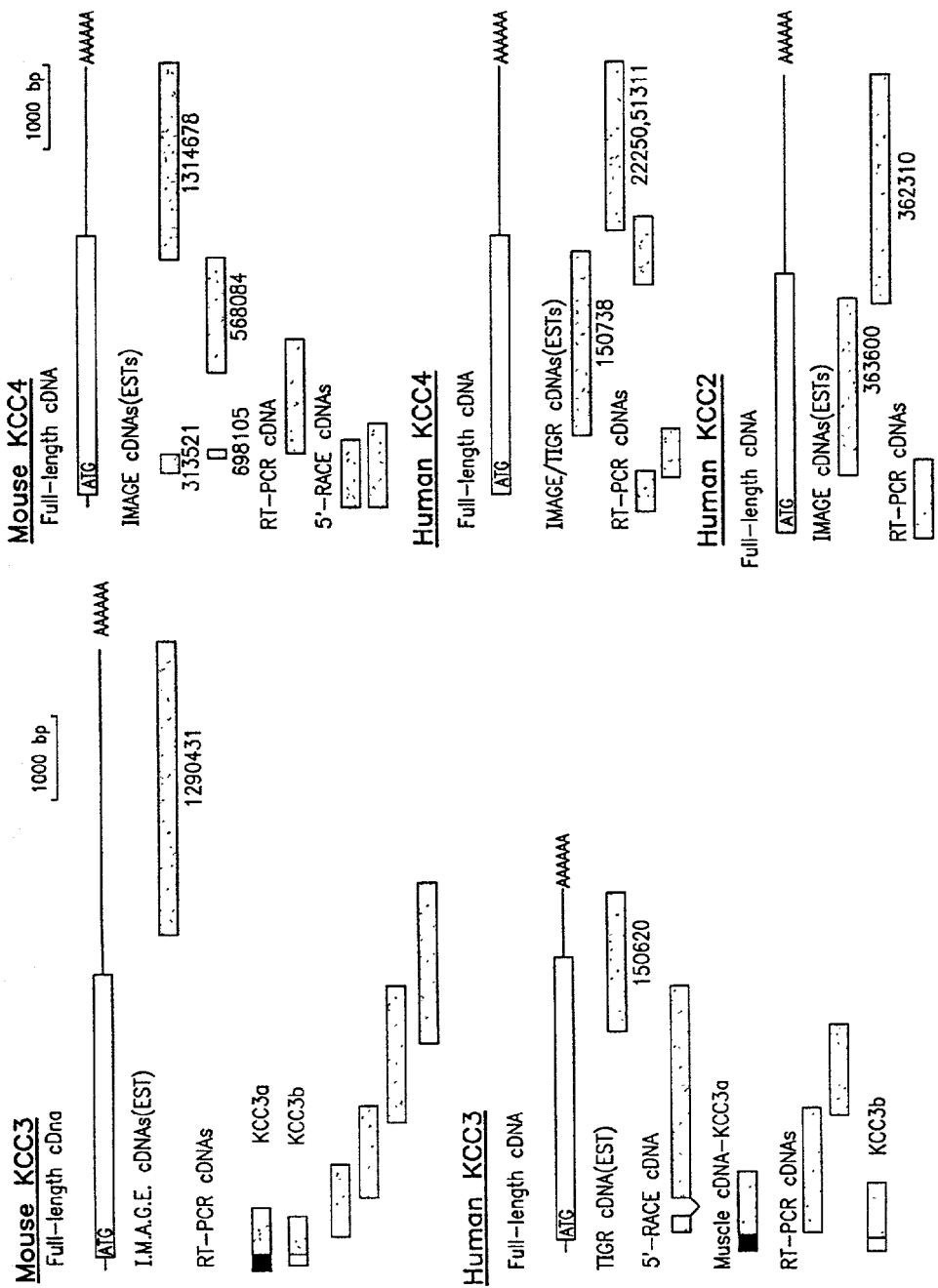
FIG. 1 is a schematic representation of the cDNAs encoding human KCC2, human, mouse and *Xenopus* KCC3 and KCC4. A full-length cDNA is shown for each isoform; coding sequence is boxed and solid lines represent 5'-and 3'-UTR. The relative positions of partial cDNAs, derived from EST cDNA clones, RT-PCR, 5'-RACE RT-PCR, and library screening, are shown as shaded rectangles below each full-length sequence. The IMAGE or TIGR clone numbers are displayed below individual EST cDNAs. The mouse KCC3a and KCC3b cDNAs were obtained by sequential RT-PCR of murine tissues, using human KCC3a and KCC3b primer pairs. The extreme 5' end of the KCC3a and KCC3b coding sequences were then determined by sequence analysis of murine exons 1a and 1b, and the 3'-UTR of was obtained from a mouse EST cDNA. In the case of hKCC2, the 5' end of the cDNA was cloned by RT-PCR, and the two 3' coding sequence ESTs (363600 and 362310) overlap at a Not I site (nucleotide 3322 in the full-length cDNA). The figure is drawn to the scale indicated.

A BLAST (basic alignment and search tool) search of the EST data base revealed a number of mouse ESTs that were homologous to rat KCC1 and KCC2. The cDNAs corresponding to four of these ESTs (IMAGE clones 568084, 633794, 313521, and 698105) were obtained from the IMAGE consortium (Research Genetics, Genome Systems and/or the American Type Culture Collection) and sequenced. These ESTs contained partial open reading frames homologous to various segments of KCC1 and KCC2 (FIG. 1). The 3' end of the open reading frame and the entire 3'-UTR were identified in a fifth IMAGE cDNA (clone 1314678).

The tissue distribution of mKCC4 was then assessed by RT-PCR, and widespread expression of mKCC4 was detected, with particularly abundant transcripts in kidney and heart. Using a primer pair spanning the gap between the IMAGE clones 313521 and 568084, a 1.2-kb fragment was amplified from mouse strain C57BL/6J kidneys and subcloned into the EcoR V site of the vector pBluescript by blunt-end ligation. PCR conditions for these and other gene-specific primers were optimized using Taq 2000 and the Opti-Prime buffer system (available from Stratagene of La Jolla, Calif.). The following amplification protocol was followed, unless specified otherwise: 30 cycles of denaturation (92° C., 2 minutes), annealing (54° C., 1 minute), and extension (72° C., 1 minute), followed by a final extension step (72° C., 8 minutes). The extreme 5'-end of mKCC4 was cloned from BALB/c mouse kidney 5'-RACE template (Clontech of Palo Alto, Calif.), using two antisense primers and the AP1 adaptor primer/S3 primer (Clontech of Palo Alto, Calif.). This PCR utilized AmpliTaq-Gold DNA polymerase (Perkin-Elmer Corp. of Boston, Mass.) and a hot-start amplification protocol, consisting of a 9-minute enzyme activation step at 94° C., followed by 35 cycles of 94° C. for 1 minute, 68° C. for 2.5 minutes, and a final 10-minute extension at 72° C.

Example 2

Cloning of Human KCC4 cDNA

A human KCC EST clone (TIGR clone 150738) was obtained from the ATCC. DNA sequencing revealed that this cDNA is derived from the human ortholog of mKCC4. The polypeptide encoded by another human 5'-EST (GenBank Accession No. F12342) exhibited strong amino acid homology with the amino terminus of the other KCCs. This EST overlaps with a large number of ESTs from the 3'-UTR of hKCC4, including the IMAGE clones 22250 and 51311 (FIG. 1). The gap between these cDNAs and the TIGR clone 150738 (FIG. 1) was bridged by RT-PCR with a primer pair, using a human kidney template (Clontech of Palo Alto, Calif.). The PCR products for this reaction were subcloned into pBluescript (Stratagene of La Jolla, Calif.). Finally, the 5'-end of hKCC4 was cloned by sequential RT-PCR of human kidney.

Example 3

Cloning of Human KCC3a cDNA

Sequence analysis of another human EST cDNA (TIGR clone 150620) indicated the existence of a fourth KCC, hKCC3A. Northern blot analysis revealed significant expression in muscle, and a single 5'-RACE cDNA was cloned from a human muscle template (Clontech of Palo Alto, Calif.). This 5'-RACE PCR used Advantage polymerase mix (Clontech of Palo Alto, Calif.) and a hot-start protocol consisting of the following: 94° C. for 1 minute, followed by 35 cycles of 94° C. for 30 seconds, 62° C. for 30 seconds, and 68° C. for 3 minutes. Screening of a random-primed human muscle cDNA library (Clontech of Palo Alto, Calif.) with a probe encompassing nucleotides 741 to 871 of hKCC3 yielded a single cDNA that extended 5' of the start codon. Finally, two overlapping PCR fragments were amplified from human brain template (Clontech of Palo Alto, Calif.), and subcloned into pCR2.1 by TA cloning (Invitrogen of Carlsbad, Calif.).

The human KCC3a cDNA shares identity with another cDNA, human KCC3b, reported by Hiki et al. (1999) *J Biol Chem* 274(15):10661–10667, but differs in the first 40 amino acids of the amino terminus of the predicted transporter protein. Genomic characterization of mouse and human KCC3 indicates that this variation is generated by transcriptional initiation at two separate promoters 5 of two separate first coding exons, which have been denoted exon 1a and exon 1b. A partial cDNA corresponding to this human KCC3b isoform was cloned by RT-PCR, using a human KCC3b sense primer derived from the sequence of reported by Hiki et al. (1999) *J Biol Chem* 274(15):10661–10667 with an anti-sense primer from within sequence common to both variants of KCC3. RT-PCR of human, mouse and *Xenopus* tissue (see FIG. 25B) also reveals conserved alternative splicing of exon 2, a 45 nucleotide exon whose alternative exclusion deletes 15 amino acids from the amino terminus while preserving the rest of the open reading frame.

Example 4

Cloning of Mouse KCC3a and KCC3b cDNAs

The sequence data and cDNA clones for human KCC3 were used to determine the full-length cDNA sequences for mouse orthologues of KCC3. First, coding sequence oligonucleotide primer pairs from the human KCC3a and KCC3b were used to "walk" along the mouse KCC3a and KCC3b cDNA sequences by sequential RT-PCR of mouse tissue RNA. The entire mouse 3'-UTR was identified by sequencing of a mouse EST cDNA (IMAGE clone 1290431) that exhibited sequence homology to the human KCC3 3'-UTR. The gap between this 3' non-coding sequence and the known 3' coding sequence was bridged by RT-PCR. To clone the two major 5' ends, which have been denoted KCC3a and KCC3b, primers designed according to human KCC3 sequences were used to amplify KCC3 partial clones from mouse RNA. The extreme 5' end of the mouse KCC3a and KCC3b sequences were then determined by sequencing of mouse genomic clones. The resultant full-length mouse KCC3a and KCC3b cDNAs are 6120 and 6052 nucleotides in length, respectively.

Example 5

Cloning of Human KCC2 cDNA

The 5' end of human KCC2 was cloned by RT-PCR of reverse-transcribed human brain poly-A$^+$ RNA using a human KCC2 anti-sense primer and a rat KCC2 sense primer. Two separate cDNAs, each extending from nucleotides 1–1650 of hKCC2, were cloned from two separate PCR reactions and subcloned into pCR2.1 (Invitrogen of Carlsbad, Calif.). Overlapping sequence for the 3' end of hKCC2 was obtained from two 3' EST cDNAs, IMAGE clones 363600 (nucleotides 1370–3327 of hKCC2) and 362310 (nucleotides 3320–5907). The two IMAGE clones overlap at a common NotI site (3322 of hKCC2).

Example 6

Sequence Analysis of KCC2, KCC3, and KCC4 cDNAs

All cDNA clones were sequenced on both strands using fluorescent dye terminator chemistry (Applied Biosystems of Foster City, Calif.). For cDNA sequence derived exclusively from PCR, at least two cDNAs from two separate PCR reactions were sequenced. Analyses of the nucleotide and amino acid sequences were performed using the GENEWORKS™ 2.5 and MACVECTOR™ 6.5 software packages (Oxford Molecular, Inc. of Campbell, Calif.). Alignments and other analyses also made use of the computer programs BLAST (ncbi.nlm.nih.gov/blast), DNASTAR (DNASTAR, Inc. of Madison, Wis.), and SMART (simple modular architecture research tool) (Schultz et al. (1998) *Proc Natl Acad Sci USA* 95:5857–5864; Schultz et al. (2000) *Nuc Acids Res* 28:231–234; available from EMBL of Heidelberg, Germany).

The complete mouse and human KCC4 cDNAs are 5132 and 5230 nucleotides long, respectively, which is close in size to the KCC3 transcripts seen on Northern blots. Both cDNAs contain open reading frames of 3248 nucleotides that are 85% identical. The predicted proteins consist of 1083 amino acids and exhibit 91% identity. The KCC4 3-UTRs are only 34% identical, close to the lower limit of conservation between mouse and human orthologs (Makalowski & Boguski (1998) *Proc Natl Acad Sci USA* 95:9407B9412).

The hKCC3a cDNA sequence is 4237 nucleotides in length, with a 5'-UTR of 165 base pairs and a 3'-UTR of 622 base pairs. There are three in-frame start codons between nucleotides 165 and 195 of the hKCC3a cDNA, at which translational initiation would result in proteins of 1150, 1141, or 1135 amino acids in length. However, homology to KCC1 and KCC4 begins before the third methionine, which is thus an unlikely translational start site. Comparison with the mouse KCC3a sequence indicates significant conservation of the first nine codons, which also contain a PKC site, and hence translation likely occurs at the first start codon. At least two KCC3 transcripts of 6B7 kb are detected by Northern blot analysis, consistent with alternative splicing. In comparison with other KCC3 cDNAs (FIG. 1), the single 5'-RACE cDNA contained a deletion of nucleotides 708B854, encoding TM1 and TM2 in the predicted KCC3 protein. The deleted region corresponds precisely to exon 4 of hKCC1, and hence at least part of the heterogeneity in KCC3 transcripts is the result of the alternative splicing of coding exons. RT-PCR experiments indicate that exon 2 of both human, mouse and *xenopus* KCC3a is omitted in a significant fraction of transcripts, corresponding to the deletion of 15 amino acids from the predicted amino terminus.

The four KCC proteins are 65B75% identical. Sequence alignments indicate that hKCC4 shares 69% identity with rat KCC2, 65% identity with hKCC1, and 66% identity with hKCC4. The hKCC3a protein shares 71% identity with hKCC1, 66% identity with rat KCC2, and 66% identity with hKCC4. Human KCC3b is marginally more similar to hKCC1 (75% identity) than is hKCC3a. The mouse and human KCC3a and KCC3b orthologues are 98% identical. Human KCC2 is in turn 99% identical to the rat KCC2 protein. The identity between the KCCs and other cation-chloride cotransporters is about 27–33%.

A phylogenetic tree indicates that the mammalian cation-chloride cotransporters fall into two groups, one composed of the Na$^+$—K$^+$-2Cl$^-$ cotransporters and the Na$^+$—Cl$^-$ cotransporter, and the other encompassing the four K$^+$—Cl$^-$ cotransporters. As indicated by direct sequence alignments, the four KCCs form two subgroups, one group comprising KCC1 and KCC4, and the other group comprising KCC3 and KCC2.

The seven mammalian cation-chloride cotransporters share a predicted membrane topology. A central core of 12 TM domains is flanked by hydrophilic amino-and carboxyl-terminal domains that have a cytoplasmic orientation (Mount et al. (1998) *J Exp Biol* 201:2091B2102). The major structural difference between the KCCs and the Na$^+$1-linked cotransporters is the position of a large glycosylated extracellular loop, which is predicted to occur between TM5 and TM6 in the KCCs and between TM7 and TM8 in the $Na^{+1}$—$K^{+1}$-$2Cl^{-2}$ cotransporters and the $Na^{+1}$—$Cl^{-2}$ cotransporter (Mount et al. (1998) *J Exp Biol* 201:2091 B2102). Homology is most marked in the TM domains, the intracellular loops, and the cytoplasmic carboxyl terminus.

A comparison of the four KCCs reveals a number of intriguing differences. KCC3a is the longest of the four because of an extension of 60 amino acids at the extreme amino-terminal end. Although highly conserved, none of the TM domains in the four KCCs are completely identical. Within the cytoplasmic domains, the four KCCs differ significantly in the distribution of consensus phosphorylation sites for tyrosine kinases, protein kinase A, and protein kinase C (PKC). A carboxyl-terminal tyrosine phosphorylation site in KCC2 (Tyr 1087) is conserved in mouse and human KCC4 (Tyr 1054). The hKCC3a sequence predicts a total of 11 PKC sites, 7 contained within the first 90 amino acids. KCC3a has two potential protein kinase A sites, one of which (Ser 939) is a predicted substrate for both protein kinases A and C. The KCC4 sequences predict fewer PKC sites, of which only two are conserved in both mouse and human (Thr 814 and Ser 1006).

Based on the primary structure of the KCCs, disclosed herein for KCC1, KCC3, and KCC4, and the kinetic characterization of NKCC1 chimeras (Isenring & Forbush (1997) *J Biol Chem* 272:24556–24562; Isenring et al. (1998a) *Proc Natl Acad Sci USA* 95:7179–7184; Isenring et al. (1998b) *J Biol Chem* 273:11295–11301; Isenring et al (1998c) *J Gen Physiol* 112:549–558), the four KCCs were proposed to differ in transport features due to variation within the central core of the transmembrane domains. In particular, TM2 is likely to control cation affinity, and TM4 and TM7 are likely to confer anion affinity. Such properties were tested by heterologous expression of KCCs in *Xenopus* oocytes as described further in Examples 11–15 herein below.

Example 7

Chromosomal Localization and Genomic Structure of hKCC2, hKCC3 and hKCC4

Chromosomal assignments for the human KCC3 and KCC4 genes were made using a PCR-based screening approach with the National Institute of General Medical Sciences (NIGMS) human/rodent somatic cell hybrid mapping panel 1. The primers used for hKCC4 mapping amplify a 377-base pair segment of the 3' noncoding region from genomic DNA, and the hKCC3 mapping primers amplify a 561-base pair segment of the 3' noncoding sequence. PCR reactions using DNA from the NIGMS panel were scored for the presence or absence of the appropriately sized product using agarose gel electrophoresis. The chromosomal localization of hKCC4 was verified by sequencing the chromosome 5 genomic clone pMS621 (set forth as SEQ ID NO:111). Fine mapping of hKCC3 was performed by PCR using radiation hybrid analysis with the Stanford G3 panel (Research Genetics of Boston, Mass.). Reaction products generated by PCR were alkali-denatured, applied to a nylon membrane using a dot-blot apparatus, and subjected to Southern blotting with a $^{32}$P-labeled internal oligonucleotide probe. Results were analyzed by querying the Stanford radiation hybrid map (http://www-shgc.stanford.edu/RH/).

The chromosomal localization of hKCC4 has been independently verified using the STS (sequence tag site) database. Thus the STS stSG1490 maps to chromosomal region 5p15, between the chromosome 5 markers D5S678 and D5S417. See the UniSTS resource available from the NCBI website.

The chromosomal localization of hKCC2 was also determined using the STS database. The STS WI-9597/stSG2530 is identical to nucleotides 5724–5896 of hKCC2. This STS maps to chromosomal region 20q13, between D20S836 and D20S888. See the UniSTS resource available from the NCBI website.

The chromosomal localization of hKCC2 was also determined using the STS database. The STS WI-9597/stSG2530 is identical to nucleotides 5724–5896 of hKCC2. This STS maps to chromosomal region 20q13, between D20S836 and D20S888. See Gene Map-99 URLs http://www.ncbi.nlm.nih.gov/genemap99/loc.cgi? ID=35899 and http://www.ncbi.nlm.nih.gov/genemap99/map.cgi? MAP=GB4&BIN=583&MARK=stSG2530.

Genomic structure of hKCC2, hKCC3, and hKCC4 has been determined from the analysis of human genomic BAC (bacterial artificial chromosome) clones. These clones were identified by PCR-based screening of a human CITB BAC pool from Research Genetics (Boston, Mass.); in the case of one hKCC3 BAC, the clone was identified through a BLAST search of the TIGR and Washington University (St. Louis, Mo.) BACend databases. The entire hKCC2 gene, at least encompassing all 24 coding exons, is found on the CITB clones 24H13 (exons 2–24) and 90C12 (exons 1–10). The entire hKCC3 gene, including at least 1.0 kb of promoter sequence 5 of exon 1a, is on the BAC clones R-122P18 (GenBank Accession No. AQ345102) and the CITB clone 278L3. Exons 2–24 of hKCC4 are contained within the CITB clone 330M20.

Intron-exon boundaries for the individual KCC exons were determined by direct sequencing of the BAC clones, using a modified chain termination protocol (BIGDYE™ available from PerkinElmer, Inc. of Boston, Mass.). In the case of hKCC2, this direct sequencing was not successful, and individual introns were amplified by PCR and long-range PCR, followed by subcloning into pCR2.1 (Clontech of Palo Alto, Calif.); these subclones were then sequenced to determine intron-exon boundaries.

Figures 2A, 2B:
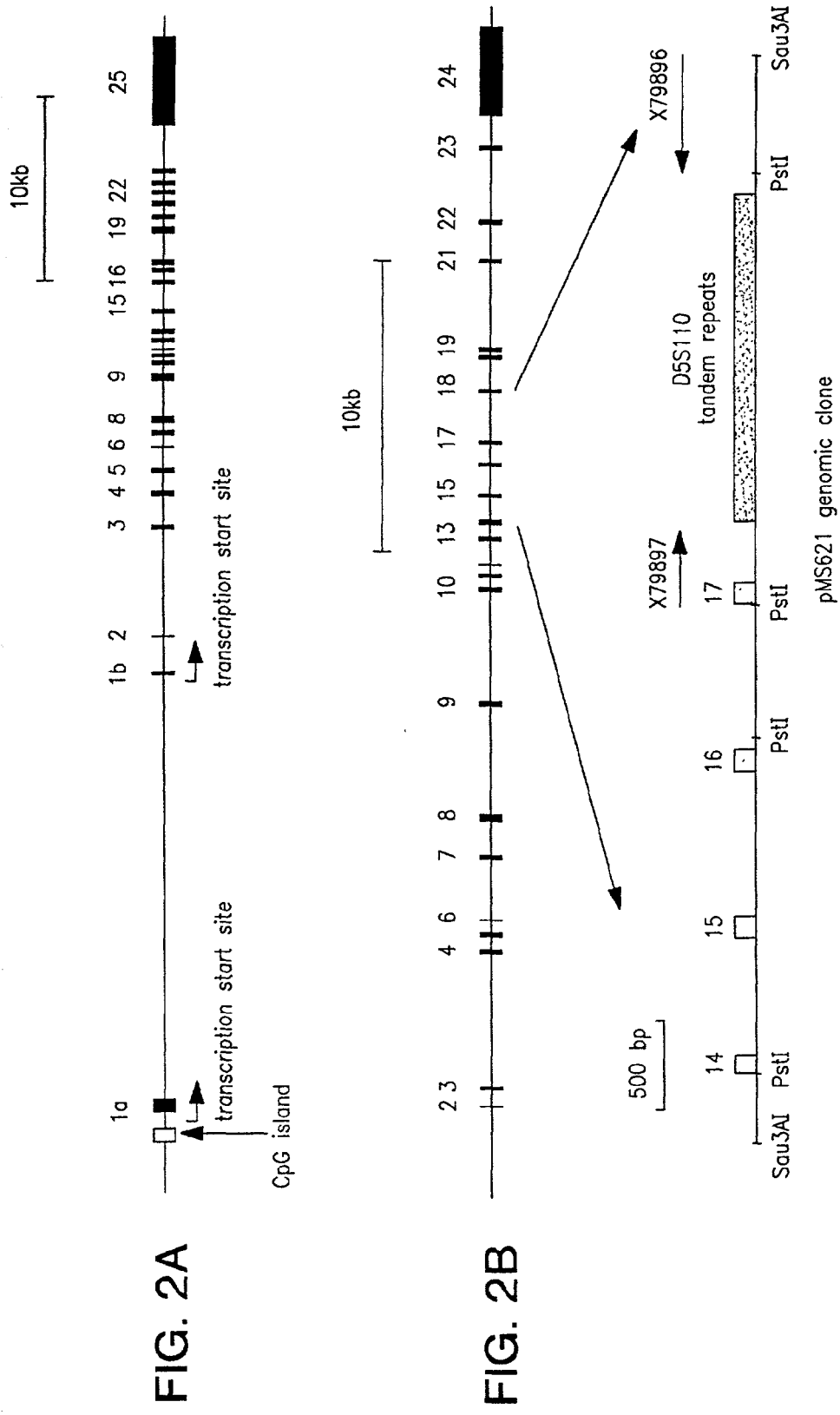
FIG. 2A is a schematic diagram depicting the genomic structure of human KCC3. Boxes represent exon sequences, numbered as indicated, and the line represents 5' UTR, 3' UTR, and intronic regions. KCC3 has two separate first coding exons, denoted 1a and 1b. 5'-RACE PCR of mouse kidney has mapped the transcriptional start site of mKCC3b just 5' of the start codon in exon 1b, hence the two isoforms are generated by transcriptional initiation at two separate promoters. Human exon 1a has a 5'-flanking CpG island (GenBank/EMBL Accession No. Z63283). The sequences for the putative mouse KCC3 exon 1a and 1b promoters are included in SEQ ID NOs:18 and 19, and that of human KCC3 exon 1a is included in SEQ ID NO:17. The figure is drawn to the scale indicated.
FIG. 2B is a schematic diagram depicting the genomic structure of exons 2–24 of human KCC4. Open boxes represent exon sequences, numbered as indicated, and the line represents 5' UTR, 3' UTR, and intronic regions. The polymorphic VNTR (variable number of tandem repeat; shaded rectangle) marker D5S110, contained in the genomic subclone pMS621, is found in the intron between exons 17 and 18 of hKCC4. The figure is drawn to the scale indicated.

FIGS. 2A and 2B show that the four human KCC genes have all been localized to different chromosomes. The genomic structure of human KCC2, KCC3, and KCC4 has been determined by the characterization of human genomic BAC (bacterial artificial chromosome) clones. Intron-exon boundary sequence is known for all of hKCC3, and most of hKCC2 and hKCC4. Intron sizes have been mapped by PCR analysis of the relevant BAC clones, using primer pairs in adjacent exons to amplify each intron.

The genomic structure of hKCC3 is shown in FIG. 2A. KCC3 has two separate first coding exons, denoted 1a and 1b. 5'-RACE PCR of mouse kidney has mapped the transcriptional start site of mKCC3b just 5' of the start codon in exon 1b, hence the two isoforms are generated by transcriptional initiation at two separate promoters. Human exon 1a has a 5-flanking CpG island (GenBank/EMBL Accession No. Z63283), previously identified by Cross et al. (1994) *Nat Genet* 6(3):236–44. The sequence for the putative mouse 1a and 1b promoters is included in SEQ ID NOs: 18–19 respectively, and that of human exon 1a is included in SEQ ID NO:17.

Genomic structure of exons 2–24 of KCC4 is shown in FIG. 2B. The polymorphic VNTR (variable number of tandem repeat) marker D5S110 (Armour et al. (1996) *Ann*

Hum Genet 60(Pt 1):11–20), contained in the genomic subclone pMS621, is found in the intron between exons 17 and 18 of hKCC4.

Example 8

Identification of a NSRE in KCC2

Figure 3:
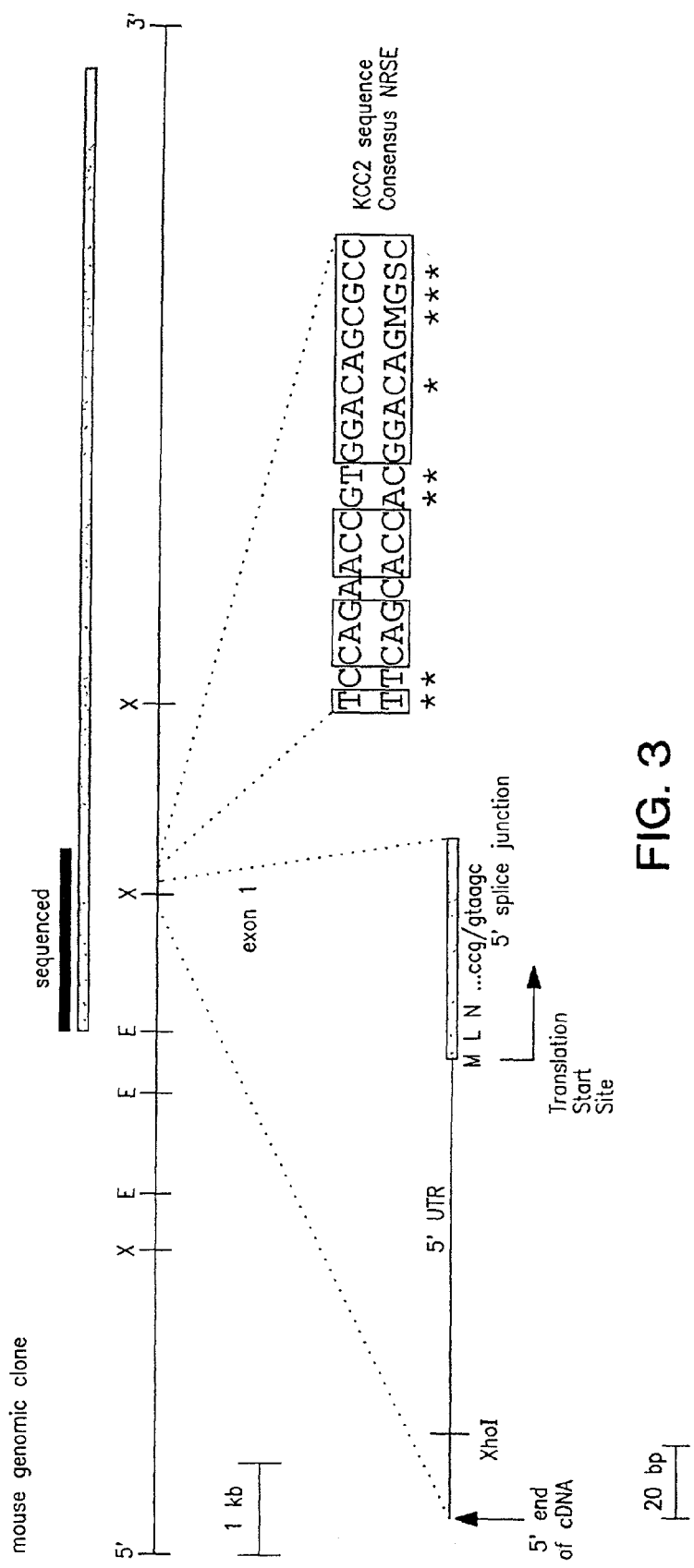
FIG. 3 is a map showing the structure of an 18-kb mouse genomic clone encoding the KCC2 gene. Magnification of exon 1 displays the position corresponding to the 5' end of the rat cDNA, the 5' untranslated region (UTR), the ATG start of the KCC2 protein (origin of arrow, M, methionine; L, leucine; N, asparagine), and the exon/intron boundary (5' splice junction). The position of the KCC2 NRSE sequence, depicted as a star, is observed downstream of exon 1. The alignment of the KCC2 putative neuronal-restrictive silencing element (NRSE) sequence with the NRSE consensus sequence is shown. Identical residues are boxed and residues that are likely subject to modifications are marked with an asterisk. M and S in the consensus sequence represent (A or C) and (C or G), respectively. Selected restrictions sites are shown as landmarks: X, XhoI; E, EcoRI. The thick black line starting at the EcoRI site indicates the fragment which was sequenced, and the thick gray line represents a 10.2-kb genomic fragment released in Genbank under Accession No. AJ011033. The genomic clone is drawn to a scale indicated by the 1 kb bar, and the magnification of exon 1 is drawn to a scale indicated by the 20 bp bar.
Figure 5:
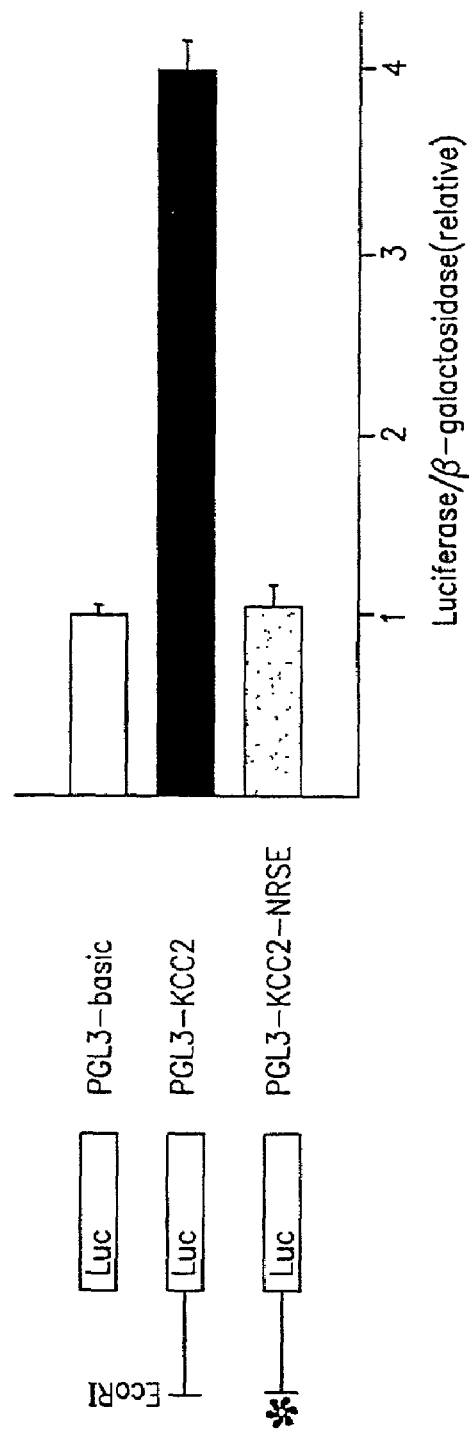
FIG. 5 is a bar graph depicting transcriptional repression conferred by the mKCC2 NSRE. Expression of the indicated reporter constructs was assayed in non-neuronal C17 cells. Relative luciferase activities were measured with promoterless PGL3-basic vector (open bar), PGL3 vector containing 1,500 base pairs of 5' flanking region of the KCC2 gene (EcoRI-XhoI fragment) (black bar), and PGL3 vector including both the KCC2 promoter and the 21-base pair NRSE element (gray bar). Significant luciferase activity is generated by the KCC2 promoter ($P<0.01$), and KCC2-induced luciferase activity is completely inhibited by the presence of the NRSE element. Each bar represents the mean±standard error of 3 measurements. Experiments shown in this figure were repeated 4 times with similar results.

The mouse KCC2 gene contains a neuronal restrictive silencing element (NSRE) in intron 1, just 3' of exon 1 (Karadesh & Delpire (2001) *J Neurophysiol* 85:995–997) (FIG. 3). As disclosed herein, this element binds nuclear proteins from a murine neural progenitor cell line using a standard electromobility shift assay (FIGS. 4A and 4B). Given the function of neuronal restrictive silencing factor (NRSF) in repressing the expression of neuronal-specific genes in non-neuronal tissues (Schoenherr et al. (1996) *Proc Natl Acad Sci USA* 93:9881–9886), the expression of a KCC2 promoter construct containing the NRSE was tested in a non-neuronal cell line. Briefly, nuclear protein (15 μg) isolated from C17 neural progenitor cells was incubated with $^{32}$P-end-labeled NSRE oligonucleotide for 15 minutes at room temperature. The reactions were resolved on a 4% acrylamide gel and visualized by autoradiographic exposure. Luciferase expression directed by a KCC2-NRSE construct in the PGL3 vector was reduced when compared to levels of luciferase expression directed by a promoter without the NRSE element in the PGL3 vector (FIG. 5). The promoter constructs used comprised the mKCC2 promoter (SEQ ID NO:131), with or without the NSRE.

Example 9

Cloning of *Xenopus* KCC

Sequence of the last 2290 nucleotides of a *Xenopus* KCC (SEQ ID NO:112) was obtained from overlapping RT-PCR cDNA (cloned using primers derived from the EST PBX0118E03) and EST (IMAGE clone 3399678) clones. The sequence of the C-terminal 358 amino acids of "xKCC" (SEQ ID NO:113) reveals 76% identity with hKCC3. A tissue survey by RT-PCR indicates that this transcript is widely expressed, including within oocytes. The expression of a highly homologous KCC in oocytes validates these cells as a model expression system for the mammalian KCCs.

Example 10

In vitro Translation of mKCC4 Protein

One (1.0) mg of the full-length mKCC4 cDNA (SEQ ID NO:13) was translated in vitro using [$^{35}$S]methionine and T7 RNA polymerase-coupled rabbit reticulocyte lysate (TNT™ T7 RNA polymerase available from Promega of Madison, Wis.), both with and without pancreatic microsomes, for 90 minutes at 30° C. Protein was resolved by 7% SDS-polyacrylamide gel electrophoresis followed by autoradiography.

KCC1, KCC2, and other members of the cation-chloride cotransporter gene family are known to be glycoproteins, and the four KCC sequences contain three identical N-linked glycosylation sites in the otherwise poorly conserved extracellular loops. The in vitro translation of mKCC4 results in a protein with an apparent molecular mass of 115 kDa, slightly lower than the predicted core weight of 119 kDa. The addition of canine pancreatic microsomes results in the appearance of an additional band of higher molecular mass, which is consistent with in vitro glycosylation. Western blot analysis with KCC3- and KCC4-specific antibodies reveals that the native proteins are 40–60 kDa greater in mass than the predicted core proteins, consistent with glycosylation of the native proteins.

Example 11

Heterologous Expression of mKCC4 and hKCC3a in *X. laevis* Oocytes

Differences in KCC transmembrane domains were predicted to confer differences in K$^+$—Cl$^-$ cotransport. Table 3 summarizes the differences among the KCCs in ion affinity, diuretic senstivity, and anion selectivity, as described further in Examples 14–15 herein below.

TABLE 3

Summary of KCC Properties

| KCC | Potassium $K_m$ (mM) | Chloride $K_m$ (mM) | Furosemide K 0.5 | Anion Series |
|---|---|---|---|---|
| KCC1 | 25.5 | 17.2 | 180 μM | Cl$^-$ > SCN$^-$ > Br$^-$ > PO$_4^-$ > I$^-$ |
| KCC2 | 9.3 | 6.3 | 90 μM | Cl$^-$ > Br$^-$ > PO$_4^-$ = I$^-$ = SCN$^-$ |
| KCC3 | 51.9 | 14.2 | 180 μM | Br$^-$ > Cl$^-$ > PO$_4^-$ = I$^-$ > SCN$^-$ |
| KCC4 | 17.5 | 15.3 | 900 μM | Cl$^-$ > Br$^-$ > PO$_4^-$ = I$^-$ > SCN$^-$ |
| xKCC | 27.7 | 15.4 | 200 μM | Cl$^-$ = PO$_4^-$ = Br$^-$ > I$^-$ > SCN$^-$ |

Oocytes were surgically collected from anesthetized female *Xenopus* adults under 0.17% tricaine and incubated for 1 hour with vigorous shaking in frog Ringer ND96 (96 mM sodium chloride, 2 mM potassium chloride, 1.8 mM calcium chloride, 1.0 mM magnesium chloride, and 5 mM Hepes/Tris, pH 7.4) in the presence of 2 mg/ml collagenase B. Oocytes were then washed four times in ND96, manually defolliculated, and incubated overnight in ND96 at 18° C. On the next day, defolliculated stage V–VI oocytes were injected with 50 nl of water or a solution containing cRNA at a concentration of 0.25–0.5 μg/μl (25 ng/oocyte). Oocytes were incubated at 17–18° C. in ND96 (96 mM sodium chloride, 2 mM potassium chloride, 1.8 mM calcium chloride, 1.0 mM magnesium chloride, and 5 mM Hepes/Tris, pH 7.4), supplemented with 2.5 mM sodium pyruvate and 5 mg/100 ml gentamicin, for 3–4 days. The incubation medium was changed every 24 hours. On the day of the experiment, oocytes were switched to Cl$^-$-free ND96 (96 mM Na$^+$ Na$^+$ isethionate, 2 mM K$^+$ gluconate, 6 mM Ca$^{2+}$ gluconate, 1 mM Mg$^{2+}$ gluconate, 5 mM Hepes, 2.5 mM sodium pyruvate, 5 mg/100 ml gentamicin, pH 7.4) for 2 hours prior to the uptake assay.

For functional expression and in vitro translation, a full-length mKCC4 cDNA was used as a standard in the *Xenopus* expression vector pGEMHE (Liman et al. (1992) *Neuron* 9:861–871). The resulting construct contains nucleotides 55–3812 of mKCC4 (SEQ ID NO:13). For functional comparison with mKCC4, a full-length rabbit KCC1 cDNA was subcloned into pGEMHE. A full-length hKCC3a construct has also been generated for functional expression, and comparative data for rabKCC1, hKCC3a, and mKCC4. To prepare a template for cRNA, the rabbit KCC1 and mKCC3 cDNAs were linearized at the 3'-end using NheI, and cRNA was transcribed in vitro using the T7 RNA polymerase and the mMESSAGE mMACHINE kit (Ambion, Inc. of Austin, Tex.). Transcription product integrity was confirmed on agarose gels, and concentration was determined by absorbance reading at 260 nm (DU 640 available from Beckman of Fullerton, Calif.).

Example 12

Assessment of $K^+$—$Cl^-$ Cotransport $K^+$—$Cl^-$ cotransport was assessed by measuring tracer $^{86}Rb^+$ uptake (NEN® Life Science Products of Boston, Mass.) in experimental groups of at least 15 oocytes. Since both KCC4 and KCC1 display minimal activity under isotonic conditions $^{86}Rb^+$ uptake was generally assessed in oocytes swollen by a 30-minute incubation period in a hypotonic $K^+$ and $Cl^-$-free medium (50 mM N-methyl-D-glucamine (NMDG) gluconate, 4.6 mM $Ca^{2+}$ gluconate, 1.0 mM $Mg^{2+}$ gluconate, 5 mM Hepes, pH 7.4) with 1 mM ouabain, followed by a 60-minute uptake period in a hypotonic $Na^+$-free medium with variable $K^+$—$Cl^-$ content. $K^+$ and $Cl^-$ concentrations were varied separately using combinations of KCl, NMDG chloride, potassium gluconate, and NMDG gluconate, for a maximal total concentration of 50 mM; an uptake solution with 50 mM $K^+$—$Cl^-$ did not contain NMDG chloride, potassium gluconate, or NMDG gluconate, for example. All uptake solutions also contained 1.8 mM $CaCl_2$, 1 mM $MgCl_2$, 5 mM Hepes, pH 7.4, and were supplemented with 1 mM ouabain and 5.0 mCi/ml $^{86}Rb^+$. Isotonic conditions were generated by supplementing the same solutions with 3.5 g/100 ml sucrose to reach isosmolar conditions for oocytes (~210 mOsm/kg). Ouabain was added to prevent $^{86}Rb^+$ uptake via the $Na^+$—$K^+$-ATPase. The absence of extracellular $Na^+$ and the hypotonicity of the uptake medium prevented $^{86}Rb^+$ uptake via the endogenous $Na^+$—$K^+$-$2Cl^-$ cotransporter that is present in oocytes (Gamba et al. (1994) *J Biol Chem* 269:17713–17722).

All uptake assays were performed at 32° C. At the end of the uptake period, oocytes were washed five times in ice-cold uptake solution without isotope to remove extracellular fluid tracer. Oocytes were dissolved in 10% SDS, and tracer activity was determined for each oocyte by β-scintillation counting.

To determine the ion transport kinetics of KCC4 and KCC1, $^{86}Rb^+$ uptake experiments were performed in variable concentrations of $K^+$ and $Cl^-$. The sensitivity for several inhibitors was assessed by exposing groups of oocytes to the inhibitors at concentrations varying from 20 mM to 2 mM. For these experiments, the desired concentration of the inhibitor was present during both the incubation and uptake periods, except when noted.

Figure 6:
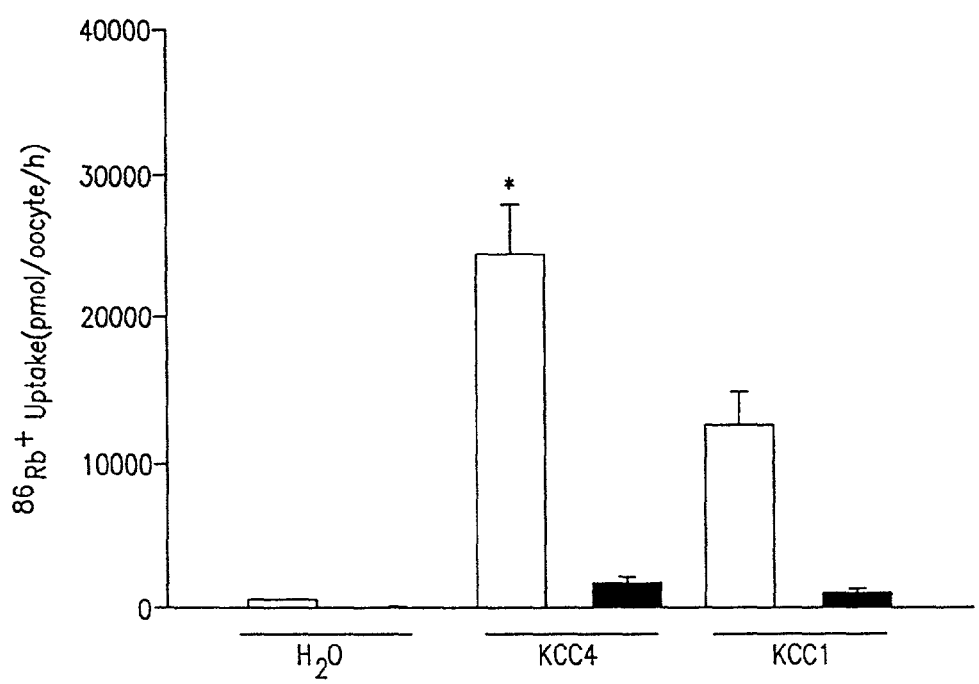
FIG. 6 is a bar graph that summarizes the baseline functional characterization of KCC1 and KCC4 expressed in *Xenopus laevis* oocytes. *Xenopus* oocytes were each injected with water ($H_2O$) or with cRNA encoding rabKCC1 or mKCC4, as indicated. $K^+$—$Cl^-$ cotransport was assayed by measuring chloride-dependent uptake of $^{86}Rb^+$, a surrogate for $K^+$, as described in Example 12. Uptakes were performed under both isotonic (200 mOsm/kg) and hypotonic (100 mOsm/kg) conditions in the presence (open bars) or absence (black bars) of extracellular chloride. Each bar represents a mean of data collected from 90 oocytes extracted from five animals. $^{86}Rb^+$ uptake was measured during a 60-minute interval. The asterisk (*) indicates that $^{86}Rb^+$ uptake in *Xenopus* oocytes expressing mKCC4 and in the presence of extracellular chloride is significantly increased when compared with $^{86}Rb^+$ uptake in control oocytes ($p<0.01$).

In isotonic conditions, no differences were observed among KCC4, KCC1, and water-injected oocytes. When uptake experiments were performed under hypotonic conditions, microinjection of KCC4 and KCC1 cRNAs resulted in significant $K^+$—$Cl^-$ transport activity, as compared with control ooctyes that were injected with water. FIG. 6 summarizes five experiments in which oocyes from difference frogs were injected with water or KCC4 or KCC1 cRNA, followed by $^{86}Rb^+$ uptake assay using a hypotonic uptake solution containing 10 mM and 50 mM of extracellular $K^+$ and $Cl^-$, respectively. In control oocytes, $^{86}Rb^+$ uptake was 588±91 pmol×oocyte$^{-1}$×hour$^{-1}$ in the presence of $Cl^-$ and 147±23 pmol×oocyte$^{-1}$×hour$^{-1}$ in the absence of $Cl^-$, indicating the presence of an endogenous $K^+$—$Cl^-$ cotransporter. Microinjection of KCC4 cRNA resulted in an increased 8Rb$^+$ uptake to 24,457±3,476 pmol×oocyte$^{-1}$×hour$^{-1}$. This $^{86}Rb^+$ uptake was $Cl^-$-dependent, in that uptake in KCC4 oocytes in the absence of extracellular $Cl^-$ was 1723±402 pmol×oocyte$^{-1}$×hour$^{-1}$. In oocytes microinjected with KCC1, $^{86}Rb^+$ uptake increased to 12,632±2205 pmol×oocyte$^{-1}$×hour$^{-1}$, and the influx was $Cl^-$-dependent. The difference in the amount of uptake between KCC4 and KCC1 was statistically significant (p<0.05). Although equal amounts of KCC4 and KCC1 cRNA were injected for all experiments, the relative expression level under hypotonic conditions was always greater for KCC4 than KCC1. In addition, for each KCC, the absolute uptake varied with each animal. Results of uptake experiments are presented as the percentage of $Cl^-$-dependent $^{86}Rb^+$ uptake. Thus, 100% generally represents the uptake observed in the KCC4 or KCC1 control group minus the uptake observed in the water-injected oocytes.

Figures 7A, 7B:
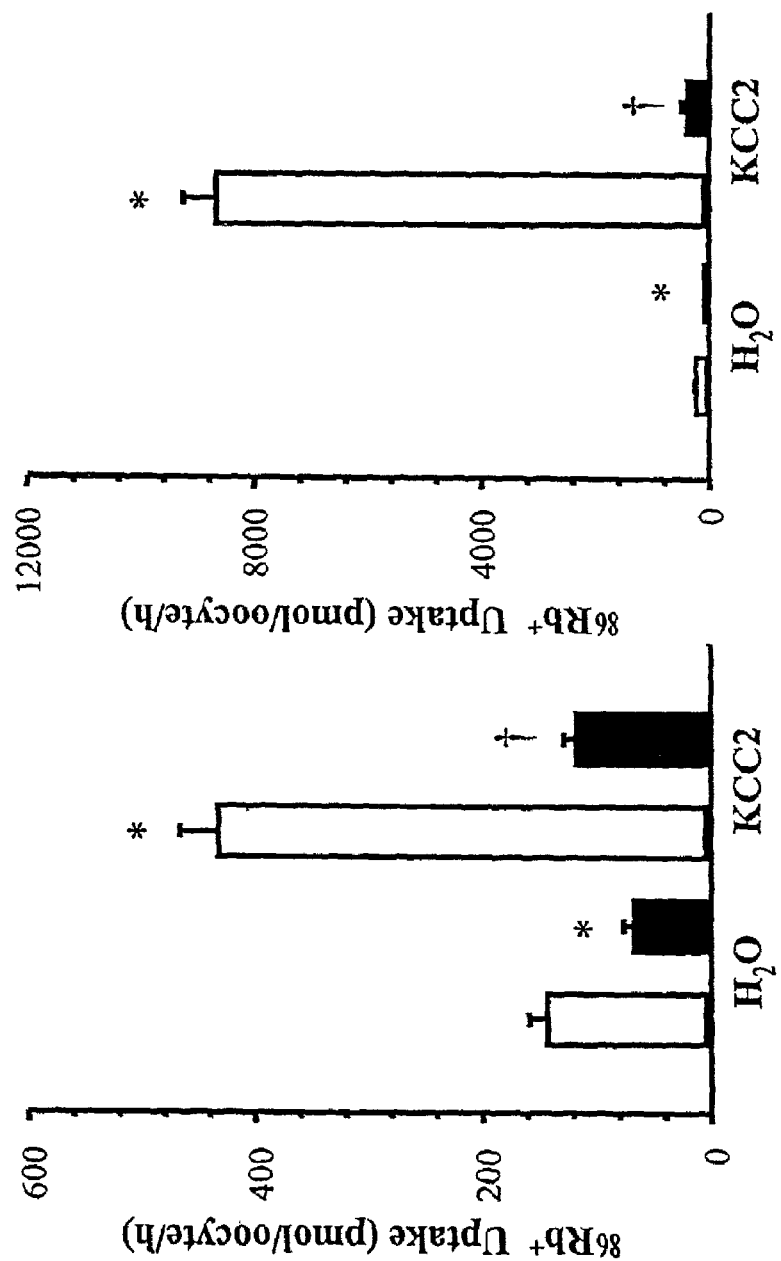
FIG. 7A shows the functional expression of a $K^+$—$Cl^-$ cotransporter in *Xenopus laevis* oocytes that were injected with water or with 25 ng of hKCC2 cRNA, as indicated. $^{86}Rb^+$ uptake assays were performed in isotonic solutions of 210 mOsm/kg, in the presence (open bars) or absence (black bars) of extracellular $Cl^-$. The uptake solutions contained 10 mM $K^+$ and 50 mM $Cl^-$. Each bar represents a mean of data obtained from 40–60 oocytes extracted from five different frogs. $^{86}Rb^+$ uptake was performed for 60 minutes. The asterisk (*) denotes a significant difference in $^{86}Rb^+$ uptake relative to $^{86}Rb^+$ uptake observed in water-injected oocytes in the presence of extracellular $Cl^-$ ($p<0.001$); the cross symbol (\) denotes significantly increased uptake in the KCC2 group in the presence of chloride ($p<0.001$) when compared to water-injected oocytes in the absence of extracellular $Cl^-$. $^{86}Rb^+$ uptake values indicate the mean+/− standard error. $H_2O$/open bars, activity of xKCC (*Xenopus* $K^+$—$Cl^-$ cotransporter) at 210 mOsm/kg=145±13; $H_2O$/black bars, activity of xKCC at 210 mOsm/kg in the absence of $Cl^-$=69.3±6.7; hKCC2/open bars, activity of KCC2 at 210 mOsm/kg=434±31; hKCC2/black bars, activity of hKCC2 at 210 mOsm/kg in the absence of $Cl^-$=119±8.5.
FIG. 7B shows the functional expression of a $K^+$—$Cl^-$ cotransporter in *Xenopus laevis* oocytes that were injected with water or with 25 ng of cRNA from hKCC2, as indicated. $^{86}Rb^+$ uptake assays were performed in hypotonic solutions with 120 mOsm/kg, in the presence (open bars) or absence (black bars) of extracellular $Cl^-$. The uptake solutions contained 10 mM $K^+$ and 50 mM $Cl^-$. Each bar represents a mean of data obtained from 40–60 oocytes extracted from five different frogs. $^{86}Rb^+$ uptake was performed for 60 minutes. The asterisk (*) denotes a significant difference from uptake in the H2O control group (p<0.001); the cross symbol (†) denotes a significant difference from uptake in the hKCC2 group in the presence of chloride (p<0.001). $^{86}Rb^+$ uptake values indicate the mean+/−standard error. H$_2$O/open bars, activity of xKCC at 120 mOsm/kg=221±11; H$_2$O/black bars, activity of xKCC at 120 mOsm/kg in the absence of $Cl^-$=71.5±6.6; hKCC2/open bars, activity of hKCC2 at 120 mOsm/kg=8713±545; hKCC2/black bars, activity of hKCC2 at 120 mOsm/kg in the absence of $Cl^-$=430±50.
Figure 8:
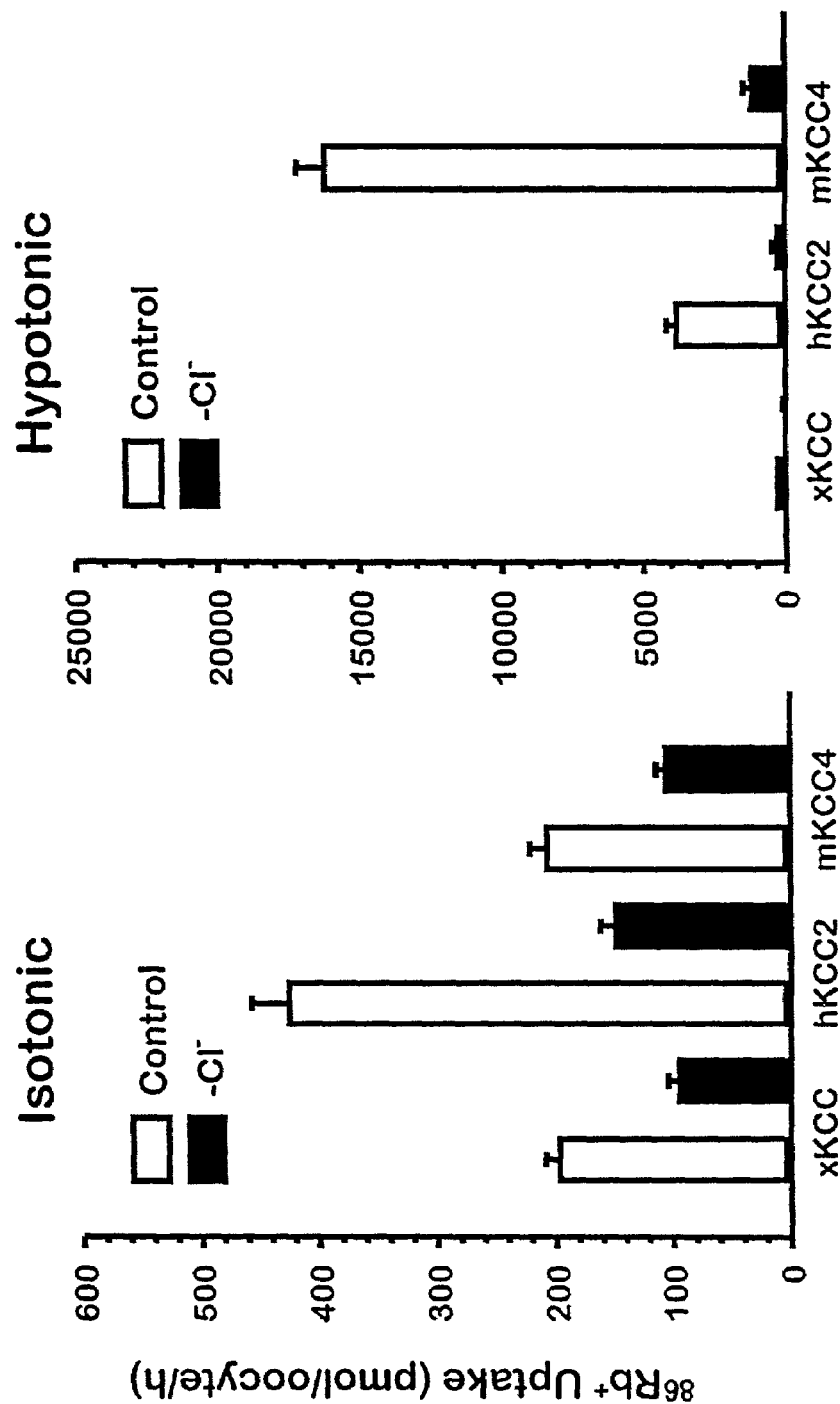
FIG. 8 presents bar graphs that compare $K^+$—$Cl^-$ cotransport mediated by xKCC, hKCC2 and mKCC4 under isotonic (210 mOsm/kg) and hypotonic (120 mOsm/kg) conditions. hKCC2 and mKCC4, which are ~70% identical, exhibit dramatic differences in their response to cell volume. Like the other KCCs, however, swelling activation of hKCC2 depends on dephosphorylation mediated by serine-threonine protein phosphatases, although baseline isotonic activity does not. KCC2 is unique among the four KCCs in mediating significant $K^+$—$Cl^-$ cotransport under isotonic conditions. Open bars, uptake assays performed in control medium containing 10 mM $K^+$ and 50 mM $Cl^-$; black bars, uptake assays performed in the absence of extracellular chloride.
Figure 9A:
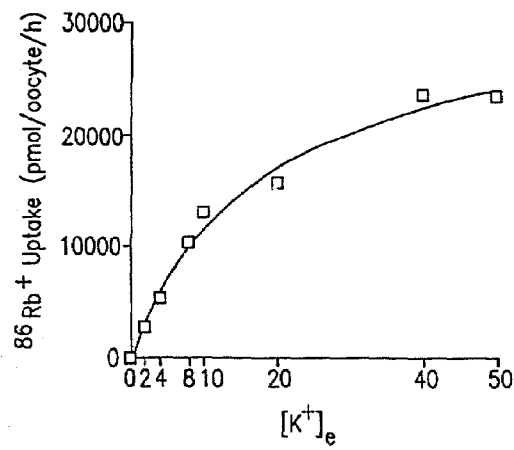
FIG. 9A is a line graph that summarizes a kinetic characterization of $^{86}Rb^+$ uptake in response to extracellular $K^+$ concentration in *Xenopus* oocytes injected with mKCC4 cRNA.
Figure 9B:
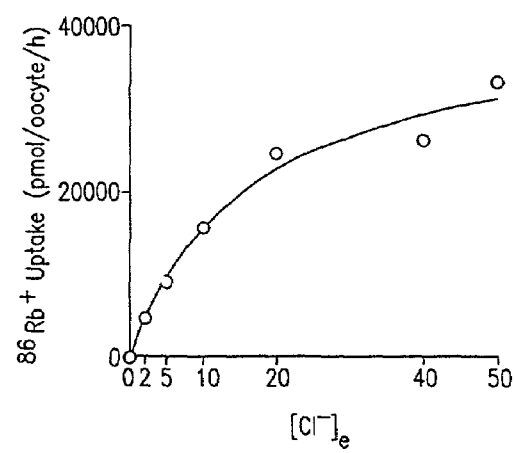
FIG. 9B is a line graph that summarizes a kinetic characterization of $^{86}Rb^+$ uptake in response to extracellular $Cl^-$ concentration in *Xenopus* oocytes injected with mKCC4 cRNA.
Figure 9C:
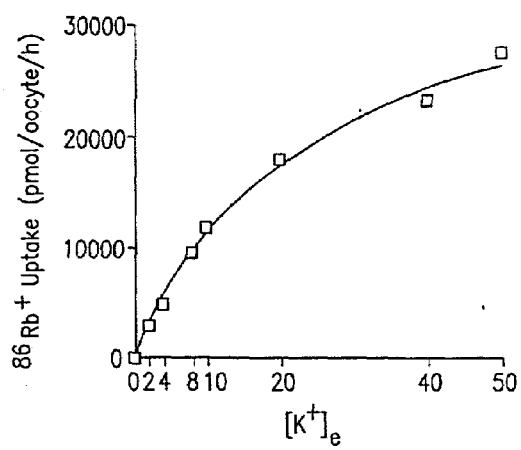
FIG. 9C is a line graph that summarizes a kinetic characterization of $^{86}Rb^+$ uptake in response to extracellular $K^+$ concentration in *Xenopus* oocytes injected with rabKCC1 cRNA.
Figure 9D:
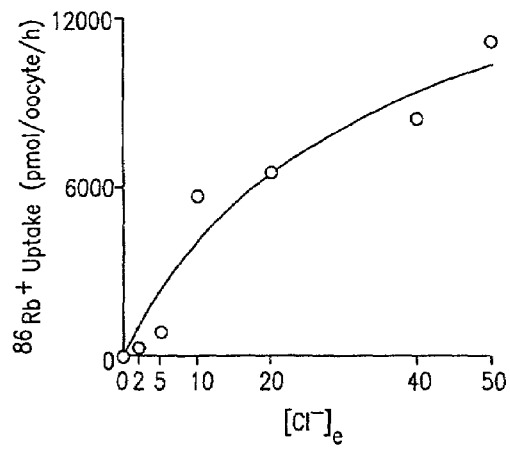
FIG. 9D is a line graph that summarizes a kinetic characterization of $^{86}Rb^+$ uptake in response to extracellular $Cl^-$ concentration in *Xenopus* oocytes injected with rabKCC1 cRNA.

Uptake assays to detect $K^+$—$Cl^-$ cotransport mediated by a hKCC2 were performed using similar methods. FIGS. 7A, 7B, and 8 depict functional expression of the hKCC2 transporter in both isotonic and hypotonic conditions.

Example 13

Kinetic Properties of KCC4 and KCC1

FIGS. 9A–9D summarize the kinetic characterization of KCC1, KCC3, and KCC4. The four KCCs differ in the sequence of key transmembrane segments (TMs), and were postulated to vary in affinity for $K^+$ and $Cl^-$ (Mount et al. (1999) *J Biol Chem* 274(23): 16355–16362). By plotting $K^+$—$Cl^-$ cotransport as a function of the external concentration of both $K^+$ and $Cl^-$ (shown for KCC3a in FIGS. 9A and 9B, respectively), the individual apparent affinity constants for these transported ions have been determined.

To determine and compare the kinetic properties of KCC4 and KCC1 in the same expression system, $^{86}Rb^+$ uptake was measured in KCC4- and KCC1-injected oocytes as a function of the concentration of each transported ion (FIG. 9). Uptake assays were performed with $K^+$ or $Cl^-$ fixed at 50 mM, and the concentration of the counterion was varied from 0 to 50 mM. Uptake assays were also performed in water-injected oocytes, and the mean values for water-injected oocytes were subtracted from corresponding KCC-injected oocytes in order to assess only the $^{86}Rb^+$ uptake mediated by each heterologously expressed isoform. As shown in FIG. 6, $^{86}Rb^+$ uptake in water-injected oocytes was low, such that this correction was generally minor.

In the case of KCC4, $^{86}Rb^+$ influx increased concomitant with increased concentration of each transported ion. A plateau phase was reached at ion concentrations greater than 20–40 mM, compatible with Michaelis-Menten behavior. The calculated apparent $K_m$ and $V_{max}$ for extracellular $K^+$ concentration were 17.5±2.7 mM and 32,370±2,115 pmol×oocyte$^{-1}$×hour$^{-1}$, respectively. The calculated apparent $K_m$ and $V_{max}$ values for extracellular $Cl^-$ concentration were 16.12±4.2 mM and 41,440±4,174 pmol×oocyte$^{-1}$×hour$^{-1}$, respectively. The Hill coefficient for both ions remained close to unity: 1.08±0.2 and 1.06±0.3 for $K^+$ and $Cl^-$, respectively. KCC1 also exhibited a similar Michaelis-Menten behavior. The apparent $K_m$ and $V_{max}$ in KCC1 were 25.5±3.2 mM and 39,540±2,199 pmol×oocyte$^{-1}$×hour$^{-1}$ for extracellular $K^+$ and 17.2±8.3 mM and 14,930±2,822 pmol×oocyte$^{-1}$×hour$^{-1}$ for $Cl^-$. Hill coefficients for $K^+$ (1.04±0.13) and $Cl^-$ (1.3±0.5) in KCC1 also were close to unity.

Figure 10:
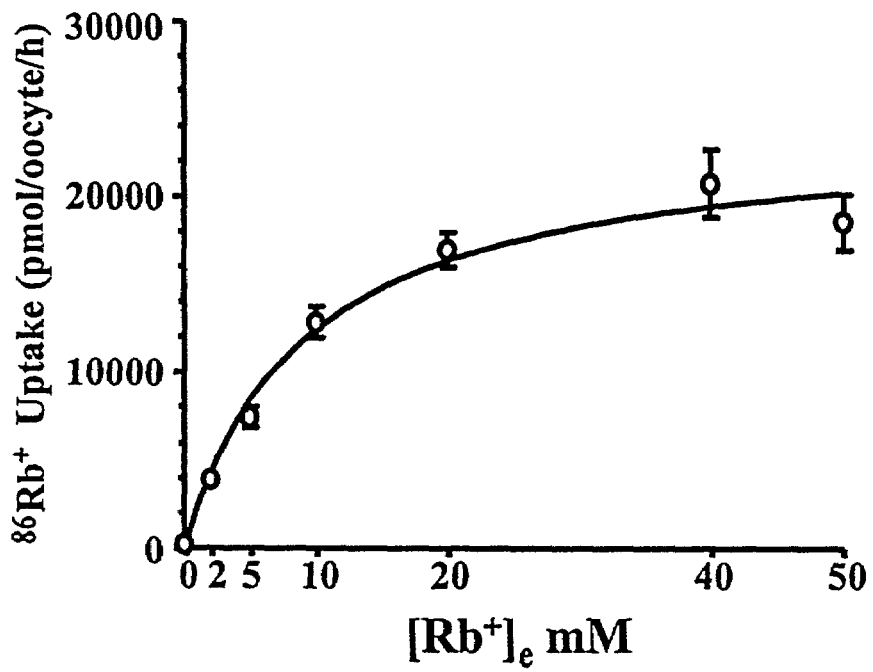
FIG. 10 presents line graphs depicting concentration dependence of $K^+$—$Cl^-$ cotransport mediated by hKCC2. Uptake assays were simultaneously assessed in water-injected oocytes. To determine $^{86}Rb^+$ uptake due to hKCC2, the mean values for water groups were subtracted from the mean values for corresponding hKCC2 groups.
Figure 10:
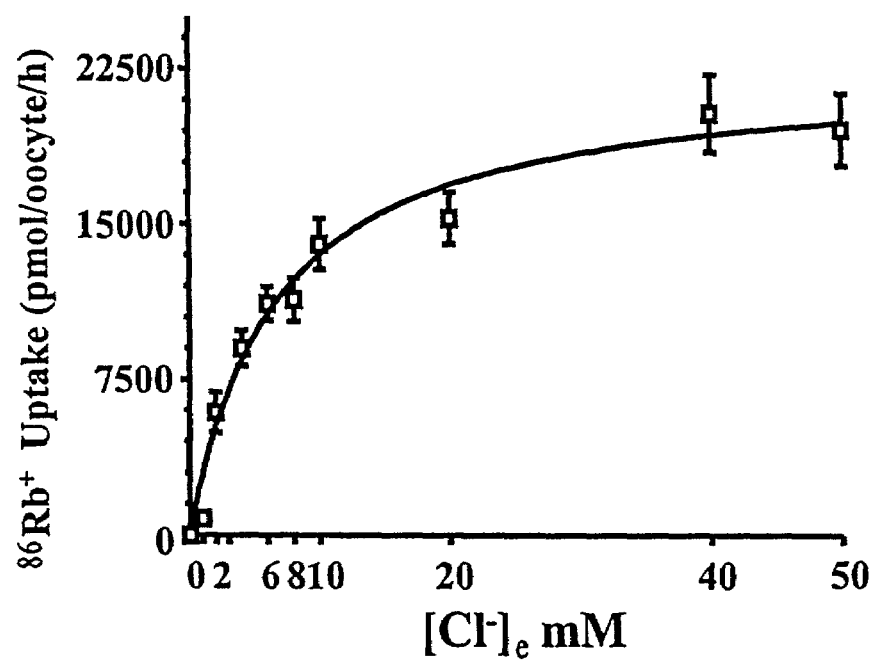

FIG. 10 presents line graphs depicting concentration dependence of $K^+$—$Cl^-$ cotransport mediated by hKCC2, which was used to calculate ion affinities using analogous methods. Uptake assays were simultaneously assessed in water-injected oocytes. To determine $^{86}Rb^+$ uptake due to KCC2, the mean values for water groups were subtracted from the mean values for corresponding KCC2 groups. Uptake assays in hypotonic media were performed for 60 minutes with a fixed concentration of $K^+$ or $Cl^-$ at 50 mM. The concentration of the counterion was varied from 0 to 50 mM as indicated. Lines were fit using the Michaelis-Menten equation, yielding a $K_m$ for $^{86}Rb^+$ (substitute for $K^+$) and $Cl^-$ of $K_m$ 9.3+/−1.8 mM and 6.31+/−0.92, respectively. This cation $K_m$ is similar to that reported for rat KCC2 analyzed in HEK293 cells (Payne et al. (1990) *Am J Physiol* 273: C1516–1525), however the chloride affinity is significantly higher (>50 mM reported for rKCC2). Of note, the measured chloride affinity for hKCC2 is closer to the chloride concentration of neurons (Hara et al. (1992) *Neurosci Lett* 143:135–138).

Figure 11:
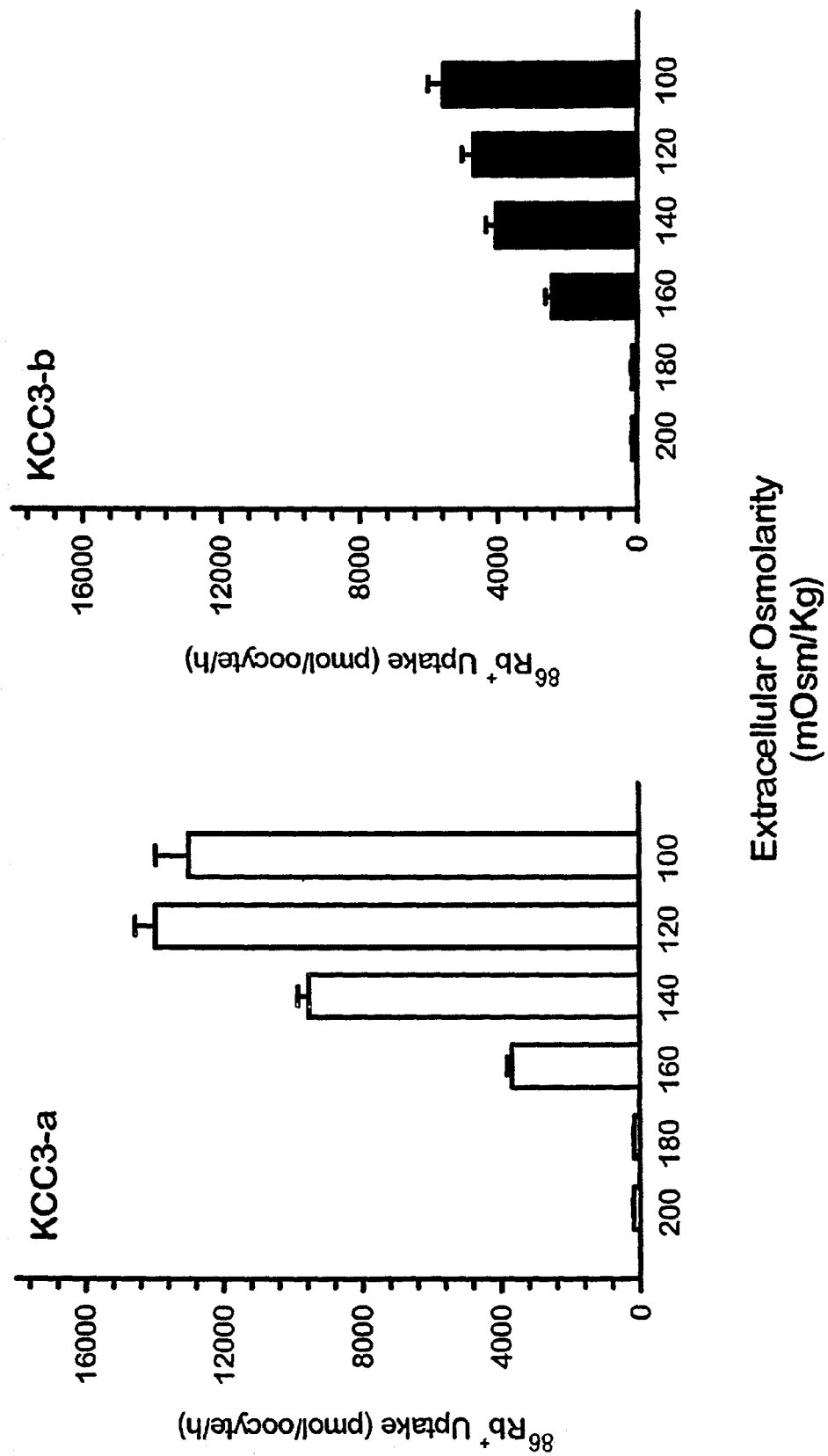
FIG. 11 presents bar graphs depicting differences in the slope of activation of hKCC3a and hKCC3b by cell swelling, but that both isoforms begin to activate at an extracellular osmolarity of 160 mOsm/kg. These differences in activation can be attributable to differences between predicted phosphorylation of their divergent amino termini (Mount et al. (1999) *J Biol Chem* 274:16355–16362).

As shown in FIG. 11, the slopes of activation of hKCC3a and hKCC3b by cell swelling, but that both isoforms begin to activate at an extracellular osmolality of 160 mOsm/kg. These differences in activation can be attributable to differences between predicted phosphorylation of their divergent amino termini (Mount et al. (1999) *J Biol Chem* 274: 16355–16362).

As shown in Table 3, the four KCCs differ significantly in affinity for $K^+$ and $Cl^-$, due presumptively to variation within TM2 (cation affinity), and within TM4 and TM7 (anion affinity) (Mount (1999) *J Biol Chem* 274(23):16355–16362). Kinetic data for rat KCC2 are from Payne (1997) *Am J Physiol* 273:C1516–C1525, "xKCC" refers to the endogenous *Xenopus* oocyte transporter. Of note, as predicted by the sequence of TM2, the four KCCs fall into two groups with respect to $K^+$ affinity, a low-affinity subgroup (KCC1 and KCC3) and a higher-affinity subgroup (KCC2 and KCC4).

Example 14

Anion Dependence of KCC1, KCC2, KCC3a, and KCC4

The anion selectivity of the three KCCs has also been determined, looking at the ability of anions other than $Cl^-$ to support $K^+/^{86}Rb^+$ transport. These results indicate that the KCCs differ in this "anion series" of $K^+$—$Cl^-$ cotransport. This data is summarized in FIGS. 12 and 13, as the percent activity (compared to chloride) for each anion. Again, this variability in anion series is likely due to variation with TM4 and TM7, segments thought to confer anion affinity on the cation-chloride cotransporters. See Mount et al. (1999) *J Biol Chem* 274(23):16355–16362; Isenring et al. (1998) *J Gen Physiol* 112(5):549–558.

Figure 12:
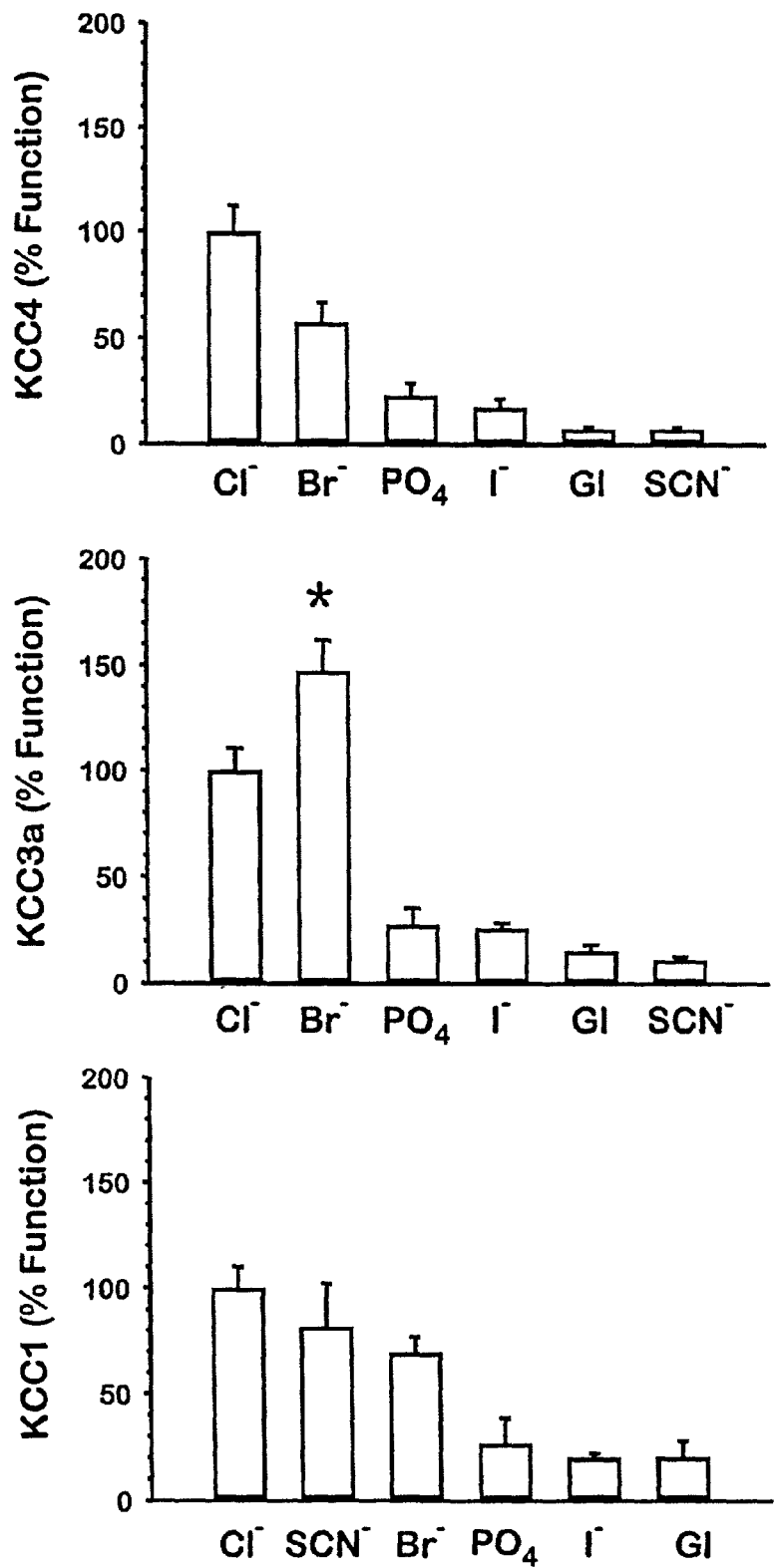
FIG. 12 is a set of bar graphs depicting the anion dependence of rabKCC1, hKCC3a, and mKCC4. $^{86}Rb^+$ influx was assessed in hypotonic uptake medium containing 40 mM NMDG gluconate plus 10 mM concentration of KCl (control group) or 10 mM potassium salts of each of the anion substitutes (KBr, KH$_2$PO4, KI, potassium gluconate, and KSCN). Preincubation was done in a solution containing 50 mM NMDG gluconate. Data was normalized by designating $^{86}Rb^+$ uptake in the control group as 100%. Each bar represents the mean±standard error determined in at least 15 oocytes. The observed differences in anion selectivity among rabKCC1, hKCC3a, and mKCC4 are likely due to variation with TM4 and TM7, segments thought to confer anion affinity on the cation-chloride cotransporters. Asterisk (*) indicates significantly increased $^{86}Rb^+$ uptake when compared to uptake observed for the control group.

It has been shown that some extracellular anions other than $Cl^-$ can support ion translocation through the $K^+$—$Cl^-$ cotransporter of both sheep and human erythrocytes (Payne et al. (1990) *Am J Physiol* 259:C819–827). Thus, $^{86}Rb^+$ transport by KCC4 and KCC1 was measure in the presence of different anions. The $^{86}Rb^+$ influx of KCC4- and KCC1-injected oocytes using an uptake solution containing 40 mM potassium gluconate and 10 mM KCl served as the reference activity for these experiments, as compared with uptake activity in oocytes exposed to medium containing 40 mM potassium gluconate and 10 mM of KBr, $KH_2PO_4$, KI, potassium gluconate, or KSCN. FIG. 12 shows the percentage of KCC4 and KCC1 function when $^{86}Rb^+$ uptake assays were performed using these different anion substitutions. KCC4 shows high $^{86}Rb^+$ influx in the presence of 10 mM KCl. $^{86}Rb^+$ influx was still observed in the presence of other anions: 58±9% with 10 mM KBr, 22±5.9% with 10 mM $KH_2PO_4$, and 17±3.8% with KI, whereas potassium gluconate and KSCN did not support transport. These results are in contrast to those observed in KCC1-injected oocytes, for which the order of anion-supported transport was $Cl^-$> SCN-=Br—>PO4-3>I>gluconate.

Figure 13:
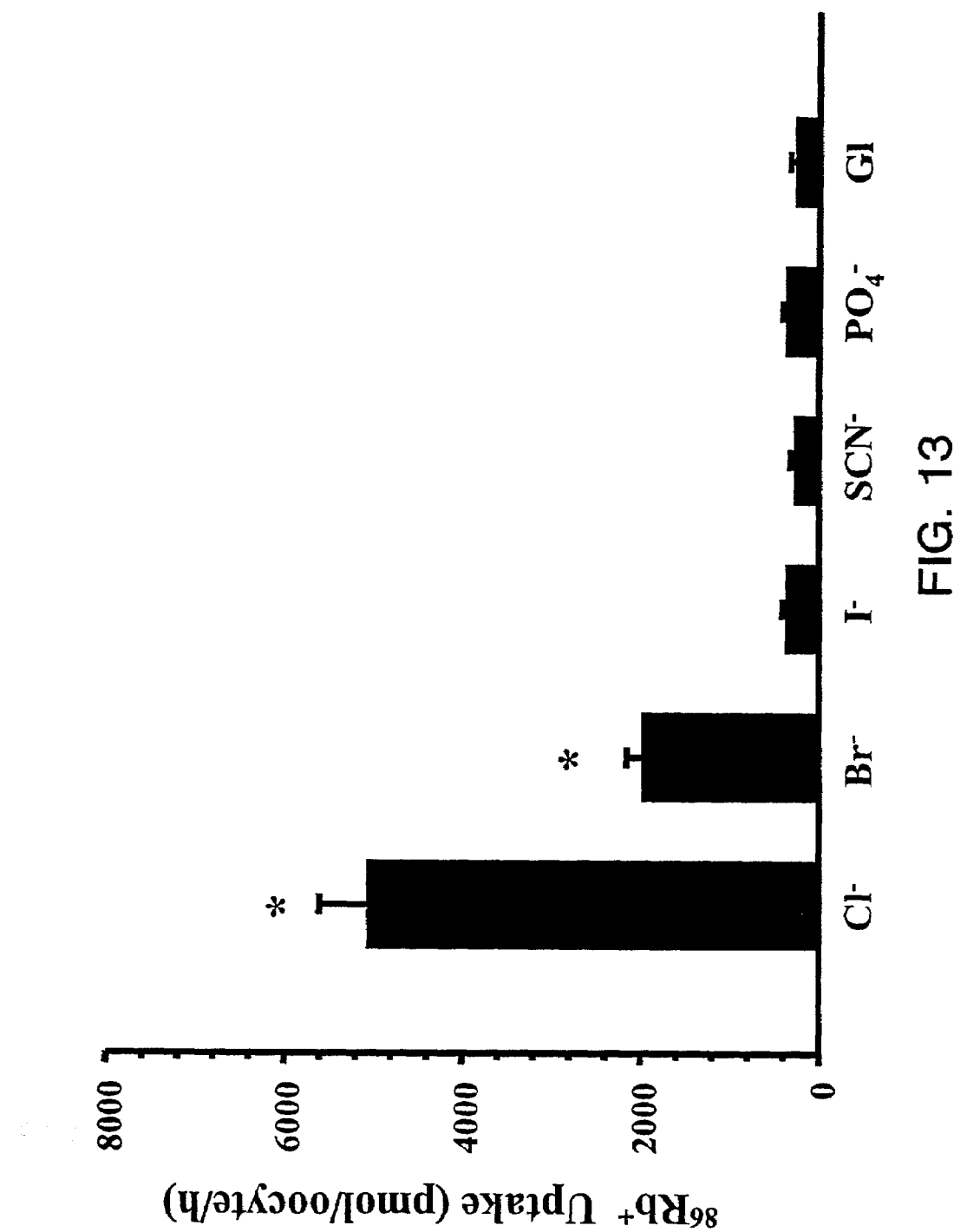
FIG. 13 is a bar graph depicting the anion dependence of $K^+$—$Cl^-$ cotransport mediated by hKCC2, i.e. the relative activity of the transporter in the presence of anions other than chloride. $^{86}Rb^+$ influx was assessed in hKCC2 injected oocytes using hypotonic uptake mediums containing 40 mM NMDG-gluconate plus 10 mM concentration of KCl (as control group) or 10 mM concentration of any of the anion substitutes (KBr, KH$_2$PO4, KI, K-gluconate and KSCN). Asterisk (*) indicates significantly increased $^{86}Rb^+$ uptake when compared to uptake observed for the control group (p<0.01).
Figure 14A:
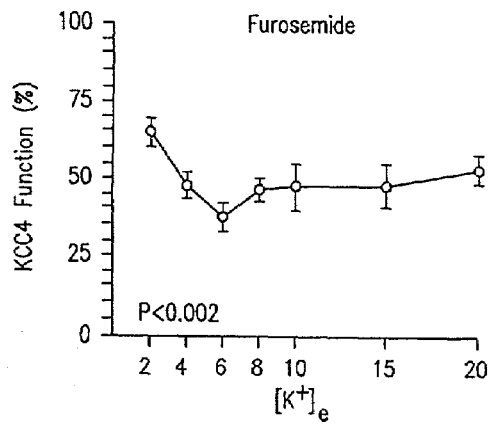
FIG. 14 presents line graphs depicting the effect of extracellular $K^+$ concentration ($[K^+]_e$) on the inhibition of $^{86}Rb^+$ uptake by the loop diuretics furosemide and bumetanide. Data from mKCC4-injected oocytes are presented in the upper panels, and data from rabKCC1-injected oocytes are shown in the lower panels. In all experiments, the $Cl^-$ concentration in the extracellular medium was 50 mM, whereas the extracellular potassium concentration was varied from 2–20 mM. The control group for each KCC comprised oocytes not treated with diuretic, and the mean uptake in the absence of loop diuretic for each KCC was designated as 100% uptake. Data from diuretic-treated groups was normalized to the uptake in the control group. Experimental groups were exposed to 2 mM furosemide or bumetanide during the incubation and uptake periods. Each point represents the mean±standard error of data obtained from at least 15 oocytes.
Figure 14B:
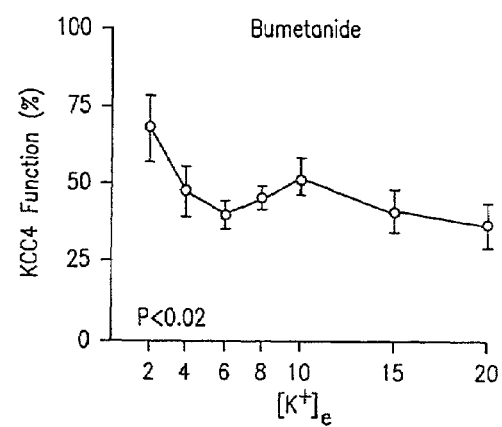
Figure 14C:
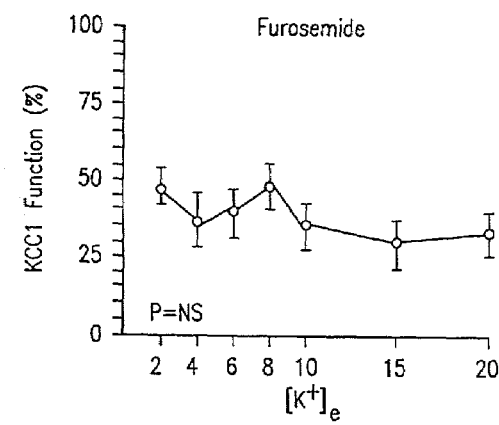
Figure 14D:
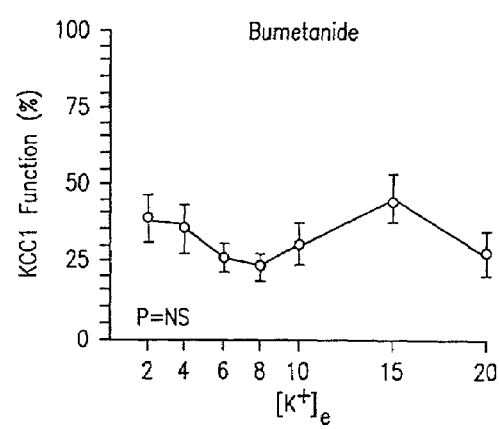

FIG. 13 shows the ion dependence of hKCC2 $K^+$—$Cl^-$ cotransport determined by $^{86}Rb^+$ uptake assays performed in the presence of different anion substitutions. KCC2 mediates $K^+$—$Cl^-$ cotransport in a similar manner to KCC4 (see Table 3).

Example 15

Inhibitor Profile of KCCs

FIGS. 14–19 summarize the pharmacological characterization of the KCCs, examining the effect of a number of different inhibitors of anion and cation transport. A particularly important finding is the universal dependence of the anion inhibitors on the presence of extracellular $K^+$. Thus in FIGS. 14–19, results are expressed as percentage function (in comparison to swelling-induced activity) of the individual KCCs.

The effect of the loop diuretics furosemide and bumetanide was initially assessed using two different concentrations of extracellular $K^+$:2 and 50 mM. In uptake medium with a $K^+$ concentration of 2 mM, relative KCC4 activity was 61±3 and 90±4% in the presence of 2 mM furosemide or bumetanide, respectively. Interestingly, the inhibition of KCC4 by loop diuretics was augmented when the uptake medium contained 50 mM $K^+$; under these conditions, the KCC4 activity was 9±4 or 17±4% in the presence of furosemide or bumetanide, respectively. In contrast, for KCC1 this effect of extracellular $K^+$ was not observed for furosemide and was marginal for bumetanide. KCC1 function in the presence of furosemide was 9±2% in 2 mM $K^+$ and 18±8% in 50 mM $K^+$ (p not significant), and in the presence of bumetanide it was 51±12 versus 19±7% in 2 and 50 mM $K^+$, respectively (p=0.05; t=1.99). To further define the differences in the $K^+$ effect on the sensitivity to loop diuretics between KCC4 and KCC1, the inhibitory effect of furosemide and bumetanide was assessed at several concentrations of extra-cellular $K^+$ (FIG. 14). The percentage inhibition of KCC4 by both furosemide and bumetanide was significantly affected by extracellular $K^+$ (FIG. 14, upper panels). The minimal and maximal inhibition by both loop diuretics was observed at 2 and 6 mM, respectively; no further effect was observed at higher $K^+$ concentrations. In contrast, the percentage of KCC1 inhibition by either furosemide or bumetanide did not vary as a function of extracellular $K^+$ concentration (FIG. 14, lower panels).

Figure 15A:
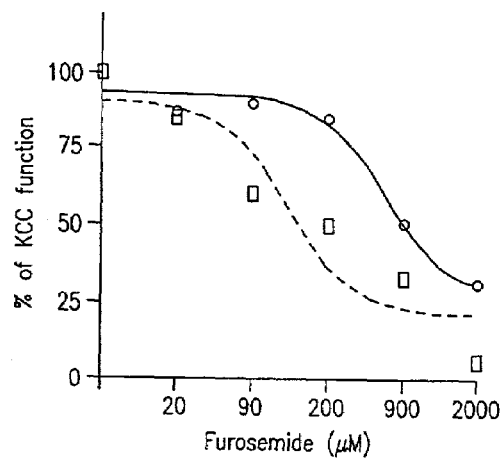
FIG. 15 presents line graphs depicting concentration-response profiles for inhibition of KCC4- and KCC1-mediated cation-chloride transport by furosemide and bumetanide. Groups of 15 *Xenopus* ooctyes microinjected with mKCC4 or rabKCC1 were exposed to 20–2000 μM furosemide or bumetanide in the preincubation and uptake media. Oocytes not exposed to loop diuretics was designated the control group, and the percentage influx observed in this group was designated as 100%. Data were normalized as the percentage of influx relative to the control group. Each point represents the mean±standard error of data obtained from at least 15 oocytes. (○)/solid line, oocytes injected with mKCC4; (□)/dashed line oocytes injected with rabKCC1.
Figure 15B:
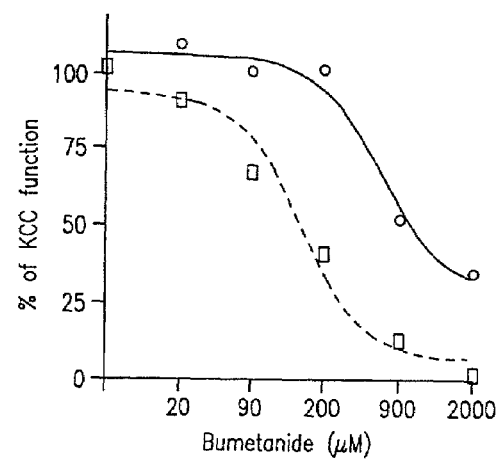

To define differences between the two KCCs in sensitivity to loop diuretics, 10 mM extracellular $K^+$ was used to assess the concentration curves for furosemide and bumetanide inhibition upon the $Cl^-$ dependent $^{86}Rb^+$ uptake induced by KCC4 or KCC1. As FIG. 15 illustrates, KCC4 exhibits apparent half-maximal inhibition (K=0.5) values of ~900 µM for both furosemide and bumetanide. These are lower than the respective values for KCC1 (~180 µM for furosemide and bumetanide). Therefore, KCC4 clearly exhibits a lower affinity for loop diuretics than does KCC1. The inhibition of KCC1 by furosemide in FIG. 14 suggests the possibility of a second affinity site for the loop diuretic. However, this inhibition fitted well to a Michaelis-Menten kinetics pattern with one inhibitor-binding site. The data did not fit to an equation with two binding sites.

Figure 16:
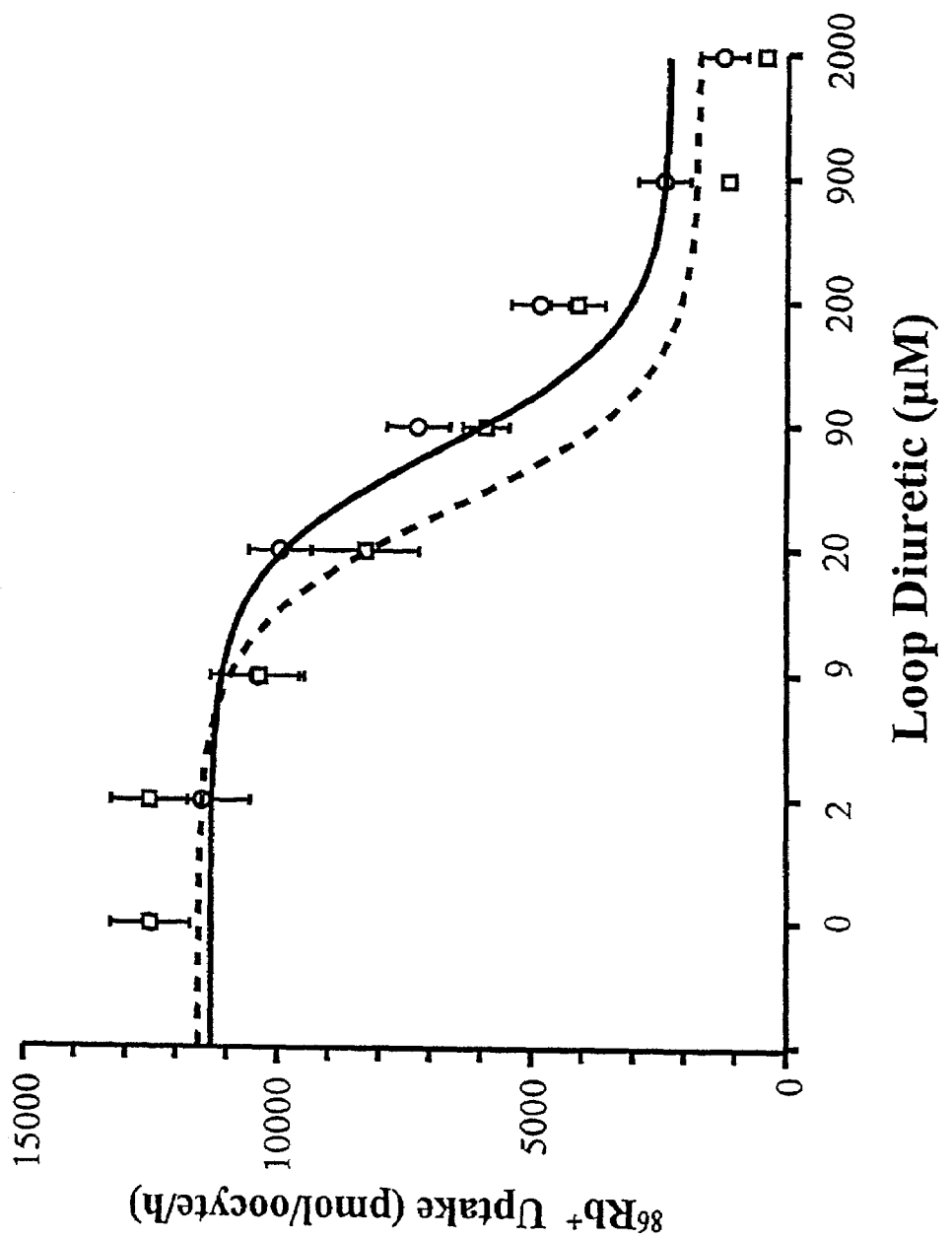
FIG. 16 is a line graph depicting dose-dependent inhibition of hKCC2-mediated cation-chloride cotransport by furosemide or bumetanide. Groups of oocytes microinjected with hKCC2 cRNA were exposed to increasing concentrations of furosemide or bumetanide in the preincubation and uptake mediums, from 2 to 2000 μM. Uptake assays were performed in hypotonic conditions. Each point represents the mean±standard error of at least 15 oocytes. (□)/dashed line, furosemide treatment; (○)/solid line, bumetanide treatment.

FIG. 16 is a line graph depicting dose-dependent inhibition of KCC2 by furosemide and bumetanide. Groups of oocytes microinjected with KCC2 cRNA were exposed to increasing concentrations of furosemide or bumetanide in the preincubation and uptake mediums, from 2 to 2000 µM. Uptake assays were performed in hypotonic conditions. Each point represents the mean±standard error of at least 15 oocytes.

Figure 17:
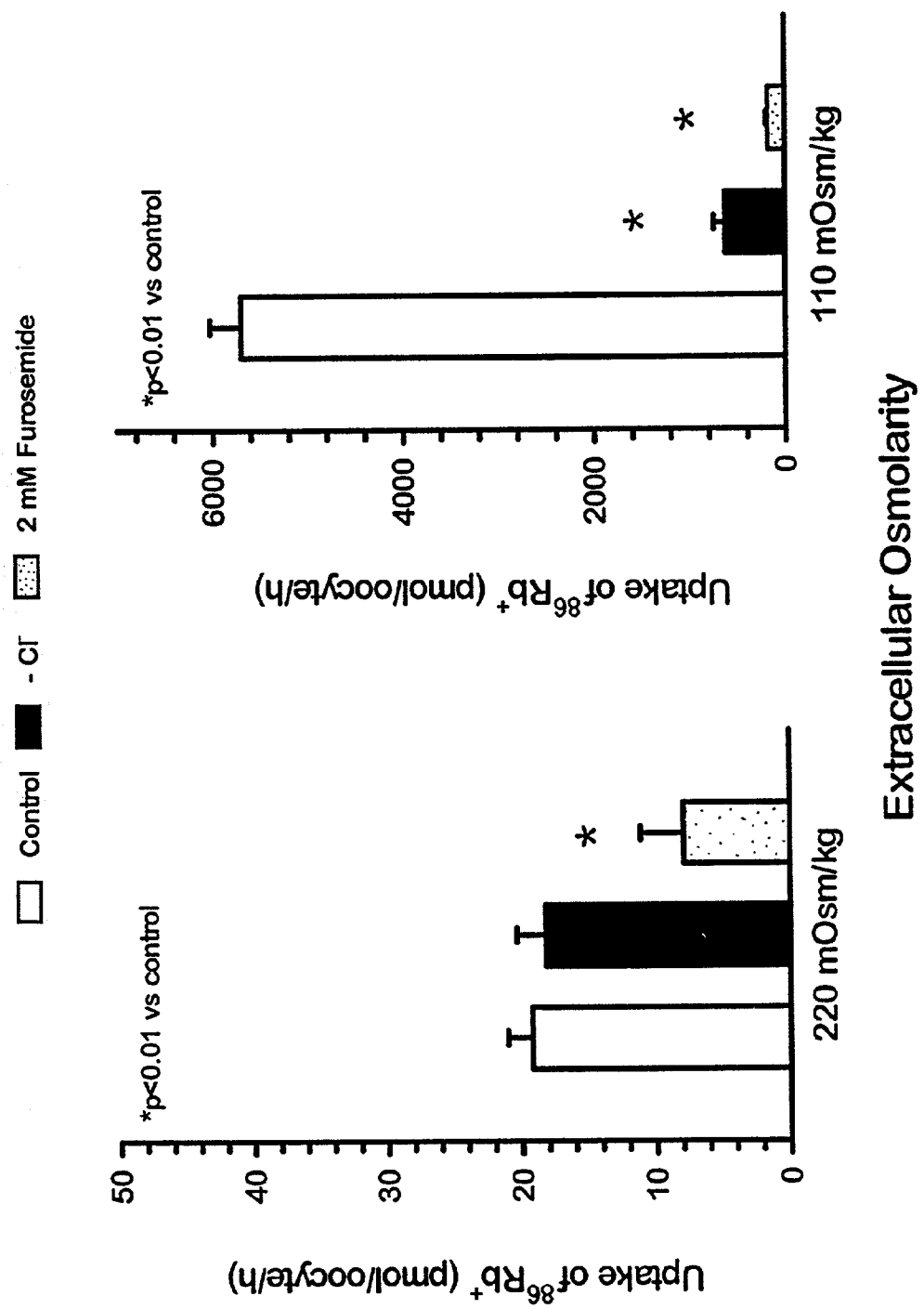
FIG. 17 presents bar graphs depicting hKCC3b-mediated $K^+$—$Cl^-$ cotransport in *Xenopus* oocytes, with minimal activity under isotonic conditions (220 mOsm/kg) and marked activation under hypotonic conditions (110 mOsm/kg). Open bars, uptake assays performed in a control medium containing 10 mM K$^+$ and 50 mM Cl$^-$; black bars, uptake assays performed in medium lacking Cl$^-$; gray bars, uptake assays performed in medium containing 2 mM furosemide. Asterisks (*) indicate a significant difference in $^{86}$Rb$^+$ uptake when compared to uptake in the corresponding control group (p<0/01).

FIG. 17 presents bar graphs depicting hKCC3b-mediated K$^+$—Cl$^-$ cotransport in *Xenopus* oocytes, with minimal activity under isotonic conditions (220 mOsm/kg) and marked activation under hypotonic conditions (110 mOsm/kg). Open bars, uptake assays performed in a control medium containing 10 mM K$^+$ and 50 mM Cl$^-$; black bars, uptake assays performed in medium lacking Cl$^-$; gray bars, uptake assays performed in medium containing 2 mM furosemide.

Figure 18A:
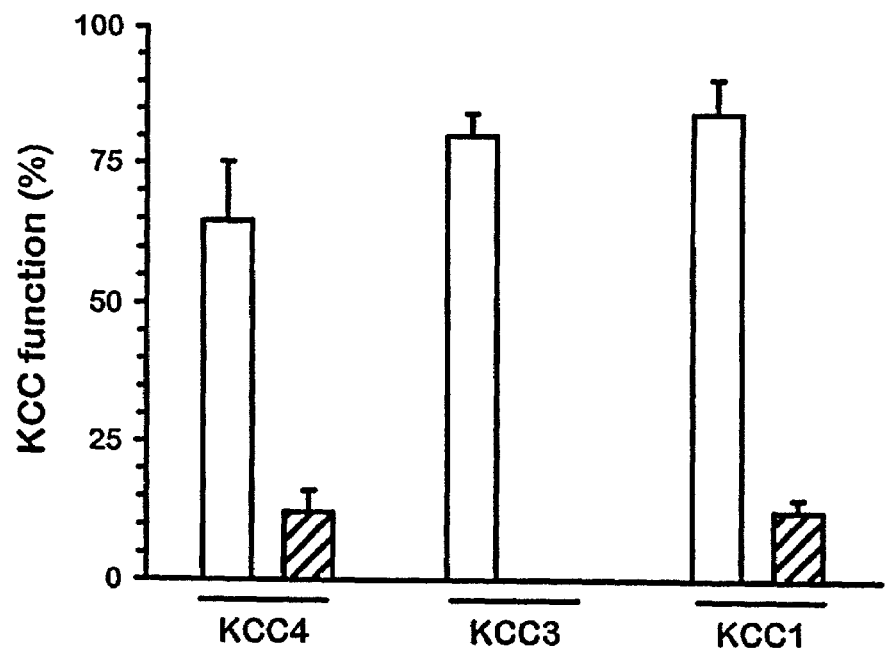
FIG. 18A is a bar graph depicting the effect of the inhibitor DIDS on $^{86}$Rb$^+$ uptake in *Xenopus* oocytes microinjected with mKCC4, hKCC3, or rabKCC1 and incubated in hypotonic conditions (120 mOsm/kg), in the presence of 2 mM extracellular K$^+$, 50 mM Cl$^-$ (open bars) or 50 mM extracellular K$^+$, 50 mM Cl$^-$ (hatched bars). $^{86}$Rb$^+$ uptake was assessed in control groups in the absence of DIDS. Experimental groups were exposed to 100 µM DIDS during the incubation and uptake periods. Each bar represents the mean±standard error of data obtained from at least 15 oocytes.
Figure 18B:
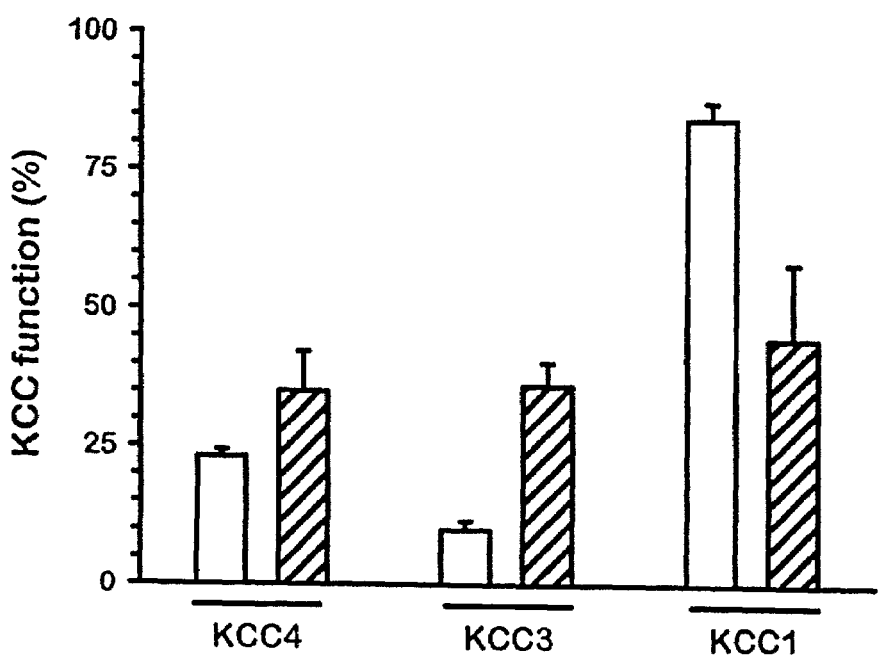
FIG. 18B is a bar graph depicting the effect of the inhibitor DIOA on $^{86}$Rb$^+$ uptake in *Xenopus* oocytes microinjected with mKCC4, hKCC3, or rabKCC1 and incubated in hypotonic conditions (120 mOsm/kg), in the presence of 2 mM extracellular K$^+$, 50 mM Cl$^-$ (open bars) or 50 mM extracellular K$^+$, 50 mM Cl$^-$ (hatched bars). $^{86}$Rb$^+$ uptake was assessed in control groups in the absence of DIOA. Experimental groups were exposed to 100 µM DIOA during the incubation and uptake periods. Each bar represents the mean±standard error of data obtained from at least 15 oocytes.

The sensitivity of the KCCs to other inhibitors of red cell K$^+$—Cl$^-$ cotransport was also assessed in oocytes injected with KCC4 or KCC1. FIG. 18 illustrates the effect of 100 µM DIDS and 100 µM DIOA on the $^{86}$Rb$^+$ uptake induced by the microinjection of each KCC cRNA. The effect of extracellular K$^+$ concentration on the inhibition of cotransport was very dramatic for DIDS. When the concentration of extracellular K$^+$ was 2 mM, the addition of DIDS to the extracellular medium resulted in reduction of KCC4 function to 65±10% (p<0.003) and of KCC1 to 85±6% (p=0.113, not significant). In contrast, when 50 mM of extracellular K$^+$ was used, DIDS resulted in significant decrease of KCC4 and KCC1 to 13±4 and 13±2%, respectively. The addition of 100 µM of DIOA to the extracellular medium also resulted in inhibition of the KCCs. However, inhibition of KCC4 was higher when extracellular K$^+$ was lower, although this was not the case for KCC1. DIOA is reportedly specific for K$^+$—Cl$^-$ cotransport over Na$^+$—K$^+$-2Cl$^-$ cotransport (Garay et al. (1988) *Mol Pharmacol* 33:696–701), and the same concentration of DIOA had no effect on the function of the Na$^+$—K$^+$-2Cl$^-$ cotransport activity of *Xenopus* oocytes (Gamba et al. (1994) *J Biol Chem* 269: 17713–17722).

The effect of a 2 mM concentration of the thiazide diuretic trichlormethiazide on the percentage of chloride-dependent $^{86}$Rb$^+$ uptake was also measured. Surprisingly, given the supposed specificity of thiazides for Na$^+$—Cl$^-$ cotransport (Rose et al. (1991) *Kidney Int* 39:336–352), KCC4 was moderately sensitive to trichlormethiazide. As observed for furosemide and DIDS, the higher the extracellular K$^+$, the higher the inhibition by thiazides, since in 2 mM of extracellular K$^{+86}$Rb$^+$ uptake was reduced to 79±3%, and at 50 mM it was reduced to 57±9%. This difference was significant (p<0.01).

Figure 19:
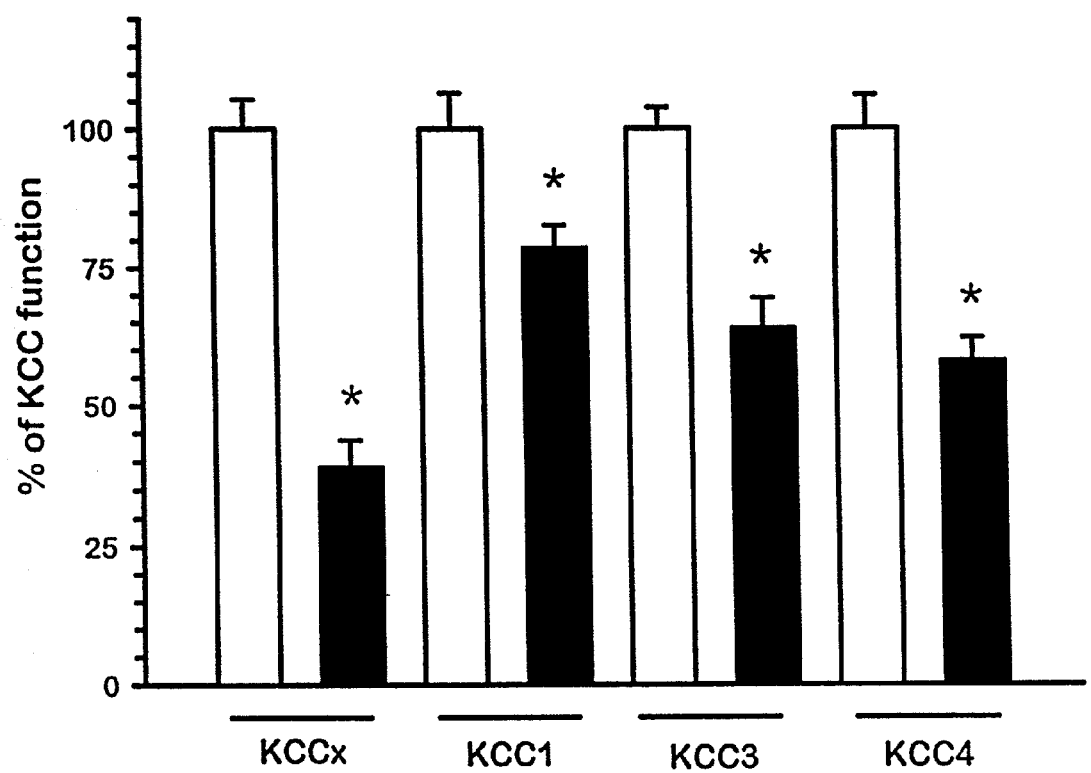
FIG. 19 presents bar graphs depicting the effect of 10 mM BaCl$_2$ on $^{86}$Rb$^+$ uptake induced by microinjection of oocytes with *Xenopus* KCC (KCCx), rabKCC1, hKCC3, or mKCC4 cRNA. $^{86}$Rb$^+$ uptake in the control groups (open bars) was measured using a hypotonic uptake medium containing 40 mM NMDG chloride and 10 mM KCl. $^{86}$Rb$^+$ uptake in oocytes treated with BaCl$_2$ (black bars) was measured using a hypotonic medium containing 30 mM NMDG chloride, 10 mM BaCl$_2$, and 10 mM KCl. Each bar represents a mean of data obtained from 20 oocytes. Asterisks (*) indicate $^{86}$Rb$^+$ uptake values of the BaCl$_2$-treated oocytes that are significantly different when compared to $^{86}$Rb$^+$ uptake in control groups (p<0.01). KCC4 in particular is partially sensitive to 10 mM barium, consistent with the localization of KCC4 at the basolateral membrane of thick ascending limb cells.

In KCC1-injected oocytes, trichlormethiazide reduced $^{86}$Rb$^+$ uptake by a statistically significant amount to 64±4% in 2 mM K$^+$; this inhibitory effect was not statistically significant at 50 mM K$^+$ (74±8% reduction in activity). Consistent sensitivity to trichlormethiazide is thus unique to KCC4. Independent studies have suggested that barium can inhibit renal K$^+$—Cl$^-$ cotransporters (Greger & Schlatter (1983) *Pflugers Arch* 396:325–334; Amlal et al. (1994) *Am J Physiol Cell Physiol* 267:C1607–1625; Di Stefano et al. (1998) *Cell Physiol Biochem* 8:89–105). In view of such, the effect of 10 mM extracellular barium on the function of KCC4 and KCC1 was determined. FIG. 19 shows that when 10 mM BaCl$_2$ was added to the uptake medium, KCC4-induced influx was reduced to 58±4.3% of the uptake observed in KCC4-injected control oocytes. KCC1 function was only reduced to 79±4.2%, hence the inhibitory effect of barium was significantly greater for KCC4 than for KCC1 (p=0.01).

Example 16

Regulation of KCC4 and KCC1 by NEM

Figure 20A:
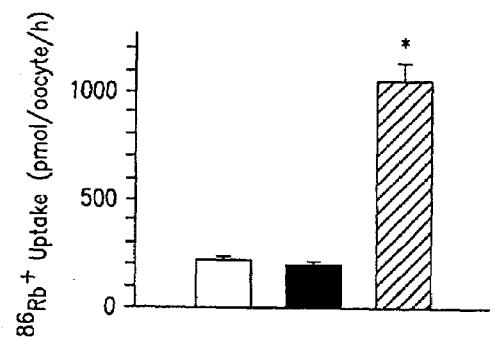
FIGS. 20A–20D present bar graphs depicting the effect of 1 mM NEM on $^{86}$Rb$^+$ uptake in mKCC4-injected and rabKCC1-injected oocytes in isotonic and hypotonic conditions.
Figure 20B:
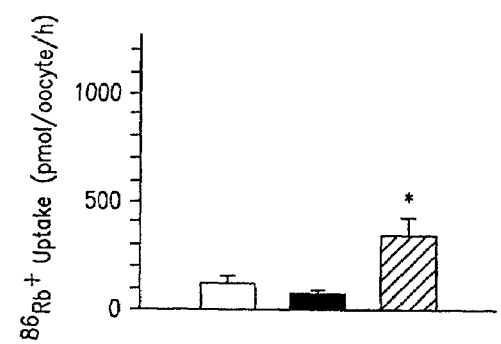
Figure 20C:
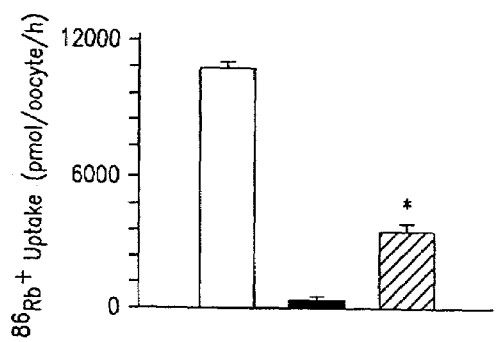
Figure 20D:
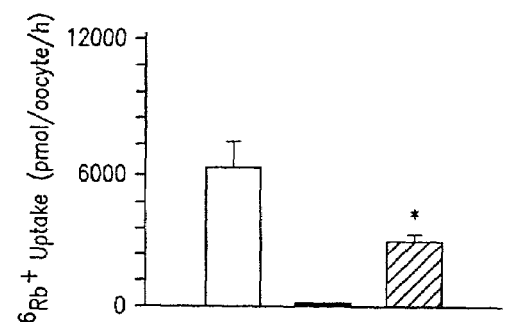

One of the most distinctive characteristics of K$^+$—Cl$^-$ cotransport in several cells and species is activation by the alkylating agent NEM (Lauf et al. (1992) *Am J Physiol* 263:C917–932). The effect of NEM on $^{86}$Rb$^+$ influx in oocytes expression KCC4 or KCC1 was assayed under isotonic or hypotonic conditions. The uptake observed in KCC4-or KCC1-injected oocytes in isotonic medium was not different from the uptake in water-injected oocytes. However, the addition of 1 mM NEM in isotonic conditions resulted in a 5-fold activation of KCC4 (214±12 pmol×oocyte$^{-1}$×hour$^{-1}$ in the KCC4 control group versus 1062±70 pmol×oocyte$^{-1}$×hour$^{-1}$ in the NEM-treated group, (p<0.001) and a 2.6-fold activation of KCC1 (120±27 versus 319±76 pmol×oocyte$^{-1}$×hour$^{-1}$ (p<0.05) (FIGS. 20A and 20B). Of note, when uptake assays were performed in hypotonic medium, the addition of NEM resulted in a dramatic inhibition of both isoforms (FIGS. 20C and 20D), such that $^{86}$Rb$^+$ uptakes induced by KCC4 and KCC1 were reduced by 68% and 55%, respectively. In the same experiments, $^{86}$Rb$^+$ uptake due to the endogenous oocyte K$^+$—Cl$^-$ cotransporter (H$_2$O-injected oocytes) was significantly increased when uptake assays were done under both isotonic and hypotonic conditions.

Example 17

Regulation of KCCs by Mercury

Figure 21:
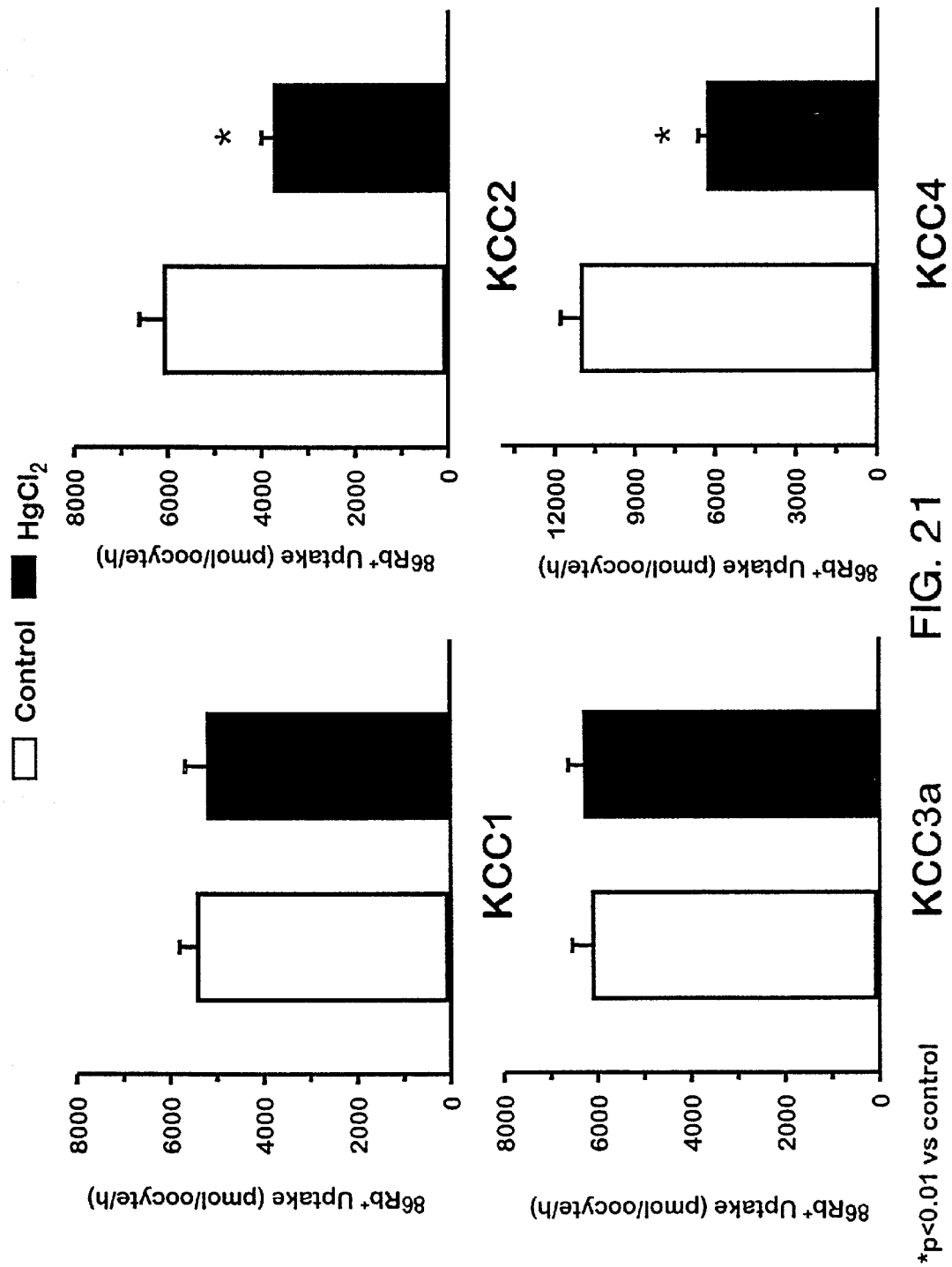
FIG. 21 presents bar graphs depicting differential response of the KCCs to 50 µM mercury (HgCl$_2$). rabKCC1 and hKCC3a activated by hypotonic conditions and are resistant to 50 µM mercury HgCl$_2$, whereas hKCC2 and in particular mKCC4 are sensitive to this agent. Open bars, uptake assays performed in control medium containing 10 mM K$^+$ and 50 mM Cl$^-$; black bars, uptake assays performed in medium containing 50 µM mercury HgCl$_2$. Asterisk (*) indicates a significant reduction in uptake activity relative to the control group (p<0.001).
Figure 22:
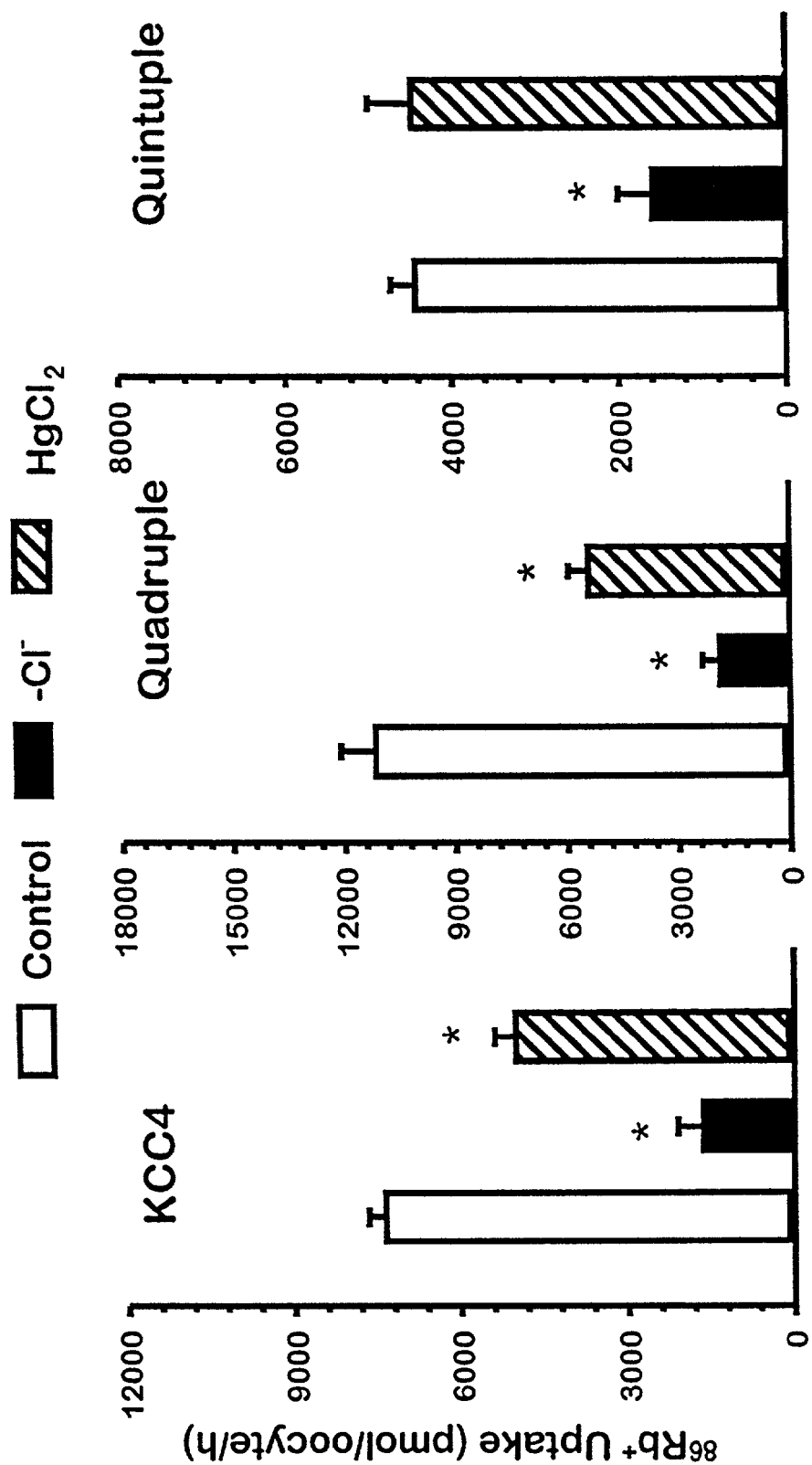
FIG. 22 presents bar graphs depicting the differential response of native and mutant mKCC4 polypeptides to HgCl$_2$. A quadruple mutant mKCC4 maintains some sensitivity to HgCl$_2$, whereas the quintuple mKCC4 mutant is resistant. Quadruple, mKCC4 mutant with four cysteines mutated (C256A/C469N/C565A/C647M); Quintuple, mKCC4 mutant with five cysteine residues mutated (C256A/C469N/C565A/C647M/C633S); open bars, uptake assays performed in control medium containing 10 mM K$^+$ and 50 mM Cl$^-$; black bars, uptake assays performed in medium lacking Cl$^-$; hatched bars, ssuptake assays performed in medium containing HgCl$_2$. Asterisk (*) indicates a significant reduction in KCC4 activity (p<0.01).

Mercury is known to inhibit several transporters via interaction with transmembrane or juxtamembrane cysteines (Kuwahara et al. (1997) *Biochemistry* 36:13973–13978; Jacoby (1999) *Am J Physiol* 277:C684–692). Given the inhibition of the KCCs by millimolar NEM at room temperature, presumed due to alkylation of cysteine residues (Mercado et al. (2000) *J Biol Chem* 275:30326–3034), the differential response of the KCCs to 50 µM mercury (Hg—Cl$_2$) was examined. KCC1 and KCC3a activated by hypotonic conditions are resistant to 50 µM mercury Hg—Cl$_2$, whereas KCC2 and in particular KCC4 are sensitive to this agent (FIG. 21). An inspection of the amino acid sequence of mKCC4 reveals a total of five transmembrane cysteines that are not found in KCC1, KCC3, and/or KCC2. A mutant with four of these five cysteines mutated (C256A/C469N/C565A/C647M) is still weakly sensitive to Hg—Cl$_2$ (quadruple mutant in FIG. 22), whereas the corresponding quintuple mutant (C256A/C469N/C565A/C647M/C633S) is resistant (quintuple mutant in FIG. 22). These results implicate cysteine-633, within transmembrane domain 12, in the sensitivity of mKCC4 to Hg—Cl$_2$. Of note, a cysteine residue in TM11 of NKCC1 is involved in the response of Na$^+$—K$^+$-2Cl$^-$ cotransport to mercury (Jacoby (1999) *Am J Physiol* 277:C684–692). This analysis supports the development of isoform-specific inhibitors of the KCCs, by targeting functionally important residues such as cysteine-633 of KCC4 and the equivalent residue in hKCC2, cysteine-613.

Example 18

Regulation of KCC Function by Phosphorylation

Figure 23:
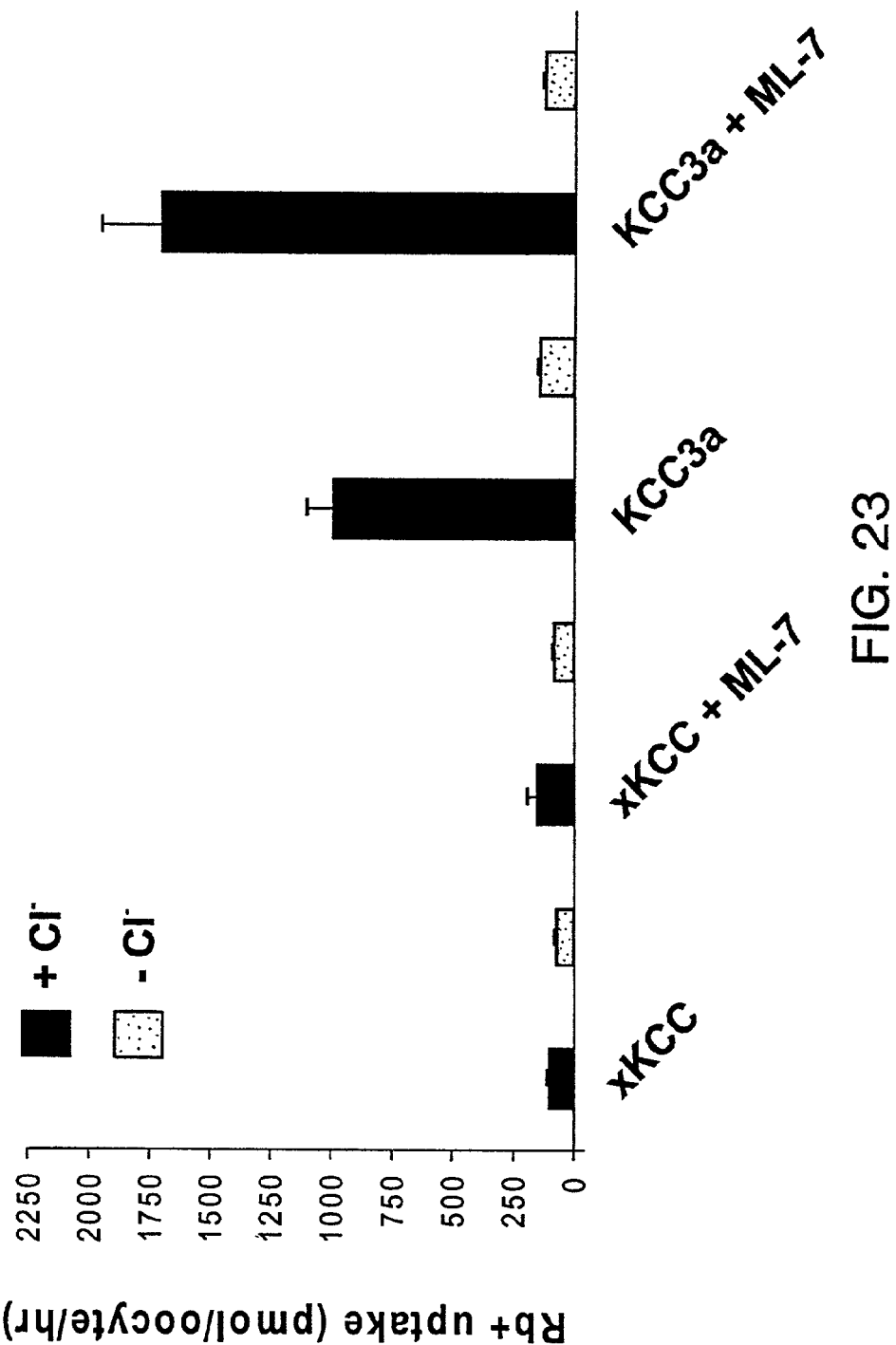
FIG. 23 is a bar graph depicting the effect of the myosin light chain kinase inhibitor ML-7 on hKCC3a activity in *Xenopus* oocytes. K$^+$—Cl$^-$ cotransport is activated by 100 µM ML-7 (989±115 pmol/oocyte/hour for KCC3a in the absence of ML-7 versus 1698±298 pmol/oocyte/hour in the presence of ML-7 at 160 mOsm/kg). Black bars from left to right, $^{86}$Rb$^+$ uptake by xKCC in the presence of Cl$^-$, $^{86}$Rb$^+$ uptake by xKCC in the presence of Cl$^-$ and ML-7, $^{86}$Rb$^+$ uptake by hKCC3a in the presence of Cl$^-$, $^{86}$Rb$^+$ uptake by hKCC3a in the presence of Cl$^-$ and ML-7; gray bars from left to right, 86Rb$^+$ uptake by xKCC in the absence of Cl$^-$, $^{86}$Rb$^+$ uptake by xKCC in the absence of Cl$^-$ and in the presence of ML-7, 86Rb$^+$ uptake by hKCC3a in the absence of Cl$^-$, $^{86}$Rb$^+$ uptake by hKCC3a in the absence of Cl$^-$ and in the presence of ML-7

The red cell K$^+$—Cl$^-$ cotransporters are thought to be phosphorylated by a volume-sensitive kinase under isotonic conditions, with dephosphorylation and activation by the serine-threonine phosphatases PP-1 and PP-2A (Bize et al. (1999) *Am J Physiol* 277:C926–936). The identity of this volume-sensitive kinase is unknown. However, insight could ultimately come from the assumption that this kinase or kinases also activates $Na^+$—$K^+$-$2Cl^-$ cotransport, a pathway that is stimulated by cell shrinkage and inhibited by staurosporine, NEM, and protein phosphatases (Lytle (1998) *Am J Physiol* 274:C1002–1010). Kelley et al. (2000) *J Membr Biol* 178:31–41 have investigated the role of myosin-light chain kinase (MLCK), another shrinkage-activated serine-threonine kinase, in the activation of $K^+$—$Cl^-$ cotransport. They found modest activation by the MLCK inhibitor ML-7 of human red cell $K^+$—$Cl^-$ cotransport at physiological osmolality. Since the kinetics of hKCC3 suggest that it is the dominant red cell $K^+$—$Cl^-$ cotransporter, as disclosed herein, the effect of ML-7 on KCC3a expression in *Xenopus* oocytes was evaluated. Just at and below the threshold for activation of KCC3a (160–180 mOsm/kg), there is clear activation of $K^+$—$Cl^-$ cotransport by 100 μM ML-7 (989±115 pmol/oocyte/hour for KCC3a in the absence of ML-7 versus 1698±298 in the presence of ML-7 at 160 mOsm/kg (FIG. 23). There is also modest activation of hKCC3a by ML-7 at 180 mOsm/kg, however ML-7 has no effect on $K^+$—$Cl^-$ cotransport under isotonic conditions. Given this absence of an effect under isotonic conditions, it is likely that the kinase(s) inhibited by ML-7 are only part of the complex signaling cascade invoked by cell swelling. However, this approach illustrates the utility of the *Xenopus* expression system in studying the regulation of expressed KCCs.

Figure 24A:
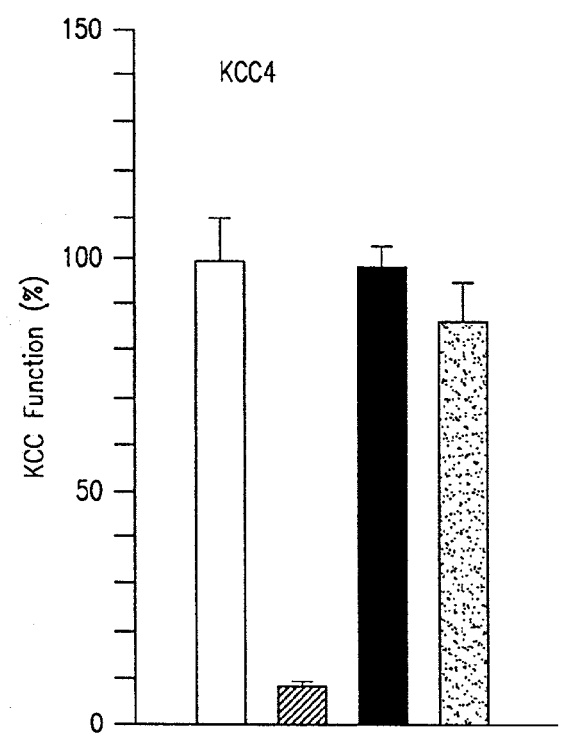
FIG. 24 presents bar graphs depicting the effect of the protein phosphatase inhibitors calyculin A, okadaic acid, and cypermethrin upon the swelling-induced activation of mKCC4 or rabKCC1. White bar, $^{86}$Rb$^+$ influx in control oocytes not treated with inhibitor in hypotonic medium; hatched bar, $^{86}$Rb$^+$ influx in oocytes treated with 100 nM calyculin A in hypotonic medium; black bar, $^{86}$Rb$^+$ influx in oocytes treated with 1 nM okadaic acid in hypotonic medium; gray bar, 86Rb$^+$ influx in oocytes treated with 100 pM cypermethrin in hypotonic medium. Each bar represents the mean±standard error observed in at least 15 oocytes.
Figure 24B:
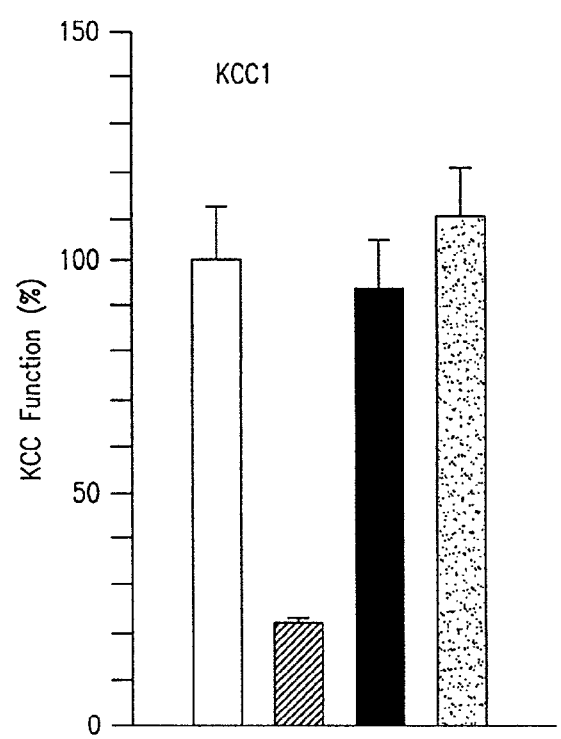

The inhibition of protein phosphatases prevents the activation of red cell $K^+$—$Cl^-$ cotransport by either cell swelling or NEM. Since the role of phosphatases in the control of the cloned KCCs is unclear, the effect of three inhibitors of protein phosphatases was evaluated. One assay included 100 nM calyculin A, which inhibits the function of protein phosphatases 1 and 2A. The relative role of specific phosphatases was assessed using okadaic acid at 1 nM, a concentration that only affects protein phosphatase 2A. Cypermethrin was used at 100 pM, a concentration in which this compound inhibits the function of protein phosphatase 2B. The addition of calyculin A completely prevents the activation of KCC4 and KCC1 by cell swelling (FIG. 24). By contrast, neither okadaic acid, nor cypermethrin prevented this activation (FIG. 24). These results indicate that protein phosphatase 1 is required for the activation of both KCC4 and KCC1 by cell swelling.

FIG. 25A is a bar graph depicting the effect of shows the effect of the protein phosphatase inhibitor calyculin A (100 nM) on the isotonic $K^+$—$Cl^-$ cotransport mediated by hKCC2. $^{86}Rb^+$ influx was assessed in a control group (white bars), in the absence of extracellular $Cl^-$ (black bars), or in the presence 100 mM calyculin (hatched bars). Each bar represents the mean±standard error of data obtained using at least 15 oocytes. Asterisk (*) indicates that $^{86}Rb^+$ influx was significantly reduced in the absence of $Cl^-$.

FIG. 25B is a bar graph depicting the effect of shows the effect of the protein phosphatase inhibitor calyculin A (100 nM) on the swelling-induced $K^+$—$Cl^-$ cotransport mediated by hKCC2. $^{86}Rb^+$ influx was assessed in a control group (white bars), in the absence of extracellular $Cl^-$ (black bars), or in the presence 100 mM calyculin (hatched bars). Each bar represents the mean±standard error of data obtained using at least 15 oocytes. Asterisk (*) indicates that $^{86}Rb^+$ influx was significantly reduced in the absence of $Cl^-$, or in the combined absence of $Cl^-$ and presence of calyculin.

Figure 26:
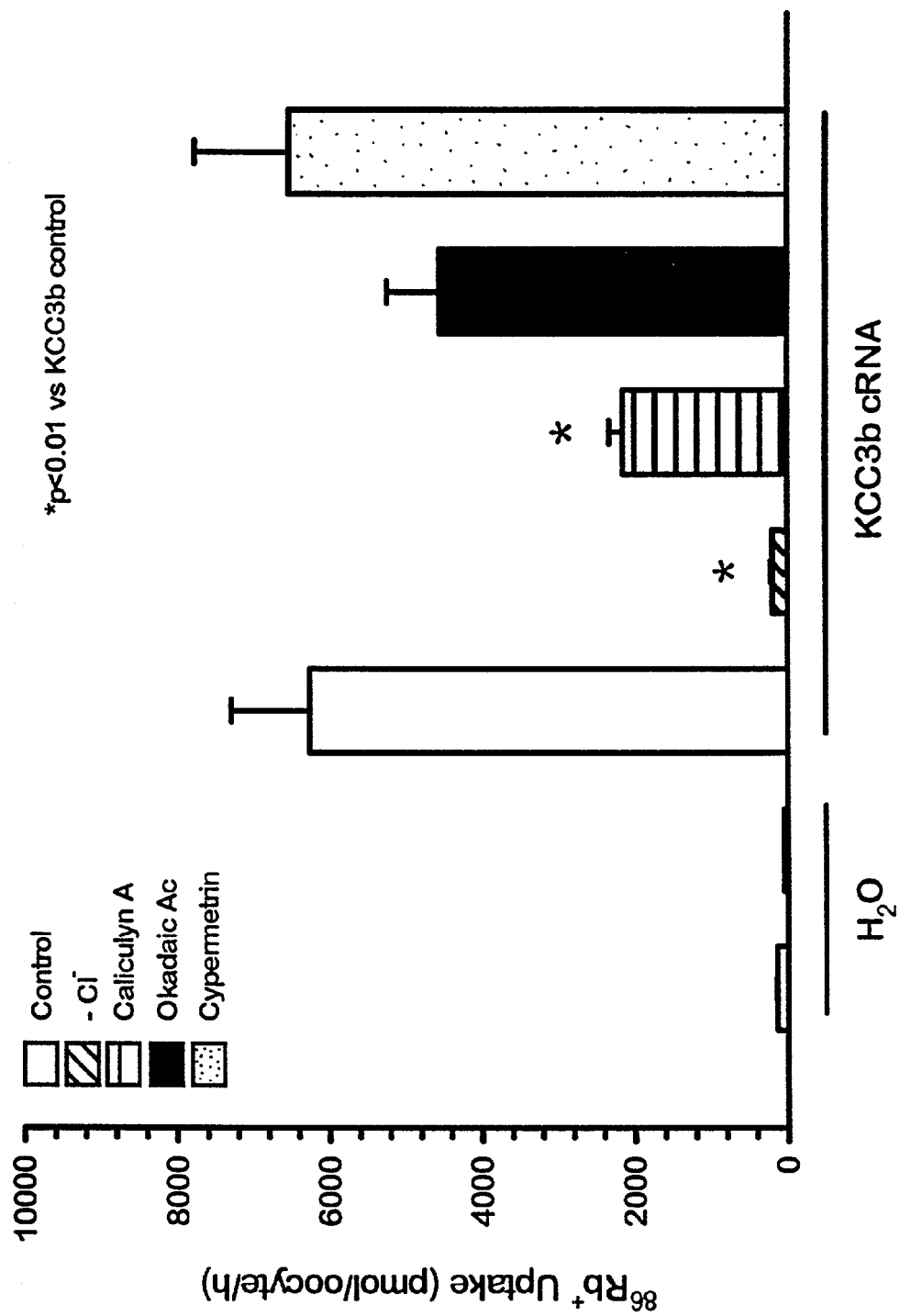
FIG. 26 is a bar graph depicting hKCC3b-mediated $K^+$—$Cl^-$ cotransport in *Xenopus* oocytes microinjected with H20 or hKCC3b cRNA as indicated, in the presence of putative inhibitors. hKCC3b-mediated $K^+$—$Cl^-$ cotransport is sensitive to furosemide treatment and blocked by calyculin A treatment. Open bars, uptake assays performed in a control medium containing 10 mM $K^+$ and 50 mM $Cl^-$; hatched bars, uptake assays performed in medium lacking $Cl^-$; bars with horizontal stripes, uptake assays performed in the presence of 100 nM calyculin A; black bars, uptake assays performed in the presence of okadaic acid; gray bars, uptake assays performed in the presence of cypermetrin.

FIG. 26 is a bar graph depicting hKCC3b-mediated $K^+$—$Cl^-$ cotransport in *Xenopus* oocytes microinjected with $H_2O$ or KCC3b cRNA as indicated, in the presence of putative inhibitors. hKCC3b-mediated $K^+$—$Cl^-$ cotransport is sensitive to furosemide treatment and blocked by Calyculin A treatment. Open bars, uptake assays performed in a control medium containing 10 mM $K^+$ and 50 mM $Cl^-$; hatched bars, uptake assays performed in medium lacking $Cl^-$; bars with horizontal stripes, uptake assays performed in the presence of 100 nM calyculin A; black bars, uptake assays performed in the presence of okadaic acid; gray bars, uptake assays performed in the presence of cypermetrin.

Example 19

Tissue Distribution of KCC3 and KCC4 Transcripts

RNA was extracted from mouse tissues (C57BL/6J strain) using guanidine isothiocyanate and cesium chloride. Total RNA (10 mg/lane) was size-fractionated by electrophoresis (5% formaldehyde, 1% agarose), transferred to a nylon membrane (Stratagene of La Jolla, Calif.), and probed sequentially with $^{32}P$-labeled randomly primed probes corresponding to full-length glyceraldehyde-3-phosphate dehydrogenase and nucleotides 4417B5062 of mKCC4 (3'-UTR). Human multiple-tissue Northern blots containing 2 mg/lane poly(A)+RNA (Clontech of Palo Alto, Calif.) were hybridized to probes generated by PCR from the 3'-UTRs of hKCC4 (nucleotides 4598–4957) and hKCC3 (nucleotides 3624–4185) and to a human beta-actin probe. Hybridization for all blots was performed overnight at 42° C. in 4×SSCP, 40% formamide, 4×Denhardt's solution, 0.5% SDS, and 200 mg of salmon sperm DNA, and membranes were washed twice for 10 minutes at room temperature in 2×SSCP, 0.1% SDS and twice for 1 hour at 65° C. in 0.1×SSCP, 0.1% SDS. Exposure times varied.

Northern blot analysis was performed with probes derived from the 3'-UTRs of KCC3 and KCC4. KCC4 probes detect 5.3-kb transcripts in a number of tissues, most prominently in the heart and kidney. Very little KCC4 transcript is detectable in adult brain. KCC3 has a more restricted expression pattern, with significant amounts of transcript found only in muscle, brain, lung, heart, and kidney. At least two different transcripts of 6B7 kb hybridize to KCC3 probes, consistent with alternative splicing.

Figure 27A:
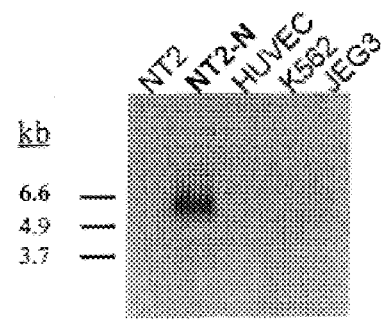
FIG. 27A is an autoradiograph of a Northern blot showing that human KCC2 is heavily induced during the in vitro differentiation of human NT2 teratocarcinoma cells, which do not express this transporter in the undifferentiated state, into "NT2-N" neuronal cells. NT2-N cells are used as a neuronal cell model, and are known to express several subtypes of $GABA_A$ receptors as well as multiple neurotrophin receptors. As such these cells provide a cell model for understanding the function, post-transcriptional regulation, and transcriptional regulation of human KCC2.

Human KCC2 is heavily induced during the in vitro differentiation of human NT2 teratocarcinoma cells, which do not express this transporter in the undifferentiated state, into "NT2-N" neuronal cells (Pleasure & Lee (1993) *J Neurosci Res* 35(6):585–602) (FIG. 27A). NT2-N cells are an increasingly well-characterized neuronal cell model, and are known to express several subtypes of $GABA_A$ receptors (Neelands et al. (1998) *J Neurosci* 18(13):4993–5007; Neelands et al. (1999) *J Neurosci* 19(16):7057–7065) as well as multiple neurotrophin receptors (Piontek et al. (1999) *J Neurochem* 73(1):139–146). As such these cells will provide an important cell model for understanding the function, post-transcriptional regulation, and transcriptional regulation of human KCC2.

Figure 27B:
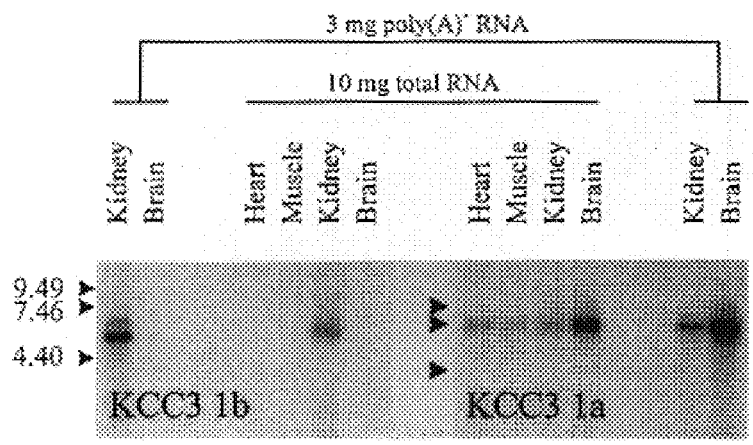
FIG. 27B is an autoradiograph of a Northern blot of mouse tissues probed with both a KCC3 exon 1a-specific and a KCC3 exon 1b-specific probe. KCC3a is particularly abundant in brain and muscle, whereas KCC3b is most abundant in kidney, indicating that the two promoters are differentially regulated.
Figure 27C:
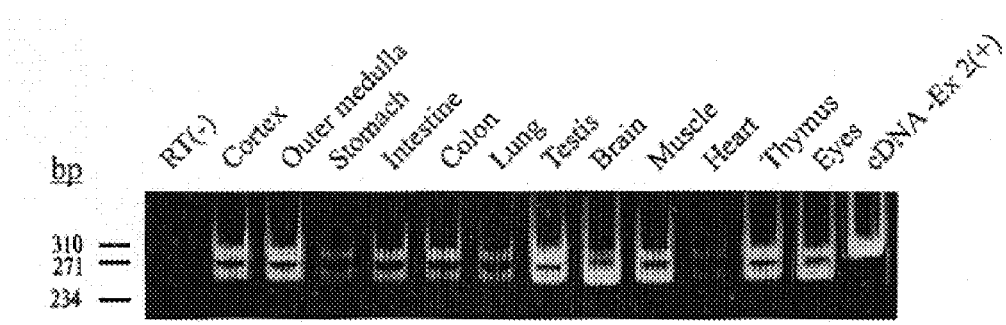
FIG. 27C is a photograph of RT-PCR of mouse tissues with a primer in KCC3 exons 1a and 4. Two bands are amplified, corresponding to alternative splicing of exon 2; the shorter band corresponds to isoforms lacking this 45 base-pair cassette exon. Sequence data for mouse and human KCC3a lacking exon 2 (KCC3a-2m) are included in SEQ ID NOs:3–6.

A Northern blot of mouse tissues probed with both a KCC3 exon 1a-specific and a KCC3b exon 1b-specific probe is shown in FIG. 27B. KCC3a is particularly abundant in brain and muscle, whereas KCC3b is most abundant in kidney, indicating that the two promoters are differentially regulated. RT-PCR of mouse tissues with primer in exons 1a and 4 is shown in FIG. 27C. Two bands are amplified, corresponding to alternative splicing of exon 2; the shorter band corresponds to isoforms lacking this 45 base-pair cassette exon. Sequence data for mouse and human KCC3a lacking exon 2 (KCC3a-2m) is included in SEQ ID NOs: 3–6.

Example 20

Generation of KCC3 and KCC4 Antibodies

Polyclonal antibodies were produced by subcutaneous injection of a KLH-coupled KCC3-specific peptide (KKARNAYLNNSNYEEGDEY; SEQ ID NO:116) to two New Zealand White rabbits (Quality Control Biochemicals of Hopkinkon, Mass.). This antigenic peptide is located within the putative intracellular amino-terminal tail of the cotransporter and shows no homology with the corresponding regions of the other three $K^+$—$Cl^-$ cotransporter isoforms, KCC1, KCC2, and KCC4, with the two $Na^+$—$K^+$-$2Cl^-$ cotransporters, NKCC1 and NKCC2, or with the $Na^+$—$Cl^-$ cotransporter, NCC. Moreover, BLAST alignments against the non-redundant and EST databases do not detect significant homology with unrelated proteins. Finally, the peptide is not a predicted substrate for major protein kinases and was predicted to be highly antigenic using MACVECTOR™ software (available from Oxford Molecular, Inc. of Campbell, Calif.). Antiserum from one rabbit with high titer was affinity purified by linking the peptide to AFFI-GEL™ 15 support (BioRad of Hercules, Calif.) and by incubating the immune serum for two days at 4° C. with the Affi-gelpeptide complex eluted in 5xphosphate-buffered saline (PBS). After washing in 5xPBS, specific antibodies were eluted with 0.1 M sodium citrate (pH 2.5), neutralized with 1 M Tris (pH 8.8) and dialysed in 1xPBS overnight at 4° C. The purified antibody was concentrated using a 30-kDa cut-off CENTRIPULUS™ column (Amicon of Beverly, Mass.) and aliquots were stored at −20° C.

Figure 28:
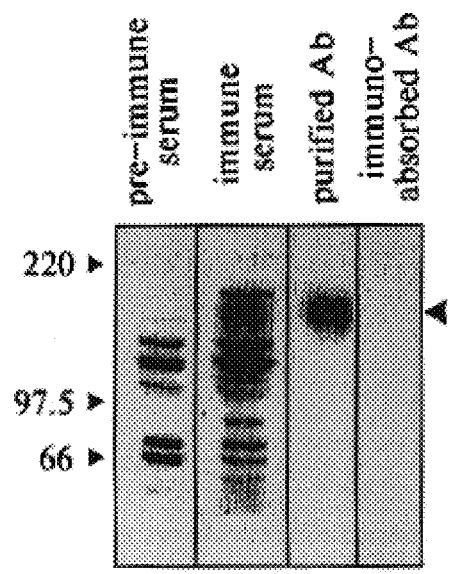
FIG. 28 is an autoradiograph of a Western blot prepared using proteins derived from mouse brain. An anti-KCC3 antibody was used to detect KCC3. Microsomal protein from mouse brain (70 g/lane) was separated by 7.5% SDS-PAGE, transferred, and probed with preimmune serum (1:300), immune serum (1:300), purified antibody (1:1000) and purified antibody preabsorbed with immune peptide. Specific KCC3 signal consisting of a protein doublet (155–165 kDa, lane 3) is also seen in immune serum but not in preimmune serum, nor in purified antibody preabsorbed with antigenic peptide.

Western blots of mouse membrane protein using anti-KCC3 immune serum detected a broad band representing a protein around 160–170 kDa, which was not observed in preimmune serum from the same rabbit (FIG. 28, lanes 1 and 2). When the immune serum was purified using specific antigen, only the 150–170 kDa band was detected (FIG. 28, lane 3). Rapid exposure of the Western blot revealed that the broad signal is composed of two distinct bands (FIG. 28, lane 2). The strong signal observed when using the affinity-purified antibody was not observed when the antibody was preabsorbed with specific antigen (FIG. 28, lane 4), demonstrating the specificity of the ~160 kDa signal as KCC3 protein.

Example 21

Tissue Distribution of KCC3 and KCC4 Proteins

Figure 27D:
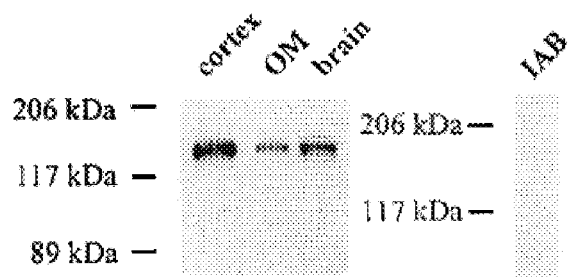
FIG. 27D is an autoradiograph of a Western blot using the amino-terminal KCC3-specific antibody, generated to a peptide antigen from exon 3 (KKARNAYLNNSNYEEGDEY; SEQ ID NO:116). Although immunoreactivity has not been tested against the five KCCs heterologously expressed in *Xenopus* oocytes, the peptide antigen is not found in the KCC1, KCC2 or KCC4 sequences, and does not detect other proteins in stringent BLAST searches of the non-redundant and EST databases. The KCC3 antibody reacts with proteins of ~160 kDa in several tissues, including brain and kidney (shown in FIG. 27D for renal cortex and outer medulla (OM), as well as brain). This reactivity is abolished when antibody is pre-incubated with peptide antigen ("IAB" sample, shown for renal cortex in FIG. 27D).
Figure 27E:
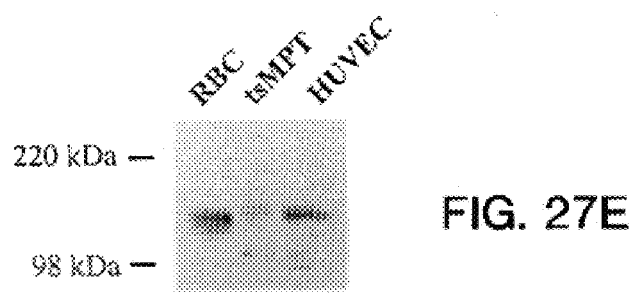
FIG. 27E is an autoradiograph of a Western blot using the amino-terminal KCC3-specific antibody, generated to a peptide antigen from exon 3 (KKARNAYLNNSNYEEGDEY; SEQ ID NO:116). A KCC3 protein is detected in membrane samples from murine red cells (RBC lane), and from a mouse proximal tubule cell line (tsMPT lane) and human umbilical vein endothelial cells (HUVEC lane). The presence of KCC3 in red cells suggests that KCC3 contributes to red cell $K^+$—$Cl^-$ cotransport activity.

Western blots using the amino-terminal KCC3-specific antibody, generated to a peptide antigen from exon 3 (KKARNAYLNNSNYEEGDEY; SEQ ID NO:116), are shown in FIGS. 27D and 27E. Although reactivity has not been tested against the five KCCs heterologously expressed in Xenopus oocytes, the peptide antigen is not found in the KCC1, KCC2 or KCC4 sequences, and does not detect other proteins in stringent BLAST searches (Altschul et al. (1997) Nucleic Acids Res 25(17):3389–3402) of the non-redundant and EST databases. The KCC3 antibody reacts with proteins of ~160 kDa in several tissues, including brain and kidney (shown in FIG. 27D, for renal cortex and outer medulla (OM), as well as brain). This reactivity is abolished when antibody is pre-incubated with peptide antigen ("IAB" sample, shown for renal cortex in FIG. 27D). KCC3 protein is also detected in membrane samples from murine red cells (RBC lane in FIG. 27E), and from a mouse proximal tubule cell line (Loghman-Adham et al. (1997) Kidney Int 52(1): 229–239) (tsMPT lane in FIG. 27E) and human umbilical vein endothelial cells (HUVEC lane in FIG. 27E). The presence of KCC3 in red cells suggests that KCC3 contributes to red cell $K^+$—$Cl^-$ cotransport activity (Lauf et al. (1992) Am J Physiol 263(5 Pt 1):C917–932).

Figure 27F:
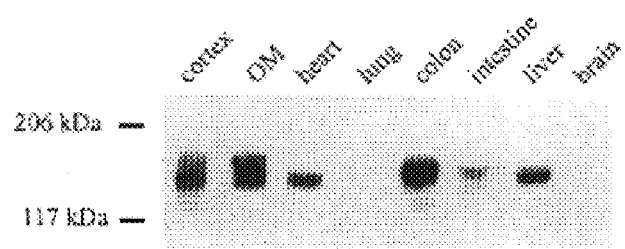
FIG. 27F is an autoradiograph of a Western blot showing that an amino-terminal KCC4-specific antibody, generated to a peptide antigen from exon 1 (AERTEEPESPES-VDQTSP; SEQ ID NO:117), detects a broad band of proteins between 160 and 180 kDa in molecular mass.
Figure 27G:
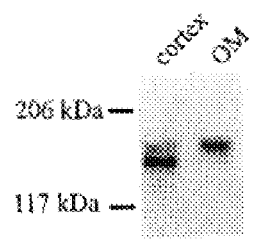
FIG. 27G is an autoradiograph of a Western blot prepared using mouse tissues showing that for an amino-terminal KCC4-specific antibody, generated to a peptide antigen from exon 1 (AERTEEPESPESVDQTSP; SEQ ID NO:117), two separate bands can be resolved in renal cortex and outer medulla (OM), with the lower mass band predominant in cortex and the higher mass band predominant in outer medulla. This heterogeneity might be due to differential glycosylation, but is more likely due to alternative splicing.
Figure 27H:
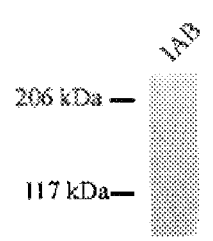
FIG. 27H is an autoradiograph of a Western blot prepared using mouse tissues showing that for an amino-terminal KCC4-specific antibody, generated to a peptide antigen from exon 1 (AERTEEPESPESVDQTSP; SEQ ID NO:117), reactivity is abolished by immunoabsorption with peptide antigen.
Figures 27I, 27J:
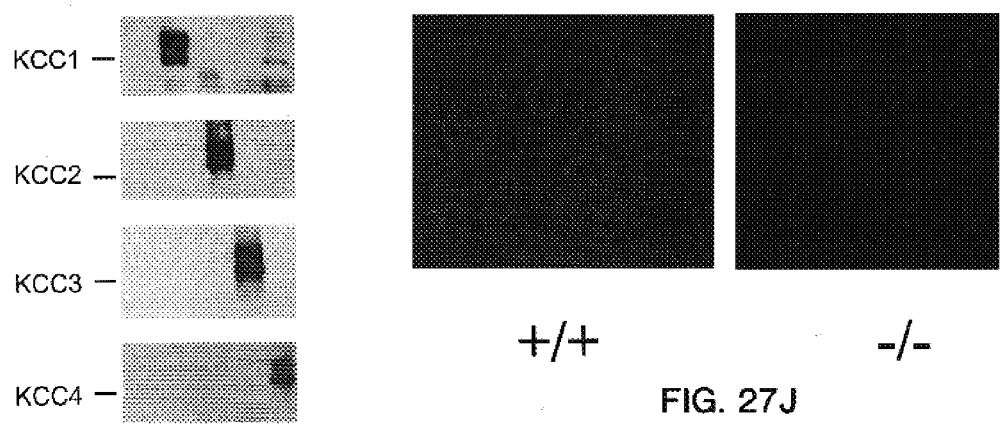
FIG. 27I is an autoradiograph of a Western blot of total protein from *Xenopus* oocytes injected with water, or singly injected with cRNA (25 ng/oocyte) encoding rabKCC1, hKCC2, hKCC3a, or mKCC4. C-terminal fusion protein-specific antibodies to KCC1 and KCC2 served as positive controls for the expression of KCC1 and KCC2. The KCC3 exon 3 antibody and the KCC4 exon 1 antibody are specific for their respective isoforms.
FIG. 27J is a photograph depicting immunofluorescence of KCC3 in mouse proximal tubules of both wildtype mice (+/+) and mice homozygous for a targeted deletion of exon 3 of mKCC3 (−/−) (KCC3 1: 4000, Alexa 594 1–5,000). The presence of KCC3 is observed as a light gray signal. Reactivity is lost in the knockout mice, demonstrating the specificity of this antibody.

An amino-terminal KCC4-specific antibody, generated to a peptide antigen from exon 1 (AERTEEPESPESVDQTSP; SEQ ID NO:117), detects a broad band of proteins between 160 and 180 kDa in molecular mass (FIG. 27F). In renal cortex and outer medulla (OM), two separate bands can be resolved, with the lower mass band predominant in cortex and the higher mass band predominant in outer medulla (FIG. 27G). This heterogeneity can be due to differential glycosylation, but is more likely generated by as-yet-uncharacterized alternative splicing. Finally, as in the case of the KCC3 antibody, reactivity is abolished by immunoabsorption with peptide antigen (FIG. 27H).

FIGS. 27A–27H show that the four KCCs have distinct but overlapping tissue distributions. KCC1 and KCC4 are widely expressed (Gillen et al. (1996) J Biol Chem 271(27): 16237–16244; Mount et al. (1999) J Biol Chem 274(23): 16355–16362), KCC3 has a slightly more restricted expression pattern (Mount et al. (1999) J Biol Chem 274(23): 16355–16362), and KCC2 is restricted to neurons in the central nervous system and retina. See Lu et al. (1999) J Neurobiology 39:558–568; Williams et al. (1999) J Biol Chem 274(18):12656–12664.

Expression of KCC3 protein in mouse brain is particularly prominent in the cell bodies and processes of oligodendrocytes, and is found in white matter tracts throughout the CNS, including the corpus callosum. This expression pattern further strengthens the genetic association with Andermann's syndrome (Casaubon et al. (1996) Am J Hum Genet 58(1):28–34) and familial spastic paraparesis (Martinez Murillo et al. (1999) Neurology 53(1):50–56). KCC3 is also expressed at the basolateral membrane of choroid plexus cells, however evidence for neuronal expression is still equivocal. Human KCC3 is however induced during the one-month in vitro differentiation of NT2 teratocarcinoma cells into NT2-N neuronal cells. NT2-N cells express hKCC2 (FIG. 27A). Human neurons thus have at least the potential to express both KCC2 and KCC3. KCC4 is expressed at very low levels in brain, however immunolocalization indicates focal expression in CA1 neurons within the hippocampus.

Example 22

Expression of KCC3 and KCC4 in Kidney

Immunofluorescence of mouse and rat kidney with the KCC3 antibody reveals expression at the basolateral membrane of proximal tubule, from S1 to S3; immunoabsorbed controls are negative. Co-immunofluorescence with distal nephron markers (antibodies to NKCC2, NCC, H-ATPase, etc.) indicates that KCC3 does not localize to the distal nephron. Despite expression in HUVEC cells, KCC3 is not detected in renal arteries. Like KCC3, KCC4 is heavily expressed at the basolateral membrane of proximal tubule cells, however expression is heaviest within S1 and weakest in S3. Neither KCC3 nor KCC4 are expressed in the glomerulus, whereas KCC1 is reportedly expressed in mesangial cells (Liapis et al. (1998) *Am J Physiol* 275(6 Pt 1):C1432–1437).

Unlike KCC3, KCC4 is expressed in the distal nephron, and co-immunofluorescence indicates expression at the basolateral membrane of the entire thick ascending limb (TAL), as well as in macula densa and distal convoluted tubule (DCT). Co-localization with aquaporin-1 suggests that descending thin limbs, thought to contain swelling-activated $K^+$—$Cl^-$ transport (Lopes et al. (1988) *Proc Natl Acad Sci USA* 85(8):2873–2877), do not express KCC4 (FIGS. 29I–29J). Finally, co-localization with $H^+$-ATPase indicates expression at the basolateral membrane of type A intercalated cells, cells that play a pivotal role in renal acid secretion.

The intra-renal localization of KCC3 and KCC4 settles the longstanding controversy regarding the presence or absence of $K^+$—$Cl^-$ transport at the basolateral membrane of proximal tubule (Seki et al. (1993) *J Clin Invest* 92(3): 1229–1235) and thick ascending limb (Di Stefano et al. (1998) *Cell Physiol Biochem* 8(1–2):89–105; Hurst et al. (1992) *Am J Physiol* 263(2 Pt 2):F262–267). The expression of KCC4 at the basolateral membrane of type A intercalated cells indicates an unexpected role in distal acid secretion.

Example 23

Expression of KCC3 Isoforms in Brain

Isoform-specific cDNA probes were used to examine the expression of KCC3a and KCC3b. The two isoforms are also distinguished by size, the KCC3a transcript being slightly larger than the KCC3b transcript (FIG. 29A). KCC3a is abundantly expressed in brain, whereas KCC3b is predominantly expressed in kidney. Total RNA was further isolated from specific brain regions or structures, including choroid plexus, hypothalamus, cerebellum, brainstem, cerebral cortex, and white matter. KCC3a was detected at equivalent levels in all noted brain regions, with the exception of reduced expression in the choroid plexus (FIG. 29B).

Brain and kidney from C5b6 mice were dissected and fresh tissue was frozen in liquid nitrogen. Total RNA was extracted using the guanidine isothiocyanate method, as described previously (Delpire et al. (1994) *J Biol Chem* 269:25, 677–25, 683). Poly(A)+RNA was purified from total RNA using RNeasy silica gel columns (Qiagen of Valencia, Calif.). Total RNA (10 µg/lane) or poly(A)+RNA (3 µg/lane) was separated on 1% agarose-0.63% formaldehyde gel, transferred onto nylon membrane, and probed with mouse-specific $^{32}$P-labeled probes consisting of 1a-or 1b-specific DNA sequences. Full-length cDNAs have been cloned from mouse KCC3a and KCC3b (GenBank Accession Nos. AF21185 and ZF211855, respectively). After overnight hybridization at 42° C. in a formamide-containing hybridization solution, the membranes were washed at high stringency (65° C.) and exposed to autoradiography.

Figure 30A:
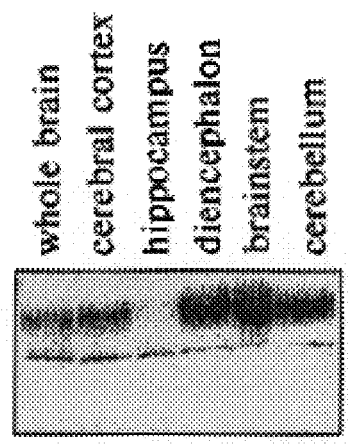
FIG. 30A is a Western blot prepared from mouse and rat microsomal protein samples (70 µg/lane) derived from the indicated brain regions. An anti-KCC3 polyclonal antibody was used to detect KCC3 protein. A protein doublet is identified in whole brain, cerebral cortex, hippocampus, diencephalon, brainstem and cerebellum. Expression was lower in the hippocampus in two of three western blot analyses.
Figure 30B:
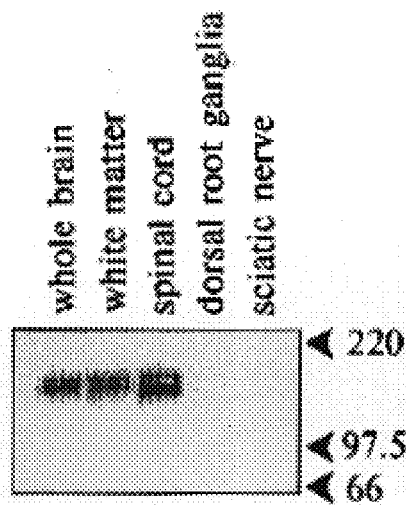
FIG. 30B is a Western blot prepared from mouse and rat microsomal protein samples derived from the indicated brain regions. An anti-KCC3 polyclonal antibody was used to detect KCC3 protein. Relatively high levels of KCC3 are detected in white matter tracts and the spinal cord, and lower levels are detected in the dorsal root ganglia and peripheral nerve.

To determine the relative abundance and distribution of KCC3 proteins in brain, microsomal protein from the cerebral cortex, hippocampus, diencephalons, brainstem, and cerebellum were used to prepare a Western blot, and the blot was analyzed using anti-KCC3 purified antibody. KCC3 protein is abundant in all regions of the brain examined (FIG. 30A). KCC3 signal was lower in the hippocampus in two of three Western blot analyses. Dissection of the white matter tracts of the internal and external capsules and corpus callosum indicated that KCC3 is highly expressing in these myelinated pathways (FIG. 30B).

For preparation of the Western blot, brain, spinal cord, dorsal root ganglia and peripheral nerves from C47b6 mice and whole brain from rats of varying age were dissected and homogenized in sucrose buffer (0.32 M sucrose, 5 mM Tris-HCl, pH 7.5, 2 mM EDTA) with a Teflon pestle. Microsomal protein was obtained by successive centrifugation at 3000 g, 20,000 g and 100,000 g. The high-speed pellet was resuspended in a buffer containing 5 nM Tris-HCl (pH 7.5) and 2 mM EDTA. Proteins were resolved by sodium dodecyl sulfate-polyacrylamide gel electrophoresis (SDS-PAGE) and electroblotted onto polyvinylidene difluoride membranes (BioRad of Hercules, Calif.). Except when indicated, membranes were probed with affinity-purified KCC3 antibody at a dilution of 1:1000. Proteins were detected using enhanced chemiluminescence (Amersham of Arlington Heights, Ill.).

To detect KCC3 protein in tissues, brain, spinal cord and peripheral nerves from C57b6 mice were dissected and fixed overnight in 4% paraformaldehyde in PBS at 4° C. Tissues were then washed with PBS and cryoprotected with 30% sucrose in PBS. For indirect immuofluorescence, 7–10 µm frozen sections were thaw mounted on SUPERFROST PLUS™ slides (VWR Scientific of West Chester, Pa.). Sections were then treated with 1% SDS and 8% 2-mercaptoethanol for 5 minutes, washed in PBS, blocked for 30 minutes at room temperature with PBS, 1% bovine serum albumin (BSA), followed by incubation with KCC3 affinity-purified antibody or antibody preabsorbed with the antigenic peptide, all at dilutions of 1:200 in PBS-1% BSA, overnight at 4° C. After washes in PBS, slides were incubated with Cy3-conjugated goat anti-rabbit immunoglobulin G (Jackson Immunoresearch of West Grove, Pa.) diluted 1:1000 in PBS, 1% BSA for 1 hour at room temperature in the dark. They were subsequently washed with PBS and mounted with Vectashield (Vector Labs of Burlingame, Calif.). For double-labeling experiments, sections were incubated successively with anti-KCC3 antibody overnight followed by Cy3-conjugated secondary antibody and then with monoclonal anti-microtubule-associated protein 2 (anti-MAP2) antibody or anti-MBP antibody overnight, followed by fluorescein isothiocyanate-conjugated anti-mouse immunoglobulin G (Jackson Immunoresearch of West Grove, Pa.). Sections were analysed with a Nikon Eclipse E800 microscope equipped with an Optronics DEI-750 color CCD camera (Optronics Engineering of Goleta, Calif.) coupled to an IBM-compatible 200 MHZ computer, connected to a color Tektronix Phaser 450 printer (Tektronics of Wilsonwill, Oreg.).

For antigen retrieval, frozen brain sections were thaw mounted on SUPERFROST PLUS™ slides, air-dried at room temperature, treated with 100% ethanol for 5 minutes at room temperature, air-dried at 42° C. and treated with 20 g/ml proteinase K in PBS, 1% BSA for 4 minutes at 37° C. After two washes in PBS, sections were treated for 5 minutes with 1% SDS and 8% 2-mercaptoethanol, and processed as indicated above.

KCC3 expression was also examined in other nervous system regions, including spinal cord, dorsal root ganglia, and peripheral nerves. Microsomal protein was prepared form the noted region. Western blot analysis revealed robust expression of KCC3 in the spinal cord (FIG. 30B). By contrast, low levels of KCC3 were detected in dorsal root ganglia, and only trace amounts were detected in sciatic and trigeminal nerves (FIG. 30B).

Figure 30C:
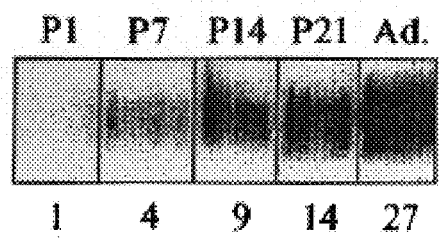
FIG. 30C is a Western blot prepared from crude membrane samples derived from rat brains at the indicated developmental stages. P1, postnatal day 1; P7, postnatal day 7; P14, postnatal day 14; P21, postnatal day 21; Ad., adult brains (>postnatal day 60). Numbers listed below each lane indicate abundance of KCC3 relative to KCC3 levels in P1 brain, as measured by densitometry.
Figure 31A:
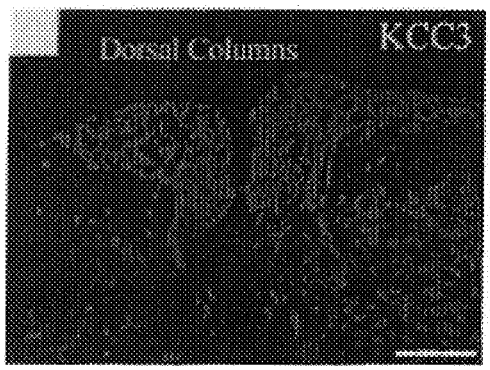
FIG. 31A is a fluorescence micrograph of adult mouse spinal cord stained using an anti-KCC3 polyclonal antibody. The presence of KCC3 is observed as regions of light gray signal. KCC3 is detected in the dorsal columns, which consist of highly myelinated axonal tracts. Scale bar=100 µm.
Figure 31D:
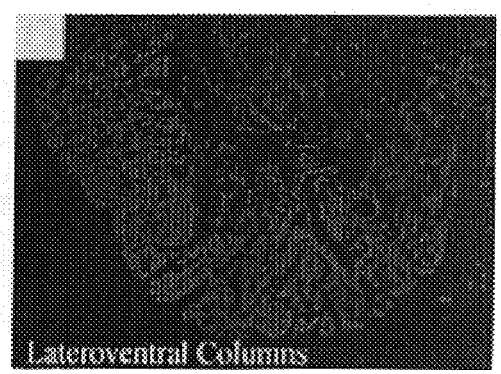
FIG. 31D is a fluorescent micrograph of an adult ventral spinal cord stained using an anti-KCC3 antibody. KCC3 is detected in the ventral white matter tracts and is observed as a light gray signal. In gray matter, KCC3 is detected only in crossing fibers.
Figure 31B:
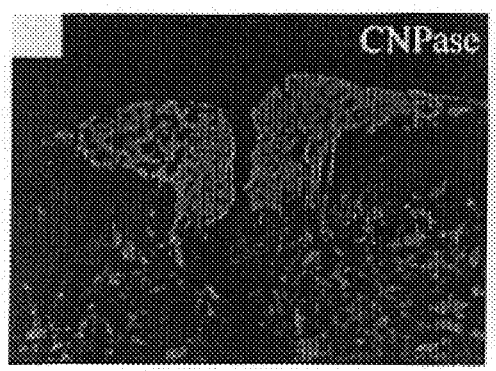
FIG. 31B is a fluorescence micrograph of the same spinal cord section depicted in FIG. 31A stained using the oligodendrocyte marker anti-CNPase antibody. The presence of CNPase is observed as regions of light gray signal.
Figure 31E:
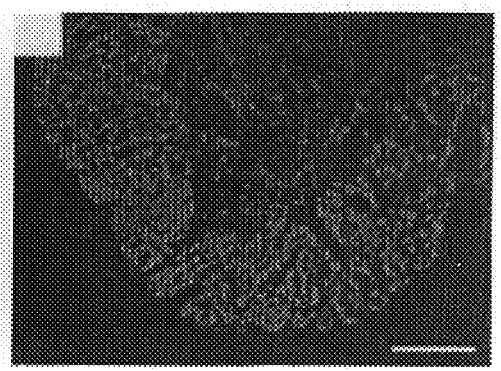
FIG. 31E is a fluorescence micrograph of the same ventral spinal cord section depicted in FIG. 17D stained using an anti-CNPase antibody. The presence of CNPase is observed as a light gray signal. CNPase is also detected in the white matter region of the ventral spinal cord, indicating co-localization of KCC3 and CNPase in the anterolateral column. Scale bar=100 µm.
Figure 31C:
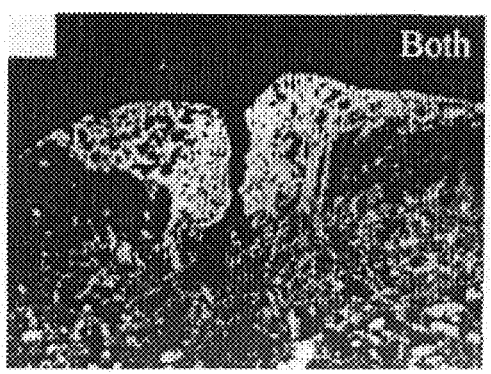
FIG. 31C is a merged image of FIGS. 32A and 32B, depicting co-staining of KCC3 and CNPase in the dorsal column. Co-staining of KCC3 and CNPase is observed as regions of white signal, representing the combined light gray signals shown in FIGS. 32A and 32B.
Figure 31F:
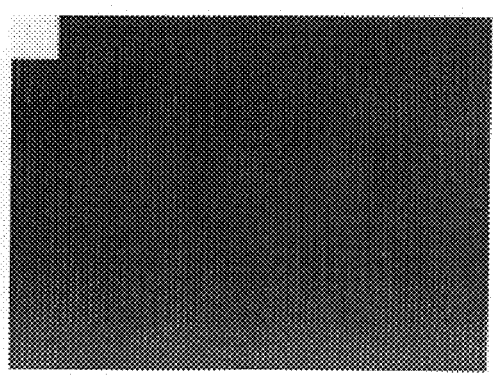
FIG. 31F is a fluorescence micrograph of an adult spinal cord stained with anti-KCC3 and anti-CNPase antibodies that were immunoabsorbed with the corresponding specific antigen prior to incubation with the tissue. KCC3 and CNPase are not detected.

To examine the postnatal developmental profile of KCC3 expression, protein derived from brains isolated at postnatal day 1 (P1), P7, P14, P21, and adult (>P60) was analyzed by Western blot analysis (FIG. 30C). KCC3 levels are low at birth and increase significantly during postnatal maturation. KCC3 levels in the adult brain are 30-fold higher than in P1 brain. At each age, double protein bands of 155 and 165 kDa were detected, confirming the specificity of the antibody throughout postnatal development. The presence of KCC3 in structures rich in white matter, together with elevated levels during postnatal development, implicate KCC3 in myelination and related biological activities.

To determine the anatomical distribution and cellular localization of KCC3 in the brain and spinal cord, polyclonal anti-KCC3 antibody was used to label 7–10 μm sections of adult mouse and spinal cord (FIG. 31). In the spinal cord, KCC3 expression was highest in highly myelinated tracts of the dorsal columns. This pattern was similar to the distribution of oligodendrocyte markers CNPase and myelin basic protein. Double-labeling using anti-KCC3 and anti-CNPase antibodies revealed substantial co-staining. White matter tracts of the ventrolateral columns were similarly labeled with both KCC3 and CNPase. KCC3 immunostaining was absent when the antibody was preabsorbed with specific antigen.

Immunolocalization of KCC3 in the brain was initially impaired by the seeming inaccessibility of the target epitope, probably due to protein-protein interactions. Using a standard immunostaining protocol, a specific signal was detected only at the base of the choroid plexus epithelium. This staining was prevented by preincubation the antibody with antigenic peptide. A high uniform background signal was also observed.

Figure 32A:
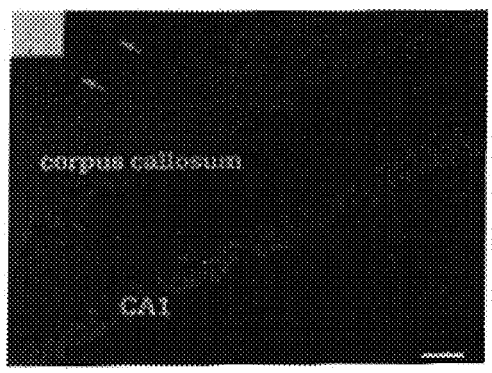
FIG. 32A is a fluorescence micrograph of a coronal section of the forebrain labeled with an anti-KCC3 antibody. The presence of KCC3 is detected as regions having a light gray signal. KCC3 is detected in the white matter tract of the corpus callosum, as well as in the CA1 neuronal layer of the hippocampus. Arrows point to KCC3-positive cell bodies in the vicinity of the white matter tract. Scale bar=50 µm.
Figure 32D:
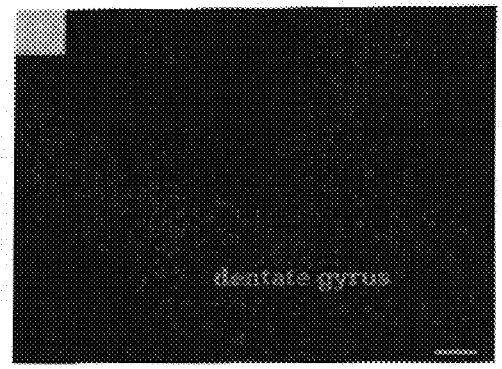
FIG. 32D is a fluorescence micrograph depicting dentate gyrus labeled with an anti-KCC3 antibody. Numerous granular cell bodies are labeled and are observed as regions of light gray signal. Scale bar=50 µm.
Figure 32B:
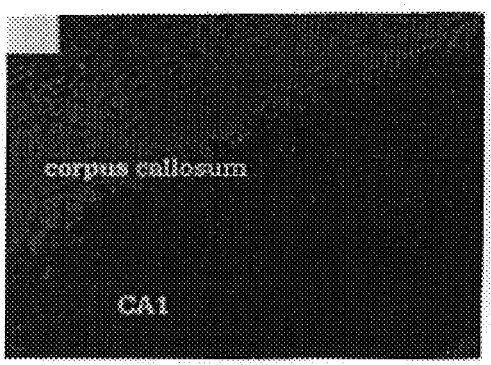
FIG. 32B is a fluorescence micrograph of the same region of the forebrain depicted in FIG. 34A stained using the oligodendrocyte (myelin) marker anti-CNPase. The presence of CNPase is observed as regions having a light gray signal. CNPase is detected in the white matter tract and is absent from the CA1 layer of the hippocampus.
Figure 32E:
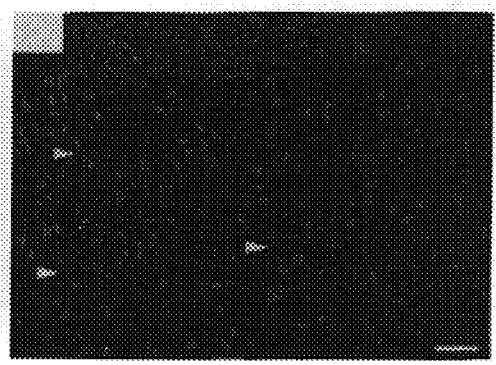
FIG. 32E is a fluorescence micrograph of deep cerebral cortex stained using an anti-KCC3 antibody. The presence of KCC3 is observed as regions of light gray signal. Numerous cortical cell bodies are labeled, as well as cell bodies and processes of pyramidal neurons (arrowheads). Scale bar=50 µm.
Figure 32C:
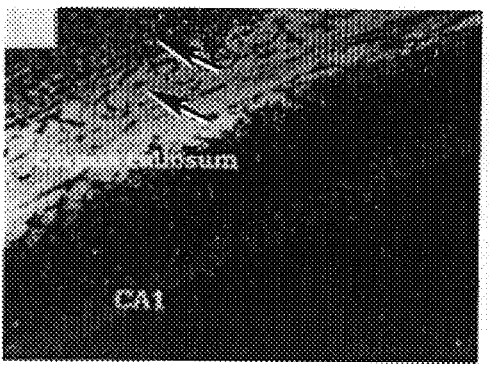
FIG. 32C is a merged image of FIGS. 34A and 34B. Co-localization of KCC3 and CNPase is observed as regions of white signal, representing the combined summation of overlapping regions of gray signal. KCC3 and CNPase are co-localized in the corpus callosum. However, numerous cell bodies are KCC3-positive but devoid of CNPase signal (arrows).
Figure 32F:
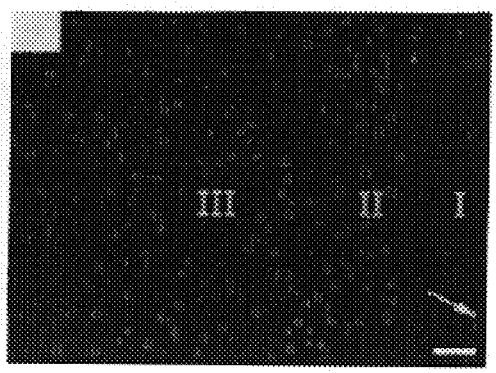
FIG. 32F is a fluorescence micrograph of large cell bodies in the superficial cortex stained using an anti-KCC3 antibody. The presence of KCC3 is observed as regions of light gray signal. KCC3 is detected in molecular layers (II) and (III), but is scarce in molecular layer (I). Arrow, edge of brain. Scale bar=50 µm.

To uncover the KCC3 epitope in brain, tissue sections were treated with proteinase K (Hardt et al. (2000) *J Comp Pathol* 122:43–53). In the forebrain, high levels of KCC3 were observed in white matter tracts (e.g., the corpus callosum, FIG. 32A). A predominant proportion of KCC3 in the corpus callosum co-localized with the oligodendrocyte markers CNPase (FIG. 32B) and myelin basic protein, although a number of KCC3-positive cell bodies were devoid of CNPase reactivity (FIG. 32B, arrows). KCC3 was also detected in packed cell layers of the hippocampus (CA1, FIGS. 32A, 32D) and cortex (FIGS. 32E, 32F), suggesting neuronal expression. Neuronal staining was distinguished by: (i) a high density of cell bodies labeled in the CA1 layer of the hippocampus (FIGS. 32A, 32C) and dentate gyrus (FIG. 32D); and (ii) the presence of labeled cells in the cerebral cortex, including a few cells in molecular layer 1, a greater number of cells in layer 11, and dispersed cells in deeper layer (FIG. 32F). In deeper cortical layers, KCC3 was detected in pyramidal neurons, which can be identified by their distinctive morphology (FIG. 32E).

In the cerebellum, KCC3 was detected in Purkinje neurons and their axons, whereas KCC3 was not detected in granular neurons. White matter tracts were also labeled with anti-KCC3 antibody. The levels of KCC3 in white matter were relatively high in vertical tracts located in the brainstem. KCC3 in white matter co-localizes with the oligodendrocyte marker CNPase, demonstrating the association of KCC3 with myelin sheaths.

Large, MAP2-positive cells in the brainstem also showed KCC3 immunoreactivity.

Example 24

KCC2 Knockout Mice

Figure 33A:
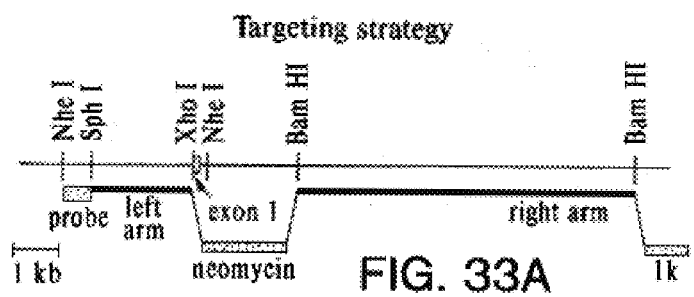
FIG. 33A is a schematic depicting a targeting strategy for the generation of a mouse strain genetically deficient in KCC2. Homozygous KCC2-mice were shown to suffer from early neonatal mortality. The targeting strategy shows the structure of the 5' end of Slc12a5/KCC2 gene, position of the 5' probe and structure of the DNA fragment inserted into the gene. The construct was created using pPNT, a vector containing both neomycin and thymidine kinase genes under phosphoglycerate kinase-1 (PGK-1) promoter. A 2.1-kb SphI-XhoI fragment (left arm) was ligated upstream of the neomycin cassette, and a 7-kb BamHI fragment (right arm) was inserted between neomycin and thymidine kinase.
Figure 33B:
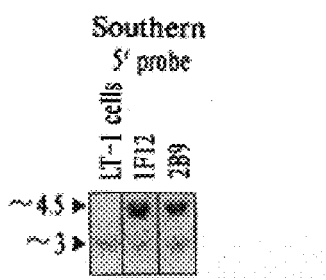
FIG. 33B is an autoradiograph depicting Southern-blot analysis of embryonic stem (ES) cell genomic DNA digested with NheI and BamHI; the 3-kb band represents the control gene and the 4.5-kb band originates from the mutant gene.

A mouse strain genetically deficient in KCC2 has been generated, and homozygous mice were shown to suffer from early neonatal mortality. The targeting strategy for this mouse strain is shown in FIG. 33A. This figure shows the structure of the 5' end of Slc12a5/KCC2 gene, position of the 5' probe and structure of the DNA fragment inserted into the gene. The construct was created using pPNT, a vector containing both neomycin and thymidine kinase genes under phosphoglycerate kinase-1 (PGK-1) promoter. A 2.1-kb SphI-XhoI fragment (left arm) was ligated upstream of the neomycin cassette, and a 7-kb BamHI fragment (right arm) was inserted between neomycin and thymidine kinase. FIG. 33B shows Southern-blot analysis of embryonic stem (ES) cell genomic DNA digested with NheI and BamHI; the 3-kb band represents the control gene and the 4.5-kb band originates from the mutant gene.

Figure 33C:
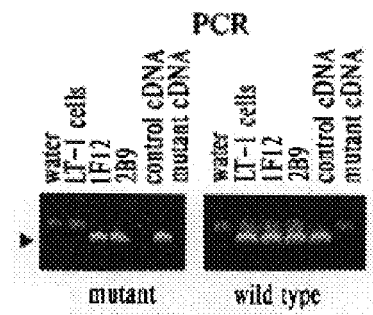
FIG. 33C is a photograph depicting PCR analysis of genomic DNA confirms the presence of the mutant gene in two ES cell mutants (1F12 & 2B9). Position of the PCR product is indicated (arrowhead). The upper band represents the primers.

As shown in FIG. 33C, PCR analysis of genomic DNA confirms the presence of the mutant gene in two ES cell mutants (1F12 & 2B9). Position of the PCR product is indicated (arrowhead). The upper band represents the primers.

Figure 33D:
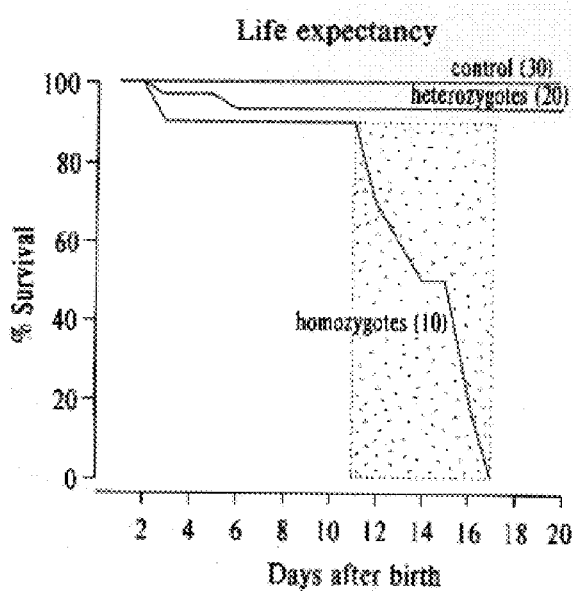
FIG. 33D is a graph that charts the life expectancy of wild type mice, heterozygote $KCC2^{-/+}$ mice, and homozygous $KCC2^{-/-}$ mice. Following birth, pups were examined and counted twice a day. Dead pups were removed and genotyped by PCR. Note the striking death rate of homozygote pups between day 11 and 17; all homozygote mutants died by day 17.

FIG. 33D charts the life expectancy of wild type mice, heterozygote $KCC2^{+/-}$ mice, and homozygous $KCC2^{-/-}$ mice. Following birth, pups were examined and counted twice a day. Dead pups were removed and genotyped by PCR. The striking death rate of homozygote pups between day 11 and 17 is shown, and all homozygote mutants died by day 17.

Figure 33E:
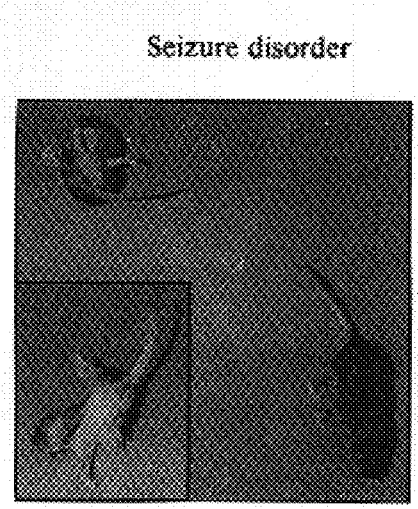
FIG. 33E is a set of photographs of seizing $KCC2^{-/-}$ mice. Homozygote mutant and control mice were placed upside-down. While the control mouse (bottom right) turned immediately back right side up, the homozygote mutants started to seize. The general stiffness of their limbs can also been seen.

FIG. 33E shows photographs of seizing $KCC2^{-/-}$ mice. Homozygote mutant and control mice were placed upside-down. While the control mouse (bottom right) turned immediately back right side up, the homozygote mutants started to seize. Note the general stiffness of the limbs of $KCC2^{-/-}$ mutant animals.

To investigate the neural defects responsible for seizure activity in KCC2 mutant animals, the brains of epileptic $KCC2^{-/-}$ mice was evaluated histologically. When compared to the brains of control animals, $KCC2^{-/-}$ brains display signs of injury, including increased immediate early gene expression (e.g., fos) and a loss of interneuronal populations (e.g., parvalbum-positive interneurons).

Figures 34A, 34B:
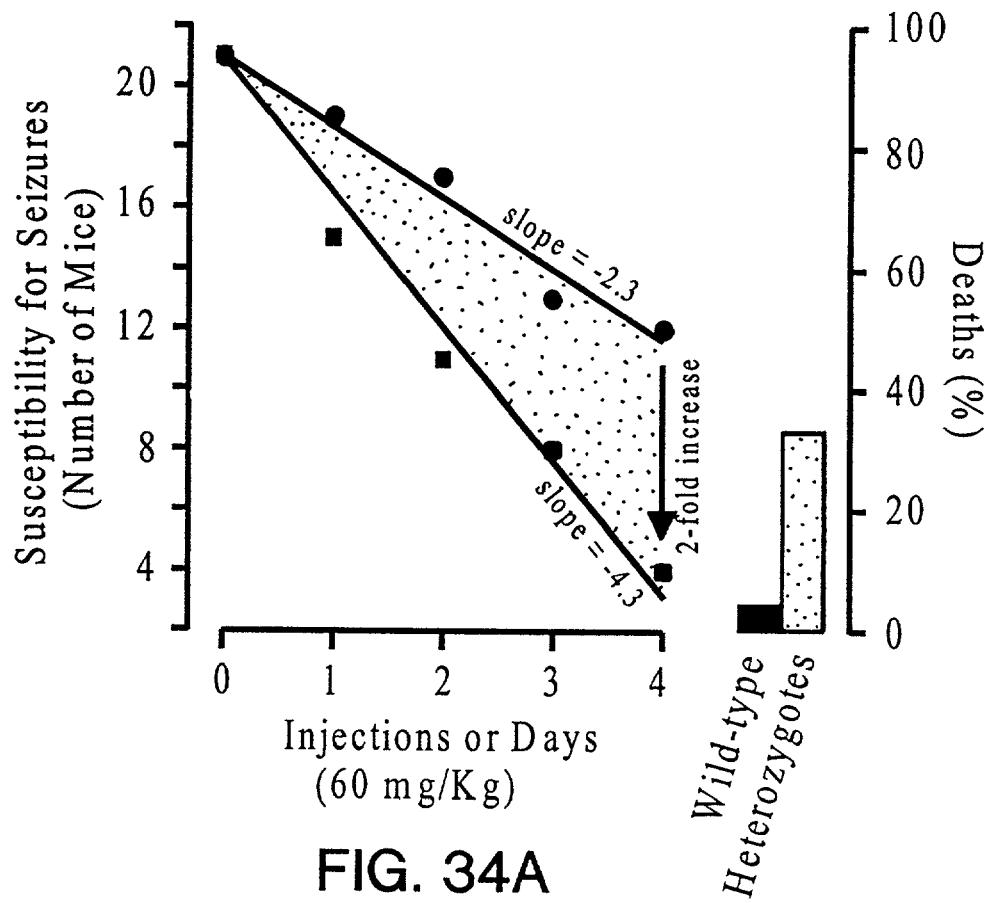
FIG. 34A is a graph depicting increased susceptibility to seizure activity in $KCC2^{+/-}$ mice (●) when compared to wild type mice (■). The number of mice showing seizure activity, assayed as described in Example 24, is plotted as a function of the number of injections received (or the number of days injections administered). In this assay, $KCC2^{+/-}$ mice (●) are about 2-fold more susceptible to seizure activity than wild type mice (■).
FIG. 34B is a bar graph depicting the percentage of deaths observed in seizure-induced KCC2$^{+/-}$ heterozygous mice (gray bar) and wild type mice (black bar). Approximately 35% of KCC2$^{+/-}$ heterozygous mice die in response to PTZ injection, whereas <5% of wild type animals die following a same PTZ injection.

A reduced threshold for induction of seizure activity was also observed in $KCC2^{+/-}$ heterozygous mice. Seizures were induced in wild type and litter-matched $KCC2^{+/-}$ mice by daily injections of 60 mg/kg pentylenetetrazole (PTZ), a blocker of the $GABA_A$ receptor. Animal behavior was observed during a one-hour interval following PTZ injection, and the severity of seizure induction was scored according to the following indicators: score=0, absence of seizure acitivity; score=1, ear and facial twitching; score=2, myoclonic body jerks; score=3, clonic forelimb convulsions with tonic extension episode and status epilepticus; score=5, death. Mice assigned a score of 3, 4, or 5 were removed from the group. FIG. 34 summarizes the number of mice assigned a score of 1 or 2 as a function of time. A significant difference between wild type and $KCC2^{+/-}$ heterozygous mice was observed, corresponding to an approximately 2-fold increase in the susceptibility of $KCC2^{+/-}$ heterozygous mice to seizure activity.

Example 25

KCC3 Knockout Mice

Figure 35:
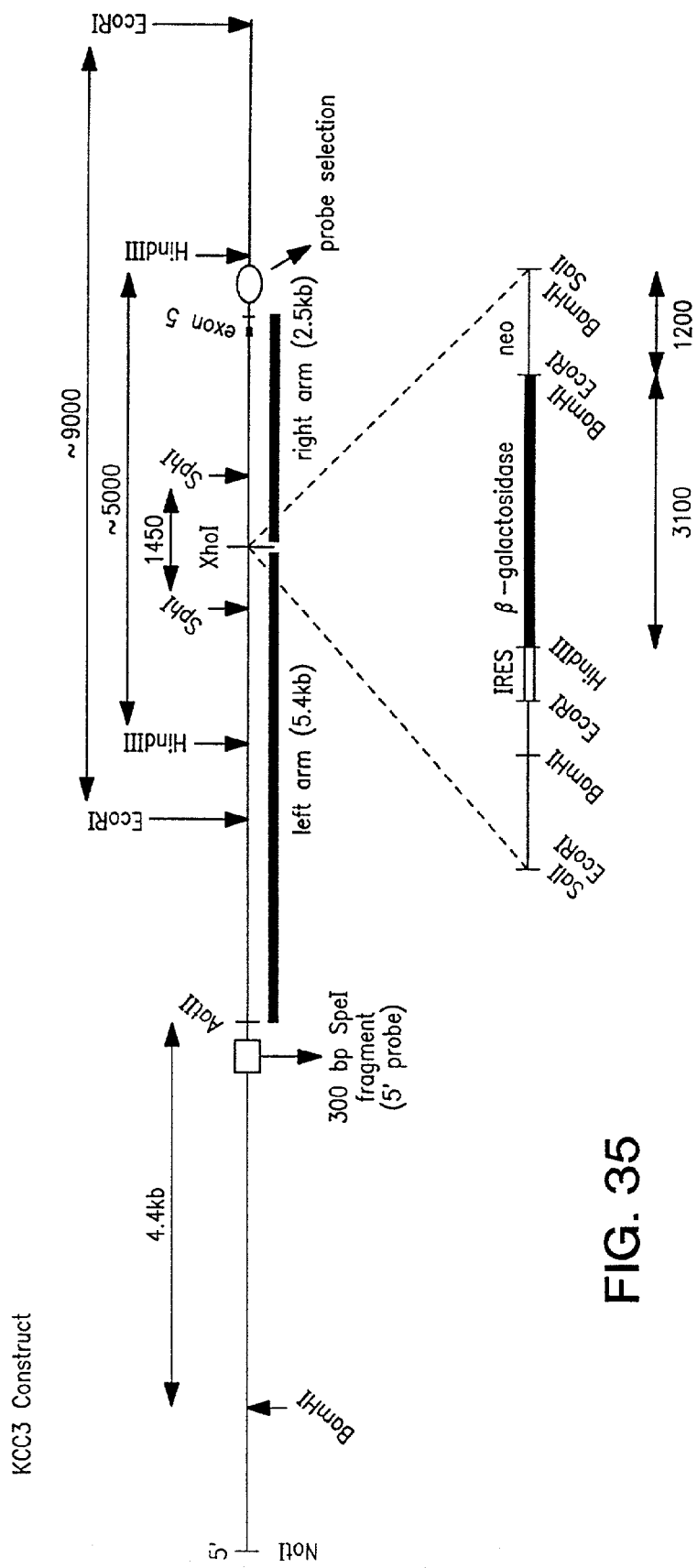
FIG. 35 is a schematic of a targeting construct for the generation of a KCC3 knockout mouse strain. Using PCR, exon 3 was removed and an XhoI site was introduced within the 1450 base pair SphI fragment. The IRES/bgeo fragment was inserted in the gene at the XhoI site. This construct deletes exon 3, which is not alternatively spliced and is utilized by both KCC3a and KCC3b transcripts.

FIG. 35 shows the targeting construct for the generation of a KCC3 knockout mouse strain. A PCR strategy was used to remove exon 3 and to introduce a XhoI site within the 1450 base pair SphI fragment. The IRES/bgeo fragment was inserted in the KCC3 gene at the XhoI site. This mutation deletes exon 3, which is not alternatively spliced and is utilized by both KCC3a and KCC3b transcripts.

KCC3$^{-/-}$ mutant mice display several abnormalities, including uncoordinated gait/locomotion, a nervous system defect manifest as reduced exploratory behavior, prepulse inhibition, and reduced myelination of peripheral axons. Human KCC3 maps to human chromosome 15q15, and this region is genetically linked with periodic catatonia, a subtype of schizophrenia (Stober et al. (2000) *Am J Hum Genet* 67:1201–1207). The phenotypes observed in KCC3$^{-/-}$ mice support the involvement of KCC3 in the genesis of schizophrenia. The early locomoter phenotype and the demyelination of peripheral nervies is similar to that observed in patients afflicted with ACCPN (peripheral neuropathy with or without agenesis of the corpus callosum) (Casaubon et al. (1996) *Am J Hum Genet* 58:28–34). Further, the strong prepulse inhibition phenotype demonstrated by KCC3$^{-/-}$ and KCC3$^{+/-}$ mice is suggestive of the schizophenia-like psychotic symptoms that have been described for ACCPN patients (Casaubon et al. (1996) *Am J Hum Genet* 58:28–34). The genomic structure of human KCC3, disclosed herein, will facilitate diagnosis of patients with schizophrenic disorders.

KCC3$^{-/-}$ mice develop an abnormal posture and gait prior to weaning (postnatal day 21). The limbs of KCC$^{-/-}$ animals are weak, manifest as a low posture and uncoordinated limb movements. To further describe this sensorimotor defect, three behavioral tasks that focus of locomotor performance (the rotorod task, the wire hang task, and the beam task) were employed, each described briefly herein below. Collectively, these data indicate locomotor deficits, involving both strength and coordination, in KCC3$^{-/-}$ mice but not in KCC3$^{+/-}$ heterozygous mice.

Figure 36A:
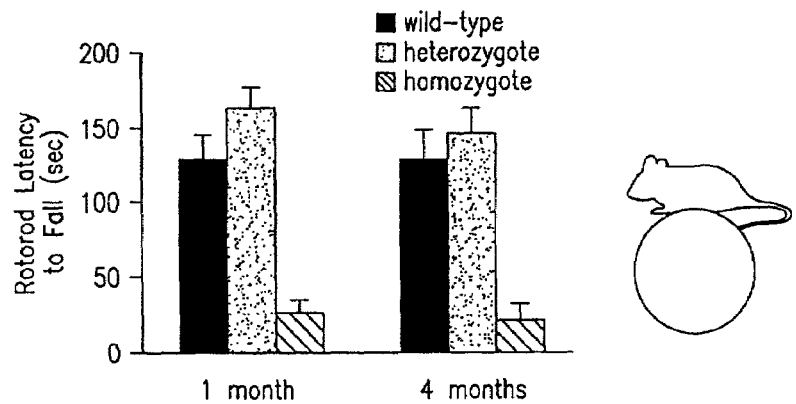
FIG. 36A is a graph depicting the performance of wild type mice (black bar), KCC3$^{+/-}$ heterozygous mice (solid gray bar), and KCC3$^{-/-}$ mutant mice (hatched gray bar) in the rotorod behavioral task. Animals of each genotype were placed on a rotorod, and the time elapsed (Rotorod Latency to Fall in seconds) until the animal fell from the rotorod was determined. All animals were tested at 1 month and 4 months of age, as indicated. A schematic drawing showing the initial position of a mouse on a rotorod is pictured adjacent to the graph.

The rotorod task involves placing an animal and scoring the animal's latency to fall. Rotorod trials were conducted 3 times per day for three days, and this test series was performed when animals were 1 month and 4 months of age. FIG. 36A summarizes the performance of the test animals on the third day of each test series. No significant difference between wild type and KCC3$^{+/-}$ heterozygous mice was observed. By contrast, KCC3$^{-/-}$ mutant mice failed the rotorod test as they fell shortly after being placed on the wheel.

Figure 36B:
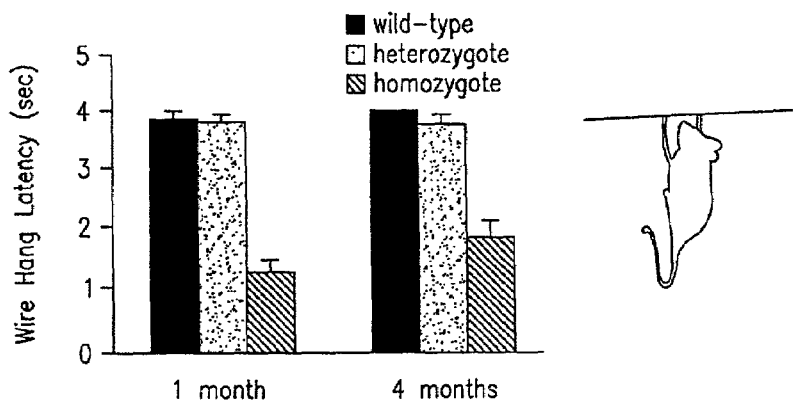
FIG. 36B is a graph depicting the performance of wild type mice (black bar), KCC3$^{+/-}$ heterozygous mice (solid gray bar), and KCC3$^{-/-}$ mutant mice (hatched gray bar) in the wire hang behavioral task. Animals of each genotype were presented with a wire, and the period of time (Wire Hang Latency in seconds) during which the mouse gripped the wire was determined. All animals were tested at 1 month and 4 months of age, as indicated. A schematic drawing showing a mouse gripping a wire is pictured adjacent to the graph.

The wire hang task involves presenting a wire to the animal's forelimbs. A normal response is characterized by gripping of the wire and pulling the body up so that the hindlimbs and tail also engage the wire. As shown in FIG. 36B, wild type and KCC3$^{+/-}$ heterozygous mice grabbed the wire without difficulty, whereas KCC3$^{-/-}$ mice performed poorly. Results were consistent when animals were tested at 1 month and 4 months of age.

Figure 36C:
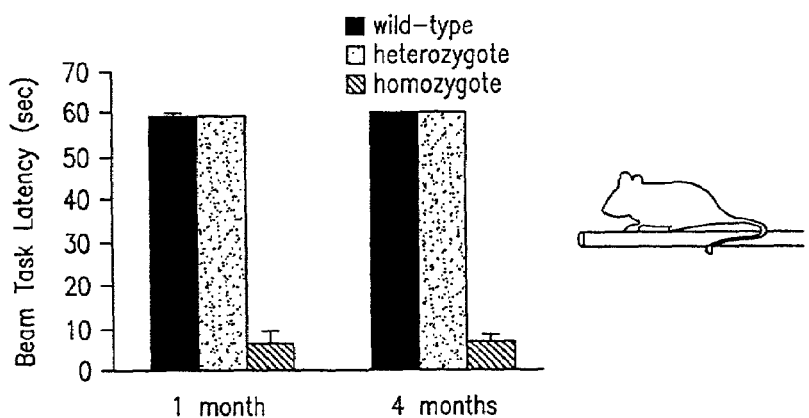
FIG. 36C is a graph depicting the performance of wild type mice (black bar), KCC3$^{+/-}$ heterozygous mice (solid gray bar), and KCC3$^{-/-}$ mutant mice (hatched gray bar) in the beam behavioral task. Animals of each genotype were placed on a narrow beam, and the time elapsed (Beam Task Latency in seconds) until the animal fell from the beam was determined during a 60-second interval. All animals were tested at 1 month and 4 months of age, as indicated. A schematic drawing showing the initial position of a mouse on a narrow beam is pictured adjacent to the graph.

The beam task involved placing the mouse on a narrow beam and measuring the latency passed until the animal fell from the beam. As shown in FIG. 36C, wild type and KCC3$^{+/-}$ heterozygous mice maintained position on the beam for one minute (the duration of the test), whereas KCC3$^{+/-}$ mice fell rapidly. Results were consistent when animals were tested at 1 month and 4 months of age.

Figure 37A:
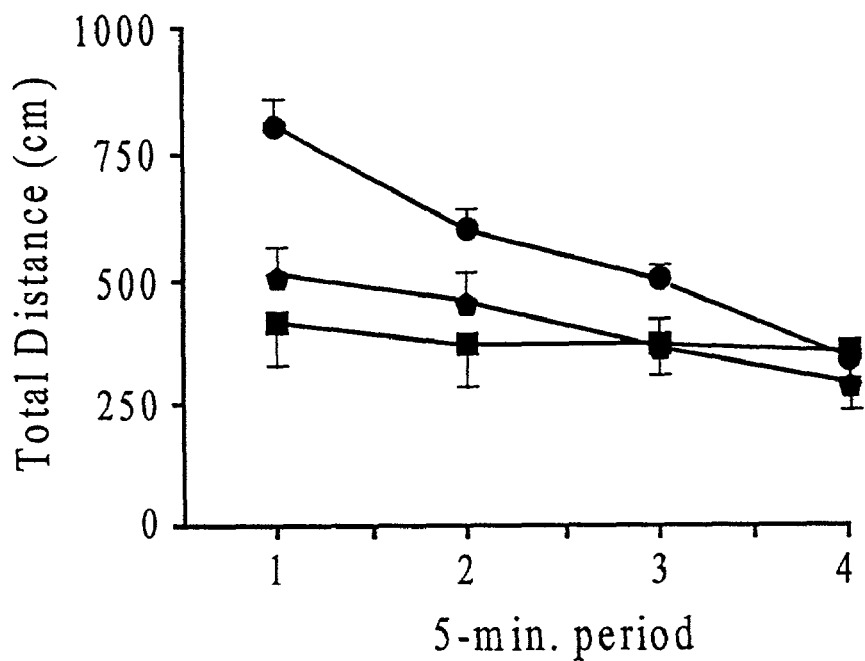
FIG. 37A is a graph depicting reduced exploratory behavior in KCC3$^{+/-}$ heterozygous mice (pentagon symbol) and KCC3$^{-/-}$ homozygous mice (■) when compared to wild type mice (●). When placed in an activity chamber, the distance traveled by each mouse was measured in 4 consecutive 5-minute intervals.
Figure 37B:
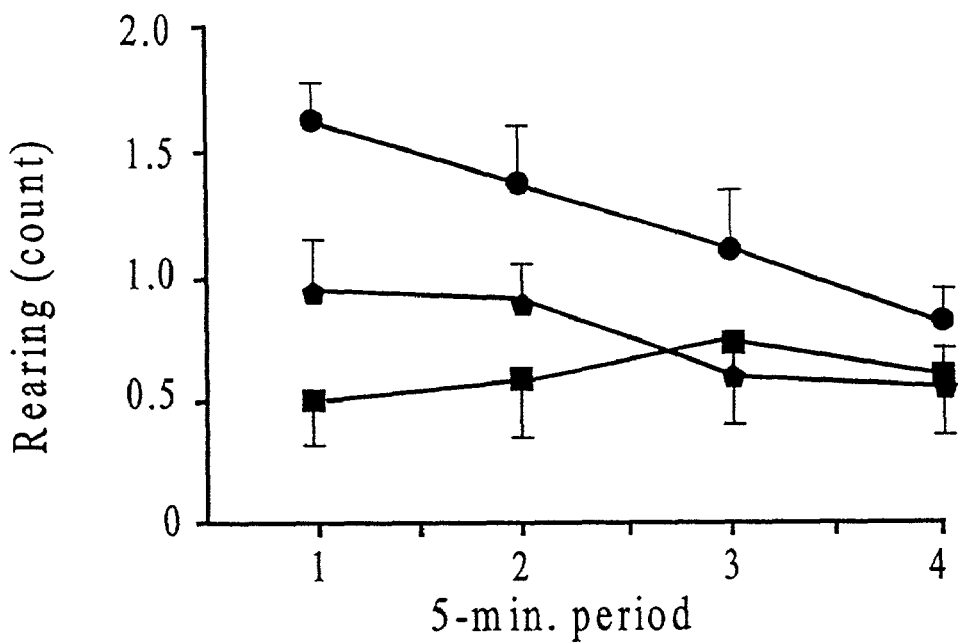
FIG. 37B is a graph depicting reduced rearing behavior in KCC3$^{+/-}$ heterozygous mice (pentagon symbol) and KCC3$^{-/-}$ homozygous mice (■) when compared to wild type mice (●). When placed in an activity chamber, the number of times each mouse displayed rearing behavior was measured in 4 consecutive 5-minute intervals.

To assess neural contributions to the locomotor phenotypes in KCC3$^{-/-}$ mutant mice, an activity chamber assay was performed. Wild type, KCC3$^{+/-}$ heterozygous mice, or KCC3$^{-/-}$ mutant mice were individually placed in an activity chamber, and the distance traveled and/or the number of rearing occurrences by the mouse was recorded in 4 contiguous 5-minute periods. The results are summarized in FIGS. 37A and 37B. Wild type mice show a high level of activity during the initial 5-minute period and a progressively decreased level of activity during each subsequent period. This behavior constitutes a normal pattern of exploration of a new environment followed by habituation. KCC3$^{-/-}$ mutant mice fail to explore their environment and also fail to habituate, as evidenced by a submaximal and constant level of activity. KCC3$^{+/-}$ heterozygous mice displayed reduced, although not absent, exploration and habituation activity. Thus, in KCC3$^{+/-}$ heterozygous animals, reduced exploratory (FIG. 37A) and rearing (FIG. 37B) behavior is observed in the absence of measurable locomoter defects (FIGS. 36A–36C), suggesting that their compromised performance in the activity chamber assay is unrelated to locomoter performance.

Figure 38:
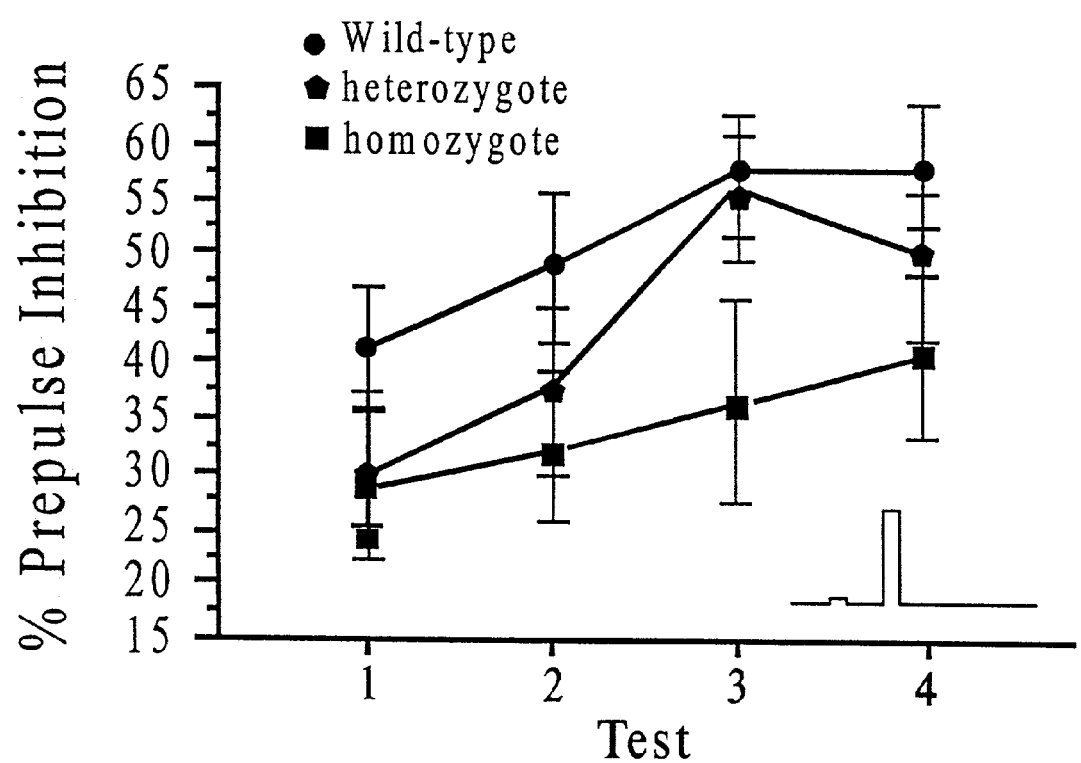
FIG. 38 is a graph depicting reduced prepulse inhibition in KCC2$^{+/-}$ heterozygous mice (pentagon symbol) and KCC3$^{-/-}$ homozygous mice (■) when compared to wild type mice (●). The percentage of animals displaying prepulse inhibition is significantly reduced in KCC3$^{-/-}$ mutant animals, and moderately reduced in KCC3$^{+/-}$ heterozygous animals. At the lower right hand corner of the graph, a schematic line drawing shows the magnitude of the acoustic prepulse and pulse stimuli, described further in Example 25.

KCC34$^{-/-}$ mice were also evaluated using a prepulse inhibition test to detect schizophrenia-like behavior. The test is based on the ability of a prepulse (in this case, an acoustic prepulse) to inhibit a sensory pulse. A wild type animal will learn to anticipate the sensory pulse based on the prepulse, whereas a schizophrenic animal will fail to learn the association. Startle response to an acoustic stimulus is recorded, and a prepulse of lower intensity is presented 100 milliseconds prior to the acoustic pulse. The results of these experiments are summarized in FIG. 38. No differences in startle response were observed between wild type and KCC3$^{-/-}$ mutant mice, indicating that auditory functions are not disrupted in KCC3$^{-/-}$ mutant mice.

Figure 39A:
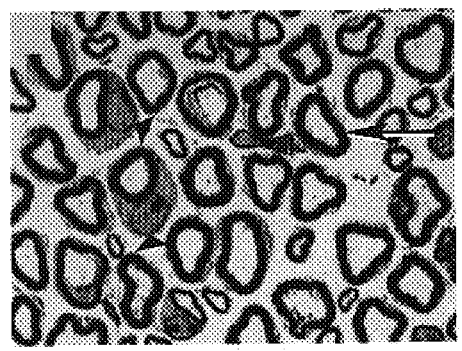
FIGS. 39A–39B are micrographs showing representative cross-sections of the sciatic nerve in wild type mice. The myelin coating is thick around large axons (thin arrows). Schwann cells are visible surrounding axons (arrowheads).
Figure 39B:
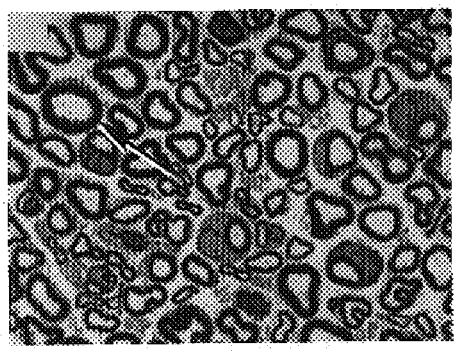
Figure 39C:
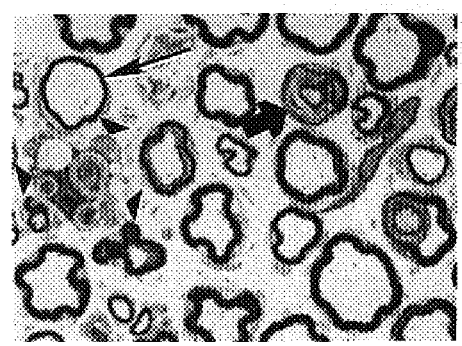
FIGS. 39C–39D are micrographs showing representative cross-sections of the sciatic nerve in KCC3$^{-/-}$ mutant mice. Numerous large axons have a relatively thin myelin coating (thin arrows) compared the degree of myelination in wild type mice. Many axons have a ring-like appearance (thick arrows), although this appearance can also be observed in axons isolated from wild type animals. Degenerating fibers and myelin deposits are also observed (arrowheads).
Figure 39D:
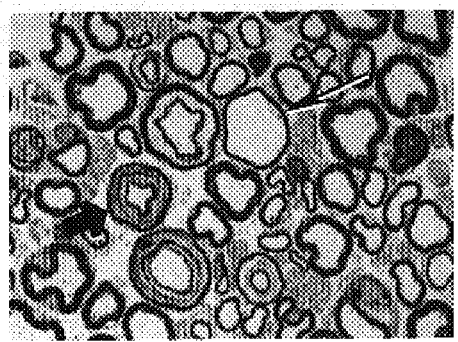

The human KCC3 gene shows genetic linkage with ACCPN, a disorder characterized in part by demyelination of peripheral nerves. To assess myelination in KCC3$^{-/-}$ mice, thick (1 μm) sections of sciatic nerve derived from wild type and KCC3$^{-/-}$ mutant mice were prepared for hisotpathological examination. Large axons isolated from wild type mice show thick myelination (FIGS. 39A–39B). By contrast, thinner myelin sheaths, degenerating axons, and numerous axons with a ring-like appearnce were observed in axons derived from KCC3$^{-/-}$ mutant mice (FIGS. 39C–39D).

Example 26

Identification of a KCC2 Polymorphism

Figure 40:
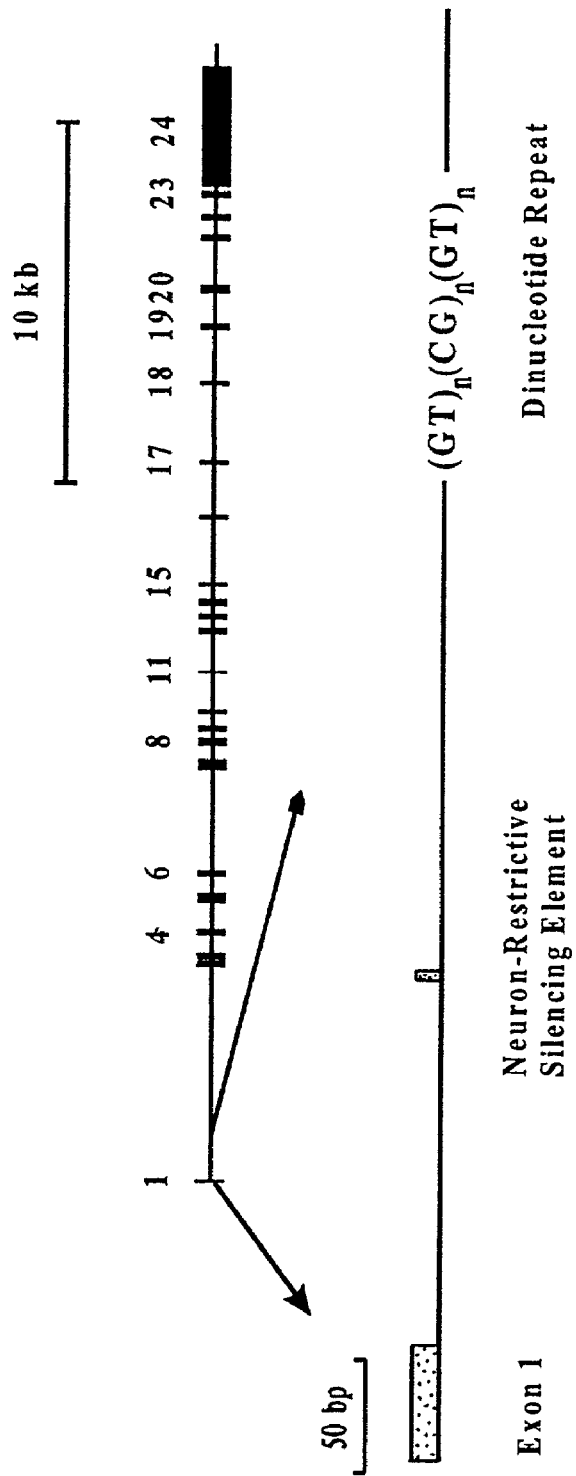
FIG. 40 is a map of the genomic region encoding hKCC2. The top line depicts organization of the KCC2 gene. Exons are represented by boxes, and a subset of the exons are numbered. The line connecting exons represents intronic regions. An enlarged view of hKCC2 exon 1 and the initial segment of intron 1 is presented below the KC2 gene map. A NSRE sequence is conserved in hKCC2, and is located in intron 1 just upstream of a $(GC)_n(CG)_n(GT)_n$ dinucleotide repeat.

Whereas targeted deletion of the mouse KCC2 gene results in repetitive seizures and early neonatal lethality (Delpire & Lovinger (2000) *J Neurosci* 26:1148), the region of chromosome 20q13 containing the hKCC2 gene is not linked to hereditary epilepsy syndromes. However, it remains possible that variability in the expression and function of hKCC2 plays a role in human disease. Of note, the NRSE observed in mouse KCC2 is conserved in the human gene, just 5' of a complex (CA/GT)n repeat (FIG. 40). To determine whether this repeat is polymorphic, primers flanking this region (SEQ ID NOs:114–115) were used to amplify genomic DNA from several individuals. Amplification conditions consisted of a 5-minute denaturation at 94° C. followed by 35 cycles of denaturation at 94° C. for 30 seconds, annealing at 60° C. for 30 seconds, extension at 72° C. for 30 seconds, and a final 5-minute extension at 72° C. The sequence of both alleles from several individuals is shown in FIG. 41, and reveals that the repeat is in fact polymorphic. This repeat might affect transcriptional regulation of the hKCC2 gene by affecting the binding of NRSF. Similar dinucleotide repeats within or near the regulatory elements of other genes have been shown to have polymorphic effects on transcription (Gebhardt et al. (1999) *J Biol Chem* 274:13176–13180; Shimajiri et al. (1999) *FEBS Lett* 455:70–74). Such genetic variability in transcription of the hKCC2 gene can impact on human seizure disorders and/or their treatment, or on other disorders that affect neuronal chloride homeostasis and the response to GABA (van den Pol et al. (1996) *J Neurosci* 16:4283–4292). Human NT2-N neuronal cells, which we have shown to express hKCC2, will be an invaluable resource in the transcriptional characterization of hKCC2, since this is evidently the only cell line that expresses KCC2 (Williams et al. (1999) *J Biol Chem* 274:12656–12664).

REFERENCES

The publications and other materials listed below and/or set forth by author and date in the text above to illuminate the background of the invention, and in particular cases, to provide additional details respecting the practice, are incorporated herein by reference. Materials used herein include but are not limited to the following listed references.

Adelman et al. (1983) *DNA* 2:183.
Altschul et al. (1990) *J Mol Biol* 215:403–410.
Altschul et al. (1 997) *Nucleic Acids Res* 25(17):3389–3402.
Amlal et al. (1994) *Am J Physiol Cell Physiol* 267:C1 607–1625.
Armour et al. (1996) *Ann Hum Genet* 60:11 B20.
Beaucage et al. (1981) *Tetrahedron Letters* 22:1859–1862.
Bize et al. (1999) *Am J Physiol* 277:C926–936.
Brookes (1999) *Gene* 234(2):177–186.
Brugnara et al. (1986) *Science* 232(4748):388–390.
Callenbach & Brouwer (1997) *Clin Neurol Neurosurg* 99(3):159–171.
Capecchi (1989) *Science* 244(4910):1288–1292.
Casaubon et al. (1996) *Am J Hum Genet* 58(1):28–34.
Chien et al. (1991) *Proc Natl Acad Sci USA* 88:9578–9582.
Clayton et al. (1998) *Brain Res Dev Brain Res* 109(2):281–292.
Conner et al. (1983) *Proc Natl Acad Sci USA* 80:278.
De Franceschi et al. (1996) *Blood* 88(7):2738–2744.
Delpire et al. (1994) *J Biol Chem* 269:25, 677–25, 683.
Delpire et al. (1999) *Nat Genet* 22(2):192–195.
Delpire & Lovinger (2000) *J Neurosci* 26:1148.
Ding et al. (1997) *J Biol Chem* 272(44):28142–28148.
Di Stefano et al. (1998) *Cell Physiol Biochem* 8:89–105.
Elmslie et al. (1997) *Hum Mol Genet*6(8):1329–1334.
Forlino et al. (1999) *J Biol Chem* 274(53):37923–37931.
Gamba et al. (1993) *Proc Natl Acad Sci USA* 90(7):2749–2753.
Gamba et al. (1994) *J Biol Chem* 269:17713–17722.
Garay et al. (1988) *Mol Pharmacol* 33:696–701.
Gatti et al. (1988) *Nature* 336:577–580.
Gebhardt et al. (1999) *J Biol Chem* 274:13176–13180.
Gillen et al. (1996) *J Biol Chem* 271(27):16237–16244.
Gimenez et al. (1999) *FASEB J* 13:A64.
Greger & Schlatter (1983) *Pflugers Arch* 396:325–334.
Gribskov et al. (1986) *Nuc Acids Res* 14(1):327–334.
Grunder et al. (1992) *Nature* 360(6406):759–762.
Hara et al. (1992) *Neurosci Lett* 143:135–138.
Hardt et al. (2000) *J Comp Pathol* 122:43–53.
Harlow & Lane (1988) *Antibodies: A Laboratory Manual*, Cold Spring Harbor Laboratory Press, Cold Spring Harbor, N.Y.
Hiki et.al. (1999) *J Biol Chem* 274: 10661–10667.
Hochman et al. (1995) *Science* 270(5233):99–102.
Holtzman et al. (1998) *Am J Physiol* 275(4 Pt 2):F550–564.
Hubner et al. (2001) *Mech Dev* 102:267–269.
Hurst et al. (1992) *Am J Physiol* 263(2 Pt 2):F262–267.
Isenring et al. (1998) *J Gen Physiol* 112(5):549–558.
Jacoby (1999) *Am J Physiol* 277:C684–692.
Ji et al. (1998) *Am J Physiol* 275(5 Pt 1):C1182–1190.
Karadesh & Delpire (2001) *J Neurophysiol* 85:995–997.
Kelley et al. (2000) *J Membr Biol* 178:31–41.
Kestila et al. (1998) *Mol Cell* 1(4), 575–582.
Kissel et al. (2000) *EMBO J* 19(6):1312–1326.
Krapivinsky et al. (1994) *Cell* 76(3):439–448.
Kuwahara et al. (1997) *Biochemistry* 36:13973–13978.
Kyte et al. (1982) *J Mol Biol* 157:105.
Lafreniere et al. (1997) *Nat Genet* 15(3):298–302.
Landgren et al. (1988) *Science* 241:1007.
Landgren et al. (1988) *Science* 242:229–237.
Lauf et al. (1992) *Am J Physiol* 263:C917–932.
Liapis et al. (1998) *Am J Physiol* 275(6 Pt 1):C1432–1437.
Liman et al. (1992) *Neuron* 9:861–871.
Loghman-Adham et al. (1997) *Kidney Int* 52(1):229–239.
Lopes et al. (1988) *Proc Natl Acad Sci USA* 85(8):2873–2877.
Lu et al. (1999) *J Neurobiology* 39:558–568.
Luyckx et al. (1999) *Proc Natl Acad Sci USA* 96(21):12174–12179.
Lytle (1998) *Am J Physiol* 274:C 1002–1010.
Makalowski & Boguski (1998) *Proc Natl Acad Sci USA* 95:9407B9412.
Maniatis et. al. (1982) in *Molecular Cloning: A Laboratory Manual*, Cold Spring Harbor Laboratory Press, New York, N.Y. Martinez Murillo et al. (1999) *Neurology* 53(1):50–56.
McPherson et al., eds. (1991) *PCR. A Practical Approach*, IRL Press, Oxford University Press, New York, N.Y.
Mercado et al. (2000) *J Biol Chem* 275:30326–3034.
Miles (1999) *Nature* 397(6716):215–216.
Misgeld et al. (1986) *Science* 232(4756):1413–141.
Mount et al. (1997) *J Membr Biol* 158:177–186.
Mount et al. (1998) *J Exp Biol* 201:2091 B2102.
Mount et al. (1999) *J Biol Chem* 274:16355–16362.
Needleman et al. (1970) *J Mol Biol* 48:443.
Neelands et al. (1998) *J Neurosci* 18(13):4993–5007.
Neelands et al. (1999) *J Neurosci* 19(16):7057–7065.
Neubauer et al. (1998) *Neurology* 51 (6):1608–1612.
Orita et al. (1989) *Proc Natl Acad Sci USA* 86(8):2766–2770.
Payne et al. (1990) *Am J Physiol* 259:C819–827.
Payne (1997) *Am J Physiol* 273:C1516–C1525.
Piontek et al. (1999) *J Neurochem* 73(1):139–146.
Pleasure & Lee (1993) *J Neurosci Res* 35(6):585–602.
Price (1993) *Blood Rev* 7:127–134.
Reed et al. (1999) *Am J Hum Genet* 64(5):1478–1480.
Rivera et al. (1999) *Nature* 397:251–255.
Rose et al. (1991) *Kidney Int* 39:336–352.
Saiki et al. (1985) *Bio/Technology* 3:1008–1012.
Sambrook et al. (1989) *Molecular Cloning: A Laboratory Manual*, Cold Spring Harbor Laboratory Press, Cold Spring Harbor, N.Y.
Sauer (1998) *Methods* 14(4):381–392.
Schoenherr et al. (1996) *Proc Natl Acad Sci USA* 93:9881–9886.
Schultz et al. (1998) *Proc Natl Acad Sci USA* 95:5857–5864.
Schultz et al. (2000) *Nuc Acids Res* 28:231–234.
Schwartz et al., (1979) *Nuc Acids Res* 6(2):745–755.
Seki et al. (1993) *J Clin Invest* 92(3):1229–1235.
Shimajiri et al. (1999) *FEBS Lett* 455:70–74.
Simon et al. (1996) *Nat Genet* 13(2):183–188.
Simon et al. (1996) *Nat Genet* 14:152–156.
Simon et al. (1997) *Nat Genet* 17:171–178.
Smith et al. (1981) *Adv Appl Math* 2:482.
Skradski et al. (1998) *Genomics* 49(2):188–192.
Stober et al. (2000) *Am J Hum Genet* 67:1201–1207.

Stoneking et al. (1991) *Am J Hum Genet* 48(2):370–382.
Su et al. (1999) *Am J Physiol* 277(5 Pt 1):C899–C912.
Thomas & Capecchi (1990) *Nature* 346(6287):847–850.
Thompson et al. (1994) *Nuc Acids Res* 22(22):4673–4680.
Timchenko & Caskey (1996) *FASEB J* 10(14):1589–1597.
Tomlinson et al. (1999) *Gastroenterology* 116(4):789–795.
Trask (1991) *Trends Genet* 7:149–154.
U.S. Pat. No. 4,196,265
U.S. Pat. No. 4,458,066
U.S. Pat. No. 4,554,101
U.S. Pat. No. 4,683,195
U.S. Pat. No. 4,683,202
U.S. Pat. No. 4,736,866
U.S. Pat. No. 4,769,331
U.S. Pat. No. 4,895,807
U.S. Pat. No. 4,965,188
U.S. Pat. No. 5,162,215
U.S. Pat. No. 5,234,933
U.S. Pat. No. 5,260,203
U.S. Pat. No. 5,279,833
U.S. Pat. No. 5,286,634
U.S. Pat. No. 5,326,902
U.S. Pat. No. 5,352,660
U.S. Pat. No. 5,399,346
U.S. Pat. No. 5,410,031
U.S. Pat. No. 5,441,875
U.S. Pat. No. 5,489,742
U.S. Pat. No. 5,550,316
U.S. Pat. No. 5,573,933
U.S. Pat. No. 5,580,722
U.S. Pat. No. 5,614,396
U.S. Pat. No. 5,625,125
U.S. Pat. No. 5,627,158
U.S. Pat. No. 5,641,484
U.S. Pat. No. 5,643,567
U.S. Pat. No. 5,645,999
U.S. Pat. No. 5,646,008
U.S. Pat. No. 5,648,061
U.S. Pat. No. 5,651,964
U.S. Pat. No. 5,734,033
U.S. Pat. No. 5,739,278
U.S. Pat. No. 5,741,957
U.S. Pat. No. 5,786,152
U.S. Pat. No. 5,834,228
U.S. Pat. No. 5,837,479
U.S. Pat. No. 5,846,720
U.S. Pat. No. 5,849,578
U.S. Pat. No. 5,872,011
van den Pol et al. (1996) *J Neurosci* 16(13):4283–4292.
Vandorpe et al. (1998) *J Biol Chem* 273(34):21542–21553.
Verma et al. (1988) *Human Chromosomes: A Manual of Basic Techniques*, Pergamon Press, New York, N.Y.
Wang et al. (1998) *Science* 280(5366):1077–1082.
Wethmur & Davidson (1968) *J Mol Biol* 31:349–370.
White et al. (1997) *Nat Genet* 17(4):404–410.
Wick et al. (1996) *Oncogene* 12(5):973–978.
Williams et al. (1999) *J Biol Chem* 274(18):12656–12664.
WO 84/03564
WO 93/25521
WO 96/34288
WO 98/29431
WO 98/37198
WO 98/53067
Yuan et al. (1999) *Hum Mutat* 14(5):440–446.

It will be understood that various details of the invention can be changed without departing from the scope of the invention. Furthermore, the foregoing description is for the purpose of illustration only, and not for the purpose of limitation—the invention being defined by the claims.

---

What is claimed is:

1. An isolated and purified nucleic acid molecule encoding a biologically active KCC3a potassium-chloride cotransporter polypeptide selected from the group consisting of:
   (a) a biologically active KCC3a polypeptide encoded by a nucleic acid sequence as set forth in SEQ ID NO 15;
   (b) a biologically active KCC3a polypeptide comprising an amino acid sequence at least 95% identical to SEQ ID NO: 16 encoded by a nucleic acid molecule comprising a nucleic acid sequence having 90% or greater sequence identity to SEQ ID NO 15;
   (c) a biologically active KCC3a polypeptide having an amino acid sequence as set forth in SEQ ID NO 16; and
   (d) a biologically active KCC3a polypeptide comprising an amino acid sequence at least 95% identical to SEQ ID NO: 16,
wherein the biologically active KCC3a polypeptide has potassium-chloride cotransporter activity.

2. The nucleic acid molecule of claim 1, further defined as under the control of a promoter.

3. An isolated recombinant host cell comprising the nucleic acid molecule of claim 1.

4. A recombinant vector comprising a nucleic acid molecule of claim 1.

5. The recombinant vector of claim 4, wherein the recombinant vector is a recombinant expression vector.

6. The recombinant vector of claim 4, further defined as comprising at least a 100 nucleotide long contiguous stretch of a polynucleic acid sequence as set forth in nucleotides 165–434 of SEQ ID NO: 15.

7. An assay kit for detecting the presence, in biological samples, of a nucleic acid encoding a KCC3a potassium-chloride cotransporter polypeptide, the kit comprising a first container that contains a nucleic acid molecule identical or fully complementary to a segment of at least ten contiguous nucleotide bases of nucleotides 1–434 of SEQ ID NO: 15.

8. An isolated and purified nucleic acid molecule encoding a biologically active KCC3a potassium-chloride cotransporter polypeptide selected from the group consisting of:
   (a) a biologically active KCC3a polypeptide having an amino acid sequence as set forth in SEQ ID NO 16; and
   (b) a biologically active KCC3a polypeptide comprising an amino acid sequence at least 95% identical to SEQ ID NO: 16,
wherein the biologically active KCC3a polypeptide has potassium-chloride cotransporter activity.

9. The nucleic acid molecule of claim 8, wherein the nucleic acid molecule is operatively linked to a promoter.

10. A recombinant host cell comprising the nucleic acid molecule of claim 8.

11. A recombinant vector comprising a nucleic acid molecule of claim 8.

12. The recombinant vector of claim 11, wherein the recombinant vector is a recombinant expression vector.

13. The recombinant vector of claim 11, wherein the recombinant vector comprises at least a 100 nucleotide long contiguous stretch of a polynucleic acid sequence as essentially set forth in nucleotides 165–434 of SEQ ID NO: 15.

* * * * *

SEQUENCE LISTING

<160> NUMBER OF SEQ ID NOS: 131

<210> SEQ ID NO 1
<211> LENGTH: 5239
<212> TYPE: DNA
<213> ORGANISM: Homo sapiens
<220> FEATURE:
<221> NAME/KEY: CDS
<222> LOCATION: (5)..(3253)
<220> FEATURE:
<221> NAME/KEY: misc_feature
<222> LOCATION: (161)
<223> OTHER INFORMATION: n=a or c, Xaa=Leu or Ile
<220> FEATURE:
<221> NAME/KEY: misc_feature
<222> LOCATION: (260)
<223> OTHER INFORMATION: n=a or t, Xaa=Leu or Ile
<220> FEATURE:
<221> NAME/KEY: misc_feature
<222> LOCATION: (3086)
<223> OTHER INFORMATION: n=a or c, Xaa=Leu or Ile

<400> SEQUENCE: 1

```
agcc atg ccc acg aac ttt acg gtg gtg ccc gtg gag gct cac gcc gac      49
     Met Pro Thr Asn Phe Thr Val Val Pro Val Glu Ala His Ala Asp
     1               5                   10                  15 ggc ggc ggg gac gag act gcc gag cgg acg gag gct ccg ggc acc ccc       97
Gly Gly Gly Asp Glu Thr Ala Glu Arg Thr Glu Ala Pro Gly Thr Pro
                20                  25                  30
```

-continued

```
gag ggc ccc gag ccc gag cgc ccc agc ccg gga gat gga aat cca aga       145
Glu Gly Pro Glu Pro Glu Arg Pro Ser Pro Gly Asp Gly Asn Pro Arg
             35                  40                  45 gaa aac agc cca ttc ntc aac aat gtc gag gtg gaa caa gag agc ttc       193
Glu Asn Ser Pro Phe Xaa Asn Asn Val Glu Val Glu Gln Glu Ser Phe
 50                  55                  60 ttt gaa ggg aag aac atg gca ctt ttc gag gag gag atg gac agt aac       241
Phe Glu Gly Lys Asn Met Ala Leu Phe Glu Glu Glu Met Asp Ser Asn
 65                  70                  75 ccc atg gtg tcc tcg ctg ntc aac aag ctg gcc aac tac acc aac ctg       289
Pro Met Val Ser Ser Leu Xaa Asn Lys Leu Ala Asn Tyr Thr Asn Leu
 80                  85                  90                  95 agc cag ggc gtg gtg gag cac gag gag gac gag gag agc cgg cgg cgg       337
Ser Gln Gly Val Val Glu His Glu Glu Asp Glu Glu Ser Arg Arg Arg
                100                 105                 110 gag gcc aag gct ccg cgc atg ggc acc ttc atc ggc gtc tac ctg ccg       385
Glu Ala Lys Ala Pro Arg Met Gly Thr Phe Ile Gly Val Tyr Leu Pro
            115                 120                 125 tgc ctg cag aac atc ctg ggc gtc atc ctc ttc ctg cgc ctg acg tgg       433
Cys Leu Gln Asn Ile Leu Gly Val Ile Leu Phe Leu Arg Leu Thr Trp
        130                 135                 140 atc gtg ggg gtg gct ggt gtc ctg gag tcc ttc ctc atc gtg gcc atg       481
Ile Val Gly Val Ala Gly Val Leu Glu Ser Phe Leu Ile Val Ala Met
145                 150                 155 tgc tgc aca tgt aca atg ctg acc gcc att tcc atg agt gcg atc gct       529
Cys Cys Thr Cys Thr Met Leu Thr Ala Ile Ser Met Ser Ala Ile Ala
160                 165                 170                 175 acc aac ggt gtg gtc cca gct ggc ggg tcc tac tac atg ata tcg cgc       577
Thr Asn Gly Val Val Pro Ala Gly Gly Ser Tyr Tyr Met Ile Ser Arg
                180                 185                 190 tcg ctg gga ccc gag ttt gga ggc gct gtc ggc ctc tgc ttc tac ctg       625
Ser Leu Gly Pro Glu Phe Gly Gly Ala Val Gly Leu Cys Phe Tyr Leu
            195                 200                 205 ggc acg acg ttt gca ggg gcc atg tat att ttg ggg acc atc gag att       673
Gly Thr Thr Phe Ala Gly Ala Met Tyr Ile Leu Gly Thr Ile Glu Ile
        210                 215                 220 ttt ctg acg tac atc tcc ccg ggt gcg gcc atc ttc cag gcg gag gct       721
Phe Leu Thr Tyr Ile Ser Pro Gly Ala Ala Ile Phe Gln Ala Glu Ala
225                 230                 235 gca ggt ggc gag gcg gcc gcc atg ctg cac aac atg cgt gtg tac ggc       769
Ala Gly Gly Glu Ala Ala Ala Met Leu His Asn Met Arg Val Tyr Gly
240                 245                 250                 255 acg tgc acg ctc gtg ctc atg gcc ctg gtg gtc ttc gtg ggc gtc aag       817
Thr Cys Thr Leu Val Leu Met Ala Leu Val Val Phe Val Gly Val Lys
                260                 265                 270 tat gtc aac aag ctg gcg ctg gtc ttc ctg gcc tgc gtc gtg ctg tcc       865
Tyr Val Asn Lys Leu Ala Leu Val Phe Leu Ala Cys Val Val Leu Ser
            275                 280                 285 atc ctg gcc atc tat gcc ggc gtc atc aag tct gcc ttc gac ccc ccg       913
Ile Leu Ala Ile Tyr Ala Gly Val Ile Lys Ser Ala Phe Asp Pro Pro
        290                 295                 300 gac atc ccg gtc tgc ctc ctg ggg aac cgc acg ctg tca cgg cgc agc       961
Asp Ile Pro Val Cys Leu Leu Gly Asn Arg Thr Leu Ser Arg Arg Ser
305                 310                 315 ttc gat gcc tgc gtc aag gcc tac ggc atc cac aac aac tca gcc acc      1009
Phe Asp Ala Cys Val Lys Ala Tyr Gly Ile His Asn Asn Ser Ala Thr
320                 325                 330                 335 tcc gcg ctc tgg ggc ctc ttc tgc aac ggc tcc cag ccc agc gcc gcc      1057
Ser Ala Leu Trp Gly Leu Phe Cys Asn Gly Ser Gln Pro Ser Ala Ala
                340                 345                 350
```

```
tgt gac gag tac ttc atc cag aac aac gtc acc gaa atc cag ggc atc      1105
Cys Asp Glu Tyr Phe Ile Gln Asn Asn Val Thr Glu Ile Gln Gly Ile
            355                 360                 365 ccg ggc gcg gcc agt ggt gtc ttc ctg gag aac ctg tgg agt acg tac      1153
Pro Gly Ala Ala Ser Gly Val Phe Leu Glu Asn Leu Trp Ser Thr Tyr
        370                 375                 380 gcg cac gcg ggg gcg ttt gtg gag aag aaa ggt gtg ccc tcg gtg ccc      1201
Ala His Ala Gly Ala Phe Val Glu Lys Lys Gly Val Pro Ser Val Pro
    385                 390                 395 gtg gca gag gag agc cgt gcc agc aca ctg ccc tac gtg ctc acc gac      1249
Val Ala Glu Glu Ser Arg Ala Ser Thr Leu Pro Tyr Val Leu Thr Asp
400                 405                 410                 415 atc gcg gcc tcc ttc acc ctg ctg gtt ggc atc tac ttc cct tcc gtg      1297
Ile Ala Ala Ser Phe Thr Leu Leu Val Gly Ile Tyr Phe Pro Ser Val
                420                 425                 430 acc ggt atc atg gcg ggt tca aac cgg tcc ggg gac ctc aag gat gca      1345
Thr Gly Ile Met Ala Gly Ser Asn Arg Ser Gly Asp Leu Lys Asp Ala
            435                 440                 445 cag aag tcc atc ccc acg ggg acc atc ctg gcc ata gtg acg acg tct      1393
Gln Lys Ser Ile Pro Thr Gly Thr Ile Leu Ala Ile Val Thr Thr Ser
        450                 455                 460 ttc atc tat ctc tcc tgc att gtg ctg ttt ggg gcc tgc att gaa ggc      1441
Phe Ile Tyr Leu Ser Cys Ile Val Leu Phe Gly Ala Cys Ile Glu Gly
    465                 470                 475 gtg gtc tta cga gat aag ttc ggg gag gcc ctg cag ggg aac ctg gtc      1489
Val Val Leu Arg Asp Lys Phe Gly Glu Ala Leu Gln Gly Asn Leu Val
480                 485                 490                 495 atc ggc atg ctg gcc tgg ccc tcc ccc tgg gtc atc gtc atc ggc tcc      1537
Ile Gly Met Leu Ala Trp Pro Ser Pro Trp Val Ile Val Ile Gly Ser
                500                 505                 510 ttc ttc tcc acc tgc ggt gcc ggc ctg cag acc ctc acg ggg gca ccg      1585
Phe Phe Ser Thr Cys Gly Ala Gly Leu Gln Thr Leu Thr Gly Ala Pro
            515                 520                 525 cgc cta ctg cag gcc att gcc cgt gac ggc atc gtc ccc ttc ctg cag      1633
Arg Leu Leu Gln Ala Ile Ala Arg Asp Gly Ile Val Pro Phe Leu Gln
        530                 535                 540 gtg ttt ggc cac ggg aag gcc aac ggg gag ccc acg tgg gcg ctg ctg      1681
Val Phe Gly His Gly Lys Ala Asn Gly Glu Pro Thr Trp Ala Leu Leu
    545                 550                 555 ctg aca gtc ctc atc tgc gag act ggc atc ctc atc gcc tct ctg gac      1729
Leu Thr Val Leu Ile Cys Glu Thr Gly Ile Leu Ile Ala Ser Leu Asp
560                 565                 570                 575 agc gtg gcc ccg atc ctc tcc atg ttc ttc ctc atg tgc tac ctg ttc      1777
Ser Val Ala Pro Ile Leu Ser Met Phe Phe Leu Met Cys Tyr Leu Phe
                580                 585                 590 gtg aac ctg gcc tgc gcc gtg cag acc ctg cta cgt acc ccc aac tgg      1825
Val Asn Leu Ala Cys Ala Val Gln Thr Leu Leu Arg Thr Pro Asn Trp
            595                 600                 605 cgt cca cgc ttc aag ttc tac cac tgg acc ctg tcc ttt ctg ggt atg      1873
Arg Pro Arg Phe Lys Phe Tyr His Trp Thr Leu Ser Phe Leu Gly Met
        610                 615                 620 agc ctg tgc ctg gcg ctg atg ttc atc tgc tcc tgg tac tac gcg ctg      1921
Ser Leu Cys Leu Ala Leu Met Phe Ile Cys Ser Trp Tyr Tyr Ala Leu
    625                 630                 635 tcc gcc atg ctc atc gct ggc tgc atc tac aag tac atc gag tac cgc      1969
Ser Ala Met Leu Ile Ala Gly Cys Ile Tyr Lys Tyr Ile Glu Tyr Arg
640                 645                 650                 655 ggg gcc gag aag gag tgg ggc gat ggc atc cgt ggc cta tcc ctg aac      2017
Gly Ala Glu Lys Glu Trp Gly Asp Gly Ile Arg Gly Leu Ser Leu Asn
                660                 665                 670
```

```
gcc gcc cgc tac gcc ctg ctg cgc gtg gag cac ggt ccc ccc cac acc    2065
Ala Ala Arg Tyr Ala Leu Leu Arg Val Glu His Gly Pro Pro His Thr
        675                 680                 685 aag aac tgg agg ccc cag gtg ctg gtg atg ctg aac ctg gac gcg gag    2113
Lys Asn Trp Arg Pro Gln Val Leu Val Met Leu Asn Leu Asp Ala Glu
    690                 695                 700 cag gcc gtg aag cac ccc cgc ctg ctg tcc ttc acg tcg cag ctg aag    2161
Gln Ala Val Lys His Pro Arg Leu Leu Ser Phe Thr Ser Gln Leu Lys
705                 710                 715 gcc ggc aag ggc ctg acc atc gtg ggc tcg gtg ctg gag ggg acg tac    2209
Ala Gly Lys Gly Leu Thr Ile Val Gly Ser Val Leu Glu Gly Thr Tyr
720                 725                 730                 735 ctg gac aag cac atg gag gct cag cgg gcc gag gag aac ata cgg tcc    2257
Leu Asp Lys His Met Glu Ala Gln Arg Ala Glu Glu Asn Ile Arg Ser
            740                 745                 750 cta atg agc aca gag aag acc aag ggc ttc tgc cag ctg gtg gtc tcg    2305
Leu Met Ser Thr Glu Lys Thr Lys Gly Phe Cys Gln Leu Val Val Ser
        755                 760                 765 tcc agc ctg cgg gat ggc atg tcc cac ctg atc cag tcg gcc ggc ctg    2353
Ser Ser Leu Arg Asp Gly Met Ser His Leu Ile Gln Ser Ala Gly Leu
    770                 775                 780 ggc ggc ctg aag cac aac acg gtg ctc atg gcc tgg ccc gca tcc tgg    2401
Gly Gly Leu Lys His Asn Thr Val Leu Met Ala Trp Pro Ala Ser Trp
785                 790                 795 aag cag gag gac aac ccc ttc tcc tgg aag aac ttt gta gac acc gtc    2449
Lys Gln Glu Asp Asn Pro Phe Ser Trp Lys Asn Phe Val Asp Thr Val
800                 805                 810                 815 cgc gac acc acc gcc gcg cac cag gct ctg ctg gtg gcc aag aac gtc    2497
Arg Asp Thr Thr Ala Ala His Gln Ala Leu Leu Val Ala Lys Asn Val
            820                 825                 830 gac tcg ttt ccg caa aac cag gag cgc ttc ggc ggg ggc cac atc gac    2545
Asp Ser Phe Pro Gln Asn Gln Glu Arg Phe Gly Gly Gly His Ile Asp
        835                 840                 845 gtg tgg tgg atc gtg cac gac ggc ggc atg ctc atg ctg ctg ccc ttc    2593
Val Trp Trp Ile Val His Asp Gly Gly Met Leu Met Leu Leu Pro Phe
    850                 855                 860 ctg ctg cgc cag cac aag gtg tgg agg aag tgc cgg atg cgt atc ttc    2641
Leu Leu Arg Gln His Lys Val Trp Arg Lys Cys Arg Met Arg Ile Phe
865                 870                 875 acc gtg gcc cag gtg gac gac aac agc atc cag atg aag aag gac ctg    2689
Thr Val Ala Gln Val Asp Asp Asn Ser Ile Gln Met Lys Lys Asp Leu
880                 885                 890                 895 cag atg ttc ttg tat cac ttg cgc atc agc gcc gag gtg gag gtg gtg    2737
Gln Met Phe Leu Tyr His Leu Arg Ile Ser Ala Glu Val Glu Val Val
            900                 905                 910 gag atg gtt gaa aac gac ata tct gct ttc acc tac gag agg aca cta    2785
Glu Met Val Glu Asn Asp Ile Ser Ala Phe Thr Tyr Glu Arg Thr Leu
        915                 920                 925 atg atg gag cag agg tcg cag atg ctg aag cag atg cag ctg tcc aag    2833
Met Met Glu Gln Arg Ser Gln Met Leu Lys Gln Met Gln Leu Ser Lys
    930                 935                 940 aac gag cag gag cga gag gcc cag ctg atc cac gac agg aac acc gcg    2881
Asn Glu Gln Glu Arg Glu Ala Gln Leu Ile His Asp Arg Asn Thr Ala
945                 950                 955 tcc cac acc gcg gcg gca gcc agg acc caa gcg ccg cct acg cca gac    2929
Ser His Thr Ala Ala Ala Ala Arg Thr Gln Ala Pro Pro Thr Pro Asp
960                 965                 970                 975 aag gtg cag atg acc tgg acc agg gag aag ctg atc gct gag aag tac    2977
Lys Val Gln Met Thr Trp Thr Arg Glu Lys Leu Ile Ala Glu Lys Tyr
            980                 985                 990
```

```
agg agc aga gac acc agc cta tcc ggt ttc aaa gac ctc ttc agc atg    3025
Arg Ser Arg Asp Thr Ser Leu Ser Gly Phe Lys Asp Leu Phe Ser Met
            995                 1000                1005 aag ccg gac cag tcc aac gtc agg cgg atg cac acg gct gtg aag ctc    3073
Lys Pro Asp Gln Ser Asn Val Arg Arg Met His Thr Ala Val Lys Leu
        1010                1015                1020 aat ggc gtc gtc ntc aac aag tcc cag gat gcg cag ctg gtc ctg ctc    3121
Asn Gly Val Val Xaa Asn Lys Ser Gln Asp Ala Gln Leu Val Leu Leu
    1025                1030                1035 aac atg cca ggt cct ccc aaa aac cgg cag gga gac gag aac tac atg    3169
Asn Met Pro Gly Pro Pro Lys Asn Arg Gln Gly Asp Glu Asn Tyr Met
1040            1045                1050                1055 gag ttt ctt gaa gtc ctg acc gag ggg ctg aac aga gtc ctc ctg gtc    3217
Glu Phe Leu Glu Val Leu Thr Glu Gly Leu Asn Arg Val Leu Leu Val
                1060                1065                1070 agg ggt ggc ggc cgg gag gtg atc acc atc tac tcc taatgcccaa         3263
Arg Gly Gly Gly Arg Glu Val Ile Thr Ile Tyr Ser
            1075                1080
```

| | |
|---|---|
| cagcatcacg gcactctggg acaggcacgg aggacggcgt gggcagcctg ggcctgggct | 3323 |
| tggcccaggg aaccagacgg cagacacacc tgtcccccag tgatgccacc caagctgccc | 3383 |
| atgggcttc ctacggaagt tctaggccc gtcacctagg gctctcctgt tcagccttaa | 3443 |
| caggctcaga aaatcagggc gtggctggac gatttccttg catctgaggg cagacgctgc | 3503 |
| taccggagtg acctggacgt ggccagatct tctcgcaggt cacaagaagc cagtgagccc | 3563 |
| ttgccttggt ttctggaagt tctttttcctt ggctggattt acccagtggt taggttgcat | 3623 |
| ttctacccca tccagaacat tcttggaaga gcacccggag ctgaagctgt ccctgatgat | 3683 |
| gaaggtgaaa cgtcagccct ggccatggct ccgctcaggg ccccggtcac ctccgagtca | 3743 |
| ctctgttcct tgactgtctt tgtgtttctg tacctcaagg cactgaagct ggaggactct | 3803 |
| gtccatgccc gtgtcaccct cgtgtgggag cctctgggct cggcaggtcc acatttcatg | 3863 |
| agctgaggcg tgggccaggg ccatctggaa agggaactcg gcttttccag aacgtggtgg | 3923 |
| atcatctgtc gggtgtgtgg tgaacacgtt cagttcatca gggcctacgc tccgggaagg | 3983 |
| ggcccccagc tgtggctctg ccatgccggg ctgtgtttgc agctgtccga gtctccatcc | 4043 |
| acctttagaa aaccagtcac ttcttttcat aagcactgac agggcccagc ccacagccac | 4103 |
| aggtgcgatc agtgcctcac gcaggcaaat gcactgaaac ccaggggcac acgcgcgcag | 4163 |
| agtgaacagt gagttccccc gacagcccac gacagccagg actgccctcc ccaccccacc | 4223 |
| ccaccccagg agcacggcac acagttcagc ctctgagctg gctcacacgt gccatcccca | 4283 |
| ccccggtgct ccaggaagg aggacacgga cccgacgtgg gaggtcctca ggcagcagtg | 4343 |
| gcgcctggtg tcaggtctgt ctggctgagt cccgggcgtc ccctgccatg gcctgtgcct | 4403 |
| tgcatggagg cggcggtggc actgaagaga tagcttttcaa gggcccaaca ctttgcactt | 4463 |
| cggctggctg tgagtttctg ctttgtaggt tgtggtcaca tttgcaggct gcgggcagtg | 4523 |
| gcaccgactt gggcctccct ttctatgtgg catatttatt tatttaaaca ccccagggag | 4583 |
| ttacgtggta acaaggttgt ccataaagag gttgcttcta tatactagag gccccagatg | 4643 |
| gcaggccttg ggctacgtct ggcttgcatg gtctcccaag ggaatcaacc ccatcaacaa | 4703 |
| agttcaaatc ggggcagagg ctgcacttgt gcccccagat gtttctgagg agccagatta | 4763 |
| gggctggcat tgctgtagag tgacggctgc tgcccagagc gtgtcccaga catcacagcg | 4823 |
| gggctcagca gttcccacag cctctgcctg ccttggctaa gcatgagtta agcagcaaaa | 4883 |
| cgctcctcca tgtctggatg gggccggcag gtcctgtgtc ccctgcacct ggaggagagc | 4943 |

-continued

```
aggctagagg cacagcggcc acatggtgct ggctctgaac gttggttggt ggctggaaaa    5003
cagccctgct tctgagggcc gctcagttct gcacacgaaa ccacctcctg agggctcagc    5063 tctgccccg ccctgggctg cagcctctgc acgcaagcac caggcatcct ttgtgttgtc     5123
aactccgtgt aaccagtaac tacagccatt tacaattgac tccgtttcct tttgtaggtt    5183
tccctgtctg tctgtgttag tagaaaaata aaatcctatg aaatctgaaa aaaaaa        5239
```

<210> SEQ ID NO 2
<211> LENGTH: 1083
<212> TYPE: PRT
<213> ORGANISM: Homo sapiens
<220> FEATURE:
<221> NAME/KEY: misc_feature
<222> LOCATION: (53)
<223> OTHER INFORMATION: Xaa=Leu or Ile
<220> FEATURE:
<221> NAME/KEY: misc_feature
<222> LOCATION: (86)
<223> OTHER INFORMATION: Xaa=Leu or Ile
<220> FEATURE:
<221> NAME/KEY: misc_feature
<222> LOCATION: (1028)
<223> OTHER INFORMATION: Xaa=Leu or Ile

<400> SEQUENCE: 2

```
Met Pro Thr Asn Phe Thr Val Val Pro Val Glu Ala His Ala Asp Gly
 1               5                  10                  15

Gly Gly Asp Glu Thr Ala Glu Arg Thr Glu Ala Pro Gly Thr Pro Glu
            20                  25                  30

Gly Pro Glu Pro Glu Arg Pro Ser Pro Gly Asp Gly Asn Pro Arg Glu
        35                  40                  45

Asn Ser Pro Phe Xaa Asn Asn Val Glu Val Gln Glu Ser Phe Phe
    50                  55                  60

Glu Gly Lys Asn Met Ala Leu Phe Glu Glu Met Asp Ser Asn Pro
65                  70                  75                  80

Met Val Ser Ser Leu Xaa Asn Lys Leu Ala Asn Tyr Thr Asn Leu Ser
                85                  90                  95

Gln Gly Val Val Glu His Glu Glu Asp Glu Glu Ser Arg Arg Arg Glu
            100                 105                 110

Ala Lys Ala Pro Arg Met Gly Thr Phe Ile Gly Val Tyr Leu Pro Cys
        115                 120                 125

Leu Gln Asn Ile Leu Gly Val Ile Leu Phe Leu Arg Leu Thr Trp Ile
    130                 135                 140

Val Gly Val Ala Gly Val Leu Glu Ser Phe Leu Ile Val Ala Met Cys
145                 150                 155                 160

Cys Thr Cys Thr Met Leu Thr Ala Ile Ser Met Ser Ala Ile Ala Thr
                165                 170                 175

Asn Gly Val Val Pro Ala Gly Gly Ser Tyr Tyr Met Ile Ser Arg Ser
            180                 185                 190

Leu Gly Pro Glu Phe Gly Gly Ala Val Gly Leu Cys Phe Tyr Leu Gly
        195                 200                 205

Thr Thr Phe Ala Gly Ala Met Tyr Ile Leu Gly Thr Ile Glu Ile Phe
    210                 215                 220

Leu Thr Tyr Ile Ser Pro Gly Ala Ala Ile Phe Gln Ala Glu Ala Ala
225                 230                 235                 240

Gly Gly Glu Ala Ala Ala Met Leu His Asn Met Arg Val Tyr Gly Thr
                245                 250                 255
```

-continued

```
Cys Thr Leu Val Leu Met Ala Leu Val Val Phe Val Gly Val Lys Tyr
            260                 265                 270

Val Asn Lys Leu Ala Leu Val Phe Leu Ala Cys Val Val Leu Ser Ile
        275                 280                 285

Leu Ala Ile Tyr Ala Gly Val Ile Lys Ser Ala Phe Asp Pro Pro Asp
    290                 295                 300

Ile Pro Val Cys Leu Leu Gly Asn Arg Thr Leu Ser Arg Arg Ser Phe
305                 310                 315                 320

Asp Ala Cys Val Lys Ala Tyr Gly Ile His Asn Asn Ser Ala Thr Ser
                325                 330                 335

Ala Leu Trp Gly Leu Phe Cys Asn Gly Ser Gln Pro Ser Ala Ala Cys
            340                 345                 350

Asp Glu Tyr Phe Ile Gln Asn Asn Val Thr Glu Ile Gln Gly Ile Pro
        355                 360                 365

Gly Ala Ala Ser Gly Val Phe Leu Glu Asn Leu Trp Ser Thr Tyr Ala
    370                 375                 380

His Ala Gly Ala Phe Val Glu Lys Lys Gly Val Pro Ser Val Pro Val
385                 390                 395                 400

Ala Glu Glu Ser Arg Ala Ser Thr Leu Pro Tyr Val Leu Thr Asp Ile
                405                 410                 415

Ala Ala Ser Phe Thr Leu Leu Val Gly Ile Tyr Phe Pro Ser Val Thr
            420                 425                 430

Gly Ile Met Ala Gly Ser Asn Arg Ser Gly Asp Leu Lys Asp Ala Gln
        435                 440                 445

Lys Ser Ile Pro Thr Gly Thr Ile Leu Ala Ile Val Thr Thr Ser Phe
    450                 455                 460

Ile Tyr Leu Ser Cys Ile Val Leu Phe Gly Ala Cys Ile Glu Gly Val
465                 470                 475                 480

Val Leu Arg Asp Lys Phe Gly Glu Ala Leu Gln Gly Asn Leu Val Ile
                485                 490                 495

Gly Met Leu Ala Trp Pro Ser Pro Trp Val Ile Val Ile Gly Ser Phe
            500                 505                 510

Phe Ser Thr Cys Gly Ala Gly Leu Gln Thr Leu Thr Gly Ala Pro Arg
        515                 520                 525

Leu Leu Gln Ala Ile Ala Arg Asp Gly Ile Val Pro Phe Leu Gln Val
    530                 535                 540

Phe Gly His Gly Lys Ala Asn Gly Glu Pro Thr Trp Ala Leu Leu Leu
545                 550                 555                 560

Thr Val Leu Ile Cys Glu Thr Gly Ile Leu Ile Ala Ser Leu Asp Ser
                565                 570                 575

Val Ala Pro Ile Leu Ser Met Phe Phe Leu Met Cys Tyr Leu Phe Val
            580                 585                 590

Asn Leu Ala Cys Ala Val Gln Thr Leu Leu Arg Thr Pro Asn Trp Arg
        595                 600                 605

Pro Arg Phe Lys Phe Tyr His Trp Thr Leu Ser Phe Leu Gly Met Ser
    610                 615                 620

Leu Cys Leu Ala Leu Met Phe Ile Cys Ser Trp Tyr Tyr Ala Leu Ser
625                 630                 635                 640

Ala Met Leu Ile Ala Gly Cys Ile Tyr Lys Tyr Ile Glu Tyr Arg Gly
                645                 650                 655

Ala Glu Lys Glu Trp Gly Asp Gly Ile Arg Gly Leu Ser Leu Asn Ala
            660                 665                 670
```

```
Ala Arg Tyr Ala Leu Leu Arg Val Glu His Gly Pro Pro His Thr Lys
        675                 680                 685

Asn Trp Arg Pro Gln Val Leu Val Met Leu Asn Leu Asp Ala Glu Gln
690                 695                 700

Ala Val Lys His Pro Arg Leu Leu Ser Phe Thr Ser Gln Leu Lys Ala
705                 710                 715                 720

Gly Lys Gly Leu Thr Ile Val Gly Ser Val Leu Glu Gly Thr Tyr Leu
                725                 730                 735

Asp Lys His Met Glu Ala Gln Arg Ala Glu Asn Ile Arg Ser Leu
        740                 745                 750

Met Ser Thr Glu Lys Thr Lys Gly Phe Cys Gln Leu Val Ser Ser
        755                 760                 765

Ser Leu Arg Asp Gly Met Ser His Leu Ile Gln Ser Ala Gly Leu Gly
770                 775                 780

Gly Leu Lys His Asn Thr Val Leu Met Ala Trp Pro Ala Ser Trp Lys
785                 790                 795                 800

Gln Glu Asp Asn Pro Phe Ser Trp Lys Asn Phe Val Asp Thr Val Arg
                805                 810                 815

Asp Thr Thr Ala Ala His Gln Ala Leu Leu Val Ala Lys Asn Val Asp
                820                 825                 830

Ser Phe Pro Gln Asn Gln Glu Arg Phe Gly Gly His Ile Asp Val
        835                 840                 845

Trp Trp Ile Val His Asp Gly Gly Met Leu Met Leu Leu Pro Phe Leu
        850                 855                 860

Leu Arg Gln His Lys Val Trp Arg Lys Cys Arg Met Arg Ile Phe Thr
865                 870                 875                 880

Val Ala Gln Val Asp Asp Asn Ser Ile Gln Met Lys Lys Asp Leu Gln
                885                 890                 895

Met Phe Leu Tyr His Leu Arg Ile Ser Ala Glu Val Glu Val Glu
                900                 905                 910

Met Val Glu Asn Asp Ile Ser Ala Phe Thr Tyr Glu Arg Thr Leu Met
        915                 920                 925

Met Glu Gln Arg Ser Gln Met Leu Lys Gln Met Gln Leu Ser Lys Asn
        930                 935                 940

Glu Gln Glu Arg Glu Ala Gln Leu Ile His Asp Arg Asn Thr Ala Ser
945                 950                 955                 960

His Thr Ala Ala Ala Arg Thr Gln Ala Pro Pro Thr Pro Asp Lys
                965                 970                 975

Val Gln Met Thr Trp Thr Arg Glu Lys Leu Ile Ala Glu Lys Tyr Arg
        980                 985                 990

Ser Arg Asp Thr Ser Leu Ser Gly Phe Lys Asp Leu Phe Ser Met Lys
        995                 1000                1005

Pro Asp Gln Ser Asn Val Arg Arg Met His Thr Ala Val Lys Leu Asn
        1010                1015                1020

Gly Val Val Xaa Asn Lys Ser Gln Asp Ala Gln Leu Val Leu Leu Asn
1025                1030                1035                1040

Met Pro Gly Pro Pro Lys Asn Arg Gln Gly Asp Glu Asn Tyr Met Glu
                1045                1050                1055

Phe Leu Glu Val Leu Thr Glu Gly Leu Asn Arg Val Leu Leu Val Arg
                1060                1065                1070

Gly Gly Gly Arg Glu Val Ile Thr Ile Tyr Ser
                1075                1080
```

-continued

```
<210> SEQ ID NO 3
<211> LENGTH: 4215
<212> TYPE: DNA
<213> ORGANISM: Homo sapiens
<220> FEATURE:
<221> NAME/KEY: CDS
<222> LOCATION: (165)..(3569)
<220> FEATURE:
<221> NAME/KEY: misc_feature
<222> LOCATION: (267)
<223> OTHER INFORMATION: n=c or a, Xaa=Leu or Ile
<220> FEATURE:
<221> NAME/KEY: misc_feature
<222> LOCATION: (1578)
<223> OTHER INFORMATION: n=c or a, Xaa=Leu or Ile
<220> FEATURE:
<221> NAME/KEY: misc_feature
<222> LOCATION: (3387)
<223> OTHER INFORMATION: n=c or a, Xaa=Leu or Ile

<400> SEQUENCE: 3
tgagtagaag tattcttagt tggggctttt tgtgtggtgt gaatcaaggt tattgaaatg      60
tgttattttt caagttatct tttgtattgc agtcaaaagt agctagcgta agaggaagat     120
tttgcgaggt tcccccact tttttgttc ttaaaaagaa caaa atg cat cct cca       176
                                              Met His Pro Pro
                                                1 gaa acc acc acc aag atg gct tca gtt cgg ttc atg gtg aca ccg aca      224
Glu Thr Thr Thr Lys Met Ala Ser Val Arg Phe Met Val Thr Pro Thr
  5                  10                  15                  20 aag atc gat gac att cca ggt ttg tca gac acc agt ccg gac ntc agc      272
Lys Ile Asp Asp Ile Pro Gly Leu Ser Asp Thr Ser Pro Asp Xaa Ser
             25                  30                  35 tct cga tct agt tcc cga gta aga ttt agc tcc cgg gaa agc gtg cct      320
Ser Arg Ser Ser Ser Arg Val Arg Phe Ser Ser Arg Glu Ser Val Pro
         40                  45                  50 gaa aca agc cgg agt gag cct atg agt gag atg tct ggg gcc acc act      368
Glu Thr Ser Arg Ser Glu Pro Met Ser Glu Met Ser Gly Ala Thr Thr
     55                  60                  65 tcg ctg gca act gtt gca ctg gat cca ccc agt gac cgg act tct cac      416
Ser Leu Ala Thr Val Ala Leu Asp Pro Pro Ser Asp Arg Thr Ser His
 70                  75                  80 ccc cag gat gtc atc gag gac gac gga cat aag aaa gct cga aat gct      464
Pro Gln Asp Val Ile Glu Asp Asp Gly His Lys Lys Ala Arg Asn Ala
 85                  90                  95                 100 tat ctc aat aat tcc aat tat gaa gaa gga gat gaa tat ttt gat aaa      512
Tyr Leu Asn Asn Ser Asn Tyr Glu Glu Gly Asp Glu Tyr Phe Asp Lys
                105                 110                 115 aat ttg gca ctc ttt gag gaa gaa atg gac acc aga ccg aag gtg tct      560
Asn Leu Ala Leu Phe Glu Glu Glu Met Asp Thr Arg Pro Lys Val Ser
            120                 125                 130 tcc ctc ctc aac cgc atg gcc aat tac act aat ctg act caa gga gca      608
Ser Leu Leu Asn Arg Met Ala Asn Tyr Thr Asn Leu Thr Gln Gly Ala
        135                 140                 145 aag gaa cat gaa gag gca gaa aac atc act gaa ggg aaa aag aag ccc      656
Lys Glu His Glu Glu Ala Glu Asn Ile Thr Glu Gly Lys Lys Lys Pro
    150                 155                 160 acc aag acc ccc caa atg ggt acc ttc atg ggt gtc tac ctc cca tgt      704
Thr Lys Thr Pro Gln Met Gly Thr Phe Met Gly Val Tyr Leu Pro Cys
165                 170                 175                 180 cta caa aat att ttt gga gtg atc ctt ttt tta cgc ctt aca tgg gtg      752
Leu Gln Asn Ile Phe Gly Val Ile Leu Phe Leu Arg Leu Thr Trp Val
                185                 190                 195
```

-continued

| | |
|---|---|
| gtg ggc aca gct gga gtt ctt cag gct ttt gca att gtc ctt atc tgc<br>Val Gly Thr Ala Gly Val Leu Gln Ala Phe Ala Ile Val Leu Ile Cys<br>200                                205                            210 | 800 |
| tgc tgc tgt aca atg ttg act gct atc tcc atg agt gcc att gcc act<br>Cys Cys Cys Thr Met Leu Thr Ala Ile Ser Met Ser Ala Ile Ala Thr<br>        215                            220                            225 | 848 |
| aat gga gtg gtg cca gct ggg ggc tca tac ttt atg att tcc cgg gca<br>Asn Gly Val Val Pro Ala Gly Gly Ser Tyr Phe Met Ile Ser Arg Ala<br>230                                235                            240 | 896 |
| ctg ggc cca gag ttt ggt ggg gct gtt ggc ctc tgc ttt tat ctt ggt<br>Leu Gly Pro Glu Phe Gly Gly Ala Val Gly Leu Cys Phe Tyr Leu Gly<br>245                            250                            255                 260 | 944 |
| acc aca ttt gca gca gcc atg tac atc ctt ggt gcc att gaa atc ttt<br>Thr Thr Phe Ala Ala Ala Met Tyr Ile Leu Gly Ala Ile Glu Ile Phe<br>                         265                            270                        275 | 992 |
| ctg gtc tat atc gtc ccc cga gct gcc atc ttt cac agt gat gac gca<br>Leu Val Tyr Ile Val Pro Arg Ala Ala Ile Phe His Ser Asp Asp Ala<br>                280                            285                            290 | 1040 |
| ctc aag gaa tca gca gcc atg cta aat aac atg cgt gtc tac ggc aca<br>Leu Lys Glu Ser Ala Ala Met Leu Asn Asn Met Arg Val Tyr Gly Thr<br>295                                300                            305 | 1088 |
| gct ttc ttg gtc ctt atg gta tta gtg gta ttt atc ggc gta cgc tat<br>Ala Phe Leu Val Leu Met Val Leu Val Val Phe Ile Gly Val Arg Tyr<br>310                                315                            320 | 1136 |
| gtg aac aag ttt gcc tca ctt ttc ctg gcc tgt gtc att gtg tcc atc<br>Val Asn Lys Phe Ala Ser Leu Phe Leu Ala Cys Val Ile Val Ser Ile<br>325                                330                            335                 340 | 1184 |
| ttg gcc atc tat gct gga gcc atc aag tct tct ttt gct cct cca cac<br>Leu Ala Ile Tyr Ala Gly Ala Ile Lys Ser Ser Phe Ala Pro Pro His<br>                         345                            350                        355 | 1232 |
| ttc ccg gtc tgc atg ctg ggt aac cgc act ctt tca tca aga cac att<br>Phe Pro Val Cys Met Leu Gly Asn Arg Thr Leu Ser Ser Arg His Ile<br>                360                            365                            370 | 1280 |
| gac gtt tgc tct aag acc aag gaa att aac aac atg aca gtc cca tca<br>Asp Val Cys Ser Lys Thr Lys Glu Ile Asn Asn Met Thr Val Pro Ser<br>                        375                            380                            385 | 1328 |
| aag tta tgg gga ttc ttc tgt aac tcg agt caa ttt ttc aat gcc acc<br>Lys Leu Trp Gly Phe Phe Cys Asn Ser Ser Gln Phe Phe Asn Ala Thr<br>390                                395                            400 | 1376 |
| tgt gat gaa tac ttt gtt cac aat aac gtc act tca atc cag ggc att<br>Cys Asp Glu Tyr Phe Val His Asn Asn Val Thr Ser Ile Gln Gly Ile<br>405                                410                            415                 420 | 1424 |
| cct gga ttg gct agt ggt ata att aca gag aat ctt tgg agt aat tac<br>Pro Gly Leu Ala Ser Gly Ile Ile Thr Glu Asn Leu Trp Ser Asn Tyr<br>                        425                            430                        435 | 1472 |
| cta ccc aag gga gag atc atc gaa aag cct tca gcc aaa tct tct gat<br>Leu Pro Lys Gly Glu Ile Ile Glu Lys Pro Ser Ala Lys Ser Ser Asp<br>                        440                            445                        450 | 1520 |
| gtc tta ggc agc tta aac cat gaa tat gtt ctt gtt gac atc acc acc<br>Val Leu Gly Ser Leu Asn His Glu Tyr Val Leu Val Asp Ile Thr Thr<br>                        455                            460                        465 | 1568 |
| tcc ttc acg ntt ctg gtg gga atc ttc ttt ccc tct gtt aca ggt atc<br>Ser Phe Thr Xaa Leu Val Gly Ile Phe Phe Pro Ser Val Thr Gly Ile<br>470                                475                            480 | 1616 |
| atg gct gga tca aac aga tct gga gat ctg aaa gat gct cag aag tct<br>Met Ala Gly Ser Asn Arg Ser Gly Asp Leu Lys Asp Ala Gln Lys Ser<br>485                                490                            495                 500 | 1664 |
| att ccg att ggt act atc ctt gcc atc ctg acc acc tcc ttt gtt tat<br>Ile Pro Ile Gly Thr Ile Leu Ala Ile Leu Thr Thr Ser Phe Val Tyr<br>                        505                            510                        515 | 1712 |

```
tta agc aat gtt gtc ctt ttt ggt gca tgt att gaa ggg gtt gtt ctc      1760
Leu Ser Asn Val Val Leu Phe Gly Ala Cys Ile Glu Gly Val Val Leu
        520                 525                 530 aga gac aag ttc ggt gat gct gtg aaa ggt aat ttg gtg gta ggc acc      1808
Arg Asp Lys Phe Gly Asp Ala Val Lys Gly Asn Leu Val Val Gly Thr
            535                 540                 545 tta tct tgg cca tcc cca tgg gtg att gtt att ggc tcc ttc ttt tca      1856
Leu Ser Trp Pro Ser Pro Trp Val Ile Val Ile Gly Ser Phe Phe Ser
550                 555                 560 aca tgt ggg gct gga ctt cag agc ctc aca ggt gca ccg agg ctg cta      1904
Thr Cys Gly Ala Gly Leu Gln Ser Leu Thr Gly Ala Pro Arg Leu Leu
565                 570                 575                 580 caa gct att gcc aag gat aac atc ata ccg ttt ctg agg gtt ttt ggc      1952
Gln Ala Ile Ala Lys Asp Asn Ile Ile Pro Phe Leu Arg Val Phe Gly
                585                 590                 595 cac agc aaa gcc aat ggg gaa cct acc tgg gct tta ctt cta act gct      2000
His Ser Lys Ala Asn Gly Glu Pro Thr Trp Ala Leu Leu Leu Thr Ala
            600                 605                 610 gcc att gca gag ctt gga ata ctc att gcc tcc ctg gat ctt gtg gcc      2048
Ala Ile Ala Glu Leu Gly Ile Leu Ile Ala Ser Leu Asp Leu Val Ala
        615                 620                 625 cca att ctt tcc atg ttt ttt ctc atg tgt tac ctc ttt gta aac ttg      2096
Pro Ile Leu Ser Met Phe Phe Leu Met Cys Tyr Leu Phe Val Asn Leu
630                 635                 640 gca tgt gcc ttg caa aca tta ctt cga aca ccc aac tgg aga ccc cga      2144
Ala Cys Ala Leu Gln Thr Leu Leu Arg Thr Pro Asn Trp Arg Pro Arg
645                 650                 655                 660 ttc cgc tac tac cat tgg gcc ctt tct ttc atg gga atg agt atc tgt      2192
Phe Arg Tyr Tyr His Trp Ala Leu Ser Phe Met Gly Met Ser Ile Cys
                665                 670                 675 ctg gct ctg atg ttc att tct tcc tgg tat tat gcc att gta gcc atg      2240
Leu Ala Leu Met Phe Ile Ser Ser Trp Tyr Tyr Ala Ile Val Ala Met
            680                 685                 690 gta ata gct ggt atg atc tac aag tac att gaa tac caa gga gct gag      2288
Val Ile Ala Gly Met Ile Tyr Lys Tyr Ile Glu Tyr Gln Gly Ala Glu
        695                 700                 705 aaa gaa tgg ggt gat ggt atc cgt ggg ctg tcc ctc agt gca gcc cgg      2336
Lys Glu Trp Gly Asp Gly Ile Arg Gly Leu Ser Leu Ser Ala Ala Arg
710                 715                 720 ttt gct ttg ctt cga ttg gag gaa gga cct cca cac act aaa aac tgg      2384
Phe Ala Leu Leu Arg Leu Glu Glu Gly Pro Pro His Thr Lys Asn Trp
725                 730                 735                 740 agg cct cag ttg ctt gta tta ctg aaa cta gat gaa gac tta cat gtc      2432
Arg Pro Gln Leu Leu Val Leu Leu Lys Leu Asp Glu Asp Leu His Val
                745                 750                 755 aag cat cct cgc ctc ctc acc ttt gcc tca cag ctc aaa gca gga aaa      2480
Lys His Pro Arg Leu Leu Thr Phe Ala Ser Gln Leu Lys Ala Gly Lys
            760                 765                 770 ggt ctc act att gtg ggc tct gtc atc gtg ggg aac ttc cta gag aac      2528
Gly Leu Thr Ile Val Gly Ser Val Ile Val Gly Asn Phe Leu Glu Asn
        775                 780                 785 tac ggt gaa gct tta gct gct gag cag acc ata aag cac cta atg gag      2576
Tyr Gly Glu Ala Leu Ala Ala Glu Gln Thr Ile Lys His Leu Met Glu
790                 795                 800 gca gag aag gta aaa gga ttc tgc cag ctg gtg gtg gcc gcc aag ctg      2624
Ala Glu Lys Val Lys Gly Phe Cys Gln Leu Val Val Ala Ala Lys Leu
805                 810                 815                 820 aga gag ggc att tcc cac ctc atc cag tca tgt ggc ctt ggg ggc atg      2672
Arg Glu Gly Ile Ser His Leu Ile Gln Ser Cys Gly Leu Gly Gly Met
                825                 830                 835
```

| | |
|---|---|
| aag cac aac acg gtg gtg atg ggc tgg cct aat ggc tgg cgt caa agc<br>Lys His Asn Thr Val Val Met Gly Trp Pro Asn Gly Trp Arg Gln Ser<br>            840                    845                    850 | 2720 |
| gaa gat gcc cgc gct tgg aag act ttt att ggc aca gtt cga gtg aca<br>Glu Asp Ala Arg Ala Trp Lys Thr Phe Ile Gly Thr Val Arg Val Thr<br>855                    860                    865 | 2768 |
| act gct gcc cat ctt gca ctg ctg gtg gct aaa aac atc tcc ttc ttt<br>Thr Ala Ala His Leu Ala Leu Leu Val Ala Lys Asn Ile Ser Phe Phe<br>870                    875                    880 | 2816 |
| ccc agc aat gtg gag caa ttt tct gag ggc aac att gat gtg tgg tgg<br>Pro Ser Asn Val Glu Gln Phe Ser Glu Gly Asn Ile Asp Val Trp Trp<br>885                    890                    895                    900 | 2864 |
| att gtg cat gat ggg ggg atg ctt atg cta cta cca ttc cta ctg aaa<br>Ile Val His Asp Gly Gly Met Leu Met Leu Leu Pro Phe Leu Leu Lys<br>            905                    910                    915 | 2912 |
| cag cac aag gtg tgg cga aag tgc agc ata cgg atc ttc aca gta gcc<br>Gln His Lys Val Trp Arg Lys Cys Ser Ile Arg Ile Phe Thr Val Ala<br>920                    925                    930 | 2960 |
| caa tta gaa gac aac agt atc caa atg aag aag gac cta gcc acc ttc<br>Gln Leu Glu Asp Asn Ser Ile Gln Met Lys Lys Asp Leu Ala Thr Phe<br>            935                    940                    945 | 3008 |
| cta tat cac tta cgc att gag gcg gag gta gaa gtg gtg gag atg cat<br>Leu Tyr His Leu Arg Ile Glu Ala Glu Val Glu Val Val Glu Met His<br>950                    955                    960 | 3056 |
| gac agt gat ata tca gca tat act tac gag cgc act ttg atg atg gaa<br>Asp Ser Asp Ile Ser Ala Tyr Thr Tyr Glu Arg Thr Leu Met Met Glu<br>965                    970                    975                    980 | 3104 |
| caa agg tcc cag atg ctt cgg cac atg cgg cta tcc aaa aca gag cga<br>Gln Arg Ser Gln Met Leu Arg His Met Arg Leu Ser Lys Thr Glu Arg<br>            985                    990                    995 | 3152 |
| gac aga gag gca caa ttg gtg aaa gac cga aac tca atg cta cga ttg<br>Asp Arg Glu Ala Gln Leu Val Lys Asp Arg Asn Ser Met Leu Arg Leu<br>1000                    1005                  1010 | 3200 |
| acc agc att ggc tct gat gag gac gaa gag aca gaa acc tat cag gag<br>Thr Ser Ile Gly Ser Asp Glu Asp Glu Glu Thr Glu Thr Tyr Gln Glu<br>              1015                  1020                  1025 | 3248 |
| aag gtg cac atg act tgg aca aaa gac aag tac atg gca tcc cgg gga<br>Lys Val His Met Thr Trp Thr Lys Asp Lys Tyr Met Ala Ser Arg Gly<br>1030                    1035                  1040 | 3296 |
| caa aaa gcg aag tca atg gaa gga ttc cag gac ctg ctt aac atg cgt<br>Gln Lys Ala Lys Ser Met Glu Gly Phe Gln Asp Leu Leu Asn Met Arg<br>1045                    1050                  1055                  1060 | 3344 |
| ccg gac cag tcc aat gtg agg cgg atg cat aca gca gtg aaa ntc aac<br>Pro Asp Gln Ser Asn Val Arg Arg Met His Thr Ala Val Lys Xaa Asn<br>              1065                  1070                  1075 | 3392 |
| gag gtt ata gtt aac aag tcc cat gaa gca aag ctg gtt tta ttg aat<br>Glu Val Ile Val Asn Lys Ser His Glu Ala Lys Leu Val Leu Leu Asn<br>1080                    1085                  1090 | 3440 |
| atg cca ggg cca ccc cga aac cct gag ggt gat gaa aac tac atg gag<br>Met Pro Gly Pro Pro Arg Asn Pro Glu Gly Asp Glu Asn Tyr Met Glu<br>1095                    1100                  1105 | 3488 |
| ttc cta gag gtg ctt acc gag gga cta gag cga gtc cta ctt gtc cgg<br>Phe Leu Glu Val Leu Thr Glu Gly Leu Glu Arg Val Leu Leu Val Arg<br>            1110                  1115                  1120 | 3536 |
| ggt ggt ggc agt gaa gtg atc acc att tat tca taacctactc tgaatgaccg<br>Gly Gly Gly Ser Glu Val Ile Thr Ile Tyr Ser<br>1125                    1130                  1135 | 3589 |
| tgcttgacct gttttcttaa aaggcctacg tcctccatgg aagtgccagc tcattactac | 3649 |
| cactcccact caactagaag cctgtgttct gtacacatca tactgaactc ttgatgagct | 3709 |

-continued

```
gagcctcaag tacctgtgta aaagagctcc catctgatct gcagtcatta cagaaaaagc   3769
aaatattccc tcaacatcag aacaatgctc aagtctttca agccactgtc tgagcagtca   3829
aaggcaaatt agaattaaca agctgagcca ataaatgaat tggtaaaagg gatgctagaa   3889
attcaactga agaaaaaaag caagtcaagt acgtattcag cattaaagat gaatctcaga   3949
agtcatggtt caatgttgac actgtgagga tacactagag acagcttcat cttactaaag   4009
aatttatggt caagtatatt tggacctatt atcctcggca agccaagatg caaacatttt   4069
ttagctatat ttctttagta tacccactgc tgtaattta  tattaggata ctaacttgaa   4129
acatggctgc agcctctact tcttcaaaaa catccccca  aaataccaga tttaaatatc   4189
caaaaaaaaa aaaaaaaaaa aaaaaa                                       4215
```

<210> SEQ ID NO 4
<211> LENGTH: 1135
<212> TYPE: PRT
<213> ORGANISM: Homo sapiens
<220> FEATURE:
<221> NAME/KEY: misc_feature
<222> LOCATION: (35)
<223> OTHER INFORMATION: Xaa=Leu or Ile
<220> FEATURE:
<221> NAME/KEY: misc_feature
<222> LOCATION: (472)
<223> OTHER INFORMATION: Xaa=Leu or Ile
<220> FEATURE:
<221> NAME/KEY: misc_feature
<222> LOCATION: (1075)
<223> OTHER INFORMATION: Xaa=Leu or Ile

<400> SEQUENCE: 4

```
Met His Pro Pro Glu Thr Thr Thr Lys Met Ala Ser Val Arg Phe Met
  1               5                  10                  15

Val Thr Pro Thr Lys Ile Asp Asp Ile Pro Gly Leu Ser Asp Thr Ser
                 20                  25                  30

Pro Asp Xaa Ser Ser Arg Ser Ser Arg Val Arg Phe Ser Ser Arg
             35                  40                  45

Glu Ser Val Pro Glu Thr Ser Arg Ser Glu Pro Met Ser Glu Met Ser
 50                  55                  60

Gly Ala Thr Thr Ser Leu Ala Thr Val Ala Leu Asp Pro Pro Ser Asp
 65                  70                  75                  80

Arg Thr Ser His Pro Gln Asp Val Ile Glu Asp Gly His Lys Lys
                 85                  90                  95

Ala Arg Asn Ala Tyr Leu Asn Asn Ser Asn Tyr Glu Glu Gly Asp Glu
                100                 105                 110

Tyr Phe Asp Lys Asn Leu Ala Leu Phe Glu Glu Met Asp Thr Arg
            115                 120                 125

Pro Lys Val Ser Ser Leu Leu Asn Arg Met Ala Asn Tyr Thr Asn Leu
130                 135                 140

Thr Gln Gly Ala Lys Glu His Glu Glu Ala Glu Asn Ile Thr Glu Gly
145                 150                 155                 160

Lys Lys Lys Pro Thr Lys Thr Pro Gln Met Gly Thr Phe Met Gly Val
                165                 170                 175

Tyr Leu Pro Cys Leu Gln Asn Ile Phe Gly Val Ile Leu Phe Leu Arg
            180                 185                 190

Leu Thr Trp Val Val Gly Thr Ala Gly Val Leu Gln Ala Phe Ala Ile
        195                 200                 205

Val Leu Ile Cys Cys Cys Cys Thr Met Leu Thr Ala Ile Ser Met Ser
210                 215                 220
```

-continued

```
Ala Ile Ala Thr Asn Gly Val Pro Ala Gly Gly Ser Tyr Phe Met
225                 230                 235                 240

Ile Ser Arg Ala Leu Gly Pro Glu Phe Gly Gly Ala Val Gly Leu Cys
            245                 250                 255

Phe Tyr Leu Gly Thr Thr Phe Ala Ala Met Tyr Ile Leu Gly Ala
        260                 265                 270

Ile Glu Ile Phe Leu Val Tyr Ile Val Pro Arg Ala Ala Ile Phe His
    275                 280                 285

Ser Asp Asp Ala Leu Lys Glu Ser Ala Ala Met Leu Asn Asn Met Arg
290                 295                 300

Val Tyr Gly Thr Ala Phe Leu Val Leu Met Val Leu Val Phe Ile
305                 310                 315                 320

Gly Val Arg Tyr Val Asn Lys Phe Ala Ser Leu Phe Leu Ala Cys Val
            325                 330                 335

Ile Val Ser Ile Leu Ala Ile Tyr Ala Gly Ala Ile Lys Ser Ser Phe
        340                 345                 350

Ala Pro Pro His Phe Pro Val Cys Met Leu Gly Asn Arg Thr Leu Ser
        355                 360                 365

Ser Arg His Ile Asp Val Cys Ser Lys Thr Lys Glu Ile Asn Asn Met
    370                 375                 380

Thr Val Pro Ser Lys Leu Trp Gly Phe Phe Cys Asn Ser Ser Gln Phe
385                 390                 395                 400

Phe Asn Ala Thr Cys Asp Glu Tyr Phe Val His Asn Asn Val Thr Ser
            405                 410                 415

Ile Gln Gly Ile Pro Gly Leu Ala Ser Gly Ile Ile Thr Glu Asn Leu
        420                 425                 430

Trp Ser Asn Tyr Leu Pro Lys Gly Glu Ile Ile Glu Lys Pro Ser Ala
    435                 440                 445

Lys Ser Ser Asp Val Leu Gly Ser Leu Asn His Glu Tyr Val Leu Val
    450                 455                 460

Asp Ile Thr Thr Ser Phe Thr Xaa Leu Val Gly Ile Phe Phe Pro Ser
465                 470                 475                 480

Val Thr Gly Ile Met Ala Gly Ser Asn Arg Ser Gly Asp Leu Lys Asp
            485                 490                 495

Ala Gln Lys Ser Ile Pro Ile Gly Thr Ile Leu Ala Ile Leu Thr Thr
        500                 505                 510

Ser Phe Val Tyr Leu Ser Asn Val Val Leu Phe Gly Ala Cys Ile Glu
        515                 520                 525

Gly Val Val Leu Arg Asp Lys Phe Gly Asp Ala Val Lys Gly Asn Leu
    530                 535                 540

Val Val Gly Thr Leu Ser Trp Pro Ser Pro Trp Val Ile Val Ile Gly
545                 550                 555                 560

Ser Phe Phe Ser Thr Cys Gly Ala Gly Leu Gln Ser Leu Thr Gly Ala
            565                 570                 575

Pro Arg Leu Leu Gln Ala Ile Ala Lys Asp Asn Ile Ile Pro Phe Leu
        580                 585                 590

Arg Val Phe Gly His Ser Lys Ala Asn Gly Glu Pro Thr Trp Ala Leu
        595                 600                 605

Leu Leu Thr Ala Ala Ile Ala Glu Leu Gly Ile Leu Ile Ala Ser Leu
    610                 615                 620

Asp Leu Val Ala Pro Ile Leu Ser Met Phe Phe Leu Met Cys Tyr Leu
625                 630                 635                 640
```

-continued

```
Phe Val Asn Leu Ala Cys Ala Leu Gln Thr Leu Leu Arg Thr Pro Asn
            645                 650                 655

Trp Arg Pro Arg Phe Arg Tyr Tyr His Trp Ala Leu Ser Phe Met Gly
        660                 665                 670

Met Ser Ile Cys Leu Ala Leu Met Phe Ile Ser Ser Trp Tyr Tyr Ala
            675                 680                 685

Ile Val Ala Met Val Ile Ala Gly Met Ile Tyr Lys Tyr Ile Glu Tyr
        690                 695                 700

Gln Gly Ala Glu Lys Glu Trp Gly Asp Gly Ile Arg Gly Leu Ser Leu
705                 710                 715                 720

Ser Ala Ala Arg Phe Ala Leu Leu Arg Leu Glu Glu Gly Pro Pro His
                725                 730                 735

Thr Lys Asn Trp Arg Pro Gln Leu Leu Val Leu Leu Lys Leu Asp Glu
            740                 745                 750

Asp Leu His Val Lys His Pro Arg Leu Leu Thr Phe Ala Ser Gln Leu
        755                 760                 765

Lys Ala Gly Lys Gly Leu Thr Ile Val Gly Ser Val Ile Val Gly Asn
    770                 775                 780

Phe Leu Glu Asn Tyr Gly Glu Ala Leu Ala Ala Glu Gln Thr Ile Lys
785                 790                 795                 800

His Leu Met Glu Ala Glu Lys Val Lys Gly Phe Cys Gln Leu Val Val
                805                 810                 815

Ala Ala Lys Leu Arg Glu Gly Ile Ser His Leu Ile Gln Ser Cys Gly
            820                 825                 830

Leu Gly Gly Met Lys His Asn Thr Val Val Met Gly Trp Pro Asn Gly
        835                 840                 845

Trp Arg Gln Ser Glu Asp Ala Arg Ala Trp Lys Thr Phe Ile Gly Thr
    850                 855                 860

Val Arg Val Thr Thr Ala Ala His Leu Ala Leu Leu Val Ala Lys Asn
865                 870                 875                 880

Ile Ser Phe Phe Pro Ser Asn Val Glu Gln Phe Ser Glu Gly Asn Ile
                885                 890                 895

Asp Val Trp Trp Ile Val His Asp Gly Gly Met Leu Met Leu Leu Pro
            900                 905                 910

Phe Leu Leu Lys Gln His Lys Val Trp Arg Lys Cys Ser Ile Arg Ile
        915                 920                 925

Phe Thr Val Ala Gln Leu Glu Asp Asn Ser Ile Gln Met Lys Lys Asp
    930                 935                 940

Leu Ala Thr Phe Leu Tyr His Leu Arg Ile Glu Ala Glu Val Glu Val
945                 950                 955                 960

Val Glu Met His Asp Ser Asp Ile Ser Ala Tyr Thr Tyr Glu Arg Thr
                965                 970                 975

Leu Met Met Glu Gln Arg Ser Gln Met Leu Arg His Met Arg Leu Ser
            980                 985                 990

Lys Thr Glu Arg Asp Arg Glu Ala Gln Leu Val Lys Asp Arg Asn Ser
        995                 1000                1005

Met Leu Arg Leu Thr Ser Ile Gly Ser Asp Glu Asp Glu Glu Thr Glu
    1010                1015                1020

Thr Tyr Gln Glu Lys Val His Met Thr Trp Thr Lys Asp Lys Tyr Met
1025                1030                1035                1040

Ala Ser Arg Gly Gln Lys Ala Lys Ser Met Glu Gly Phe Gln Asp Leu
                1045                1050                1055
```

-continued

```
Leu Asn Met Arg Pro Asp Gln Ser Asn Val Arg Arg Met His Thr Ala
            1060                1065                1070

Val Lys Xaa Asn Glu Val Ile Val Asn Lys Ser His Glu Ala Lys Leu
        1075                1080                1085

Val Leu Leu Asn Met Pro Gly Pro Pro Arg Asn Pro Glu Gly Asp Glu
    1090                1095                1100

Asn Tyr Met Glu Phe Leu Glu Val Leu Thr Glu Gly Leu Glu Arg Val
1105                1110                1115                1120

Leu Leu Val Arg Gly Gly Gly Ser Glu Val Ile Thr Ile Tyr Ser
                1125                1130                1135

<210> SEQ ID NO 5
<211> LENGTH: 6075
<212> TYPE: DNA
<213> ORGANISM: mouse
<220> FEATURE:
<221> NAME/KEY: CDS
<222> LOCATION: (4)..(3408)
<220> FEATURE:
<221> NAME/KEY: misc_feature
<222> LOCATION: (307)
<223> OTHER INFORMATION: n=c or a, Xaa=Leu or Ile
<220> FEATURE:
<221> NAME/KEY: misc_feature
<222> LOCATION: (1894)
<223> OTHER INFORMATION: n=c or a, Xaa=Leu or Ile
<220> FEATURE:
<221> NAME/KEY: misc_feature
<222> LOCATION: (3340)
<223> OTHER INFORMATION: n=c or a, Xaa=Leu or Ile

<400> SEQUENCE: 5 aaa atg cat cca cca gaa gcc acc acc aag atg tcc tca gtt cgg ttc      48
    Met His Pro Pro Glu Ala Thr Thr Lys Met Ser Ser Val Arg Phe
    1               5                   10                  15 atg gtg aca cca act aag att gat gac att cca ggt ttg tca gac acc      96
Met Val Thr Pro Thr Lys Ile Asp Asp Ile Pro Gly Leu Ser Asp Thr
            20                  25                  30 agc ccg gac ctc agc tct cgg tct agt tct cga gta aga ttt agc tcc     144
Ser Pro Asp Leu Ser Ser Arg Ser Ser Ser Arg Val Arg Phe Ser Ser
        35                  40                  45 cga gaa agt gtg cca gaa aca agc cgt agt gag cct atg agc gaa ctg     192
Arg Glu Ser Val Pro Glu Thr Ser Arg Ser Glu Pro Met Ser Glu Leu
    50                  55                  60 tct ggg gct act act tct ctg gca act gtt gcc cta gat cct tcc agt     240
Ser Gly Ala Thr Thr Ser Leu Ala Thr Val Ala Leu Asp Pro Ser Ser
65                  70                  75 gac cgg act tct aat ccc cag gat gtt acg gag gat gac ggc cat aaa     288
Asp Arg Thr Ser Asn Pro Gln Asp Val Thr Glu Asp Asp Gly His Lys
80                  85                  90                  95 aaa gcc cga aat gct tat ntc aat aat tcc aac tat gaa gaa gga gac     336
Lys Ala Arg Asn Ala Tyr Xaa Asn Asn Ser Asn Tyr Glu Glu Gly Asp
                100                 105                 110 gaa tat ttt gat aaa aat ttg gca ctc ttt gag gaa gaa atg gac acc     384
Glu Tyr Phe Asp Lys Asn Leu Ala Leu Phe Glu Glu Glu Met Asp Thr
            115                 120                 125 aga cca aag gtg tct tct ctc ctc aac cgc atg gcc aac tat aca aat     432
Arg Pro Lys Val Ser Ser Leu Leu Asn Arg Met Ala Asn Tyr Thr Asn
        130                 135                 140 ctg aca caa gga gca aag gaa cat gaa gag gca gag aac atc act gaa     480
Leu Thr Gln Gly Ala Lys Glu His Glu Glu Ala Glu Asn Ile Thr Glu
    145                 150                 155
```

-continued

| | | |
|---|---|---|
| ggg aaa aag aag cct acc aag agc ccc caa atg ggt act ttc atg ggt<br>Gly Lys Lys Lys Pro Thr Lys Ser Pro Gln Met Gly Thr Phe Met Gly<br>160                        165                    170                  175 | 528 |
| gtc tac ctc cca tgt cta cag aac atc ttt gga gtg atc ctc ttc ctg<br>Val Tyr Leu Pro Cys Leu Gln Asn Ile Phe Gly Val Ile Leu Phe Leu<br>                    180                    185                  190 | 576 |
| cgt ctt acc tgg gta gtg gga aca gct gga atc ctt cag gcc ttt gca<br>Arg Leu Thr Trp Val Val Gly Thr Ala Gly Ile Leu Gln Ala Phe Ala<br>        195                    200                    205 | 624 |
| att gtc ctc atc tgc tgc tgt aca atg tta act gcc atc tcc atg<br>Ile Val Leu Ile Cys Cys Cys Thr Met Leu Thr Ala Ile Ser Met<br>210                    215                    220 | 672 |
| agc gcc atc gcc act aac gga gtg gtg cca gct ggg ggc tca tac ttc<br>Ser Ala Ile Ala Thr Asn Gly Val Val Pro Ala Gly Gly Ser Tyr Phe<br>225                    230                    235 | 720 |
| atg att tcc aga gcc ctg ggc cca gag ttt ggc ggg gct gta ggc ctc<br>Met Ile Ser Arg Ala Leu Gly Pro Glu Phe Gly Gly Ala Val Gly Leu<br>240                        245                  250                  255 | 768 |
| tgc ttt tat ctt ggc acc aca ttt gca gca gcc atg tat att ctt ggt<br>Cys Phe Tyr Leu Gly Thr Thr Phe Ala Ala Ala Met Tyr Ile Leu Gly<br>                    260                    265                  270 | 816 |
| gcc att gaa atc ttt ctg gta tac att gtc ccc cga gct gcc atc ttt<br>Ala Ile Glu Ile Phe Leu Val Tyr Ile Val Pro Arg Ala Ala Ile Phe<br>            275                    280                    285 | 864 |
| cgg agt gac gat gca ctc aag gag tca gca gct atg ctg aac aac atg<br>Arg Ser Asp Asp Ala Leu Lys Glu Ser Ala Ala Met Leu Asn Asn Met<br>        290                    295                    300 | 912 |
| cgc gtc tat ggt aca gcc ttc ttg gtc ctc atg gtc ttg gtg gta ttc<br>Arg Val Tyr Gly Thr Ala Phe Leu Val Leu Met Val Leu Val Val Phe<br>305                        310                  315 | 960 |
| atc ggc gta cgc tat gtg aat aag ttt gcc tca ctc ttc ctg gcc tgt<br>Ile Gly Val Arg Tyr Val Asn Lys Phe Ala Ser Leu Phe Leu Ala Cys<br>320                        325                  330                  335 | 1008 |
| gta att gtg tcg atc ttg gct atc tat gct ggt gcc atc aag tct tcc<br>Val Ile Val Ser Ile Leu Ala Ile Tyr Ala Gly Ala Ile Lys Ser Ser<br>                    340                    345                  350 | 1056 |
| ttt gct cca cca cac ttc ccg gtc tgt atg ctg ggc aac cgt acc ctg<br>Phe Ala Pro Pro His Phe Pro Val Cys Met Leu Gly Asn Arg Thr Leu<br>            355                    360                    365 | 1104 |
| tca tca aga cac ctt gac att tgc tct aag acc aag gag gtt gac aac<br>Ser Ser Arg His Leu Asp Ile Cys Ser Lys Thr Lys Glu Val Asp Asn<br>        370                    375                    380 | 1152 |
| atg aca gta cca tca aag tta tgg gga ttc ttc tgc aac tcg agt cag<br>Met Thr Val Pro Ser Lys Leu Trp Gly Phe Phe Cys Asn Ser Ser Gln<br>385                        390                  395 | 1200 |
| ttc ttt aat gcc acc tgt gat gag tac ttt gtt cac aat aac gtc atc<br>Phe Phe Asn Ala Thr Cys Asp Glu Tyr Phe Val His Asn Asn Val Ile<br>400                        405                  410                  415 | 1248 |
| tca atc caa ggc att cca ggg ttg gct agt ggt atc att act gaa aat<br>Ser Ile Gln Gly Ile Pro Gly Leu Ala Ser Gly Ile Ile Thr Glu Asn<br>                    420                    425                  430 | 1296 |
| ctt tgg agt aat tat tta cca aag ggt gag ata att gaa aag cca tca<br>Leu Trp Ser Asn Tyr Leu Pro Lys Gly Glu Ile Ile Glu Lys Pro Ser<br>            435                    440                    445 | 1344 |
| gcc aag tca tct gat gtc tta ggc aac tta aac cat gaa tat gtt ctt<br>Ala Lys Ser Ser Asp Val Leu Gly Asn Leu Asn His Glu Tyr Val Leu<br>        450                    455                    460 | 1392 |
| gct gat atc acc acc tcc ttc act ctg ctg gtg ggg atc ttc ttt ccc<br>Ala Asp Ile Thr Thr Ser Phe Thr Leu Leu Val Gly Ile Phe Phe Pro<br>465                        470                  475 | 1440 |

-continued

| | | |
|---|---|---|
| tcg gtc aca ggt atc atg gct ggg tca aac aga tct gga gat ctg aaa<br>Ser Val Thr Gly Ile Met Ala Gly Ser Asn Arg Ser Gly Asp Leu Lys<br>480                        485                     490                   495 | 1488 |
| gat gcc cag aag tct att ccc att ggg acc atc ctt gcc atc ctg acc<br>Asp Ala Gln Lys Ser Ile Pro Ile Gly Thr Ile Leu Ala Ile Leu Thr<br>                  500                   505                   510 | 1536 |
| aca tcc ttt gtg tat tta agc aat gtt gtc ctt ttt ggt gca tgt att<br>Thr Ser Phe Val Tyr Leu Ser Asn Val Val Leu Phe Gly Ala Cys Ile<br>              515                   520                   525 | 1584 |
| gaa gga gtc gtt ctc aga gac aaa ttt ggg gat gct gta aaa ggg aat<br>Glu Gly Val Val Leu Arg Asp Lys Phe Gly Asp Ala Val Lys Gly Asn<br>          530                   535                   540 | 1632 |
| ttg gtt gta ggc acc tta tcc tgg cca tcc ccg tgg gtg atc gtt att<br>Leu Val Val Gly Thr Leu Ser Trp Pro Ser Pro Trp Val Ile Val Ile<br>545                        550                     555 | 1680 |
| ggc tcc ttc ttt tca aca tgt ggg gct ggg ctg cag agc ctc aca ggt<br>Gly Ser Phe Phe Ser Thr Cys Gly Ala Gly Leu Gln Ser Leu Thr Gly<br>560                        565                     570                   575 | 1728 |
| gcg cct cgg ctg ctg cag gct atc gcc aag gat aac atc ata cct ttc<br>Ala Pro Arg Leu Leu Gln Ala Ile Ala Lys Asp Asn Ile Ile Pro Phe<br>                  580                   585                   590 | 1776 |
| ctt agg gtt ttt ggt cac agc aaa gct aat ggg gaa cct acc tgg gct<br>Leu Arg Val Phe Gly His Ser Lys Ala Asn Gly Glu Pro Thr Trp Ala<br>             595                   600                   605 | 1824 |
| tta ctt cta act gct gcc ata gca gag ctg gga att ctc atc gcc tcc<br>Leu Leu Leu Thr Ala Ala Ile Ala Glu Leu Gly Ile Leu Ile Ala Ser<br>          610                   615                   620 | 1872 |
| ctg gat ctc gtg gcc cca att ntt tcc atg ttt ttt ctc atg tgt tac<br>Leu Asp Leu Val Ala Pro Ile Xaa Ser Met Phe Phe Leu Met Cys Tyr<br>625                        630                     635 | 1920 |
| ctc ttt gtg aac ttg gct tgt gcc ttg caa aca ttg ctg cga acc ccc<br>Leu Phe Val Asn Leu Ala Cys Ala Leu Gln Thr Leu Leu Arg Thr Pro<br>640                        645                     650                   655 | 1968 |
| aac tgg agg cct cga ttc cgc tat tat cac tgg gcc ctc tct ttc atg<br>Asn Trp Arg Pro Arg Phe Arg Tyr Tyr His Trp Ala Leu Ser Phe Met<br>                  660                   665                   670 | 2016 |
| gga atg agt atc tgt cta gct ctg atg ttc att tct tct tgg tat tat<br>Gly Met Ser Ile Cys Leu Ala Leu Met Phe Ile Ser Ser Trp Tyr Tyr<br>             675                   680                   685 | 2064 |
| gcc att gta gct atg gta ata gct ggc atg atc tac aag tac att gaa<br>Ala Ile Val Ala Met Val Ile Ala Gly Met Ile Tyr Lys Tyr Ile Glu<br>          690                   695                   700 | 2112 |
| tat caa ggg gct gag aaa gaa tgg ggg gat ggt atc cgt ggg ctg tcg<br>Tyr Gln Gly Ala Glu Lys Glu Trp Gly Asp Gly Ile Arg Gly Leu Ser<br>705                        710                     715 | 2160 |
| ctc agt gca gcc cgc ttc gct ttg ctc cgt cta gag gaa gga cct cct<br>Leu Ser Ala Ala Arg Phe Ala Leu Leu Arg Leu Glu Glu Gly Pro Pro<br>720                        725                     730                   735 | 2208 |
| cac act aaa aac tgg agg cct cag ctg ctc gtc cta ctg aag ctg gat<br>His Thr Lys Asn Trp Arg Pro Gln Leu Leu Val Leu Leu Lys Leu Asp<br>                  740                   745                   750 | 2256 |
| gaa gat tta cac gtc aag cac cct cgc ctc ctc acc ttt gcc tcc cag<br>Glu Asp Leu His Val Lys His Pro Arg Leu Leu Thr Phe Ala Ser Gln<br>             755                   760                   765 | 2304 |
| ctc aag gca gga aag gga ctc acg att gtg ggc tct gtc atc gtg ggg<br>Leu Lys Ala Gly Lys Gly Leu Thr Ile Val Gly Ser Val Ile Val Gly<br>          770                   775                   780 | 2352 |
| aac ttc ttg gag aac tat ggt gac gcg ctc gcg gca gag cag acc att<br>Asn Phe Leu Glu Asn Tyr Gly Asp Ala Leu Ala Ala Glu Gln Thr Ile<br>785                        790                     795 | 2400 |

| | | |
|---|---|---|
| aag cac cta atg gag gca gaa aag gta aaa gga ttc tgc caa ttg gtg<br>Lys His Leu Met Glu Ala Glu Lys Val Lys Gly Phe Cys Gln Leu Val<br>800                805                    810                815 | | 2448 |
| gtg gct gcc aag ctg aaa gag ggc att tca cac ctc atc cag tcc tgt<br>Val Ala Ala Lys Leu Lys Glu Gly Ile Ser His Leu Ile Gln Ser Cys<br>                    820                    825                    830 | | 2496 |
| ggc ctc gga ggc atg aaa cac aac aca gtg gtg atg ggc tgg ccc aat<br>Gly Leu Gly Gly Met Lys His Asn Thr Val Val Met Gly Trp Pro Asn<br>835                840                    845 | | 2544 |
| ggc tgg cgt cag agt gaa gat gct cgc gct tgg aag act ttc att ggc<br>Gly Trp Arg Gln Ser Glu Asp Ala Arg Ala Trp Lys Thr Phe Ile Gly<br>    850                    855                    860 | | 2592 |
| aca gta cga gtg aca act gct gcc cat cta gcc ctg ctg gtg gct aaa<br>Thr Val Arg Val Thr Thr Ala Ala His Leu Ala Leu Leu Val Ala Lys<br>865                870                    875 | | 2640 |
| aat gtc tcc ttc ttt ccc agc aat gtg gag cag ttt tct gag ggc aac<br>Asn Val Ser Phe Phe Pro Ser Asn Val Glu Gln Phe Ser Glu Gly Asn<br>880                885                    890                895 | | 2688 |
| att gat gtg cgg tgg att gtg cat gat ggg ggc atg ctc atg cta tta<br>Ile Asp Val Arg Trp Ile Val His Asp Gly Gly Met Leu Met Leu Leu<br>                    900                    905                    910 | | 2736 |
| ccg ttc ctg ctg aaa cag cac aag gtt tgg cgg aaa tgc agc ata cgg<br>Pro Phe Leu Leu Lys Gln His Lys Val Trp Arg Lys Cys Ser Ile Arg<br>                915                    920                    925 | | 2784 |
| atc ttc aca gta gcc caa cta gaa gac aac agt atc cag atg aag aag<br>Ile Phe Thr Val Ala Gln Leu Glu Asp Asn Ser Ile Gln Met Lys Lys<br>            930                    935                    940 | | 2832 |
| gat ctg gcc acc ttt ctg tac cac ctg cgc att gag gca gaa gtg gaa<br>Asp Leu Ala Thr Phe Leu Tyr His Leu Arg Ile Glu Ala Glu Val Glu<br>945                950                    955 | | 2880 |
| gtg gtg gag atg cac gac agt gac ata tct gcc tat aca tat gag cgc<br>Val Val Glu Met His Asp Ser Asp Ile Ser Ala Tyr Thr Tyr Glu Arg<br>960                965                    970                975 | | 2928 |
| acc ctg atg atg gag cag agg tcc cag atg ctt cgg cat atg cgg ctg<br>Thr Leu Met Met Glu Gln Arg Ser Gln Met Leu Arg His Met Arg Leu<br>                    980                    985                    990 | | 2976 |
| tcc aaa aca gag cga gac agg gag gca cag ctg gtg aaa gat cga aac<br>Ser Lys Thr Glu Arg Asp Arg Glu Ala Gln Leu Val Lys Asp Arg Asn<br>              995                    1000                  1005 | | 3024 |
| tca atg cta cgc ttg acc agc att ggc tct gat gag gac gaa gag aca<br>Ser Met Leu Arg Leu Thr Ser Ile Gly Ser Asp Glu Asp Glu Glu Thr<br>            1010                    1015                  1020 | | 3072 |
| gaa acg tac cag gag aag gtg cac atg act tgg acc aag gat aaa tac<br>Glu Thr Tyr Gln Glu Lys Val His Met Thr Trp Thr Lys Asp Lys Tyr<br>1025                1030                    1035 | | 3120 |
| atg gca tcc cgg ggg caa aag gtc aag tca atg gaa gga ttc cag gac<br>Met Ala Ser Arg Gly Gln Lys Val Lys Ser Met Glu Gly Phe Gln Asp<br>1040                1045                    1050                  1055 | | 3168 |
| cta ctt aat atg cgt ccg gac cag tcc aac gtg aga cgg atg cat aca<br>Leu Leu Asn Met Arg Pro Asp Gln Ser Asn Val Arg Arg Met His Thr<br>                1060                    1065                  1070 | | 3216 |
| gca gtg aag ctc aat gaa gtt ata gtc aac aag tct cat gaa gca aag<br>Ala Val Lys Leu Asn Glu Val Ile Val Asn Lys Ser His Glu Ala Lys<br>            1075                    1080                  1085 | | 3264 |
| ctg gtt ttg ttg aat atg cca gga cca ccc cgg aac cct gaa ggt gat<br>Leu Val Leu Leu Asn Met Pro Gly Pro Pro Arg Asn Pro Glu Gly Asp<br>                1090                    1095                  1100 | | 3312 |
| gaa aac tac atg gaa ttt cta gaa gtg ntc act gag gga tta gaa cga<br>Glu Asn Tyr Met Glu Phe Leu Glu Val Xaa Thr Glu Gly Leu Glu Arg<br>1105                1110                    1115 | | 3360 |

-continued

| | | |
|---|---|---|
| gtc ctt ctt gtc cgg ggt ggt ggc agt gag gtc atc acc att tac tca<br>Val Leu Leu Val Arg Gly Gly Gly Ser Glu Val Ile Thr Ile Tyr Ser<br>1120                     1125                    1130                    1135 | 3408 |
| taatcagctg tgggagattc tgcgtggtcc gacttcccta agactcatcg tccatggaga | 3468 |
| tgatagctct ttcctaccac tcccactcta ttcttgcaga gctgagcccc atctatgctc | 3528 |
| ttggctgcaa catgatctgc catcccagca gaaacaaata tccctcaac agaagaatgg | 3588 |
| tcaagtccta aaagctattt ctatggcagg agaaggcaag tcaaaattaa caagctaagc | 3648 |
| caaagggaac cttttggcac acagaaggta atgagttagt aaaacatatg ctagaaatgt | 3708 |
| aactggcaac agaaagcaat gttcatatct aacattcagg acgagtttca gaagacacgg | 3768 |
| gtcagtgagc accagaaagt taacaggcag ttaagcttca ccttagtaaa aaatgagttc | 3828 |
| ccattataga gacagcctgc agcagccagg atggaaacag gatactgata tataaaacct | 3888 |
| gagacatagc tgcagccact acttcttcct catggtttat tgtctgtact gtaccactgt | 3948 |
| acattttaac tgtctttgtt ttaaaaccca ttctgtggtt ataatgcaga cagtagtgtt | 4008 |
| actatagaaa tgttttttg aaaggctaga atgttttttt caggttttca aatgctgaac | 4068 |
| taaggggatt ccaaagagtg cgtattaaaa tatatagaaa cacagtggtt agctatgcaa | 4128 |
| cataaagcac acaagctatt atcttaacaa atgtgggttg ttatgtagtt aaccagaagg | 4188 |
| gtctcttcta ctcttagtag gcattggtct taaaaaccaa acaaaccaaa cctgtaagga | 4248 |
| agagacgcca gggctgtgtg atgccacctc caaggcccca gggttcagag gttcagcagt | 4308 |
| ggaactgggg gtgtgaaagc catacccttt ccactgtgcc aaaatcgtct gctcactggc | 4368 |
| agacaggttt gcaagtggcc tgacacaagc accttttctt tcacaagaaa tccatctgtg | 4428 |
| gcctcttcac caaagccata gtgcagattt gaggcactcg acctccatgc ccagagcttt | 4488 |
| tcccgtctca atattattat tattcattct gacttcggaa acttggctct gaaacaaatg | 4548 |
| gttcactaag ctaatgatct gctgtattgg ttttgctttc aaaaagctct aactgtgcca | 4608 |
| aggaaatact tgtgtaagat cagatttttt ttttttttt aatttactga tcacaaacac | 4668 |
| ttggcttacc agcataggca gcctttgtgg ctgagcagta ttcccagggt gtgaaacctc | 4728 |
| catacccttt ccaagatagt tactgaagaa actgtcttct tgcttagatt cacggctgct | 4788 |
| tttacatttc cttcactga cagtaaattg tgccactctc catacccgt aggacaatga | 4848 |
| acacccagaa ttcaacccaa gacagaagaa acccctcaaa tatggcttaa gaagctgagt | 4908 |
| catatggttt gttcttcctc ctcccaggcc cacttgagta gcaaaggatc cagcatgttt | 4968 |
| tcctttgctt cctgcagagg gtagaaacta ctcgtagttc tctttccaac actccattgc | 5028 |
| atacttgagt ataatcccct aggctccaag gcattggagc gcccattctg taaaagccag | 5088 |
| cctgcccagg aactgcctaa cacatccacc cctgaccaaa gtgacacata cttttttccat | 5148 |
| atcaaacaaa catgggaaga gaataaggtt tctttaagaa aggctgtttg tggttagagc | 5208 |
| tacataagaa tctgttaaag ggtagagtat agtcttcatt ccccaagata aaatcactg | 5268 |
| ttacatggac aaatggttat taggccagat ttgtactcat ctctgtctag aacatttcat | 5328 |
| gtctatgtgt tgcttatgtt gtctgtctgc aaagtgtctt agctctttta atcactgcaa | 5388 |
| ataaagcaat actgaaaact tgagagagaa aatgcacctt aggggaaggg gccaaatgtt | 5448 |
| tctagaggga agaggaagac cttctcctgc ctttcttata agacccagct tgtgtcttac | 5508 |
| ccatgagttt attagcaggg caggctgtaa cattcgttct cccccaactg tcctcagcc | 5568 |
| ttccgtagct acccttaaaag ctggagtttg aattgcaggg cctggttgac aggtgccagc | 5628 |
| ttcctcgtgg cagagcaaaa gctgctgctt ttcatattct gtgcctcctt ttcttgtggc | 5688 |

-continued

```
cccaaggatc ccaccaatcc tcattccccc taaatgttaa agaaaattc cttattgtgg    5748 atattaagtt acactgtaag catatttaca tgctcttttt ccccctggt ttttcttttc    5808 atcatgtata atttgaatcc agtgatagtc tcacatcttc caaaaaagtc tgcttatgtg    5868
atatagaaga gaaatattaa agtagactga aggggaactt gtgaaacatt aagcattgtt    5928
ctcaaccgtt taatttattg aaaggagaag ctgctactga gcagctgcta ttcttttgtt    5988
tacatagagt ctggttttgt ttgttttgct ctgtgctggg aacataaata aagttttcta    6048
cattattttc aaaaaaaaaa aaaaaaa                                       6075
```

<210> SEQ ID NO 6
<211> LENGTH: 1135
<212> TYPE: PRT
<213> ORGANISM: mouse
<220> FEATURE:
<221> NAME/KEY: misc_feature
<222> LOCATION: (102)
<223> OTHER INFORMATION: Xaa=Leu or Ile
<220> FEATURE:
<221> NAME/KEY: misc_feature
<222> LOCATION: (631)
<223> OTHER INFORMATION: Xaa=Leu or Ile
<220> FEATURE:
<221> NAME/KEY: misc_feature
<222> LOCATION: (1113)
<223> OTHER INFORMATION: Xaa=Leu or Ile

<400> SEQUENCE: 6

```
Met His Pro Pro Glu Ala Thr Thr Lys Met Ser Ser Val Arg Phe Met
  1               5                  10                  15

Val Thr Pro Thr Lys Ile Asp Asp Ile Pro Gly Leu Ser Asp Thr Ser
                 20                  25                  30

Pro Asp Leu Ser Ser Arg Ser Ser Arg Val Arg Phe Ser Ser Arg
             35                  40                  45

Glu Ser Val Pro Glu Thr Ser Arg Ser Glu Pro Met Ser Glu Leu Ser
         50                  55                  60

Gly Ala Thr Thr Ser Leu Ala Thr Val Ala Leu Asp Pro Ser Ser Asp
 65                  70                  75                  80

Arg Thr Ser Asn Pro Gln Asp Val Thr Glu Asp Asp Gly His Lys Lys
                 85                  90                  95

Ala Arg Asn Ala Tyr Xaa Asn Asn Ser Asn Tyr Glu Glu Gly Asp Glu
            100                 105                 110

Tyr Phe Asp Lys Asn Leu Ala Leu Phe Glu Glu Glu Met Asp Thr Arg
        115                 120                 125

Pro Lys Val Ser Ser Leu Leu Asn Arg Met Ala Asn Tyr Thr Asn Leu
    130                 135                 140

Thr Gln Gly Ala Lys Glu His Glu Glu Ala Glu Asn Ile Thr Glu Gly
145                 150                 155                 160

Lys Lys Lys Pro Thr Lys Ser Pro Gln Met Gly Thr Phe Met Gly Val
                165                 170                 175

Tyr Leu Pro Cys Leu Gln Asn Ile Phe Gly Val Ile Leu Phe Leu Arg
            180                 185                 190

Leu Thr Trp Val Val Gly Thr Ala Gly Ile Leu Gln Ala Phe Ala Ile
        195                 200                 205

Val Leu Ile Cys Cys Cys Cys Thr Met Leu Thr Ala Ile Ser Met Ser
    210                 215                 220

Ala Ile Ala Thr Asn Gly Val Val Pro Ala Gly Gly Ser Tyr Phe Met
225                 230                 235                 240
```

-continued

```
Ile Ser Arg Ala Leu Gly Pro Glu Phe Gly Ala Val Gly Leu Cys
            245                 250                 255

Phe Tyr Leu Gly Thr Thr Phe Ala Ala Ala Met Tyr Ile Leu Gly Ala
            260                 265                 270

Ile Glu Ile Phe Leu Val Tyr Ile Val Pro Arg Ala Ala Ile Phe Arg
            275                 280                 285

Ser Asp Asp Ala Leu Lys Glu Ser Ala Ala Met Leu Asn Asn Met Arg
290                 295                 300

Val Tyr Gly Thr Ala Phe Leu Val Leu Met Val Leu Val Phe Ile
305                 310                 315                 320

Gly Val Arg Tyr Val Asn Lys Phe Ala Ser Leu Phe Leu Ala Cys Val
                325                 330                 335

Ile Val Ser Ile Leu Ala Ile Tyr Ala Gly Ala Ile Lys Ser Ser Phe
                340                 345                 350

Ala Pro Pro His Phe Pro Val Cys Met Leu Gly Asn Arg Thr Leu Ser
                355                 360                 365

Ser Arg His Leu Asp Ile Cys Ser Lys Thr Lys Glu Val Asp Asn Met
            370                 375                 380

Thr Val Pro Ser Lys Leu Trp Gly Phe Phe Cys Asn Ser Ser Gln Phe
385                 390                 395                 400

Phe Asn Ala Thr Cys Asp Glu Tyr Phe Val His Asn Asn Val Ile Ser
                405                 410                 415

Ile Gln Gly Ile Pro Gly Leu Ala Ser Gly Ile Ile Thr Glu Asn Leu
                420                 425                 430

Trp Ser Asn Tyr Leu Pro Lys Gly Glu Ile Glu Lys Pro Ser Ala
            435                 440                 445

Lys Ser Ser Asp Val Leu Gly Asn Leu Asn His Glu Tyr Val Leu Ala
450                 455                 460

Asp Ile Thr Thr Ser Phe Thr Leu Leu Val Gly Ile Phe Phe Pro Ser
465                 470                 475                 480

Val Thr Gly Ile Met Ala Gly Ser Asn Arg Ser Gly Asp Leu Lys Asp
                485                 490                 495

Ala Gln Lys Ser Ile Pro Ile Gly Thr Ile Leu Ala Ile Leu Thr Thr
                500                 505                 510

Ser Phe Val Tyr Leu Ser Asn Val Val Leu Phe Gly Ala Cys Ile Glu
            515                 520                 525

Gly Val Val Leu Arg Asp Lys Phe Gly Asp Ala Val Lys Gly Asn Leu
            530                 535                 540

Val Val Gly Thr Leu Ser Trp Pro Ser Pro Trp Val Ile Val Ile Gly
545                 550                 555                 560

Ser Phe Phe Ser Thr Cys Gly Ala Gly Leu Gln Ser Leu Thr Gly Ala
                565                 570                 575

Pro Arg Leu Leu Gln Ala Ile Ala Lys Asp Asn Ile Ile Pro Phe Leu
            580                 585                 590

Arg Val Phe Gly His Ser Lys Ala Asn Gly Glu Pro Thr Trp Ala Leu
            595                 600                 605

Leu Leu Thr Ala Ala Ile Ala Glu Leu Gly Ile Leu Ile Ala Ser Leu
            610                 615                 620

Asp Leu Val Ala Pro Ile Xaa Ser Met Phe Leu Met Cys Tyr Leu
625                 630                 635                 640

Phe Val Asn Leu Ala Cys Ala Leu Gln Thr Leu Leu Arg Thr Pro Asn
                645                 650                 655
```

-continued

```
Trp Arg Pro Arg Phe Arg Tyr Tyr His Trp Ala Leu Ser Phe Met Gly
            660                 665                 670

Met Ser Ile Cys Leu Ala Leu Met Phe Ile Ser Ser Trp Tyr Tyr Ala
            675                 680                 685

Ile Val Ala Met Val Ile Ala Gly Met Ile Tyr Lys Tyr Ile Glu Tyr
            690                 695                 700

Gln Gly Ala Glu Lys Glu Trp Gly Asp Gly Ile Arg Gly Leu Ser Leu
705                 710                 715                 720

Ser Ala Ala Arg Phe Ala Leu Leu Arg Leu Glu Gly Pro Pro His
                725                 730                 735

Thr Lys Asn Trp Arg Pro Gln Leu Leu Val Leu Leu Lys Leu Asp Glu
            740                 745                 750

Asp Leu His Val Lys His Pro Arg Leu Leu Thr Phe Ala Ser Gln Leu
            755                 760                 765

Lys Ala Gly Lys Gly Leu Thr Ile Val Gly Ser Val Ile Val Gly Asn
770                 775                 780

Phe Leu Glu Asn Tyr Gly Asp Ala Leu Ala Ala Glu Gln Thr Ile Lys
785                 790                 795                 800

His Leu Met Glu Ala Glu Lys Val Lys Gly Phe Cys Gln Leu Val Val
            805                 810                 815

Ala Ala Lys Leu Lys Glu Gly Ile Ser His Leu Ile Gln Ser Cys Gly
            820                 825                 830

Leu Gly Gly Met Lys His Asn Thr Val Val Met Gly Trp Pro Asn Gly
            835                 840                 845

Trp Arg Gln Ser Glu Asp Ala Arg Ala Trp Lys Thr Phe Ile Gly Thr
850                 855                 860

Val Arg Val Thr Thr Ala Ala His Leu Ala Leu Leu Val Ala Lys Asn
865                 870                 875                 880

Val Ser Phe Phe Pro Ser Asn Val Glu Gln Phe Ser Glu Gly Asn Ile
                885                 890                 895

Asp Val Arg Trp Ile Val His Asp Gly Gly Met Leu Met Leu Leu Pro
            900                 905                 910

Phe Leu Leu Lys Gln His Lys Val Trp Arg Lys Cys Ser Ile Arg Ile
            915                 920                 925

Phe Thr Val Ala Gln Leu Glu Asp Asn Ser Ile Gln Met Lys Lys Asp
            930                 935                 940

Leu Ala Thr Phe Leu Tyr His Leu Arg Ile Glu Ala Glu Val Glu Val
945                 950                 955                 960

Val Glu Met His Asp Ser Asp Ile Ser Ala Tyr Thr Tyr Glu Arg Thr
                965                 970                 975

Leu Met Met Glu Gln Arg Ser Gln Met Leu Arg His Met Arg Leu Ser
            980                 985                 990

Lys Thr Glu Arg Asp Arg Glu Ala Gln Leu Val Lys Asp Arg Asn Ser
            995                 1000                1005

Met Leu Arg Leu Thr Ser Ile Gly Ser Asp Glu Asp Glu Glu Thr Glu
    1010                1015                1020

Thr Tyr Gln Glu Lys Val His Met Thr Trp Thr Lys Asp Lys Tyr Met
1025                1030                1035                1040

Ala Ser Arg Gly Gln Lys Val Lys Ser Met Glu Gly Phe Gln Asp Leu
                1045                1050                1055

Leu Asn Met Arg Pro Asp Gln Ser Asn Val Arg Arg Met His Thr Ala
            1060                1065                1070
```

-continued

```
Val Lys Leu Asn Glu Val Ile Val Asn Lys Ser His Glu Ala Lys Leu
        1075                1080                1085

Val Leu Leu Asn Met Pro Gly Pro Pro Arg Asn Pro Glu Gly Asp Glu
        1090                1095                1100

Asn Tyr Met Glu Phe Leu Glu Val Xaa Thr Glu Gly Leu Glu Arg Val
1105                1110                1115                1120

Leu Leu Val Arg Gly Gly Gly Ser Glu Val Ile Thr Ile Tyr Ser
                1125                1130                1135

<210> SEQ ID NO 7
<211> LENGTH: 6120
<212> TYPE: DNA
<213> ORGANISM: mouse
<220> FEATURE:
<221> NAME/KEY: CDS
<222> LOCATION: (4)..(3453)
<220> FEATURE:
<221> NAME/KEY: misc_feature
<222> LOCATION: (106)
<223> OTHER INFORMATION: n=c or a, Xaa=Leu or Ile
<220> FEATURE:
<221> NAME/KEY: misc_feature
<222> LOCATION: (925)
<223> OTHER INFORMATION: n=c or a, Xaa=Leu or Ile
<220> FEATURE:
<221> NAME/KEY: misc_feature
<222> LOCATION: (2545)
<223> OTHER INFORMATION: n=c or a, Xaa=Leu or Ile

<400> SEQUENCE: 7 aaa atg cat cca cca gaa gcc acc acc aag atg tcc tca gtt cgg ttc     48
    Met His Pro Pro Glu Ala Thr Thr Lys Met Ser Ser Val Arg Phe
    1               5                  10                  15 atg gtg aca cca act aag att gac gac att cca ggt ttg tca gac acc     96
Met Val Thr Pro Thr Lys Ile Asp Asp Ile Pro Gly Leu Ser Asp Thr
            20                  25                  30 agc ccg gac ntc agc tct cgg tct agt tct cga gta aga ttt agc tcc    144
Ser Pro Asp Xaa Ser Ser Arg Ser Ser Ser Arg Val Arg Phe Ser Ser
                35                  40                  45 cga gaa agt gtg cca gaa aca agc cgt agt gag cct atg agc gaa ctg    192
Arg Glu Ser Val Pro Glu Thr Ser Arg Ser Glu Pro Met Ser Glu Leu
        50                  55                  60 tct ggg gct act act tct ctg gca act gtt gcc cta gat cct tcc agt    240
Ser Gly Ala Thr Thr Ser Leu Ala Thr Val Ala Leu Asp Pro Ser Ser
65                  70                  75 gac cgg act tct aat ccc cag gat gtt acg gag gac ccg agt cag aac    288
Asp Arg Thr Ser Asn Pro Gln Asp Val Thr Glu Asp Pro Ser Gln Asn
80                  85                  90                  95 tcc atc aca ggg gag cac agc cag ctg tta gat gac ggc cat aaa aaa    336
Ser Ile Thr Gly Glu His Ser Gln Leu Leu Asp Asp Gly His Lys Lys
                100                 105                 110 gcc cga aat gct tat ctc aat aat tcc aac tat gaa gaa gga gac gaa    384
Ala Arg Asn Ala Tyr Leu Asn Asn Ser Asn Tyr Glu Glu Gly Asp Glu
            115                 120                 125 tat ttt gat aaa aat ttg gca ctc ttt gag gaa gaa atg gac acc aga    432
Tyr Phe Asp Lys Asn Leu Ala Leu Phe Glu Glu Glu Met Asp Thr Arg
        130                 135                 140 cca aag gtg tct tct ctc ctc aac cgc atg gcc aac tat aca aat ctg    480
Pro Lys Val Ser Ser Leu Leu Asn Arg Met Ala Asn Tyr Thr Asn Leu
    145                 150                 155 aca caa gga gca aag gaa cat gaa gag gca gag aac atc act gaa ggg    528
Thr Gln Gly Ala Lys Glu His Glu Glu Ala Glu Asn Ile Thr Glu Gly
160                 165                 170                 175
```

| | |
|---|---|
| aaa aag aag cct acc aag agc ccc caa atg ggt act ttc atg ggt gtc<br>Lys Lys Lys Pro Thr Lys Ser Pro Gln Met Gly Thr Phe Met Gly Val<br>180 185 190 | 576 |
| tac ctc cca tgt cta cag aac atc ttt gga gtg atc ctc ttc ctg cgt<br>Tyr Leu Pro Cys Leu Gln Asn Ile Phe Gly Val Ile Leu Phe Leu Arg<br>195 200 205 | 624 |
| ctt acc tgg gta gtg gga aca gct gga atc ctt cag gcc ttt gca att<br>Leu Thr Trp Val Val Gly Thr Ala Gly Ile Leu Gln Ala Phe Ala Ile<br>210 215 220 | 672 |
| gtc ctc atc tgc tgc tgc tgt aca atg tta act gcc atc tcc atg agc<br>Val Leu Ile Cys Cys Cys Cys Thr Met Leu Thr Ala Ile Ser Met Ser<br>225 230 235 | 720 |
| gcc atc gcc act aac gga gtg gtg cca gct ggg ggc tca tac ttc atg<br>Ala Ile Ala Thr Asn Gly Val Val Pro Ala Gly Gly Ser Tyr Phe Met<br>240 245 250 255 | 768 |
| att tcc aga gcc ctg ggc cca gag ttt ggc ggg gct gta ggc ctc tgc<br>Ile Ser Arg Ala Leu Gly Pro Glu Phe Gly Gly Ala Val Gly Leu Cys<br>260 265 270 | 816 |
| ttt tat ctt ggc acc aca ttt gca gca gcc atg tat att ctt ggt gcc<br>Phe Tyr Leu Gly Thr Thr Phe Ala Ala Ala Met Tyr Ile Leu Gly Ala<br>275 280 285 | 864 |
| att gaa atc ttt ctg gta tac att gtc ccc cga gct gcc atc ttt cgg<br>Ile Glu Ile Phe Leu Val Tyr Ile Val Pro Arg Ala Ala Ile Phe Arg<br>290 295 300 | 912 |
| agt gac gat gca ntc aag gag tca gca gct atg ctg aac aac atg cgc<br>Ser Asp Asp Ala Xaa Lys Glu Ser Ala Ala Met Leu Asn Asn Met Arg<br>305 310 315 | 960 |
| gtc tat ggt aca gcc ttc ttg gtc ctc atg gtc ttg gtg gta ttc atc<br>Val Tyr Gly Thr Ala Phe Leu Val Leu Met Val Leu Val Val Phe Ile<br>320 325 330 335 | 1008 |
| ggc gta cgc tat gtg aat aag ttt gcc tca ctc ttc ctg gcc tgt gta<br>Gly Val Arg Tyr Val Asn Lys Phe Ala Ser Leu Phe Leu Ala Cys Val<br>340 345 350 | 1056 |
| att gtg tcg atc ttg gct atc tat gct ggt gcc atc aag tct tcc ttt<br>Ile Val Ser Ile Leu Ala Ile Tyr Ala Gly Ala Ile Lys Ser Ser Phe<br>355 360 365 | 1104 |
| gct cca cca cac ttc ccg gtc tgt atg ctg ggc aac cgt acc ctg tca<br>Ala Pro Pro His Phe Pro Val Cys Met Leu Gly Asn Arg Thr Leu Ser<br>370 375 380 | 1152 |
| tca aga cac ctt gac att tgc tct aag acc aag gag gtt gac aac atg<br>Ser Arg His Leu Asp Ile Cys Ser Lys Thr Lys Glu Val Asp Asn Met<br>385 390 395 | 1200 |
| aca gta cca tca aag tta tgg gga ttc ttc tgc aac tcg agt cag ttc<br>Thr Val Pro Ser Lys Leu Trp Gly Phe Phe Cys Asn Ser Ser Gln Phe<br>400 405 410 415 | 1248 |
| ttt aat gcc acc tgt gat gag tac ttt gtt cac aat aac gtc atc tca<br>Phe Asn Ala Thr Cys Asp Glu Tyr Phe Val His Asn Asn Val Ile Ser<br>420 425 430 | 1296 |
| atc caa ggc att cca ggg ttg gct agt ggt atc att act gaa aat ctt<br>Ile Gln Gly Ile Pro Gly Leu Ala Ser Gly Ile Ile Thr Glu Asn Leu<br>435 440 445 | 1344 |
| tgg agt aat tat tta cca aag ggt gag ata att gaa aag cca tca gcc<br>Trp Ser Asn Tyr Leu Pro Lys Gly Glu Ile Ile Glu Lys Pro Ser Ala<br>450 455 460 | 1392 |
| aag tca tct gat gtc tta ggc aac tta aac cat gaa tat gtt ctt gct<br>Lys Ser Ser Asp Val Leu Gly Asn Leu Asn His Glu Tyr Val Leu Ala<br>465 470 475 | 1440 |
| gat atc acc acc tcc ttc act ctg ctg gtg ggg atc ttc ttt ccc tcg<br>Asp Ile Thr Thr Ser Phe Thr Leu Leu Val Gly Ile Phe Phe Pro Ser<br>480 485 490 495 | 1488 |

-continued

| | | |
|---|---|---|
| gtc aca ggt atc atg gct ggg tca aac aga tct gga gat ctg aaa gat<br>Val Thr Gly Ile Met Ala Gly Ser Asn Arg Ser Gly Asp Leu Lys Asp<br>            500                        505                        510 | 1536 |
| gcc cag aag tct att ccc att ggg acc atc ctt gcc atc ctg acc aca<br>Ala Gln Lys Ser Ile Pro Ile Gly Thr Ile Leu Ala Ile Leu Thr Thr<br>515                        520                        525 | 1584 |
| tcc ttt gtg tat tta agc aat gtt gtc ctt ttt ggt gca tgt att gaa<br>Ser Phe Val Tyr Leu Ser Asn Val Val Leu Phe Gly Ala Cys Ile Glu<br>        530                        535                        540 | 1632 |
| gga gtc gtt ctc aga gac aaa ttt ggg gat gct gta aaa ggg aat ttg<br>Gly Val Val Leu Arg Asp Lys Phe Gly Asp Ala Val Lys Gly Asn Leu<br>545                        550                        555 | 1680 |
| gtt gta ggc acc tta tcc tgg cca tcc ccg tgg gtg atc gtt att ggc<br>Val Val Gly Thr Leu Ser Trp Pro Ser Pro Trp Val Ile Val Ile Gly<br>560                        565                        570                        575 | 1728 |
| tcc ttc ttt tca aca tgt ggg gct ggg ctg cag agc ctc aca ggt gcg<br>Ser Phe Phe Ser Thr Cys Gly Ala Gly Leu Gln Ser Leu Thr Gly Ala<br>                        580                        585                        590 | 1776 |
| cct cgg ctg ctg cag gct atc gcc aag gat aac atc ata cct ttc ctt<br>Pro Arg Leu Leu Gln Ala Ile Ala Lys Asp Asn Ile Ile Pro Phe Leu<br>595                        600                        605 | 1824 |
| agg gtt ttt ggt cac agc aaa gct aat ggg gaa cct acc tgg gct tta<br>Arg Val Phe Gly His Ser Lys Ala Asn Gly Glu Pro Thr Trp Ala Leu<br>        610                        615                        620 | 1872 |
| ctt cta act gct gcc ata gca gag ctg gga att ctc atc gcc tcc ctg<br>Leu Leu Thr Ala Ala Ile Ala Glu Leu Gly Ile Leu Ile Ala Ser Leu<br>625                        630                        635 | 1920 |
| gat ctc gtg gcc cca att ctt tcc atg ttt ttt ctc atg tgt tac ctc<br>Asp Leu Val Ala Pro Ile Leu Ser Met Phe Phe Leu Met Cys Tyr Leu<br>640                        645                        650                        655 | 1968 |
| ttt gtg aac ttg gct tgt gcc ttg caa aca ttg ctg cga acc ccc aac<br>Phe Val Asn Leu Ala Cys Ala Leu Gln Thr Leu Leu Arg Thr Pro Asn<br>                660                        665                        670 | 2016 |
| tgg agg cct cga ttc cgc tat tat cac tgg gcc ctc tct ttc atg gga<br>Trp Arg Pro Arg Phe Arg Tyr Tyr His Trp Ala Leu Ser Phe Met Gly<br>                        675                        680                        685 | 2064 |
| atg agt atc tgt cta gct ctg atg ttc att tct tct tgg tat tat gcc<br>Met Ser Ile Cys Leu Ala Leu Met Phe Ile Ser Ser Trp Tyr Tyr Ala<br>        690                        695                        700 | 2112 |
| att gta gct atg gta ata gct ggc atg atc tac aag tac att gaa tat<br>Ile Val Ala Met Val Ile Ala Gly Met Ile Tyr Lys Tyr Ile Glu Tyr<br>705                        710                        715 | 2160 |
| caa ggg gct gag aaa gaa tgg ggg gat ggt atc cgt ggg ctg tcg ctc<br>Gln Gly Ala Glu Lys Glu Trp Gly Asp Gly Ile Arg Gly Leu Ser Leu<br>720                        725                        730                        735 | 2208 |
| agt gca gcc cgc ttc gct ttg ctc cgt cta gag gaa gga cct cct cac<br>Ser Ala Ala Arg Phe Ala Leu Leu Arg Leu Glu Glu Gly Pro Pro His<br>                        740                        745                        750 | 2256 |
| act aaa aac tgg agg cct cag ctg ctc gtc cta ctg aag ctg gat gaa<br>Thr Lys Asn Trp Arg Pro Gln Leu Leu Val Leu Leu Lys Leu Asp Glu<br>                755                        760                        765 | 2304 |
| gat tta cac gtc aag cac cct cgc ctc ctc acc ttt gcc tcc cag ctc<br>Asp Leu His Val Lys His Pro Arg Leu Leu Thr Phe Ala Ser Gln Leu<br>                        770                        775                        780 | 2352 |
| aag gca gga aag gga ctc acg att gtg ggc tct gtc atc gtg ggg aac<br>Lys Ala Gly Lys Gly Leu Thr Ile Val Gly Ser Val Ile Val Gly Asn<br>785                        790                        795 | 2400 |
| ttc ttg gag aac tat ggt gac gcg ctc gcg gca gag cag acc att aag<br>Phe Leu Glu Asn Tyr Gly Asp Ala Leu Ala Ala Glu Gln Thr Ile Lys<br>800                        805                        810                        815 | 2448 |

```
                                                              -continued cac cta atg gag gca gaa aag gta aaa gga ttc tgc caa ttg gtg gtg        2496
His Leu Met Glu Ala Glu Lys Val Lys Gly Phe Cys Gln Leu Val Val
            820                 825                 830 gct gcc aag ctg aaa gag ggc att tca cac ctc atc cag tcc tgt ggc        2544
Ala Ala Lys Leu Lys Glu Gly Ile Ser His Leu Ile Gln Ser Cys Gly
        835                 840                 845 ntc gga ggc atg aaa cac aac aca gtg gtg atg ggc tgg ccc aat ggc        2592
Xaa Gly Gly Met Lys His Asn Thr Val Val Met Gly Trp Pro Asn Gly
    850                 855                 860 tgg cgt cag agt gaa gat gct cgc gct tgg aag act ttc att ggc aca        2640
Trp Arg Gln Ser Glu Asp Ala Arg Ala Trp Lys Thr Phe Ile Gly Thr
865                 870                 875 gta cga gtg aca act gct gcc cat cta gcc ctg ctg gtg gct aaa aat        2688
Val Arg Val Thr Thr Ala Ala His Leu Ala Leu Leu Val Ala Lys Asn
880                 885                 890                 895 gtc tcc ttc ttt ccc agc aat gtg gag cag ttt tct gag ggc aac att        2736
Val Ser Phe Phe Pro Ser Asn Val Glu Gln Phe Ser Glu Gly Asn Ile
                900                 905                 910 gat gtg cgg tgg att gtg cat gat ggg ggc atg ctc atg cta tta ccg        2784
Asp Val Arg Trp Ile Val His Asp Gly Gly Met Leu Met Leu Leu Pro
            915                 920                 925 ttc ctg ctg aaa cag cac aag gtt tgg cgg aaa tgc agc ata cgg atc        2832
Phe Leu Leu Lys Gln His Lys Val Trp Arg Lys Cys Ser Ile Arg Ile
        930                 935                 940 ttc aca gta gcc caa cta gaa gac aac agt atc cag atg aag aag gat        2880
Phe Thr Val Ala Gln Leu Glu Asp Asn Ser Ile Gln Met Lys Lys Asp
    945                 950                 955 ctg gcc acc ttt ctg tac cac ctg cgc att gag gca gaa gtg gaa gtg        2928
Leu Ala Thr Phe Leu Tyr His Leu Arg Ile Glu Ala Glu Val Glu Val
960                 965                 970                 975 gtg gag atg cac gac agt gac ata tct gcc tat aca tat gag cgc acc        2976
Val Glu Met His Asp Ser Asp Ile Ser Ala Tyr Thr Tyr Glu Arg Thr
                980                 985                 990 ctg atg atg gag cag agg tcc cag atg ctt cgg cat atg cgg ctg tcc        3024
Leu Met Met Glu Gln Arg Ser Gln Met Leu Arg His Met Arg Leu Ser
            995                 1000                1005 aaa aca gag cga gac agg gag gca cag ctg gtg aaa gat cga aac tca        3072
Lys Thr Glu Arg Asp Arg Glu Ala Gln Leu Val Lys Asp Arg Asn Ser
        1010                1015                1020 atg cta cgc ttg acc agc att ggc tct gat gag gac gaa gag aca gaa        3120
Met Leu Arg Leu Thr Ser Ile Gly Ser Asp Glu Asp Glu Glu Thr Glu
    1025                1030                1035 acg tac cag gag aag gtg cac atg act tgg acc aag gat aaa tac atg        3168
Thr Tyr Gln Glu Lys Val His Met Thr Trp Thr Lys Asp Lys Tyr Met
1040                1045                1050                1055 gca tcc cgg ggg caa aag gtc aag tca atg gaa gga ttc cag gac cta        3216
Ala Ser Arg Gly Gln Lys Val Lys Ser Met Glu Gly Phe Gln Asp Leu
                1060                1065                1070 ctt aat atg cgt ccg gac cag tcc aac gtg aga cgg atg cat aca gca        3264
Leu Asn Met Arg Pro Asp Gln Ser Asn Val Arg Arg Met His Thr Ala
            1075                1080                1085 gtg aag ctc aat gaa gtt ata gtc aac aag tct cat gaa gca aag ctg        3312
Val Lys Leu Asn Glu Val Ile Val Asn Lys Ser His Glu Ala Lys Leu
        1090                1095                1100 gtt ttg ttg aat atg cca gga cca ccc cgg aac cct gaa ggt gat gaa        3360
Val Leu Leu Asn Met Pro Gly Pro Pro Arg Asn Pro Glu Gly Asp Glu
    1105                1110                1115 aac tac atg gaa ttt cta gaa gtg ctc act gag gga tta gaa cga gtc        3408
Asn Tyr Met Glu Phe Leu Glu Val Leu Thr Glu Gly Leu Glu Arg Val
1120                1125                1130                1135
```

| | | |
|---|---|---|
| ctt ctt gtc cgg ggt ggt ggc agt gag gtc atc acc att tac tca<br>Leu Leu Val Arg Gly Gly Gly Ser Glu Val Ile Thr Ile Tyr Ser<br>    1140            1145            1150 | 3453 |
| taatcagctg tgggagattc tgcgtggtcc gacttcccta agactcatcg tccatggaga | 3513 |
| tgatagctct ttcctaccac tcccactcta ttcttgcaga gctgagcccc atctatgctc | 3573 |
| ttggctgcaa catgatctgc catcccagca gaaacaaata tccctcaac agaagaatgg | 3633 |
| tcaagtccta aaagctattt ctatggcagg agaaggcaag tcaaaattaa caagctaagc | 3693 |
| caaagggaac cttttggcac acagaaggta atgagttagt aaaacatatg ctagaaatgt | 3753 |
| aactggcaac agaaagcaat gttcatatct aacattcagg acgagtttca gaagacacgg | 3813 |
| gtcagtgagc accagaaagt taacaggcag ttaagcttca ccttagtaaa aatgagttc | 3873 |
| ccattataga gacagcctgc agcagccagg atggaaacag gatactgata tataaaacct | 3933 |
| gagacatagc tgcagccact acttcttcct catggtttat tgtctgtact gtaccactgt | 3993 |
| acattttaac tgtctttgtt ttaaaaccca ttctgtggtt ataatgcaga cagtagtgtt | 4053 |
| actatagaaa tgttttttg aaaggctaga atgttttttt caggttttca aatgctgaac | 4113 |
| taagggatt ccaaagagtg cgtattaaaa tatatagaaa cacagtggtt agctatgcaa | 4173 |
| cataaagcac acaagctatt atcttaacaa atgtgggttg ttatgtagtt aaccagaagg | 4233 |
| gtctcttcta ctcttagtag gcattggtct taaaaaccaa acaaaccaaa cctgtaagga | 4293 |
| agagacgcca gggctgtgtg atgccacctc caaggcccca gggttcagag gttcagcagt | 4353 |
| ggaactgggg gtgtgaaagc catacccttt ccactgtgcc aaaatcgtct gctcactggc | 4413 |
| agacaggttt gcaagtggcc tgacacaagc accttttctt tcacaagaaa tccatctgtg | 4473 |
| gcctcttcac caaagccata gtgcagattt gaggcactcg acctccatgc ccagagcttt | 4533 |
| tcccgtctca atattattat tattcattct gacttcggaa acttggctct gaaacaaatg | 4593 |
| gttcactaag ctaatgatct gctgtattgg ttttgctttc aaaagctct aactgtgcca | 4653 |
| aggaaatact tgtgtaagat cagatttttt ttttttttt aatttactga tcacaaacac | 4713 |
| ttggcttacc agcataggca gcctttgtgg ctgagcagta ttcccagggt gtgaaacctc | 4773 |
| catacccttt ccaagatagt tactgaagaa actgtcttct tgcttagatt cacggctgct | 4833 |
| tttacatttc ctttcactga cagtaaattg tgccactctc cataccctgt aggacaatga | 4893 |
| acacccagaa ttcaacccaa gacagaagaa accctcaaa tatggcttaa gaagctgagt | 4953 |
| catatggttt gttcttcctc ctcccaggcc cacttgagta gcaaaggatc cagcatgttt | 5013 |
| tcctttgctt cctgcagagg gtagaaacta ctcgtagttc tctttccaac actccattgc | 5073 |
| atacttgagt ataatcccct aggctccaag gcattggagc gcccattctg taaaagccag | 5133 |
| cctgcccagg aactgcctaa cacatccacc cctgaccaaa gtgacacata cttttccat | 5193 |
| atcaaacaaa catgggaaga gaataaggtt tctttaagaa aggctgtttg tggttagagc | 5253 |
| tacataagaa tctgttaaag ggtagagtat agtcttcatt ccccaagata aaatcactg | 5313 |
| ttacatggac aaatggttat taggccagat ttgtactcat ctctgtctag aacatttcat | 5373 |
| gtctatgtgt tgcttatgtt gtctgtctgc aaagtgtctt agctcttta atcactgcaa | 5433 |
| ataaagcaat actgaaaact tgagagagaa aatgcacctt aggggaaggg gccaaatgtt | 5493 |
| tctagaggga agaggaagac cttctcctgc ctttcttata agacccagct tgtgtcttac | 5553 |
| ccatgagttt attagcaggg caggctgtaa cattcgttct ccccaactg tcctcagcc | 5613 |
| ttccgtagct acccttaaaag ctggagtttg aattgcaggg cctggttgac aggtgccagc | 5673 |
| ttcctcgtgg cagagcaaaa gctgctgctt ttcatattct gtgcctcctt ttcttgtggc | 5733 |

```
cccaaggatc ccaccaatcc tcattccccc taaatgttaa agaaaaattc cttattgtgg    5793
atattaagtt acactgtaag catatttaca tgctcttttt ccccccctggt ttttcttttc    5853 atcatgtata atttgaatcc agtgatagtc tcacatcttc caaaaaagtc tgcttatgtg    5913
atatagaaga gaaatattaa agtagactga aggggaactt gtgaaacatt aagcattgtt    5973
ctcaaccgtt taatttattg aaaggagaag ctgctactga gcagctgcta ttcttttgtt    6033
tacatagagt ctggttttgt ttgttttgct ctgtgctggg aacataaata aagttttcta    6093
cattattttc aaaaaaaaaa aaaaaa                                         6120
```

```
<210> SEQ ID NO 8
<211> LENGTH: 1150
<212> TYPE: PRT
<213> ORGANISM: mouse
<220> FEATURE:
<221> NAME/KEY: misc_feature
<222> LOCATION: (35)
<223> OTHER INFORMATION: Xaa=Leu or Ile
<220> FEATURE:
<221> NAME/KEY: misc_feature
<222> LOCATION: (308)
<223> OTHER INFORMATION: Xaa=Leu or Ile
<220> FEATURE:
<221> NAME/KEY: misc_feature
<222> LOCATION: (848)
<223> OTHER INFORMATION: Xaa=Leu or Ile

<400> SEQUENCE: 8

Met His Pro Pro Glu Ala Thr Thr Lys Met Ser Ser Val Arg Phe Met
  1               5                  10                  15

Val Thr Pro Thr Lys Ile Asp Asp Ile Pro Gly Leu Ser Asp Thr Ser
                 20                  25                  30

Pro Asp Leu Ser Ser Arg Ser Ser Arg Val Arg Phe Ser Ser Arg
             35                  40                  45

Glu Ser Val Pro Glu Thr Ser Arg Ser Glu Pro Met Ser Glu Leu Ser
         50                  55                  60

Gly Ala Thr Thr Ser Leu Ala Thr Val Ala Leu Asp Pro Ser Ser Asp
 65                  70                  75                  80

Arg Thr Ser Asn Pro Gln Asp Val Thr Glu Asp Pro Ser Gln Asn Ser
                 85                  90                  95

Ile Thr Gly Glu His Ser Gln Leu Leu Asp Asp Gly His Lys Lys Ala
            100                 105                 110

Arg Asn Ala Tyr Leu Asn Asn Ser Asn Tyr Glu Glu Gly Asp Glu Tyr
        115                 120                 125

Phe Asp Lys Asn Leu Ala Leu Phe Glu Glu Met Asp Thr Arg Pro
    130                 135                 140

Lys Val Ser Ser Leu Leu Asn Arg Met Ala Asn Tyr Thr Asn Leu Thr
145                 150                 155                 160

Gln Gly Ala Lys Glu His Glu Glu Ala Glu Asn Ile Thr Glu Gly Lys
                165                 170                 175

Lys Lys Pro Thr Lys Ser Pro Gln Met Gly Thr Phe Met Gly Val Tyr
            180                 185                 190

Leu Pro Cys Leu Gln Asn Ile Phe Gly Val Ile Leu Phe Leu Arg Leu
        195                 200                 205

Thr Trp Val Val Gly Thr Ala Gly Ile Leu Gln Ala Phe Ala Ile Val
    210                 215                 220

Leu Ile Cys Cys Cys Cys Thr Met Leu Thr Ala Ile Ser Met Ser Ala
225                 230                 235                 240
```

-continued

```
Ile Ala Thr Asn Gly Val Val Pro Ala Gly Gly Ser Tyr Phe Met Ile
            245                 250                 255

Ser Arg Ala Leu Gly Pro Glu Phe Gly Gly Ala Val Gly Leu Cys Phe
        260                 265                 270

Tyr Leu Gly Thr Thr Phe Ala Ala Ala Met Tyr Ile Leu Gly Ala Ile
        275                 280                 285

Glu Ile Phe Leu Val Tyr Ile Val Pro Arg Ala Ile Phe Arg Ser
290                 295                 300

Asp Asp Ala Leu Lys Glu Ser Ala Ala Met Leu Asn Asn Met Arg Val
305                 310                 315                 320

Tyr Gly Thr Ala Phe Leu Val Leu Met Val Leu Val Phe Ile Gly
                325                 330                 335

Val Arg Tyr Val Asn Lys Phe Ala Ser Leu Phe Leu Ala Cys Val Ile
            340                 345                 350

Val Ser Ile Leu Ala Ile Tyr Ala Gly Ala Ile Lys Ser Ser Phe Ala
        355                 360                 365

Pro Pro His Phe Pro Val Cys Met Leu Gly Asn Arg Thr Leu Ser Ser
370                 375                 380

Arg His Leu Asp Ile Cys Ser Lys Thr Lys Glu Val Asp Asn Met Thr
385                 390                 395                 400

Val Pro Ser Lys Leu Trp Gly Phe Phe Cys Asn Ser Ser Gln Phe Phe
            405                 410                 415

Asn Ala Thr Cys Asp Glu Tyr Phe Val His Asn Asn Val Ile Ser Ile
        420                 425                 430

Gln Gly Ile Pro Gly Leu Ala Ser Gly Ile Ile Thr Glu Asn Leu Trp
        435                 440                 445

Ser Asn Tyr Leu Pro Lys Gly Glu Ile Ile Glu Lys Pro Ser Ala Lys
    450                 455                 460

Ser Ser Asp Val Leu Gly Asn Leu Asn His Glu Tyr Val Leu Ala Asp
465                 470                 475                 480

Ile Thr Thr Ser Phe Thr Leu Leu Val Gly Ile Phe Phe Pro Ser Val
                485                 490                 495

Thr Gly Ile Met Ala Gly Ser Asn Arg Ser Gly Asp Leu Lys Asp Ala
            500                 505                 510

Gln Lys Ser Ile Pro Ile Gly Thr Ile Leu Ala Ile Leu Thr Thr Ser
        515                 520                 525

Phe Val Tyr Leu Ser Asn Val Val Leu Phe Gly Ala Cys Ile Glu Gly
    530                 535                 540

Val Val Leu Arg Asp Lys Phe Gly Asp Ala Val Lys Gly Asn Leu Val
545                 550                 555                 560

Val Gly Thr Leu Ser Trp Pro Ser Pro Trp Val Ile Val Ile Gly Ser
                565                 570                 575

Phe Phe Ser Thr Cys Gly Ala Gly Leu Gln Ser Leu Thr Gly Ala Pro
            580                 585                 590

Arg Leu Leu Gln Ala Ile Ala Lys Asp Asn Ile Ile Pro Phe Leu Arg
        595                 600                 605

Val Phe Gly His Ser Lys Ala Asn Gly Glu Pro Thr Trp Ala Leu Leu
    610                 615                 620

Leu Thr Ala Ala Ile Ala Glu Leu Gly Ile Leu Ile Ala Ser Leu Asp
625                 630                 635                 640

Leu Val Ala Pro Ile Leu Ser Met Phe Phe Leu Met Cys Tyr Leu Phe
                645                 650                 655
```

```
Val Asn Leu Ala Cys Ala Leu Gln Thr Leu Arg Thr Pro Asn Trp
            660                 665                 670

Arg Pro Arg Phe Arg Tyr Tyr His Trp Ala Leu Ser Phe Met Gly Met
        675                 680                 685

Ser Ile Cys Leu Ala Leu Met Phe Ile Ser Ser Trp Tyr Tyr Ala Ile
    690                 695                 700

Val Ala Met Val Ile Ala Gly Met Ile Tyr Lys Tyr Ile Glu Tyr Gln
705                 710                 715                 720

Gly Ala Glu Lys Glu Trp Gly Asp Gly Ile Arg Gly Leu Ser Leu Ser
                725                 730                 735

Ala Ala Arg Phe Ala Leu Leu Arg Leu Glu Gly Pro Pro His Thr
                740                 745                 750

Lys Asn Trp Arg Pro Gln Leu Leu Val Leu Leu Lys Leu Asp Glu Asp
            755                 760                 765

Leu His Val Lys His Pro Arg Leu Leu Thr Phe Ala Ser Gln Leu Lys
    770                 775                 780

Ala Gly Lys Gly Leu Thr Ile Val Gly Ser Val Ile Val Gly Asn Phe
785                 790                 795                 800

Leu Glu Asn Tyr Gly Asp Ala Leu Ala Ala Glu Gln Thr Ile Lys His
                805                 810                 815

Leu Met Glu Ala Glu Lys Val Lys Gly Phe Cys Gln Leu Val Val Ala
            820                 825                 830

Ala Lys Leu Lys Glu Gly Ile Ser His Leu Ile Gln Ser Cys Gly Leu
    835                 840                 845

Gly Gly Met Lys His Asn Thr Val Val Met Gly Trp Pro Asn Gly Trp
850                 855                 860

Arg Gln Ser Glu Asp Ala Arg Ala Trp Lys Thr Phe Ile Gly Thr Val
865                 870                 875                 880

Arg Val Thr Thr Ala Ala His Leu Ala Leu Leu Val Ala Lys Asn Val
                885                 890                 895

Ser Phe Phe Pro Ser Asn Val Glu Gln Phe Ser Glu Gly Asn Ile Asp
            900                 905                 910

Val Arg Trp Ile Val His Asp Gly Gly Met Leu Met Leu Leu Pro Phe
    915                 920                 925

Leu Leu Lys Gln His Lys Val Trp Arg Lys Cys Ser Ile Arg Ile Phe
    930                 935                 940

Thr Val Ala Gln Leu Glu Asp Asn Ser Ile Gln Met Lys Lys Asp Leu
945                 950                 955                 960

Ala Thr Phe Leu Tyr His Leu Arg Ile Glu Ala Glu Val Glu Val Val
                965                 970                 975

Glu Met His Asp Ser Asp Ile Ser Ala Tyr Thr Tyr Glu Arg Thr Leu
            980                 985                 990

Met Met Glu Gln Arg Ser Gln Met Leu Arg His Met Arg Leu Ser Lys
            995                 1000                1005

Thr Glu Arg Asp Arg Glu Ala Gln Leu Val Lys Asp Arg Asn Ser Met
    1010                1015                1020

Leu Arg Leu Thr Ser Ile Gly Ser Asp Glu Asp Glu Thr Glu Thr
1025                1030                1035                1040

Tyr Gln Glu Lys Val His Met Thr Trp Thr Lys Asp Lys Tyr Met Ala
                1045                1050                1055

Ser Arg Gly Gln Lys Val Lys Ser Met Glu Gly Phe Gln Asp Leu Leu
                1060                1065                1070
```

-continued

```
Asn Met Arg Pro Asp Gln Ser Asn Val Arg Arg Met His Thr Ala Val
        1075                1080                1085

Lys Leu Asn Glu Val Ile Val Asn Lys Ser His Glu Ala Lys Leu Val
    1090                1095                1100

Leu Leu Asn Met Pro Gly Pro Pro Arg Asn Pro Glu Gly Asp Glu Asn
1105                1110                1115                1120

Tyr Met Glu Phe Leu Glu Val Leu Thr Glu Gly Leu Glu Arg Val Leu
                1125                1130                1135

Leu Val Arg Gly Gly Gly Ser Glu Val Ile Thr Ile Tyr Ser
            1140                1145                1150

<210> SEQ ID NO 9
<211> LENGTH: 6052
<212> TYPE: DNA
<213> ORGANISM: mouse
<220> FEATURE:
<221> NAME/KEY: CDS
<222> LOCATION: (89)..(3385)
<220> FEATURE:
<221> NAME/KEY: misc_feature
<222> LOCATION: (284)
<223> OTHER INFORMATION: n=c or a, Xaa=Leu or Ile
<220> FEATURE:
<221> NAME/KEY: misc_feature
<222> LOCATION: (1697)
<223> OTHER INFORMATION: n=c or a, Xaa=Leu or Ile
<220> FEATURE:
<221> NAME/KEY: misc_feature
<222> LOCATION: (3008)
<223> OTHER INFORMATION: n=c or a, Xaa=Leu or Ile

<400> SEQUENCE: 9
ggctgtgctc tgagtgtgga gggagagagg cagggacgca cgggaaggaa atttaaactc       60
ttaaagcaag ggtctgtctg taagaaca atg ccg cac ttc act gtg acc aag        112
                                Met Pro His Phe Thr Val Thr Lys
                                  1               5 gta gaa gac cca gag gag ggg gca gct ggc ccc ctc tct cct gag ccc        160
Val Glu Asp Pro Glu Glu Gly Ala Ala Gly Pro Leu Ser Pro Glu Pro
     10                  15                  20 agc tca gca gaa gta aaa gcc cgg att cag gat ccc caa gaa cca gac        208
Ser Ser Ala Glu Val Lys Ala Arg Ile Gln Asp Pro Gln Glu Pro Asp
 25                  30                  35                  40 ccg agt cag aac tcc atc aca ggg gag cac agc cag ctg tta gat gac        256
Pro Ser Gln Asn Ser Ile Thr Gly Glu His Ser Gln Leu Leu Asp Asp
                 45                  50                  55 ggc cat aaa aaa gcc cga aat gct tat ntc aat aat tcc aac tat gaa        304
Gly His Lys Lys Ala Arg Asn Ala Tyr Xaa Asn Asn Ser Asn Tyr Glu
             60                  65                  70 gaa gga gac gaa tat ttt gat aaa aat ttg gca ctc ttt gag gaa gaa        352
Glu Gly Asp Glu Tyr Phe Asp Lys Asn Leu Ala Leu Phe Glu Glu Glu
         75                  80                  85 atg gac acc aga cca aag gtg tct tct ctc ctc aac cgc atg gcc aac        400
Met Asp Thr Arg Pro Lys Val Ser Ser Leu Leu Asn Arg Met Ala Asn
     90                  95                 100 tat aca aat ctg aca caa gga gca aag gaa cat gaa gag gca gag aac        448
Tyr Thr Asn Leu Thr Gln Gly Ala Lys Glu His Glu Glu Ala Glu Asn
105                 110                 115                 120 atc act gaa ggg aaa aag aag cct acc aag agc ccc caa atg ggt act        496
Ile Thr Glu Gly Lys Lys Lys Pro Thr Lys Ser Pro Gln Met Gly Thr
                125                 130                 135 ttc atg ggt gtc tac ctc cca tgt cta cag aac atc ttt gga gtg atc        544
Phe Met Gly Val Tyr Leu Pro Cys Leu Gln Asn Ile Phe Gly Val Ile
            140                 145                 150
```

| | | | | | | | | | | | | | | | | |
|---|---|---|---|---|---|---|---|---|---|---|---|---|---|---|---|---|
| ctc | ttc | ctg | cgt | ctt | acc | tgg | gta | gtg | gga | aca | gct | gga | atc | ctt | cag | 592 |
| Leu | Phe | Leu | Arg | Leu | Thr | Trp | Val | Val | Gly | Thr | Ala | Gly | Ile | Leu | Gln | |
| | | | 155 | | | | 160 | | | | | 165 | | | | |
| gcc | ttt | gca | att | gtc | ctc | atc | tgc | tgc | tgc | tgt | aca | atg | tta | act | gcc | 640 |
| Ala | Phe | Ala | Ile | Val | Leu | Ile | Cys | Cys | Cys | Cys | Thr | Met | Leu | Thr | Ala | |
| | 170 | | | | | 175 | | | | | 180 | | | | | |
| atc | tcc | atg | agc | gcc | atc | gcc | act | aac | gga | gtg | gtg | cca | gct | ggg | ggc | 688 |
| Ile | Ser | Met | Ser | Ala | Ile | Ala | Thr | Asn | Gly | Val | Val | Pro | Ala | Gly | Gly | |
| 185 | | | | | 190 | | | | | 195 | | | | | 200 | |
| tca | tac | ttc | atg | att | tcc | aga | gcc | ctg | ggc | cca | gag | ttt | ggc | ggg | gct | 736 |
| Ser | Tyr | Phe | Met | Ile | Ser | Arg | Ala | Leu | Gly | Pro | Glu | Phe | Gly | Gly | Ala | |
| | | | | 205 | | | | | 210 | | | | | 215 | | |
| gta | ggc | ctc | tgc | ttt | tat | ctt | ggc | acc | aca | ttt | gca | gca | gcc | atg | tat | 784 |
| Val | Gly | Leu | Cys | Phe | Tyr | Leu | Gly | Thr | Thr | Phe | Ala | Ala | Ala | Met | Tyr | |
| | | | 220 | | | | | 225 | | | | | 230 | | | |
| att | ctt | ggt | gcc | att | gaa | atc | ttt | ctg | gta | tac | att | gtc | ccc | cga | gct | 832 |
| Ile | Leu | Gly | Ala | Ile | Glu | Ile | Phe | Leu | Val | Tyr | Ile | Val | Pro | Arg | Ala | |
| | | 235 | | | | | 240 | | | | | 245 | | | | |
| gcc | atc | ttt | cgg | agt | gac | gat | gca | ctc | aag | gag | tca | gca | gct | atg | ctg | 880 |
| Ala | Ile | Phe | Arg | Ser | Asp | Asp | Ala | Leu | Lys | Glu | Ser | Ala | Ala | Met | Leu | |
| | 250 | | | | | 255 | | | | | 260 | | | | | |
| aac | aac | atg | cgc | gtc | tat | ggt | aca | gcc | ttc | ttg | gtc | ctc | atg | gtc | ttg | 928 |
| Asn | Asn | Met | Arg | Val | Tyr | Gly | Thr | Ala | Phe | Leu | Val | Leu | Met | Val | Leu | |
| 265 | | | | | 270 | | | | | 275 | | | | | 280 | |
| gtg | gta | ttc | atc | ggc | gta | cgc | tat | gtg | aat | aag | ttt | gcc | tca | ctc | ttc | 976 |
| Val | Val | Phe | Ile | Gly | Val | Arg | Tyr | Val | Asn | Lys | Phe | Ala | Ser | Leu | Phe | |
| | | | | 285 | | | | | 290 | | | | | 295 | | |
| ctg | gcc | tgt | gta | att | gtg | tcg | atc | ttg | gct | atc | tat | gct | ggt | gcc | atc | 1024 |
| Leu | Ala | Cys | Val | Ile | Val | Ser | Ile | Leu | Ala | Ile | Tyr | Ala | Gly | Ala | Ile | |
| | | | 300 | | | | | 305 | | | | | 310 | | | |
| aag | tct | tcc | ttt | gct | cca | cca | cac | ttc | ccg | gtc | tgt | atg | ctg | ggc | aac | 1072 |
| Lys | Ser | Ser | Phe | Ala | Pro | Pro | His | Phe | Pro | Val | Cys | Met | Leu | Gly | Asn | |
| | | 315 | | | | | 320 | | | | | 325 | | | | |
| cgt | acc | ctg | tca | tca | aga | cac | ctt | gac | att | tgc | tct | aag | acc | aag | gag | 1120 |
| Arg | Thr | Leu | Ser | Ser | Arg | His | Leu | Asp | Ile | Cys | Ser | Lys | Thr | Lys | Glu | |
| | 330 | | | | | 335 | | | | | 340 | | | | | |
| gtt | gac | aac | atg | aca | gta | cca | tca | aag | tta | tgg | gga | ttc | ttc | tgc | aac | 1168 |
| Val | Asp | Asn | Met | Thr | Val | Pro | Ser | Lys | Leu | Trp | Gly | Phe | Phe | Cys | Asn | |
| 345 | | | | | 350 | | | | | 355 | | | | | 360 | |
| tcg | agt | cag | ttc | ttt | aat | gcc | acc | tgt | gat | gag | tac | ttt | gtt | cac | aat | 1216 |
| Ser | Ser | Gln | Phe | Phe | Asn | Ala | Thr | Cys | Asp | Glu | Tyr | Phe | Val | His | Asn | |
| | | | | 365 | | | | | 370 | | | | | 375 | | |
| aac | gtc | atc | tca | atc | caa | ggc | att | cca | ggg | ttg | gct | agt | ggt | atc | att | 1264 |
| Asn | Val | Ile | Ser | Ile | Gln | Gly | Ile | Pro | Gly | Leu | Ala | Ser | Gly | Ile | Ile | |
| | | | 380 | | | | | 385 | | | | | 390 | | | |
| act | gaa | aat | ctt | tgg | agt | aat | tat | tta | cca | aag | ggt | gag | ata | att | gaa | 1312 |
| Thr | Glu | Asn | Leu | Trp | Ser | Asn | Tyr | Leu | Pro | Lys | Gly | Glu | Ile | Ile | Glu | |
| | | 395 | | | | | 400 | | | | | 405 | | | | |
| aag | cca | tca | gcc | aag | tca | tct | gat | gtc | tta | ggc | aac | tta | aac | cat | gaa | 1360 |
| Lys | Pro | Ser | Ala | Lys | Ser | Ser | Asp | Val | Leu | Gly | Asn | Leu | Asn | His | Glu | |
| | 410 | | | | | 415 | | | | | 420 | | | | | |
| tat | gtt | ctt | gct | gat | atc | acc | acc | tcc | ttc | act | ctg | ctg | gtg | ggg | atc | 1408 |
| Tyr | Val | Leu | Ala | Asp | Ile | Thr | Thr | Ser | Phe | Thr | Leu | Leu | Val | Gly | Ile | |
| 425 | | | | | 430 | | | | | 435 | | | | | 440 | |
| ttc | ttt | ccc | tcg | gtc | aca | ggt | atc | atg | gct | ggg | tca | aac | aga | tct | gga | 1456 |
| Phe | Phe | Pro | Ser | Val | Thr | Gly | Ile | Met | Ala | Gly | Ser | Asn | Arg | Ser | Gly | |
| | | | | 445 | | | | | 450 | | | | | 455 | | |
| gat | ctg | aaa | gat | gcc | cag | aag | tct | att | ccc | att | ggg | acc | atc | ctt | gcc | 1504 |
| Asp | Leu | Lys | Asp | Ala | Gln | Lys | Ser | Ile | Pro | Ile | Gly | Thr | Ile | Leu | Ala | |
| | | | 460 | | | | | 465 | | | | | 470 | | | |

```
                                            -continued
atc ctg acc aca tcc ttt gtg tat tta agc aat gtt gtc ctt ttt ggt       1552
Ile Leu Thr Thr Ser Phe Val Tyr Leu Ser Asn Val Val Leu Phe Gly
        475                 480                 485 gca tgt att gaa gga gtc gtt ctc aga gac aaa ttt ggg gat gct gta       1600
Ala Cys Ile Glu Gly Val Val Leu Arg Asp Lys Phe Gly Asp Ala Val
490                 495                 500 aaa ggg aat ttg gtt gta ggc acc tta tcc tgg cca tcc ccg tgg gtg       1648
Lys Gly Asn Leu Val Val Gly Thr Leu Ser Trp Pro Ser Pro Trp Val
505                 510                 515                 520 atc gtt att ggc tcc ttc ttt tca aca tgt ggg gct ggg ctg cag agc       1696
Ile Val Ile Gly Ser Phe Phe Ser Thr Cys Gly Ala Gly Leu Gln Ser
                525                 530                 535 ntc aca ggt gcg cct cgg ctg ctg cag gct atc gcc aag gat aac atc       1744
Xaa Thr Gly Ala Pro Arg Leu Leu Gln Ala Ile Ala Lys Asp Asn Ile
        540                 545                 550 ata cct ttc ctt agg gtt ttt ggt cac agc aaa gct aat ggg gaa cct       1792
Ile Pro Phe Leu Arg Val Phe Gly His Ser Lys Ala Asn Gly Glu Pro
        555                 560                 565 acc tgg gct tta ctt cta act gct gcc ata gca gag ctg gga att ctc       1840
Thr Trp Ala Leu Leu Leu Thr Ala Ala Ile Ala Glu Leu Gly Ile Leu
        570                 575                 580 atc gcc tcc ctg gat ctc gtg gcc cca att ctt tcc atg ttt ttt ctc       1888
Ile Ala Ser Leu Asp Leu Val Ala Pro Ile Leu Ser Met Phe Phe Leu
585                 590                 595                 600 atg tgt tac ctc ttt gtg aac ttg gct tgt gcc ttg caa aca ttg ctg       1936
Met Cys Tyr Leu Phe Val Asn Leu Ala Cys Ala Leu Gln Thr Leu Leu
                605                 610                 615 cga acc ccc aac tgg agg cct cga ttc cgc tat tat cac tgg gcc ctc       1984
Arg Thr Pro Asn Trp Arg Pro Arg Phe Arg Tyr Tyr His Trp Ala Leu
        620                 625                 630 tct ttc atg gga atg agt atc tgt cta gct ctg atg ttc att tct tct       2032
Ser Phe Met Gly Met Ser Ile Cys Leu Ala Leu Met Phe Ile Ser Ser
        635                 640                 645 tgg tat tat gcc att gta gct atg gta ata gct ggc atg atc tac aag       2080
Trp Tyr Tyr Ala Ile Val Ala Met Val Ile Ala Gly Met Ile Tyr Lys
        650                 655                 660 tac att gaa tat caa ggg gct gag aaa gaa tgg ggg gat ggt atc cgt       2128
Tyr Ile Glu Tyr Gln Gly Ala Glu Lys Glu Trp Gly Asp Gly Ile Arg
665                 670                 675                 680 ggg ctg tcg ctc agt gca gcc cgc ttc gct ttg ctc cgt cta gag gaa       2176
Gly Leu Ser Leu Ser Ala Ala Arg Phe Ala Leu Leu Arg Leu Glu Glu
                685                 690                 695 gga cct cct cac act aaa aac tgg agg cct cag ctg ctc gtc cta ctg       2224
Gly Pro Pro His Thr Lys Asn Trp Arg Pro Gln Leu Leu Val Leu Leu
        700                 705                 710 aag ctg gat gaa gat tta cac gtc aag cac cct cgc ctc ctc acc ttt       2272
Lys Leu Asp Glu Asp Leu His Val Lys His Pro Arg Leu Leu Thr Phe
        715                 720                 725 gcc tcc cag ctc aag gca gga aag gga ctc acg att gtg ggc tct gtc       2320
Ala Ser Gln Leu Lys Ala Gly Lys Gly Leu Thr Ile Val Gly Ser Val
        730                 735                 740 atc gtg ggg aac ttc ttg gag aac tat ggt gac gcg ctc gcg gca gag       2368
Ile Val Gly Asn Phe Leu Glu Asn Tyr Gly Asp Ala Leu Ala Ala Glu
745                 750                 755                 760 cag acc att aag cac cta atg gag gca gaa aag gta aaa gga ttc tgc       2416
Gln Thr Ile Lys His Leu Met Glu Ala Glu Lys Val Lys Gly Phe Cys
                765                 770                 775 caa ttg gtg gtg gct gcc aag ctg aaa gag ggc att tca cac ctc atc       2464
Gln Leu Val Val Ala Ala Lys Leu Lys Glu Gly Ile Ser His Leu Ile
        780                 785                 790
```

-continued

| | | |
|---|---|---|
| cag tcc tgt ggc ctc gga ggc atg aaa cac aac aca gtg gtg atg ggc<br>Gln Ser Cys Gly Leu Gly Gly Met Lys His Asn Thr Val Val Met Gly<br>     795                   800                 805 | 2512 |
| tgg ccc aat ggc tgg cgt cag agt gaa gat gct cgc gct tgg aag act<br>Trp Pro Asn Gly Trp Arg Gln Ser Glu Asp Ala Arg Ala Trp Lys Thr<br>810                     815                 820 | 2560 |
| ttc att ggc aca gta cga gtg aca act gct gcc cat cta gcc ctg ctg<br>Phe Ile Gly Thr Val Arg Val Thr Thr Ala Ala His Leu Ala Leu Leu<br>825                   830                 835                 840 | 2608 |
| gtg gct aaa aat gtc tcc ttc ttt ccc agc aat gtg gag cag ttt tct<br>Val Ala Lys Asn Val Ser Phe Phe Pro Ser Asn Val Glu Gln Phe Ser<br>                   845                 850                 855 | 2656 |
| gag ggc aac att gat gtg cgg tgg att gtg cat gat ggg ggc atg ctc<br>Glu Gly Asn Ile Asp Val Arg Trp Ile Val His Asp Gly Gly Met Leu<br>860                     865                 870 | 2704 |
| atg cta tta ccg ttc ctg ctg aaa cag cac aag gtt tgg cgg aaa tgc<br>Met Leu Leu Pro Phe Leu Leu Lys Gln His Lys Val Trp Arg Lys Cys<br>875                   880                 885 | 2752 |
| agc ata cgg atc ttc aca gta gcc caa cta gaa gac aac agt atc cag<br>Ser Ile Arg Ile Phe Thr Val Ala Gln Leu Glu Asp Asn Ser Ile Gln<br>890                   895                 900 | 2800 |
| atg aag aag gat ctg gcc acc ttt ctg tac cac ctg cgc att gag gca<br>Met Lys Lys Asp Leu Ala Thr Phe Leu Tyr His Leu Arg Ile Glu Ala<br>905                     910                 915                 920 | 2848 |
| gaa gtg gaa gtg gtg gag atg cac gac agt gac ata tct gcc tat aca<br>Glu Val Glu Val Val Glu Met His Asp Ser Asp Ile Ser Ala Tyr Thr<br>                   925                 930                 935 | 2896 |
| tat gag cgc acc ctg atg atg gag cag agg tcc cag atg ctt cgg cat<br>Tyr Glu Arg Thr Leu Met Met Glu Gln Arg Ser Gln Met Leu Arg His<br>940                     945                 950 | 2944 |
| atg cgg ctg tcc aaa aca gag cga gac agg gag gca cag ctg gtg aaa<br>Met Arg Leu Ser Lys Thr Glu Arg Asp Arg Glu Ala Gln Leu Val Lys<br>955                     960                 965 | 2992 |
| gat cga aac tca atg nta cgc ttg acc agc att ggc tct gat gag gac<br>Asp Arg Asn Ser Met Xaa Arg Leu Thr Ser Ile Gly Ser Asp Glu Asp<br>970                     975                 980 | 3040 |
| gaa gag aca gaa acg tac cag gag aag gtg cac atg act tgg acc aag<br>Glu Glu Thr Glu Thr Tyr Gln Glu Lys Val His Met Thr Trp Thr Lys<br>985                     990                 995               1000 | 3088 |
| gat aaa tac atg gca tcc cgg ggg caa aag gtc aag tca atg gaa gga<br>Asp Lys Tyr Met Ala Ser Arg Gly Gln Lys Val Lys Ser Met Glu Gly<br>                   1005                1010                1015 | 3136 |
| ttc cag gac cta ctt aat atg cgt ccg gac cag tcc aac gtg aga cgg<br>Phe Gln Asp Leu Leu Asn Met Arg Pro Asp Gln Ser Asn Val Arg Arg<br>1020                  1025                1030 | 3184 |
| atg cat aca gca gtg aag ctc aat gaa gtt ata gtc aac aag tct cat<br>Met His Thr Ala Val Lys Leu Asn Glu Val Ile Val Asn Lys Ser His<br>                   1035                1040                1045 | 3232 |
| gaa gca aag ctg gtt ttg ttg aat atg cca gga cca ccc cgg aac cct<br>Glu Ala Lys Leu Val Leu Leu Asn Met Pro Gly Pro Pro Arg Asn Pro<br>1050                  1055                1060 | 3280 |
| gaa ggt gat gaa aac tac atg gaa ttt cta gaa gtg ctc act gag gga<br>Glu Gly Asp Glu Asn Tyr Met Glu Phe Leu Glu Val Leu Thr Glu Gly<br>1065                  1070                1075                1080 | 3328 |
| tta gaa cga gtc ctt ctt gtc cgg ggt ggt ggc agt gag gtc atc acc<br>Leu Glu Arg Val Leu Leu Val Arg Gly Gly Gly Ser Glu Val Ile Thr<br>                   1085                1090                1095 | 3376 |
| att tac tca taatcagctg tgggagattc tgcgtggtcc gacttcccta<br>Ile Tyr Ser | 3425 |

```
agactcatcg tccatggaga tgatagctct ttcctaccac tcccactcta ttcttgcaga    3485
gctgagcccc atctatgctc ttggctgcaa catgatctgc catcccagca gaaacaaata    3545
atccctcaac agaagaatgg tcaagtccta aaagctattt ctatggcagg agaaggcaag    3605
tcaaaattaa caagctaagc caaagggaac cttttggcac acagaaggta atgagttagt    3665
aaaacatatg ctagaaatgt aactggcaac agaaagcaat gttcatatct aacattcagg    3725
acgagtttca gaagacacgg gtcagtgagc accagaaagt taacaggcag ttaagcttca    3785
ccttagtaaa aaatgagttc ccattataga gacagcctgc agcagccagg atggaaacag    3845
gatactgata tataaaacct gagacatagc tgcagccact acttcttcct catggtttat    3905
tgtctgtact gtaccactgt acattttaac tgtctttgtt ttaaaaccca ttctgtggtt    3965
ataatgcaga cagtagtgtt actatagaaa tgttttttg aaaggctaga aatgtttttt     4025
caggttttca aatgctgaac taagggggatt ccaagagtg cgtattaaaa tatatagaaa    4085
cacagtggtt agctatgcaa cataaagcac acaagctatt atcttaacaa atgtgggttg    4145
ttatgtagtt aaccagaagg gtctcttcta ctcttagtag gcattggtct taaaaaccaa    4205
acaaaccaaa cctgtaagga agagacgcca gggctgtgtg atgccacctc caaggcccca    4265
gggttcagag gttcagcagt ggaactgggg gtgtgaaagc catcccttt ccactgtgcc     4325
aaaatcgtct gctcactggc agacaggttt gcaagtggcc tgacacaagc acctttctt    4385
tcacaagaaa tccatctgtg gcctcttcac caaagccata gtgcagattt gaggcactcg    4445
acctccatgc ccagagcttt tcccgtctca atattattat tattcattct gacttcggaa    4505
acttggctct gaaacaaatg gttcactaag ctaatgatct gctgtattgg ttttgctttc    4565
aaaaagctct aactgtgcca aggaaatact tgtgtaagat cagatttttt tttttttttt    4625
aatttactga tcacaaacac ttggcttacc agcataggca gcctttgtgg ctgagcagta    4685
ttcccagggt gtgaaacctc catcccttt ccaagatagt tactgaagaa actgtcttct     4745
tgcttagatt cacggctgct tttacatttc cttcactga cagtaaattg tgccactctc     4805
catacccctgt aggacaatga acacccagaa ttcaacccaa gacagaagaa acccctcaaa   4865
tatggcttaa gaagctgagt catatggttt gttcttcctc ctcccaggcc cacttgagta    4925
gcaaaggatc cagcatgttt tccttttgctt cctgcagagg gtagaaacta ctcgtagttc   4985
tctttccaac actccattgc atacttgagt ataatcccct aggctccaag gcattggagc    5045
gcccattctg taaaagccag cctgcccagg aactgcctaa cacatccacc cctgaccaaa    5105
gtgacacata cttttccat atcaaacaaa catgggaaga gaataaggtt tctttaagaa     5165
aggctgtttg tggttagagc tacataagaa tctgttaaag ggtagagtat agtcttcatt    5225
ccccaagata aaaatcactg ttacatggac aaatggttat taggccagat ttgtactcat    5285
ctctgtctag aacatttcat gtctatgtgt tgcttatgtt gtctgtctgc aaagtgtctt    5345
agctctttta atcactgcaa ataaagcaat actgaaaact tgagagagaa aatgcacctt    5405
aggggaaggg gccaaatgtt tctagaggga agaggaagac cttctcctgc ctttcttata    5465
agacccagct tgtgtcttac ccatgagttt attagcaggg caggctgtaa cattcgttct    5525
cccccaactg gtcctcagcc ttccgtagct accttaaaag ctggagtttg aattgcaggg    5585
cctggttgac aggtgccagc ttcctcgtgg cagagcaaaa gctgctgctt ttcatattct    5645
gtgcctcctt ttcttgtggc cccaaggatc ccaccaatcc tcattccccc taaatgttaa    5705
aagaaaattc cttattgtgg atattaagtt acactgtaag catatttaca tgctctttt    5765
ccccccctggt ttttcttttc atcatgtata atttgaatcc agtgatagtc tcacatcttc   5825
```

-continued

```
caaaaaagtc tgcttatgtg atatagaaga gaaatattaa agtagactga agggggaactt      5885 gtgaaacatt aagcattgtt ctcaaccgtt taatttattg aaaggagaag ctgctactga      5945
gcagctgcta ttcttttgtt tacatagagt ctggttttgt ttgttttgct ctgtgctggg      6005
aacataaata aagttttcta cattattttc aaaaaaaaaa aaaaaaa                    6052
```

<210> SEQ ID NO 10
<211> LENGTH: 1099
<212> TYPE: PRT
<213> ORGANISM: mouse
<220> FEATURE:
<221> NAME/KEY: misc_feature
<222> LOCATION: (66)
<223> OTHER INFORMATION: Xaa=Leu or Ile
<220> FEATURE:
<221> NAME/KEY: misc_feature
<222> LOCATION: (537)
<223> OTHER INFORMATION: Xaa=Leu or Ile
<220> FEATURE:
<221> NAME/KEY: misc_feature
<222> LOCATION: (974)
<223> OTHER INFORMATION: n=c or a, Xaa=Leu or Ile

<400> SEQUENCE: 10

```
Met Pro His Phe Thr Val Thr Lys Val Glu Asp Pro Glu Glu Gly Ala
 1               5                  10                  15

Ala Gly Pro Leu Ser Pro Glu Pro Ser Ala Glu Val Lys Ala Arg
                20                  25                  30

Ile Gln Asp Pro Gln Glu Pro Asp Pro Ser Gln Asn Ser Ile Thr Gly
            35                  40                  45

Glu His Ser Gln Leu Leu Asp Asp Gly His Lys Lys Ala Arg Asn Ala
        50                  55                  60

Tyr Xaa Asn Asn Ser Asn Tyr Glu Glu Gly Asp Glu Tyr Phe Asp Lys
 65                  70                  75                  80

Asn Leu Ala Leu Phe Glu Glu Met Asp Thr Arg Pro Lys Val Ser
                85                  90                  95

Ser Leu Leu Asn Arg Met Ala Asn Tyr Thr Asn Leu Thr Gln Gly Ala
            100                 105                 110

Lys Glu His Glu Glu Ala Glu Asn Ile Thr Glu Gly Lys Lys Lys Pro
        115                 120                 125

Thr Lys Ser Pro Gln Met Gly Thr Phe Met Gly Val Tyr Leu Pro Cys
    130                 135                 140

Leu Gln Asn Ile Phe Gly Val Ile Leu Phe Leu Arg Leu Thr Trp Val
145                 150                 155                 160

Val Gly Thr Ala Gly Ile Leu Gln Ala Phe Ala Ile Val Leu Ile Cys
                165                 170                 175

Cys Cys Cys Thr Met Leu Thr Ala Ile Ser Met Ser Ala Ile Ala Thr
            180                 185                 190

Asn Gly Val Val Pro Ala Gly Gly Ser Tyr Phe Met Ile Ser Arg Ala
        195                 200                 205

Leu Gly Pro Glu Phe Gly Gly Ala Val Gly Leu Cys Phe Tyr Leu Gly
    210                 215                 220

Thr Thr Phe Ala Ala Ala Met Tyr Ile Leu Gly Ala Ile Glu Ile Phe
225                 230                 235                 240

Leu Val Tyr Ile Val Pro Arg Ala Ala Ile Phe Arg Ser Asp Asp Ala
                245                 250                 255

Leu Lys Glu Ser Ala Ala Met Leu Asn Asn Met Arg Val Tyr Gly Thr
            260                 265                 270
```

```
Ala Phe Leu Val Leu Met Val Leu Val Val Phe Ile Gly Val Arg Tyr
        275                 280                 285
Val Asn Lys Phe Ala Ser Leu Phe Leu Ala Cys Val Ile Val Ser Ile
        290                 295                 300
Leu Ala Ile Tyr Ala Gly Ala Ile Lys Ser Ser Phe Ala Pro Pro His
305                 310                 315                 320
Phe Pro Val Cys Met Leu Gly Asn Arg Thr Leu Ser Ser Arg His Leu
                325                 330                 335
Asp Ile Cys Ser Lys Thr Lys Glu Val Asp Asn Met Thr Val Pro Ser
                340                 345                 350
Lys Leu Trp Gly Phe Phe Cys Asn Ser Ser Gln Phe Asn Ala Thr
        355                 360                 365
Cys Asp Glu Tyr Phe Val His Asn Asn Val Ile Ser Ile Gln Gly Ile
370                 375                 380
Pro Gly Leu Ala Ser Gly Ile Ile Thr Glu Asn Leu Trp Ser Asn Tyr
385                 390                 395                 400
Leu Pro Lys Gly Glu Ile Glu Lys Pro Ser Ala Lys Ser Ser Asp
                405                 410                 415
Val Leu Gly Asn Leu Asn His Glu Tyr Val Leu Ala Asp Ile Thr Thr
                420                 425                 430
Ser Phe Thr Leu Leu Val Gly Ile Phe Phe Pro Ser Val Thr Gly Ile
        435                 440                 445
Met Ala Gly Ser Asn Arg Ser Gly Asp Leu Lys Asp Ala Gln Lys Ser
450                 455                 460
Ile Pro Ile Gly Thr Ile Leu Ala Ile Leu Thr Thr Ser Phe Val Tyr
465                 470                 475                 480
Leu Ser Asn Val Val Leu Phe Gly Ala Cys Ile Glu Gly Val Val Leu
                485                 490                 495
Arg Asp Lys Phe Gly Asp Ala Val Lys Gly Asn Leu Val Val Gly Thr
                500                 505                 510
Leu Ser Trp Pro Ser Pro Trp Val Ile Val Gly Ser Phe Phe Ser
        515                 520                 525
Thr Cys Gly Ala Gly Leu Gln Ser Xaa Thr Gly Ala Pro Arg Leu Leu
530                 535                 540
Gln Ala Ile Ala Lys Asp Asn Ile Ile Pro Phe Leu Arg Val Phe Gly
545                 550                 555                 560
His Ser Lys Ala Asn Gly Glu Pro Thr Trp Ala Leu Leu Leu Thr Ala
                565                 570                 575
Ala Ile Ala Glu Leu Gly Ile Leu Ile Ala Ser Leu Asp Leu Val Ala
                580                 585                 590
Pro Ile Leu Ser Met Phe Phe Leu Met Cys Tyr Leu Phe Val Asn Leu
        595                 600                 605
Ala Cys Ala Leu Gln Thr Leu Leu Arg Thr Pro Asn Trp Arg Pro Arg
610                 615                 620
Phe Arg Tyr Tyr His Trp Ala Leu Ser Phe Met Gly Met Ser Ile Cys
625                 630                 635                 640
Leu Ala Leu Met Phe Ile Ser Ser Trp Tyr Tyr Ala Ile Val Ala Met
                645                 650                 655
Val Ile Ala Gly Met Ile Tyr Lys Tyr Ile Glu Tyr Gln Gly Ala Glu
                660                 665                 670
Lys Glu Trp Gly Asp Gly Ile Arg Gly Leu Ser Leu Ser Ala Ala Arg
        675                 680                 685
```

-continued

```
Phe Ala Leu Leu Arg Leu Glu Glu Gly Pro Pro His Thr Lys Asn Trp
    690                 695                 700
Arg Pro Gln Leu Leu Val Leu Leu Lys Leu Asp Glu Asp Leu His Val
705                 710                 715                 720
Lys His Pro Arg Leu Leu Thr Phe Ala Ser Gln Leu Lys Ala Gly Lys
                725                 730                 735
Gly Leu Thr Ile Val Gly Ser Val Ile Val Gly Asn Phe Leu Glu Asn
                740                 745                 750
Tyr Gly Asp Ala Leu Ala Ala Glu Gln Thr Ile Lys His Leu Met Glu
            755                 760                 765
Ala Glu Lys Val Lys Gly Phe Cys Gln Leu Val Val Ala Ala Lys Leu
    770                 775                 780
Lys Glu Gly Ile Ser His Leu Ile Gln Ser Cys Gly Leu Gly Gly Met
785                 790                 795                 800
Lys His Asn Thr Val Val Met Gly Trp Pro Asn Gly Trp Arg Gln Ser
                805                 810                 815
Glu Asp Ala Arg Ala Trp Lys Thr Phe Ile Gly Thr Val Arg Val Thr
            820                 825                 830
Thr Ala Ala His Leu Ala Leu Leu Val Ala Lys Asn Val Ser Phe Phe
        835                 840                 845
Pro Ser Asn Val Glu Gln Phe Ser Glu Gly Asn Ile Asp Val Arg Trp
    850                 855                 860
Ile Val His Asp Gly Gly Met Leu Met Leu Leu Pro Phe Leu Leu Lys
865                 870                 875                 880
Gln His Lys Val Trp Arg Lys Cys Ser Ile Arg Ile Phe Thr Val Ala
                885                 890                 895
Gln Leu Glu Asp Asn Ser Ile Gln Met Lys Lys Asp Leu Ala Thr Phe
            900                 905                 910
Leu Tyr His Leu Arg Ile Glu Ala Glu Val Glu Val Glu Met His
        915                 920                 925
Asp Ser Asp Ile Ser Ala Tyr Thr Tyr Glu Arg Thr Leu Met Met Glu
    930                 935                 940
Gln Arg Ser Gln Met Leu Arg His Met Arg Leu Ser Lys Thr Glu Arg
945                 950                 955                 960
Asp Arg Glu Ala Gln Leu Val Lys Asp Arg Asn Ser Met Xaa Arg Leu
                965                 970                 975
Thr Ser Ile Gly Ser Asp Glu Asp Glu Thr Glu Thr Tyr Gln Glu
            980                 985                 990
Lys Val His Met Thr Trp Thr Lys Asp Lys Tyr Met Ala Ser Arg Gly
        995                 1000                1005
Gln Lys Val Lys Ser Met Glu Gly Phe Gln Asp Leu Leu Asn Met Arg
    1010                1015                1020
Pro Asp Gln Ser Asn Val Arg Arg Met His Thr Ala Val Lys Leu Asn
1025                1030                1035                1040
Glu Val Ile Val Asn Lys Ser His Glu Ala Lys Leu Val Leu Leu Asn
                1045                1050                1055
Met Pro Gly Pro Pro Arg Asn Pro Glu Gly Asp Glu Asn Tyr Met Glu
            1060                1065                1070
Phe Leu Glu Val Leu Thr Glu Gly Leu Glu Arg Val Leu Leu Val Arg
        1075                1080                1085
Gly Gly Gly Ser Glu Val Ile Thr Ile Tyr Ser
    1090                1095
```

-continued

```
<210> SEQ ID NO 11
<211> LENGTH: 5907
<212> TYPE: DNA
<213> ORGANISM: Homo sapiens
<220> FEATURE:
<221> NAME/KEY: CDS
<222> LOCATION: (1)..(3348)
<220> FEATURE:
<221> NAME/KEY: misc_feature
<222> LOCATION: (358)
<223> OTHER INFORMATION: n=c or a, Xaa=Leu or Ile
<220> FEATURE:
<221> NAME/KEY: misc_feature
<222> LOCATION: (1072)
<223> OTHER INFORMATION: n=c or a, Xaa=Leu or Ile
<220> FEATURE:
<221> NAME/KEY: misc_feature
<222> LOCATION: (2746)
<223> OTHER INFORMATION: n=c or a, Xaa=Leu or Ile

<400> SEQUENCE: 11 atg ccc aac aac ctg acg gac tgc gag gac ggc gat ggg gga gcc aac     48
Met Pro Asn Asn Leu Thr Asp Cys Glu Asp Gly Asp Gly Gly Ala Asn
 1               5                  10                  15 ccg ggt gat ggc aac ccc aag gaa agc agt ccc ttc atc aac agc acc     96
Pro Gly Asp Gly Asn Pro Lys Glu Ser Ser Pro Phe Ile Asn Ser Thr
             20                  25                  30 gac aca gag aag gga aag gag tat gat ggc aag aac atg gcc ttg ttt    144
Asp Thr Glu Lys Gly Lys Glu Tyr Asp Gly Lys Asn Met Ala Leu Phe
         35                  40                  45 gag gag gag atg gac acc agc cct atg gtg tcc tcc ttg ctc agt ggc    192
Glu Glu Glu Met Asp Thr Ser Pro Met Val Ser Ser Leu Leu Ser Gly
     50                  55                  60 ctg gcc aac tac acc aac ctg ccc cag gga agt agg gag cat gaa gag    240
Leu Ala Asn Tyr Thr Asn Leu Pro Gln Gly Ser Arg Glu His Glu Glu
 65                  70                  75                  80 gca gaa aac aat gag ggt gga aaa aag aag ccg gtg cag gcc cca cgc    288
Ala Glu Asn Asn Glu Gly Gly Lys Lys Lys Pro Val Gln Ala Pro Arg
                 85                  90                  95 atg ggc acc ttc atg ggc gtg tac ctg ccg tgc ctg cag aac atc ttt    336
Met Gly Thr Phe Met Gly Val Tyr Leu Pro Cys Leu Gln Asn Ile Phe
            100                 105                 110 ggc gtc atc ctc ttc ctg cgg ntc acc tgg gtg gtg ggc att gca ggc    384
Gly Val Ile Leu Phe Leu Arg Xaa Thr Trp Val Val Gly Ile Ala Gly
        115                 120                 125 atc atg gag tcc ttc tgc atg gtg ttc atc tgc tgc tcc tgt acg atg    432
Ile Met Glu Ser Phe Cys Met Val Phe Ile Cys Cys Ser Cys Thr Met
    130                 135                 140 ctc acg gcc atc tcc atg agt gca att gca acg aat ggt gtt gtg cct    480
Leu Thr Ala Ile Ser Met Ser Ala Ile Ala Thr Asn Gly Val Val Pro
145                 150                 155                 160 gct ggt ggc tcc tac tac atg att tcc agg tct ctg ggc cca gag ttt    528
Ala Gly Gly Ser Tyr Tyr Met Ile Ser Arg Ser Leu Gly Pro Glu Phe
                165                 170                 175 ggg ggt gcc gtg ggc ctc tgc ttc tac ctg ggc act acc ttt gca gga    576
Gly Gly Ala Val Gly Leu Cys Phe Tyr Leu Gly Thr Thr Phe Ala Gly
            180                 185                 190 gcc atg tac atc ctg ggc acc atc gaa atc ctg ctg gct tac ctc ttc    624
Ala Met Tyr Ile Leu Gly Thr Ile Glu Ile Leu Leu Ala Tyr Leu Phe
        195                 200                 205 cca gcc atg gcc atc ttc aag gca gaa gat gcc agt ggg gag gca gca    672
Pro Ala Met Ala Ile Phe Lys Ala Glu Asp Ala Ser Gly Glu Ala Ala
    210                 215                 220
```

-continued

```
gcc atg ctg aac aac atg cgt gtt tac ggc acc tgt gtg ctc acc tgc      720
Ala Met Leu Asn Asn Met Arg Val Tyr Gly Thr Cys Val Leu Thr Cys
225                 230                 235                 240 atg gcc act gtg gtg ttt gtg ggt gtc aag tat gtc aac aag ttt gcc      768
Met Ala Thr Val Val Phe Val Gly Val Lys Tyr Val Asn Lys Phe Ala
        245                 250                 255 ctt gtc ttc ctg ggt tgt gtc atc ctc tcc atc ctg gcc atc tat gct      816
Leu Val Phe Leu Gly Cys Val Ile Leu Ser Ile Leu Ala Ile Tyr Ala
    260                 265                 270 ggg gtc atc aag tct gcc ttc gac cca ccc aac ttc ccg atc tgc ctc      864
Gly Val Ile Lys Ser Ala Phe Asp Pro Pro Asn Phe Pro Ile Cys Leu
275                 280                 285 ctg ggt aac cgc acg ctg tct cgc cat ggc ttt gat gtc tgt gcc aag      912
Leu Gly Asn Arg Thr Leu Ser Arg His Gly Phe Asp Val Cys Ala Lys
290                 295                 300 ctg gct tgg gaa gga aat gag acg gtg acc aca cgg cta tgg ggc ctt      960
Leu Ala Trp Glu Gly Asn Glu Thr Val Thr Thr Arg Leu Trp Gly Leu
305                 310                 315                 320 ttc tgc tcc tct cgc ttc ctc aac gcc acc tgt gat gaa tac ttc acc     1008
Phe Cys Ser Ser Arg Phe Leu Asn Ala Thr Cys Asp Glu Tyr Phe Thr
            325                 330                 335 cga aac aat gtc aca gag atc cag ggc atc cct ggt gct gcc agt ggc     1056
Arg Asn Asn Val Thr Glu Ile Gln Gly Ile Pro Gly Ala Ala Ser Gly
        340                 345                 350 ctc atc aaa gag aac ntc tgg agc tcc tac ctg acc aag ggc gtg att     1104
Leu Ile Lys Glu Asn Xaa Trp Ser Ser Tyr Leu Thr Lys Gly Val Ile
    355                 360                 365 gtg gag agg agt ggg atg acc tcg gtg ggc ctg gcc gat ggc act cct     1152
Val Glu Arg Ser Gly Met Thr Ser Val Gly Leu Ala Asp Gly Thr Pro
370                 375                 380 atc gac atg gac cac cct tat gtc ttc agt gat atg acc tcc tac ttc     1200
Ile Asp Met Asp His Pro Tyr Val Phe Ser Asp Met Thr Ser Tyr Phe
385                 390                 395                 400 acc ctg ctg gtt ggc atc tac ttc ccc tca gtc aca ggg atc atg gct     1248
Thr Leu Leu Val Gly Ile Tyr Phe Pro Ser Val Thr Gly Ile Met Ala
            405                 410                 415 ggt tct aac cgc tct ggg gac ctg agg gat gcc cag aag tca atc ccc     1296
Gly Ser Asn Arg Ser Gly Asp Leu Arg Asp Ala Gln Lys Ser Ile Pro
        420                 425                 430 act ggc acc atc ctg gcc atc gcc acc acc tct gct gtc tac atc agc     1344
Thr Gly Thr Ile Leu Ala Ile Ala Thr Thr Ser Ala Val Tyr Ile Ser
    435                 440                 445 tcc gtt gtt ctg ttt ggg gcc tgc att gag ggg gtc gtc ctg cgg gac     1392
Ser Val Val Leu Phe Gly Ala Cys Ile Glu Gly Val Val Leu Arg Asp
450                 455                 460 aag ttt ggc gaa gct gtg aat ggc aac ctc gtg gtg ggc act ctg gcc     1440
Lys Phe Gly Glu Ala Val Asn Gly Asn Leu Val Val Gly Thr Leu Ala
465                 470                 475                 480 tgg cca tct cca tgg gta att gtc atc gga tcc ttc ttc tcc acc tgt     1488
Trp Pro Ser Pro Trp Val Ile Val Ile Gly Ser Phe Phe Ser Thr Cys
            485                 490                 495 ggg gct ggg ctg cag agc ctc acg ggg gcc cca cgc ctg ctg cag gcc     1536
Gly Ala Gly Leu Gln Ser Leu Thr Gly Ala Pro Arg Leu Leu Gln Ala
        500                 505                 510 atc tcg agg gat ggc att gtg ccc ttc ctg cag gtc ttt ggc cat ggc     1584
Ile Ser Arg Asp Gly Ile Val Pro Phe Leu Gln Val Phe Gly His Gly
    515                 520                 525 aag gcc aat gga gag ccg acc tgg gcc ctg ctc ctg act gcc tgc atc     1632
Lys Ala Asn Gly Glu Pro Thr Trp Ala Leu Leu Leu Thr Ala Cys Ile
530                 535                 540
```

-continued

| | |
|---|---|
| tgc gag att ggc atc ctc att gca tcc ctc gac gag gtg gcc ccc atc<br>Cys Glu Ile Gly Ile Leu Ile Ala Ser Leu Asp Glu Val Ala Pro Ile<br>545                     550                  555                  560 | 1680 |
| ctc tct atg ttc ttc ctg atg tgc tac atg ttt gtg aat ctg gcc tgt<br>Leu Ser Met Phe Phe Leu Met Cys Tyr Met Phe Val Asn Leu Ala Cys<br>                        565                  570                  575 | 1728 |
| gca gtg cag acg ctg ctg agg aca ccc aac tgg agg cca cgc ttt cga<br>Ala Val Gln Thr Leu Leu Arg Thr Pro Asn Trp Arg Pro Arg Phe Arg<br>580                     585                  590 | 1776 |
| tat tac cac tgg acc ctc tcc ttc ctg ggc atg agc ctc tgc ctg gcc<br>Tyr Tyr His Trp Thr Leu Ser Phe Leu Gly Met Ser Leu Cys Leu Ala<br>                     595                  600                  605 | 1824 |
| ctc atg ttc atc tgc tcc tgg tat tat gca ctg gta gcc atg ctc att<br>Leu Met Phe Ile Cys Ser Trp Tyr Tyr Ala Leu Val Ala Met Leu Ile<br>610                     615                  620 | 1872 |
| gct gga ctc atc tac aag tac att gag tac cgt ggg gca gag aag gag<br>Ala Gly Leu Ile Tyr Lys Tyr Ile Glu Tyr Arg Gly Ala Glu Lys Glu<br>625                     630                  635                  640 | 1920 |
| tgg ggc gat ggg ata cga ggt ctg tct ctc agt gcg gct cgc tat gcc<br>Trp Gly Asp Gly Ile Arg Gly Leu Ser Leu Ser Ala Ala Arg Tyr Ala<br>                     645                  650                  655 | 1968 |
| ctc tta cgc ctg gag gaa ggg ccc cca cac acc aag aac tgg agg cca<br>Leu Leu Arg Leu Glu Glu Gly Pro Pro His Thr Lys Asn Trp Arg Pro<br>660                     665                  670 | 2016 |
| cag ctg ctg gtg ctg gtg cgt gtg gac caa gac cag aat gtg gtg cac<br>Gln Leu Leu Val Leu Val Arg Val Asp Gln Asp Gln Asn Val Val His<br>                     675                  680                  685 | 2064 |
| ccc cag ctg ctc tca ctg acc tcc cag ctg aag gca ggg aag ggc ctg<br>Pro Gln Leu Leu Ser Leu Thr Ser Gln Leu Lys Ala Gly Lys Gly Leu<br>690                     695                  700 | 2112 |
| acc atc gtg ggc tct gtc ctt gag ggc acc ttt ctg gaa aat cat cca<br>Thr Ile Val Gly Ser Val Leu Glu Gly Thr Phe Leu Glu Asn His Pro<br>705                     710                  715                  720 | 2160 |
| cag gcc cag cgg gca gaa gag tct atc agg cgc ctg atg gag gca gag<br>Gln Ala Gln Arg Ala Glu Glu Ser Ile Arg Arg Leu Met Glu Ala Glu<br>                     725                  730                  735 | 2208 |
| aag gtg aag ggc ttc tgc cag gtg gtg atc tcc tcc aac ttg cgt gat<br>Lys Val Lys Gly Phe Cys Gln Val Val Ile Ser Ser Asn Leu Arg Asp<br>740                     745                  750 | 2256 |
| ggc gtg tcc cat ctg atc cag tcc ggg ggc ctc ggg ggg ctg cag cac<br>Gly Val Ser His Leu Ile Gln Ser Gly Gly Leu Gly Gly Leu Gln His<br>                     755                  760                  765 | 2304 |
| aac act gtg ctt gtt ggc tgg ccc cgc aac tgg cgc cag aag gaa gat<br>Asn Thr Val Leu Val Gly Trp Pro Arg Asn Trp Arg Gln Lys Glu Asp<br>770                     775                  780 | 2352 |
| cat cag acg tgg agg aac ttc att gag ctg gtc cgg gaa acc aca gct<br>His Gln Thr Trp Arg Asn Phe Ile Glu Leu Val Arg Glu Thr Thr Ala<br>785                     790                  795                  800 | 2400 |
| ggc cac tta gcc ctg ctg gtc acc aag aac gtt tcc atg ttt cct ggg<br>Gly His Leu Ala Leu Leu Val Thr Lys Asn Val Ser Met Phe Pro Gly<br>                     805                  810                  815 | 2448 |
| aac cct gag cgc ttc tct gag ggc agc atc gac gtt tgg tgg att gtg<br>Asn Pro Glu Arg Phe Ser Glu Gly Ser Ile Asp Val Trp Trp Ile Val<br>820                     825                  830 | 2496 |
| cac gat gga ggc atg ctc atg ctg ctc ccc ttc ctg ctg cgg cac cac<br>His Asp Gly Gly Met Leu Met Leu Leu Pro Phe Leu Leu Arg His His<br>                     835                  840                  845 | 2544 |
| aag gtc tgg cgg aag tgc aag atg cgt atc ttc act gtg gcc cag atg<br>Lys Val Trp Arg Lys Cys Lys Met Arg Ile Phe Thr Val Ala Gln Met<br>850                     855                  860 | 2592 |

-continued

```
gat gac aat agc atc cag atg aag aag gat ctg acc aca ttt ctg tat      2640
Asp Asp Asn Ser Ile Gln Met Lys Lys Asp Leu Thr Thr Phe Leu Tyr
865                 870                 875                 880 cat tta cgc atc act gcg gag gtc gag gtg gtg gag atg cat gag agc      2688
His Leu Arg Ile Thr Ala Glu Val Glu Val Val Glu Met His Glu Ser
                885                 890                 895 gac atc tca gct tac acc tat gag aag acg ttg gtg atg gag cag cgt      2736
Asp Ile Ser Ala Tyr Thr Tyr Glu Lys Thr Leu Val Met Glu Gln Arg
            900                 905                 910 tcc cag atc ntc aaa cag atg cat tta acc aag aat gag cgg gag cgg      2784
Ser Gln Ile Xaa Lys Gln Met His Leu Thr Lys Asn Glu Arg Glu Arg
        915                 920                 925 gag atc cag agt atc aca gat gag tca cga ggc tca atc cgg aga aag      2832
Glu Ile Gln Ser Ile Thr Asp Glu Ser Arg Gly Ser Ile Arg Arg Lys
    930                 935                 940 aat cca gcc aac acg cgg ctc cgc ctg aac gtc cca gaa gag acg gct      2880
Asn Pro Ala Asn Thr Arg Leu Arg Leu Asn Val Pro Glu Glu Thr Ala
945                 950                 955                 960 ggt gac agt gaa gag aag cca gag gag gag gtg cag ctg atc cac gat      2928
Gly Asp Ser Glu Glu Lys Pro Glu Glu Glu Val Gln Leu Ile His Asp
                965                 970                 975 cag agt gct ccc agc tgc ccc agc agc tcc ccg tcc cca ggg gag gag      2976
Gln Ser Ala Pro Ser Cys Pro Ser Ser Ser Pro Ser Pro Gly Glu Glu
            980                 985                 990 cct gag ggg gaa ggg gag aca gat ccg gag aag gtg cat ctc acc tgg      3024
Pro Glu Gly Glu Gly Glu Thr Asp Pro Glu Lys Val His Leu Thr Trp
        995                 1000                1005 acc aag gac aag tcg gtg gca gag aag aat aag ggc ccc agt cct gtc      3072
Thr Lys Asp Lys Ser Val Ala Glu Lys Asn Lys Gly Pro Ser Pro Val
    1010                1015                1020 tcc tct gag ggc atc aag gac ttc ttc agc atg aag ccg gag tgg gag      3120
Ser Ser Glu Gly Ile Lys Asp Phe Phe Ser Met Lys Pro Glu Trp Glu
1025                1030                1035                1040 aac ttg aac cag tcc aac gtg cgg cgc atg cac acg gcc gtg cgg ctg      3168
Asn Leu Asn Gln Ser Asn Val Arg Arg Met His Thr Ala Val Arg Leu
                1045                1050                1055 aac gag gtc atc gtg aag aaa tcc cgg gac gcc aag ctt gtt ttg ctc      3216
Asn Glu Val Ile Val Lys Lys Ser Arg Asp Ala Lys Leu Val Leu Leu
            1060                1065                1070 aac atg cct ggg cct ccc cgc aac cgc aat ggt gat gaa aac tac atg      3264
Asn Met Pro Gly Pro Pro Arg Asn Arg Asn Gly Asp Glu Asn Tyr Met
        1075                1080                1085 gag ttt ctc gag gtc ctc aca gag cac ctg gac cgg gtg atg ctg gtc      3312
Glu Phe Leu Glu Val Leu Thr Glu His Leu Asp Arg Val Met Leu Val
    1090                1095                1100 cgc ggc ggc ggc cgc gag gtc atc acc atc tac tcc tgagaaccag           3358
Arg Gly Gly Gly Arg Glu Val Ile Thr Ile Tyr Ser
1105                1110                1115 gtcctgccac ccgggcccga gcgcgcccgg cccgcggctc cggagccctc gccgcgcccc   3418
ccgccgctgt caccgtttac atacagaccc tgtgcccgtg tcctggcccc ttaccccgct   3478
gcctgaagcc cggaggccac gcctgttggg gctgattcgg agagggcgcc ccgccgcgca   3538
gagaccagag ctcctcagtg ccagtttggc ccctgggtct tcgctgccct ttttctaagc   3598
ccggcctcgt ctcgccggag gagacgctgc aataaaggtt gggagaaggc gcggaaagga   3658
gaggagctgg ggccttgggg accccaggt agtccatgcg gcccattcct ccccttccca    3718
ctcccgccgc ggtcctcgct ctgcgctcct ccggcgctgc tccctggctc ccggcggccc   3778
ggaggcccgc ggggtgggaa ggccgcgctt gccgtctccg ccgccccttc tcgccgagcc   3838
```

-continued

```
gtggggcgcg ggcggccgag cctatacata gtgtacagga gacatcgcgt gtatttttaa    3898
cgtccccata tttatgtgac tagaagcgca acagacttct cgccatagtc gagctctccc    3958
gctgggggca ctgcggggag gcgaggcctc gggaagctga attttccttg acgtccaaga    4018
gtttgagagc gaaagtgctt taggcccagg cgggggtcgt ggcctcgttc cctcgacacc    4078
tccgtcctgc tctcgcctct tcgccctttc cgcgcgccct tggcttccca ccctcctctc    4138
cagtcctttt ccgagatgag gtgagacaag ggtccaactt ttcctggatt cgcctcccag    4198
cggacgtgag cttccactgc ggctgcagag acgcgagcaa cctcttctca tcggctctta    4258
tgcaagttgg ggccaggata ggggagggggt gctcctcaag aggaagaaac cgagaggccc    4318
gcgccccacc gaggaagccc cgccccggtg ccttcgctgg ggagcaggcg tctctcctca    4378
gtcggcttgt cgcctgctcc ccgtatccca tggctcctcg ccaaagactg aaattgtgga    4438
gctggagggc gccccctccc cggagttttcc tccctgggac aagtgaggga ggaggggggcc   4498
gattctggtt taggggccgg acccactgag aggcccccaga gccgcccgtg atgttcctcc    4558
cccgtcccca tctggcagct cctgtctcgc ctgagggacc cagccgcctt ctccgtgctc    4618
tggggccggg cctcgctgct tagcagcggc ctctagctcc gtctcccggg gacctgggcc    4678
tgagggaggg ctggagtcag cacgcgcttt gtccttagcg cctgtctgct ctcctctaac    4738
taggacccag ggcctttggc ttccccagct catccttggc ccttccgctc caccagcctg    4798
gtctgaggcg tgctctgtcc ttagagaagg cgcggtggcc gggttcccctt cccctagggc    4858
acattactaa gggggtcagg cactgcatgc tcgttccagc accatctggg actgggtaca    4918
gtacctccag ccccagggcc ctgacctgcg cacctagctt gacatctcac gcacctccca    4978
gagctggcgc cactgagtaa tccggacctc accacctctt ttcctttgag cccaaggcag    5038
agctagagct ggagctggcg ccacccagac agcgtcaggt gtggctgggg taggtttgga    5098
ggtctgccag ttacgccaag tcccctctga gattcgatca ggggactgga tagattcttt    5158
caggtactca atcaggaagc tggaggtgtt agacaccagc cccctgcatc cttcagtaga    5218
cctccctctg aacaccacag ccaggtcctg ccttctgggg gcctgaatat tccagagctg    5278
atgtgatggg ctgtgcagaa ggggggctgta tcaacatcaa ttagggaacc aaagttgcac    5338
tatctgggcc cagattgtct ggttggcaag agcaaagttt ccgttgatga aacagacatc    5398
ccacaacaaa aacccaagtt ttctgtgcta catgtgcaat atttgttatg aatgttatca    5458
caagtcattc atcaagttat ctttataatc actgtagtta gatgtttcat gtccattcaa    5518
gtgactttta ttctgagtgc aatatttcaa tagccttgta gtgataacta gtgttgcttt    5578
tgtttagatg atctatgtgc agggcaatgc aatgaagttg aaaccccttg gtaataggag    5638
aggttgcaaa ccaaatcaag agtatttatt actattactg ctattattat taggcctgcc    5698
tttaattttc agtgtaagtg ttcagtatgc cgcatcctgc ctcagtattg atcttgtgtt    5758
ctttgtgcca atatgaaaag gagagggttg gttctttcct ttattgttga atgctcccat    5818
ttaatgcttt atggcttta ctgtattact ttttttagact cccgtctgca caaaatgcaa    5878
taaaaataat tttattataa aaaaaaaa                                      5907
```

<210> SEQ ID NO 12
<211> LENGTH: 1116
<212> TYPE: PRT
<213> ORGANISM: Homo sapiens
<220> FEATURE:
<221> NAME/KEY: misc_feature
<222> LOCATION: (120)
<223> OTHER INFORMATION: Xaa=Leu or Ile

```
<220> FEATURE:
<221> NAME/KEY: misc_feature
<222> LOCATION: (358)
<223> OTHER INFORMATION: Xaa=Leu or Ile
<220> FEATURE:
<221> NAME/KEY: misc_feature
<222> LOCATION: (916)
<223> OTHER INFORMATION: Xaa=Leu or Ile

<400> SEQUENCE: 12

Met Pro Asn Asn Leu Thr Asp Cys Glu Asp Gly Asp Gly Gly Ala Asn
 1               5                  10                  15

Pro Gly Asp Gly Asn Pro Lys Glu Ser Ser Pro Phe Ile Asn Ser Thr
            20                  25                  30

Asp Thr Glu Lys Gly Lys Glu Tyr Asp Gly Lys Asn Met Ala Leu Phe
        35                  40                  45

Glu Glu Glu Met Asp Thr Ser Pro Met Val Ser Ser Leu Leu Ser Gly
    50                  55                  60

Leu Ala Asn Tyr Thr Asn Leu Pro Gln Gly Ser Arg Glu His Glu Glu
65                  70                  75                  80

Ala Glu Asn Asn Glu Gly Gly Lys Lys Lys Pro Val Gln Ala Pro Arg
                85                  90                  95

Met Gly Thr Phe Met Gly Val Tyr Leu Pro Cys Leu Gln Asn Ile Phe
            100                 105                 110

Gly Val Ile Leu Phe Leu Arg Xaa Thr Trp Val Val Gly Ile Ala Gly
        115                 120                 125

Ile Met Glu Ser Phe Cys Met Val Phe Ile Cys Cys Ser Cys Thr Met
    130                 135                 140

Leu Thr Ala Ile Ser Met Ser Ala Ile Ala Thr Asn Gly Val Val Pro
145                 150                 155                 160

Ala Gly Gly Ser Tyr Tyr Met Ile Ser Arg Ser Leu Gly Pro Glu Phe
                165                 170                 175

Gly Gly Ala Val Gly Leu Cys Phe Tyr Leu Gly Thr Thr Phe Ala Gly
            180                 185                 190

Ala Met Tyr Ile Leu Gly Thr Ile Glu Ile Leu Leu Ala Tyr Leu Phe
        195                 200                 205

Pro Ala Met Ala Ile Phe Lys Ala Glu Asp Ala Ser Gly Glu Ala Ala
    210                 215                 220

Ala Met Leu Asn Asn Met Arg Val Tyr Gly Thr Cys Val Leu Thr Cys
225                 230                 235                 240

Met Ala Thr Val Val Phe Val Gly Val Lys Tyr Val Asn Lys Phe Ala
                245                 250                 255

Leu Val Phe Leu Gly Cys Val Ile Leu Ser Ile Leu Ala Ile Tyr Ala
            260                 265                 270

Gly Val Ile Lys Ser Ala Phe Asp Pro Pro Asn Phe Pro Ile Cys Leu
        275                 280                 285

Leu Gly Asn Arg Thr Leu Ser Arg His Gly Phe Asp Val Cys Ala Lys
    290                 295                 300

Leu Ala Trp Glu Gly Asn Glu Thr Val Thr Thr Arg Leu Trp Gly Leu
305                 310                 315                 320

Phe Cys Ser Ser Arg Phe Leu Asn Ala Thr Cys Asp Glu Tyr Phe Thr
                325                 330                 335

Arg Asn Asn Val Thr Glu Ile Gln Gly Ile Pro Gly Ala Ala Ser Gly
            340                 345                 350

Leu Ile Lys Glu Asn Xaa Trp Ser Ser Tyr Leu Thr Lys Gly Val Ile
        355                 360                 365
```

-continued

```
Val Glu Arg Ser Gly Met Thr Ser Val Gly Leu Ala Asp Gly Thr Pro
    370                 375                 380

Ile Asp Met Asp His Pro Tyr Val Phe Ser Asp Met Thr Ser Tyr Phe
385                 390                 395                 400

Thr Leu Leu Val Gly Ile Tyr Phe Pro Ser Val Thr Gly Ile Met Ala
                405                 410                 415

Gly Ser Asn Arg Ser Gly Asp Leu Arg Asp Ala Gln Lys Ser Ile Pro
            420                 425                 430

Thr Gly Thr Ile Leu Ala Ile Ala Thr Thr Ser Ala Val Tyr Ile Ser
        435                 440                 445

Ser Val Val Leu Phe Gly Ala Cys Ile Glu Gly Val Val Leu Arg Asp
    450                 455                 460

Lys Phe Gly Glu Ala Val Asn Gly Asn Leu Val Val Gly Thr Leu Ala
465                 470                 475                 480

Trp Pro Ser Pro Trp Val Ile Val Ile Gly Ser Phe Phe Ser Thr Cys
                485                 490                 495

Gly Ala Gly Leu Gln Ser Leu Thr Gly Ala Pro Arg Leu Leu Gln Ala
            500                 505                 510

Ile Ser Arg Asp Gly Ile Val Pro Phe Leu Gln Val Phe Gly His Gly
        515                 520                 525

Lys Ala Asn Gly Glu Pro Thr Trp Ala Leu Leu Leu Thr Ala Cys Ile
530                 535                 540

Cys Glu Ile Gly Ile Leu Ile Ala Ser Leu Asp Glu Val Ala Pro Ile
545                 550                 555                 560

Leu Ser Met Phe Phe Leu Met Cys Tyr Met Phe Val Asn Leu Ala Cys
                565                 570                 575

Ala Val Gln Thr Leu Leu Arg Thr Pro Asn Trp Arg Pro Arg Phe Arg
            580                 585                 590

Tyr Tyr His Trp Thr Leu Ser Phe Leu Gly Met Ser Leu Cys Leu Ala
        595                 600                 605

Leu Met Phe Ile Cys Ser Trp Tyr Tyr Ala Leu Val Ala Met Leu Ile
    610                 615                 620

Ala Gly Leu Ile Tyr Lys Tyr Ile Glu Tyr Arg Gly Ala Glu Lys Glu
625                 630                 635                 640

Trp Gly Asp Gly Ile Arg Gly Leu Ser Leu Ser Ala Ala Arg Tyr Ala
                645                 650                 655

Leu Leu Arg Leu Glu Glu Gly Pro Pro His Thr Lys Asn Trp Arg Pro
            660                 665                 670

Gln Leu Leu Val Leu Val Arg Val Asp Gln Asp Gln Asn Val Val His
        675                 680                 685

Pro Gln Leu Leu Ser Leu Thr Ser Gln Leu Lys Ala Gly Lys Gly Leu
    690                 695                 700

Thr Ile Val Gly Ser Val Leu Glu Gly Thr Phe Leu Glu Asn His Pro
705                 710                 715                 720

Gln Ala Gln Arg Ala Glu Glu Ser Ile Arg Arg Leu Met Glu Ala Glu
                725                 730                 735

Lys Val Lys Gly Phe Cys Gln Val Val Ile Ser Ser Asn Leu Arg Asp
            740                 745                 750

Gly Val Ser His Leu Ile Gln Ser Gly Gly Leu Gly Gly Leu Gln His
        755                 760                 765

Asn Thr Val Leu Val Gly Trp Pro Arg Asn Trp Arg Gln Lys Glu Asp
    770                 775                 780
```

-continued

```
His Gln Thr Trp Arg Asn Phe Ile Glu Leu Val Arg Glu Thr Thr Ala
785                 790                 795                 800

Gly His Leu Ala Leu Leu Val Thr Lys Asn Val Ser Met Phe Pro Gly
            805                 810                 815

Asn Pro Glu Arg Phe Ser Glu Gly Ser Ile Asp Val Trp Trp Ile Val
        820                 825                 830

His Asp Gly Gly Met Leu Met Leu Leu Pro Phe Leu Leu Arg His His
    835                 840                 845

Lys Val Trp Arg Lys Cys Lys Met Arg Ile Phe Thr Val Ala Gln Met
850                 855                 860

Asp Asp Asn Ser Ile Gln Met Lys Lys Asp Leu Thr Thr Phe Leu Tyr
865                 870                 875                 880

His Leu Arg Ile Thr Ala Glu Val Glu Val Glu Met His Glu Ser
            885                 890                 895

Asp Ile Ser Ala Tyr Thr Tyr Glu Lys Thr Leu Val Met Glu Gln Arg
        900                 905                 910

Ser Gln Ile Xaa Lys Gln Met His Leu Thr Lys Asn Glu Arg Glu Arg
            915                 920                 925

Glu Ile Gln Ser Ile Thr Asp Glu Ser Arg Gly Ser Ile Arg Arg Lys
        930                 935                 940

Asn Pro Ala Asn Thr Arg Leu Arg Leu Asn Val Pro Glu Glu Thr Ala
945                 950                 955                 960

Gly Asp Ser Glu Glu Lys Pro Glu Glu Val Gln Leu Ile His Asp
            965                 970                 975

Gln Ser Ala Pro Ser Cys Pro Ser Ser Pro Ser Pro Gly Glu Glu
        980                 985                 990

Pro Glu Gly Glu Gly Glu Thr Asp Pro Glu Lys Val His Leu Thr Trp
        995                 1000                1005

Thr Lys Asp Lys Ser Val Ala Glu Lys Asn Lys Gly Pro Ser Pro Val
    1010                1015                1020

Ser Ser Glu Gly Ile Lys Asp Phe Phe Ser Met Lys Pro Glu Trp Glu
1025                1030                1035                1040

Asn Leu Asn Gln Ser Asn Val Arg Arg Met His Thr Ala Val Arg Leu
                1045                1050                1055

Asn Glu Val Ile Val Lys Lys Ser Arg Asp Ala Lys Leu Val Leu Leu
                1060                1065                1070

Asn Met Pro Gly Pro Pro Arg Asn Arg Asn Gly Asp Glu Asn Tyr Met
            1075                1080                1085

Glu Phe Leu Glu Val Leu Thr Glu His Leu Asp Arg Val Met Leu Val
    1090                1095                1100

Arg Gly Gly Gly Arg Glu Val Ile Thr Ile Tyr Ser
1105                1110                1115
```

<210> SEQ ID NO 13
<211> LENGTH: 5155
<212> TYPE: DNA
<213> ORGANISM: mouse
<220> FEATURE:
<221> NAME/KEY: CDS
<222> LOCATION: (73)..(3321)
<220> FEATURE:
<221> NAME/KEY: misc_feature
<222> LOCATION: (283)
<223> OTHER INFORMATION: n=c or a, Xaa=Leu or Ile
<220> FEATURE:
<221> NAME/KEY: misc_feature
<222> LOCATION: (535)
<223> OTHER INFORMATION: n=a or c, Xaa=Leu or Ile -continued

```
<220> FEATURE:
<221> NAME/KEY: misc_feature
<222> LOCATION: (1471)
<223> OTHER INFORMATION: n=c or a, Xaa=Leu or Ile
<220> FEATURE:
<221> NAME/KEY: misc_feature
<222> LOCATION: (1828)
<223> OTHER INFORMATION: n=a or c, Xaa=Leu or Ile
<220> FEATURE:
<221> NAME/KEY: misc_feature
<222> LOCATION: (1987)
<223> OTHER INFORMATION: n=c or a, Xaa=Leu or Ile
<220> FEATURE:
<221> NAME/KEY: misc_feature
<222> LOCATION: (3139)
<223> OTHER INFORMATION: n=a or c, Xaa=Leu or Ile

<400> SEQUENCE: 13
```

| | |
|---|---:|
| ctacgccgga gtccggcggc tgctactgga gcaagcgtgt ggctgcgagg gacagcagag | 60 |
| tctaacggag cc atg ccc acg aac ttt acg gtg gtg ccg gtg gag gcg cgc <br>             Met Pro Thr Asn Phe Thr Val Val Pro Val Glu Ala Arg <br>              1           5                10 | 111 |
| gcc gac ggc gcc ggg gac gaa gct gct gag cgc acg gaa gaa ccc gag <br> Ala Asp Gly Ala Gly Asp Glu Ala Ala Glu Arg Thr Glu Glu Pro Glu <br>  15                   20                25 | 159 |
| tct ccc gag agc gtg gat caa acc tcc cct acg ccg gga gat gga aac <br> Ser Pro Glu Ser Val Asp Gln Thr Ser Pro Thr Pro Gly Asp Gly Asn <br> 30                  35                40                45 | 207 |
| ccc agg gaa aac agc cct ttc atc aat aat gtg gag gtg gaa aga gag <br> Pro Arg Glu Asn Ser Pro Phe Ile Asn Asn Val Glu Val Glu Arg Glu <br>             50                55                60 | 255 |
| agc tac ttc gag ggg aag aac atg gca ntt ttt gag gaa gag atg gac <br> Ser Tyr Phe Glu Gly Lys Asn Met Ala Xaa Phe Glu Glu Glu Met Asp <br>         65                70                75 | 303 |
| agc aac ccc atg gtg tca tca ctg ctg aac aag ctg gcc aac tat acc <br> Ser Asn Pro Met Val Ser Ser Leu Leu Asn Lys Leu Ala Asn Tyr Thr <br> 80                  85                90 | 351 |
| aac ctg agc cag ggt gtg gta gag cat gag gaa gat gag gac agc cgg <br> Asn Leu Ser Gln Gly Val Val Glu His Glu Glu Asp Glu Asp Ser Arg <br>         95                100             105 | 399 |
| agg cga gag gtc aag gcc cca cgc atg ggc acc ttc atc gga gtc tac <br> Arg Arg Glu Val Lys Ala Pro Arg Met Gly Thr Phe Ile Gly Val Tyr <br> 110                115             120             125 | 447 |
| ctg ccg tgc ctg cag aac atc ttg ggt gtt atc ctt ttc ctg cgt ctg <br> Leu Pro Cys Leu Gln Asn Ile Leu Gly Val Ile Leu Phe Leu Arg Leu <br>             130             135            140 | 495 |
| acc tgg att gtg ggg gca gct ggt gtt atg gag tcc ttc ntc att gtg <br> Thr Trp Ile Val Gly Ala Ala Gly Val Met Glu Ser Phe Xaa Ile Val <br>               145             150            155 | 543 |
| gcc atg tgc tgc acc tgt aca atg ctg aca gcc atc tcc atg agc gcc <br> Ala Met Cys Cys Thr Cys Thr Met Leu Thr Ala Ile Ser Met Ser Ala <br> 160                165             170 | 591 |
| atc gct acc aac ggc gtg gtc cca gcg gga ggc tcg tac tac atg atc <br> Ile Ala Thr Asn Gly Val Val Pro Ala Gly Gly Ser Tyr Tyr Met Ile <br>             175             180            185 | 639 |
| tcc cgt tcg ctg ggg cct gag ttt gga ggt gct gtt ggc ctc tgc ttc <br> Ser Arg Ser Leu Gly Pro Glu Phe Gly Gly Ala Val Gly Leu Cys Phe <br> 190                195             200            205 | 687 |
| tac ttg ggc aca aca ttt gca ggc gcc atg tac atc ctg ggt acc atc <br> Tyr Leu Gly Thr Thr Phe Ala Gly Ala Met Tyr Ile Leu Gly Thr Ile <br>               210             215            220 | 735 |

```
                                                              -continued gag atc ttc ctg acc tac atc tct cca agt gcg gcc atc ttc cag gca      783
Glu Ile Phe Leu Thr Tyr Ile Ser Pro Ser Ala Ala Ile Phe Gln Ala
            225                 230                 235 gag acg gcg gat ggc gag gcg gcc gca ctg ttg aac aac atg cgt gtg      831
Glu Thr Ala Asp Gly Glu Ala Ala Ala Leu Leu Asn Asn Met Arg Val
240                 245                 250 tat ggc agc tgt gcc ctg gca ctc atg gcg gtg gtg gtc ttt gtt ggt      879
Tyr Gly Ser Cys Ala Leu Ala Leu Met Ala Val Val Val Phe Val Gly
    255                 260                 265 gtc aaa tat gtc aac aag ctg gca ctg gtc ttc tta gcc tgt gtt gtg      927
Val Lys Tyr Val Asn Lys Leu Ala Leu Val Phe Leu Ala Cys Val Val
270                 275                 280                 285 ctt tct atc ctg gcc atc tat gct ggt gtc atc aag aca gcc ttt gcc      975
Leu Ser Ile Leu Ala Ile Tyr Ala Gly Val Ile Lys Thr Ala Phe Ala
                290                 295                 300 cca cct gac atc ccg gtc tgc ctt cta ggg aac cgc acg ctg gca aat     1023
Pro Pro Asp Ile Pro Val Cys Leu Leu Gly Asn Arg Thr Leu Ala Asn
                305                 310                 315 cgc aac ttt gat acc tgt gcc aag atg cag gtt gtc agc aac ggt aca     1071
Arg Asn Phe Asp Thr Cys Ala Lys Met Gln Val Val Ser Asn Gly Thr
                320                 325                 330 gtg acc act gca ctc tgg cgc ctc ttc tgc aat ggc tcc agc ttg ggt     1119
Val Thr Thr Ala Leu Trp Arg Leu Phe Cys Asn Gly Ser Ser Leu Gly
            335                 340                 345 gcc acc tgt gat gag tac ttt gca cag aac aac gtt act gag ata cag     1167
Ala Thr Cys Asp Glu Tyr Phe Ala Gln Asn Asn Val Thr Glu Ile Gln
350                 355                 360                 365 ggc atc cct ggt gtg gcc agt ggt gtc ttc ctg gat aac ctg tgg agc     1215
Gly Ile Pro Gly Val Ala Ser Gly Val Phe Leu Asp Asn Leu Trp Ser
                370                 375                 380 aca tat tca gac aag ggg gca ttt gtg gaa aag aaa ggt gtg tcc tca     1263
Thr Tyr Ser Asp Lys Gly Ala Phe Val Glu Lys Lys Gly Val Ser Ser
                385                 390                 395 gtg cct gtg tcc gag gag agc cgg cct ggt gga ttg cca tac gtc ctc     1311
Val Pro Val Ser Glu Glu Ser Arg Pro Gly Gly Leu Pro Tyr Val Leu
            400                 405                 410 aca gac atc atg acc tac ttc acc atg cta gtt ggc atc tac ttc ccg     1359
Thr Asp Ile Met Thr Tyr Phe Thr Met Leu Val Gly Ile Tyr Phe Pro
            415                 420                 425 tct gta act ggg atc atg gca gga tcc aac cgc tcc ggg gac ctc aaa     1407
Ser Val Thr Gly Ile Met Ala Gly Ser Asn Arg Ser Gly Asp Leu Lys
430                 435                 440                 445 gac gcc cag aag tct att cca aca ggg acc att ctg gcc atc gtg act     1455
Asp Ala Gln Lys Ser Ile Pro Thr Gly Thr Ile Leu Ala Ile Val Thr
                450                 455                 460 aca tct ttc att tat ntt tcc tgc ata gtg ctg ttt ggg gcc tgc att     1503
Thr Ser Phe Ile Tyr Xaa Ser Cys Ile Val Leu Phe Gly Ala Cys Ile
                465                 470                 475 gaa ggt gta gtc ctg cga gat aag ttt ggg gag gcc ttg caa ggg aac     1551
Glu Gly Val Val Leu Arg Asp Lys Phe Gly Glu Ala Leu Gln Gly Asn
            480                 485                 490 ctg gtc att ggc atg ctg gcc tgg cca tct ccc tgg gtc att gtg att     1599
Leu Val Ile Gly Met Leu Ala Trp Pro Ser Pro Trp Val Ile Val Ile
            495                 500                 505 ggc tcc ttc ttc tcc acc tgt ggt gct ggc ctg cag agc ctg act ggg     1647
Gly Ser Phe Phe Ser Thr Cys Gly Ala Gly Leu Gln Ser Leu Thr Gly
510                 515                 520                 525 gca ccc cgc cta ctg cag gcc att gcg cgt gac gga atc atc ccc ttc     1695
Ala Pro Arg Leu Leu Gln Ala Ile Ala Arg Asp Gly Ile Ile Pro Phe
                530                 535                 540
```

-continued

| | |
|---|---|
| cta cag gtg ttt ggt cat gga aag gcc aac ggg gag ccc aca tgg gcc<br>Leu Gln Val Phe Gly His Gly Lys Ala Asn Gly Glu Pro Thr Trp Ala<br>545 550 555 | 1743 |
| ctg ctg ctc acg gct ctc atc tgt gag acc ggt atc ctc atc gcc tcc<br>Leu Leu Leu Thr Ala Leu Ile Cys Glu Thr Gly Ile Leu Ile Ala Ser<br>560 565 570 | 1791 |
| ctg gac agt gtg gcc ccc atc ctg tcc atg ttc ttc ntc atg tgc tac<br>Leu Asp Ser Val Ala Pro Ile Leu Ser Met Phe Phe Xaa Met Cys Tyr<br>575 580 585 | 1839 |
| atg ttc gtc aat ctg gcc tgt gcc gta cag acc ctg cta cgc aca ccc<br>Met Phe Val Asn Leu Ala Cys Ala Val Gln Thr Leu Leu Arg Thr Pro<br>590 595 600 605 | 1887 |
| aac tgg cgt cca cgc ttc aag ttc tac cac tgg acc ctc tcc ttc ctt<br>Asn Trp Arg Pro Arg Phe Lys Phe Tyr His Trp Thr Leu Ser Phe Leu<br>610 615 620 | 1935 |
| ggg atg agt ctc tgc ctc gcg ctg atg ttc atc tgc tcc tgg tac tac<br>Gly Met Ser Leu Cys Leu Ala Leu Met Phe Ile Cys Ser Trp Tyr Tyr<br>625 630 635 | 1983 |
| gcc ntt ttc gcc atg ctc att gcc ggc tgc atc tac aag tac atc gag<br>Ala Xaa Phe Ala Met Leu Ile Ala Gly Cys Ile Tyr Lys Tyr Ile Glu<br>640 645 650 | 2031 |
| tac cgc ggg gct gag aag gag tgg ggg gat ggc atc agg ggc ctg tca<br>Tyr Arg Gly Ala Glu Lys Glu Trp Gly Asp Gly Ile Arg Gly Leu Ser<br>655 660 665 | 2079 |
| ctg aat gct gcc cgc tac gcc ctg ctg cgt gtg gaa cat ggg ccc cca<br>Leu Asn Ala Ala Arg Tyr Ala Leu Leu Arg Val Glu His Gly Pro Pro<br>670 675 680 685 | 2127 |
| cat acc aag aac tgg agg ccc cag gtg ttg gtg atg ctg aac ctg gac<br>His Thr Lys Asn Trp Arg Pro Gln Val Leu Val Met Leu Asn Leu Asp<br>690 695 700 | 2175 |
| tcg gag cag tgt gta aag cac ccc cgc ctg ctg tcc ttc acc tct cag<br>Ser Glu Gln Cys Val Lys His Pro Arg Leu Leu Ser Phe Thr Ser Gln<br>705 710 715 | 2223 |
| ctg aag gct ggc aag ggc ctg acc atc gtg gga tct gtg cta gag ggc<br>Leu Lys Ala Gly Lys Gly Leu Thr Ile Val Gly Ser Val Leu Glu Gly<br>720 725 730 | 2271 |
| acc tac tta gac aag cat gtg gag gcc cag agg gct gaa gag aat atc<br>Thr Tyr Leu Asp Lys His Val Glu Ala Gln Arg Ala Glu Glu Asn Ile<br>735 740 745 | 2319 |
| cgg tct ctg atg agt gca gag aag acg aag ggc ttc tgc cag ctg gtg<br>Arg Ser Leu Met Ser Ala Glu Lys Thr Lys Gly Phe Cys Gln Leu Val<br>750 755 760 765 | 2367 |
| gtg tcc tcc aac ctg cga gat ggt gcg tcc cac ctg atc cag tcg gct<br>Val Ser Ser Asn Leu Arg Asp Gly Ala Ser His Leu Ile Gln Ser Ala<br>770 775 780 | 2415 |
| ggc ctc ggt ggc atg aaa cac aac act gtc ctc atg gcc tgg cca gag<br>Gly Leu Gly Gly Met Lys His Asn Thr Val Leu Met Ala Trp Pro Glu<br>785 790 795 | 2463 |
| gct tgg aag gag gca gat aat cct ttc tcc tgg aag aac ttt gta gac<br>Ala Trp Lys Glu Ala Asp Asn Pro Phe Ser Trp Lys Asn Phe Val Asp<br>800 805 810 | 2511 |
| aca gtc cgt gac act aca gca gca cat cag gcc ttg ttg gtg gcc aag<br>Thr Val Arg Asp Thr Thr Ala Ala His Gln Ala Leu Leu Val Ala Lys<br>815 820 825 | 2559 |
| aac att gac tta ttc cca caa aac caa gag cgc ttc agc gac ggg aac<br>Asn Ile Asp Leu Phe Pro Gln Asn Gln Glu Arg Phe Ser Asp Gly Asn<br>830 835 840 845 | 2607 |
| att gat gtg tgg tgg atc gtg cat gac ggg ggc atg ctc atg ctt ctg<br>Ile Asp Val Trp Trp Ile Val His Asp Gly Gly Met Leu Met Leu Leu<br>850 855 860 | 2655 |

```
ccc ttt ctg ctg cgc cag cac aag gtg tgg cga aag tgc cgg atg cgc      2703
Pro Phe Leu Leu Arg Gln His Lys Val Trp Arg Lys Cys Arg Met Arg
            865                 870                 875 atc ttc act gtg gcc cag gtg gat gat aac agc atc cag atg aag aag      2751
Ile Phe Thr Val Ala Gln Val Asp Asp Asn Ser Ile Gln Met Lys Lys
        880                 885                 890 gac ctg cag atg ttc ctg tac cac ctc agg atc agt gcc gag gtg gag      2799
Asp Leu Gln Met Phe Leu Tyr His Leu Arg Ile Ser Ala Glu Val Glu
    895                 900                 905 gtg gtg gag atg gtt gaa aat gat att tcc gca ttc acc tat gag aag      2847
Val Val Glu Met Val Glu Asn Asp Ile Ser Ala Phe Thr Tyr Glu Lys
910                 915                 920                 925 acg cta atg atg gag cag agg tca cag atg ctg aaa cag atg cag ttg      2895
Thr Leu Met Met Glu Gln Arg Ser Gln Met Leu Lys Gln Met Gln Leu
            930                 935                 940 tca aag aat gag cgg gag aga gag gcc cag ctg att cat gac agg aac      2943
Ser Lys Asn Glu Arg Glu Arg Glu Ala Gln Leu Ile His Asp Arg Asn
        945                 950                 955 act gca tcc cat acc aca gca act gct aga acc caa gcc cca cca aca      2991
Thr Ala Ser His Thr Thr Ala Thr Ala Arg Thr Gln Ala Pro Pro Thr
    960                 965                 970 ccc gac aaa gtg cag atg aca tgg acg aaa gag aaa ctc att gca gag      3039
Pro Asp Lys Val Gln Met Thr Trp Thr Lys Glu Lys Leu Ile Ala Glu
975                 980                 985 aaa cac agg aac aag gac act ggc cca tca ggc ttc aaa gac ctc ttc      3087
Lys His Arg Asn Lys Asp Thr Gly Pro Ser Gly Phe Lys Asp Leu Phe
990                 995                 1000                1005 agc cta aag ccg gac cag tcc aac gtc agg agg atg cat act gct gtg      3135
Ser Leu Lys Pro Asp Gln Ser Asn Val Arg Arg Met His Thr Ala Val
            1010                1015                1020 aag ntc aac ggc gta gtt ctc aac aag tcc cag gat gcc caa ctg gtc      3183
Lys Xaa Asn Gly Val Val Leu Asn Lys Ser Gln Asp Ala Gln Leu Val
        1025                1030                1035 ctg ctg aat atg cca ggc ccc cca aaa agt cgg cag ggg gac gag aac      3231
Leu Leu Asn Met Pro Gly Pro Pro Lys Ser Arg Gln Gly Asp Glu Asn
    1040                1045                1050 tac atg gag ttc ctc gag gtc ctg acg gaa ggg ctg aac agg gtc ctc      3279
Tyr Met Glu Phe Leu Glu Val Leu Thr Glu Gly Leu Asn Arg Val Leu
1055                1060                1065 ctg gtc agg ggt ggt ggc cga gaa gtc atc acc atc tac tcc              3321
Leu Val Arg Gly Gly Gly Arg Glu Val Ile Thr Ile Tyr Ser
1070                1075                1080 taacacctgc aacctggaca cacctggatg gggtcaggac tgtgcaagct gcctgtggcc    3381
aggctgggac tcgccagcat gccactgtga tagccactgc tctggcactc attgcctggc    3441
ctaccaacat gttgcagtga ttctggtcac cctgacacac acggcttccc acagacataa    3501
cagctcctag gcttcctcca aacagaagat gctatatggc ggggagtatc tagagctgtt    3561
ctggtaggaa cggctcctta cattgttgtc ggcaatggta ggtatacccca ggagatctgg    3621 ggcagctctt cctattactg gcagggcctc gcctcctgac actaggatca cctttctgca    3681
gatggctgtc cagcattttg tggcagttat atttttacttc caccagagaa cagtacaaag    3741
gcgcctctgt acttttcatg aacctgacag ataaaccaga actcgtgaac aagcacacag    3801
ttccttgggt ctagaatgtc actgagttgt tccccattgg cttctttgtt cctttgagta    3861
tccttgctgt gctttctgta cagtaagcac actgaggact gtccaccctc acctcctcat    3921
tctctccccc accctcctca gacatgggcc aggtaccac tgggaaattg agatagtgtt     3981
tacagggtag gagtgggtca ccattggaac cagtggtacc tgacagctgt gttcccatct    4041
```

```
gagtcgatgc cctaggagct cctgcagaga gaacctttgt tctgcagggc tatctgcagc    4101
tagcctgctt tctcttctca tgggaactca gccactttat ttcatacgca ccgagctggg    4161
aacttcaagc aggtgactac ggagagccac agtgtaacaa gcaaacggca ggaactctga    4221
gaattctgca catagtccac cacagcaggc agcatccaga gtgtgaacca tgatgtgtct    4281
cagcatacag ctttttgcaca tgaaatgccg tcccatccct caccctcctg gagagaaaag    4341
ccaggcccag cccaacaccc tcagcctcag cagccacagc cctgggtgtg tgtctttctg    4401
gctgagtgtc tcctgccata gatccttact cagccggggg ccataggcgc ctctgcactt    4461
ttcaagaacc tgacagatga tttgcacttt acccttgggc attctgctct gtaggtcatg    4521
gtttgttcac aggctgtagg caacagcact gatccgttcc tcacgttctg tatggcgtat    4581
ttatttattt aaccctcccc ggggaagctt gatagaggtg gcttctatgt ggatggcccg    4641
tggtgccagg ctctgggcat tccgacttc ctccaagaga atcagccctg tccacattca    4701
cgacgttcca gttagggtag aggccacgtt tgcacctgca caggttcttc aggctttgtt    4761
aggcacccag gtaagctcgc cagagtgact gctgcccagt gtgtgtccct gtcagcatag    4821
tgatttccac acctgctttt gcctcaattc tgaacttggc tcagactcct gagccctgga    4881
tgtctagagc agagcaggtg gctcgcctcg cctctcccag ctgttaggaa tgccctgggc    4941
agctggcctt tgcaggttct gggtcgctgc ttacaagaga tgcctgtcaa gagcgtccag    5001
cctcctttct gttgcaatct ccatgttcct ggtaactgtg gccgttcaga tcagtttcat    5061
gttttttcct ttttatagac ttttgtcttt gtatgacttt gttagtagca gagtaaagtt    5121
ctataaaata taaaaaaaaa aaaaaaaaaa aaaa                                 5155
```

<210> SEQ ID NO 14
<211> LENGTH: 1083
<212> TYPE: PRT
<213> ORGANISM: mouse
<220> FEATURE:
<221> NAME/KEY: misc_feature
<222> LOCATION: (71)
<223> OTHER INFORMATION: Xaa=Leu or Ile
<220> FEATURE:
<221> NAME/KEY: misc_feature
<222> LOCATION: (155)
<223> OTHER INFORMATION: Xaa=Leu or Ile
<220> FEATURE:
<221> NAME/KEY: misc_feature
<222> LOCATION: (467)
<223> OTHER INFORMATION: Xaa=Leu or Ile
<220> FEATURE:
<221> NAME/KEY: misc_feature
<222> LOCATION: (586)
<223> OTHER INFORMATION: Xaa=Leu or Ile
<220> FEATURE:
<221> NAME/KEY: misc_feature
<222> LOCATION: (639)
<223> OTHER INFORMATION: Xaa=Leu or Ile
<220> FEATURE:
<221> NAME/KEY: misc_feature
<222> LOCATION: (1023)
<223> OTHER INFORMATION: Xaa=Leu or Ile

<400> SEQUENCE: 14

Met Pro Thr Asn Phe Thr Val Val Pro Val Glu Ala Arg Ala Asp Gly
 1               5                  10                  15

Ala Gly Asp Glu Ala Ala Glu Arg Thr Glu Glu Pro Glu Ser Pro Glu
            20                  25                  30

Ser Val Asp Gln Thr Ser Pro Thr Pro Gly Asp Gly Asn Pro Arg Glu
        35                  40                  45

-continued

```
Asn Ser Pro Phe Ile Asn Asn Val Glu Val Glu Arg Glu Ser Tyr Phe
    50                  55                  60

Glu Gly Lys Asn Met Ala Xaa Phe Glu Glu Glu Met Asp Ser Asn Pro
 65                  70                  75                  80

Met Val Ser Ser Leu Leu Asn Lys Leu Ala Asn Tyr Thr Asn Leu Ser
                 85                  90                  95

Gln Gly Val Val Glu His Glu Glu Asp Glu Asp Ser Arg Arg Arg Glu
                100                 105                 110

Val Lys Ala Pro Arg Met Gly Thr Phe Ile Gly Val Tyr Leu Pro Cys
            115                 120                 125

Leu Gln Asn Ile Leu Gly Val Ile Leu Phe Leu Arg Leu Thr Trp Ile
    130                 135                 140

Val Gly Ala Ala Gly Val Met Glu Ser Phe Xaa Ile Val Ala Met Cys
145                 150                 155                 160

Cys Thr Cys Thr Met Leu Thr Ala Ile Ser Met Ser Ala Ile Ala Thr
                165                 170                 175

Asn Gly Val Val Pro Ala Gly Gly Ser Tyr Tyr Met Ile Ser Arg Ser
                180                 185                 190

Leu Gly Pro Glu Phe Gly Gly Ala Val Gly Leu Cys Phe Tyr Leu Gly
            195                 200                 205

Thr Thr Phe Ala Gly Ala Met Tyr Ile Leu Gly Thr Ile Glu Ile Phe
    210                 215                 220

Leu Thr Tyr Ile Ser Pro Ser Ala Ala Ile Phe Gln Ala Glu Thr Ala
225                 230                 235                 240

Asp Gly Glu Ala Ala Ala Leu Leu Asn Asn Met Arg Val Tyr Gly Ser
                245                 250                 255

Cys Ala Leu Ala Leu Met Ala Val Val Val Phe Val Gly Val Lys Tyr
            260                 265                 270

Val Asn Lys Leu Ala Leu Val Phe Leu Ala Cys Val Val Leu Ser Ile
    275                 280                 285

Leu Ala Ile Tyr Ala Gly Val Ile Lys Thr Ala Phe Ala Pro Pro Asp
    290                 295                 300

Ile Pro Val Cys Leu Leu Gly Asn Arg Thr Leu Ala Asn Arg Asn Phe
305                 310                 315                 320

Asp Thr Cys Ala Lys Met Gln Val Val Ser Asn Gly Thr Val Thr Thr
                325                 330                 335

Ala Leu Trp Arg Leu Phe Cys Asn Gly Ser Ser Leu Gly Ala Thr Cys
            340                 345                 350

Asp Glu Tyr Phe Ala Gln Asn Asn Val Thr Glu Ile Gln Gly Ile Pro
    355                 360                 365

Gly Val Ala Ser Gly Val Phe Leu Asp Asn Leu Trp Ser Thr Tyr Ser
    370                 375                 380

Asp Lys Gly Ala Phe Val Glu Lys Lys Gly Val Ser Ser Val Pro Val
385                 390                 395                 400

Ser Glu Glu Ser Arg Pro Gly Gly Leu Pro Tyr Val Leu Thr Asp Ile
                405                 410                 415

Met Thr Tyr Phe Thr Met Leu Val Gly Ile Tyr Phe Pro Ser Val Thr
            420                 425                 430

Gly Ile Met Ala Gly Ser Asn Arg Ser Gly Asp Leu Lys Asp Ala Gln
    435                 440                 445

Lys Ser Ile Pro Thr Gly Thr Ile Leu Ala Ile Val Thr Thr Ser Phe
    450                 455                 460
```

```
Ile Tyr Xaa Ser Cys Ile Val Leu Phe Gly Ala Cys Ile Glu Gly Val
465                 470                 475                 480

Val Leu Arg Asp Lys Phe Gly Glu Ala Leu Gln Gly Asn Leu Val Ile
            485                 490                 495

Gly Met Leu Ala Trp Pro Ser Pro Trp Val Ile Val Ile Gly Ser Phe
        500                 505                 510

Phe Ser Thr Cys Gly Ala Gly Leu Gln Ser Leu Thr Gly Ala Pro Arg
    515                 520                 525

Leu Leu Gln Ala Ile Ala Arg Asp Gly Ile Ile Pro Phe Leu Gln Val
530                 535                 540

Phe Gly His Gly Lys Ala Asn Gly Glu Pro Thr Trp Ala Leu Leu Leu
545                 550                 555                 560

Thr Ala Leu Ile Cys Glu Thr Gly Ile Leu Ile Ala Ser Leu Asp Ser
            565                 570                 575

Val Ala Pro Ile Leu Ser Met Phe Phe Xaa Met Cys Tyr Met Phe Val
        580                 585                 590

Asn Leu Ala Cys Ala Val Gln Thr Leu Leu Arg Thr Pro Asn Trp Arg
    595                 600                 605

Pro Arg Phe Lys Phe Tyr His Trp Thr Leu Ser Phe Leu Gly Met Ser
610                 615                 620

Leu Cys Leu Ala Leu Met Phe Ile Cys Ser Trp Tyr Tyr Ala Xaa Phe
625                 630                 635                 640

Ala Met Leu Ile Ala Gly Cys Ile Tyr Lys Tyr Ile Glu Tyr Arg Gly
            645                 650                 655

Ala Glu Lys Glu Trp Gly Asp Gly Ile Arg Gly Leu Ser Leu Asn Ala
        660                 665                 670

Ala Arg Tyr Ala Leu Leu Arg Val Glu His Gly Pro Pro His Thr Lys
    675                 680                 685

Asn Trp Arg Pro Gln Val Leu Val Met Leu Asn Leu Asp Ser Glu Gln
690                 695                 700

Cys Val Lys His Pro Arg Leu Leu Ser Phe Thr Ser Gln Leu Lys Ala
705                 710                 715                 720

Gly Lys Gly Leu Thr Ile Val Gly Ser Val Leu Glu Gly Thr Tyr Leu
            725                 730                 735

Asp Lys His Val Glu Ala Gln Arg Ala Glu Glu Asn Ile Arg Ser Leu
        740                 745                 750

Met Ser Ala Glu Lys Thr Lys Gly Phe Cys Gln Leu Val Val Ser Ser
    755                 760                 765

Asn Leu Arg Asp Gly Ala Ser His Leu Ile Gln Ser Ala Gly Leu Gly
770                 775                 780

Gly Met Lys His Asn Thr Val Leu Met Ala Trp Pro Glu Ala Trp Lys
785                 790                 795                 800

Glu Ala Asp Asn Pro Phe Ser Trp Lys Asn Phe Val Asp Thr Val Arg
            805                 810                 815

Asp Thr Thr Ala Ala His Gln Ala Leu Leu Val Ala Lys Asn Ile Asp
        820                 825                 830

Leu Phe Pro Gln Asn Gln Glu Arg Phe Ser Asp Gly Asn Ile Asp Val
    835                 840                 845

Trp Trp Ile Val His Asp Gly Gly Met Leu Met Leu Leu Pro Phe Leu
850                 855                 860

Leu Arg Gln His Lys Val Trp Arg Lys Cys Arg Met Arg Ile Phe Thr
865                 870                 875                 880
```

```
Val Ala Gln Val Asp Asp Asn Ser Ile Gln Met Lys Lys Asp Leu Gln
            885                 890                 895

Met Phe Leu Tyr His Leu Arg Ile Ser Ala Glu Val Glu Val Val Glu
        900                 905                 910

Met Val Glu Asn Asp Ile Ser Ala Phe Thr Tyr Glu Lys Thr Leu Met
            915                 920                 925

Met Glu Gln Arg Ser Gln Met Leu Lys Gln Met Gln Leu Ser Lys Asn
        930                 935                 940

Glu Arg Glu Arg Glu Ala Gln Leu Ile His Asp Arg Asn Thr Ala Ser
945                 950                 955                 960

His Thr Thr Ala Thr Ala Arg Thr Gln Ala Pro Pro Thr Pro Asp Lys
            965                 970                 975

Val Gln Met Thr Trp Thr Lys Glu Lys Leu Ile Ala Glu Lys His Arg
        980                 985                 990

Asn Lys Asp Thr Gly Pro Ser Gly Phe Lys Asp Leu Phe Ser Leu Lys
            995                 1000                1005

Pro Asp Gln Ser Asn Val Arg Arg Met His Thr Ala Val Lys Xaa Asn
    1010                1015                1020

Gly Val Val Leu Asn Lys Ser Gln Asp Ala Gln Leu Val Leu Leu Asn
1025                1030                1035                1040

Met Pro Gly Pro Pro Lys Ser Arg Gln Gly Asp Glu Asn Tyr Met Glu
            1045                1050                1055

Phe Leu Glu Val Leu Thr Glu Gly Leu Asn Arg Val Leu Leu Val Arg
        1060                1065                1070

Gly Gly Gly Arg Glu Val Ile Thr Ile Tyr Ser
        1075                1080

<210> SEQ ID NO 15
<211> LENGTH: 4260
<212> TYPE: DNA
<213> ORGANISM: Homo sapiens
<220> FEATURE:
<221> NAME/KEY: CDS
<222> LOCATION: (165)..(3614)
<220> FEATURE:
<221> NAME/KEY: misc_feature
<222> LOCATION: (267)
<223> OTHER INFORMATION: n=c or a, Xaa=Leu or Ile
<220> FEATURE:
<221> NAME/KEY: misc_feature
<222> LOCATION: (1200)
<223> OTHER INFORMATION: n=c or a, Xaa=Leu or Ile
<220> FEATURE:
<221> NAME/KEY: misc_feature
<222> LOCATION: (2529)
<223> OTHER INFORMATION: n=c or a, Xaa=Leu or Ile

<400> SEQUENCE: 15
tgagtagaag tattcttagt tggggctttt tgtgtggtgt gaatcaaggt tattgaaatg      60
tgttattttt caagttatct tttgtattgc agtcaaaagt agctagcgta agaggaagat     120
tttgcgaggt tccccccact tttttttgttc ttaaaaagaa caaa atg cat cct cca    176
                                                Met His Pro Pro
                                                 1 gaa acc acc acc aag atg gct tca gtt cgg ttc atg gtg aca ccg aca     224
Glu Thr Thr Thr Lys Met Ala Ser Val Arg Phe Met Val Thr Pro Thr
  5                  10                  15                  20 aag atc gat gac att cca ggt ttg tca gac acc agt ccg gac ntc agc     272
Lys Ile Asp Asp Ile Pro Gly Leu Ser Asp Thr Ser Pro Asp Xaa Ser
                 25                  30                  35
```

```
tct cga tct agt tcc cga gta aga ttt agc tcc cgg gaa agc gtg cct    320
Ser Arg Ser Ser Ser Arg Val Arg Phe Ser Ser Arg Glu Ser Val Pro
             40                  45                  50 gaa aca agc cgg agt gag cct atg agt gag atg tct ggg gcc acc act    368
Glu Thr Ser Arg Ser Glu Pro Met Ser Glu Met Ser Gly Ala Thr Thr
         55                  60                  65 tcg ctg gca act gtt gca ctg gat cca ccc agt gac cgg act tct cac    416
Ser Leu Ala Thr Val Ala Leu Asp Pro Pro Ser Asp Arg Thr Ser His
     70                  75                  80 ccc cag gat gtc atc gag gac ctg agt cag aac tcc atc aca ggg gaa    464
Pro Gln Asp Val Ile Glu Asp Leu Ser Gln Asn Ser Ile Thr Gly Glu
 85                  90                  95                 100 cac agc caa ctg tta gac gac gga cat aag aaa gct cga aat gct tat    512
His Ser Gln Leu Leu Asp Asp Gly His Lys Lys Ala Arg Asn Ala Tyr
                105                 110                 115 ctc aat aat tcc aat tat gaa gaa gga gat gaa tat ttt gat aaa aat    560
Leu Asn Asn Ser Asn Tyr Glu Glu Gly Asp Glu Tyr Phe Asp Lys Asn
            120                 125                 130 ttg gca ctc ttt gag gaa gaa atg gac acc aga ccg aag gtg tct tcc    608
Leu Ala Leu Phe Glu Glu Glu Met Asp Thr Arg Pro Lys Val Ser Ser
        135                 140                 145 ctc ctc aac cgc atg gcc aat tac act aat ctg act caa gga gca aag    656
Leu Leu Asn Arg Met Ala Asn Tyr Thr Asn Leu Thr Gln Gly Ala Lys
    150                 155                 160 gaa cat gaa gag gca gaa aac atc act gaa ggg aaa aag aag ccc acc    704
Glu His Glu Glu Ala Glu Asn Ile Thr Glu Gly Lys Lys Lys Pro Thr
165                 170                 175                 180 aag acc ccc caa atg ggt acc ttc atg ggt gtc tac ctc cca tgt cta    752
Lys Thr Pro Gln Met Gly Thr Phe Met Gly Val Tyr Leu Pro Cys Leu
                185                 190                 195 caa aat att ttt gga gtg atc ctt ttt tta cgc ctt aca tgg gtg gtg    800
Gln Asn Ile Phe Gly Val Ile Leu Phe Leu Arg Leu Thr Trp Val Val
            200                 205                 210 ggc aca gct gga gtt ctt cag gct ttt gca att gtc ctt atc tgc tgc    848
Gly Thr Ala Gly Val Leu Gln Ala Phe Ala Ile Val Leu Ile Cys Cys
        215                 220                 225 tgc tgt aca atg ttg act gct atc tcc atg agt gcc att gcc act aat    896
Cys Cys Thr Met Leu Thr Ala Ile Ser Met Ser Ala Ile Ala Thr Asn
    230                 235                 240 gga gtg gtg cca gct ggg ggc tca tac ttt atg att tcc cgg gca ctg    944
Gly Val Val Pro Ala Gly Gly Ser Tyr Phe Met Ile Ser Arg Ala Leu
245                 250                 255                 260 ggc cca gag ttt ggt ggg gct gtt ggc ctc tgc ttt tat ctt ggt acc    992
Gly Pro Glu Phe Gly Gly Ala Val Gly Leu Cys Phe Tyr Leu Gly Thr
                265                 270                 275 aca ttt gca gca gcc atg tac atc ctt ggt gcc att gaa atc ttt ctg   1040
Thr Phe Ala Ala Ala Met Tyr Ile Leu Gly Ala Ile Glu Ile Phe Leu
            280                 285                 290 gtc tat atc gtc ccc cga gct gcc atc ttt cac agt gat gac gca ctc   1088
Val Tyr Ile Val Pro Arg Ala Ala Ile Phe His Ser Asp Asp Ala Leu
        295                 300                 305 aag gaa tca gca gcc atg cta aat aac atg cgt gtc tac ggc aca gct   1136
Lys Glu Ser Ala Ala Met Leu Asn Asn Met Arg Val Tyr Gly Thr Ala
    310                 315                 320 ttc ttg gtc ctt atg gta tta gtg gta ttt atc ggc gta cgc tat gtg   1184
Phe Leu Val Leu Met Val Leu Val Val Phe Ile Gly Val Arg Tyr Val
325                 330                 335                 340 aac aag ttt gcc tca ntt ttc ctg gcc tgt gtc att gtg tcc atc ttg   1232
Asn Lys Phe Ala Ser Xaa Phe Leu Ala Cys Val Ile Val Ser Ile Leu
                345                 350                 355
```

-continued

```
gcc atc tat gct gga gcc atc aag tct tct ttt gct cct cca cac ttc      1280
Ala Ile Tyr Ala Gly Ala Ile Lys Ser Ser Phe Ala Pro Pro His Phe
        360                 365                 370 ccg gtc tgc atg ctg ggt aac cgc act ctt tca tca aga cac att gac      1328
Pro Val Cys Met Leu Gly Asn Arg Thr Leu Ser Ser Arg His Ile Asp
            375                 380                 385 gtt tgc tct aag acc aag gaa att aac aac atg aca gtc cca tca aag      1376
Val Cys Ser Lys Thr Lys Glu Ile Asn Asn Met Thr Val Pro Ser Lys
390                 395                 400 tta tgg gga ttc ttc tgt aac tcg agt caa ttt ttc aat gcc acc tgt      1424
Leu Trp Gly Phe Phe Cys Asn Ser Ser Gln Phe Phe Asn Ala Thr Cys
405                 410                 415                 420 gat gaa tac ttt gtt cac aat aac gtc act tca atc cag ggc att cct      1472
Asp Glu Tyr Phe Val His Asn Asn Val Thr Ser Ile Gln Gly Ile Pro
                425                 430                 435 gga ttg gct agt ggt ata att aca gag aat ctt tgg agt aat tac cta      1520
Gly Leu Ala Ser Gly Ile Ile Thr Glu Asn Leu Trp Ser Asn Tyr Leu
            440                 445                 450 ccc aag gga gag atc atc gaa aag cct tca gcc aaa tct tct gat gtc      1568
Pro Lys Gly Glu Ile Ile Glu Lys Pro Ser Ala Lys Ser Ser Asp Val
        455                 460                 465 tta ggc agc tta aac cat gaa tat gtt ctt gtt gac atc acc acc tcc      1616
Leu Gly Ser Leu Asn His Glu Tyr Val Leu Val Asp Ile Thr Thr Ser
    470                 475                 480 ttc acg ctt ctg gtg gga atc ttc ttt ccc tct gtt aca ggt atc atg      1664
Phe Thr Leu Leu Val Gly Ile Phe Phe Pro Ser Val Thr Gly Ile Met
485                 490                 495                 500 gct gga tca aac aga tct gga gat ctg aaa gat gct cag aag tct att      1712
Ala Gly Ser Asn Arg Ser Gly Asp Leu Lys Asp Ala Gln Lys Ser Ile
                505                 510                 515 ccg att ggt act atc ctt gcc atc ctg acc acc tcc ttt gtt tat tta      1760
Pro Ile Gly Thr Ile Leu Ala Ile Leu Thr Thr Ser Phe Val Tyr Leu
            520                 525                 530 agc aat gtt gtc ctt ttt ggt gca tgt att gaa ggg gtt gtt ctc aga      1808
Ser Asn Val Val Leu Phe Gly Ala Cys Ile Glu Gly Val Val Leu Arg
        535                 540                 545 gac aag ttc ggt gat gct gtg aaa ggt aat ttg gtg gta ggc acc tta      1856
Asp Lys Phe Gly Asp Ala Val Lys Gly Asn Leu Val Val Gly Thr Leu
    550                 555                 560 tct tgg cca tcc cca tgg gtg att gtt att ggc tcc ttc ttt tca aca      1904
Ser Trp Pro Ser Pro Trp Val Ile Val Ile Gly Ser Phe Phe Ser Thr
565                 570                 575                 580 tgt ggg gct gga ctt cag agc ctc aca ggt gca ccg agg ctg cta caa      1952
Cys Gly Ala Gly Leu Gln Ser Leu Thr Gly Ala Pro Arg Leu Leu Gln
                585                 590                 595 gct att gcc aag gat aac atc ata ccg ttt ctg agg gtt ttt ggc cac      2000
Ala Ile Ala Lys Asp Asn Ile Ile Pro Phe Leu Arg Val Phe Gly His
            600                 605                 610 agc aaa gcc aat ggg gaa cct acc tgg gct tta ctt cta act gct gcc      2048
Ser Lys Ala Asn Gly Glu Pro Thr Trp Ala Leu Leu Leu Thr Ala Ala
        615                 620                 625 att gca gag ctt gga ata ctc att gcc tcc ctg gat ctt gtg gcc cca      2096
Ile Ala Glu Leu Gly Ile Leu Ile Ala Ser Leu Asp Leu Val Ala Pro
    630                 635                 640 att ctt tcc atg ttt ttt ctc atg tgt tac ctc ttt gta aac ttg gca      2144
Ile Leu Ser Met Phe Phe Leu Met Cys Tyr Leu Phe Val Asn Leu Ala
645                 650                 655                 660 tgt gcc ttg caa aca tta ctt cga aca ccc aac tgg aga ccc cga ttc      2192
Cys Ala Leu Gln Thr Leu Leu Arg Thr Pro Asn Trp Arg Pro Arg Phe
                665                 670                 675
```

|     |     |     |     |     |     |     |     |     |     |     |     |     |     |     |     | |
|---|---|---|---|---|---|---|---|---|---|---|---|---|---|---|---|---|
| cgc | tac | tac | cat | tgg | gcc | ctt | tct | ttc | atg | gga | atg | agt | atc | tgt | ctg | 2240 |
| Arg | Tyr | Tyr | His | Trp | Ala | Leu | Ser | Phe | Met | Gly | Met | Ser | Ile | Cys | Leu | |
|     |     |     | 680 |     |     |     | 685 |     |     |     |     | 690 |     |     |     | |
| gct | ctg | atg | ttc | att | tct | tcc | tgg | tat | tat | gcc | att | gta | gcc | atg | gta | 2288 |
| Ala | Leu | Met | Phe | Ile | Ser | Ser | Trp | Tyr | Tyr | Ala | Ile | Val | Ala | Met | Val | |
|     |     | 695 |     |     |     |     | 700 |     |     |     |     | 705 |     |     |     | |
| ata | gct | ggt | atg | atc | tac | aag | tac | att | gaa | tac | caa | gga | gct | gag | aaa | 2336 |
| Ile | Ala | Gly | Met | Ile | Tyr | Lys | Tyr | Ile | Glu | Tyr | Gln | Gly | Ala | Glu | Lys | |
|     | 710 |     |     |     |     | 715 |     |     |     |     | 720 |     |     |     |     | |
| gaa | tgg | ggt | gat | ggt | atc | cgt | ggg | ctg | tcc | ctc | agt | gca | gcc | cgg | ttt | 2384 |
| Glu | Trp | Gly | Asp | Gly | Ile | Arg | Gly | Leu | Ser | Leu | Ser | Ala | Ala | Arg | Phe | |
| 725 |     |     |     |     | 730 |     |     |     |     | 735 |     |     |     |     | 740 | |
| gct | ttg | ctt | cga | ttg | gag | gaa | gga | cct | cca | cac | act | aaa | aac | tgg | agg | 2432 |
| Ala | Leu | Leu | Arg | Leu | Glu | Glu | Gly | Pro | Pro | His | Thr | Lys | Asn | Trp | Arg | |
|     |     |     |     | 745 |     |     |     |     | 750 |     |     |     |     | 755 |     | |
| cct | cag | ttg | ctt | gta | tta | ctg | aaa | cta | gat | gaa | gac | tta | cat | gtc | aag | 2480 |
| Pro | Gln | Leu | Leu | Val | Leu | Leu | Lys | Leu | Asp | Glu | Asp | Leu | His | Val | Lys | |
|     |     |     | 760 |     |     |     | 765 |     |     |     |     | 770 |     |     |     | |
| cat | cct | cgc | ctc | ctc | acc | ttt | gcc | tca | cag | ctc | aaa | gca | gga | aaa | ggt | 2528 |
| His | Pro | Arg | Leu | Leu | Thr | Phe | Ala | Ser | Gln | Leu | Lys | Ala | Gly | Lys | Gly | |
|     |     | 775 |     |     |     |     | 780 |     |     |     |     | 785 |     |     |     | |
| ntc | act | att | gtg | ggc | tct | gtc | atc | gtg | ggg | aac | ttc | cta | gag | aac | tac | 2576 |
| Xaa | Thr | Ile | Val | Gly | Ser | Val | Ile | Val | Gly | Asn | Phe | Leu | Glu | Asn | Tyr | |
|     | 790 |     |     |     |     | 795 |     |     |     |     | 800 |     |     |     |     | |
| ggt | gaa | gct | tta | gct | gct | gag | cag | acc | ata | aag | cac | cta | atg | gag | gca | 2624 |
| Gly | Glu | Ala | Leu | Ala | Ala | Glu | Gln | Thr | Ile | Lys | His | Leu | Met | Glu | Ala | |
| 805 |     |     |     | 810 |     |     |     |     | 815 |     |     |     |     | 820 |     | |
| gag | aag | gta | aaa | gga | ttc | tgc | cag | ctg | gtg | gtg | gcc | gcc | aag | ctg | aga | 2672 |
| Glu | Lys | Val | Lys | Gly | Phe | Cys | Gln | Leu | Val | Val | Ala | Ala | Lys | Leu | Arg | |
|     |     |     |     | 825 |     |     |     |     | 830 |     |     |     |     | 835 |     | |
| gag | ggc | att | tcc | cac | ctc | atc | cag | tca | tgt | ggc | ctt | ggg | ggc | atg | aag | 2720 |
| Glu | Gly | Ile | Ser | His | Leu | Ile | Gln | Ser | Cys | Gly | Leu | Gly | Gly | Met | Lys | |
|     |     |     | 840 |     |     |     | 845 |     |     |     |     | 850 |     |     |     | |
| cac | aac | acg | gtg | gtg | atg | ggc | tgg | cct | aat | ggc | tgg | cgt | caa | agc | gaa | 2768 |
| His | Asn | Thr | Val | Val | Met | Gly | Trp | Pro | Asn | Gly | Trp | Arg | Gln | Ser | Glu | |
|     |     | 855 |     |     |     |     | 860 |     |     |     |     | 865 |     |     |     | |
| gat | gcc | cgc | gct | tgg | aag | act | ttt | att | ggc | aca | gtt | cga | gtg | aca | act | 2816 |
| Asp | Ala | Arg | Ala | Trp | Lys | Thr | Phe | Ile | Gly | Thr | Val | Arg | Val | Thr | Thr | |
|     | 870 |     |     |     |     | 875 |     |     |     |     | 880 |     |     |     |     | |
| gct | gcc | cat | ctt | gca | ctg | ctg | gtg | gct | aaa | aac | atc | tcc | ttc | ttt | ccc | 2864 |
| Ala | Ala | His | Leu | Ala | Leu | Leu | Val | Ala | Lys | Asn | Ile | Ser | Phe | Phe | Pro | |
| 885 |     |     |     | 890 |     |     |     |     | 895 |     |     |     |     | 900 |     | |
| agc | aat | gtg | gag | caa | ttt | tct | gag | ggc | aac | att | gat | gtg | tgg | tgg | att | 2912 |
| Ser | Asn | Val | Glu | Gln | Phe | Ser | Glu | Gly | Asn | Ile | Asp | Val | Trp | Trp | Ile | |
|     |     |     |     | 905 |     |     |     |     | 910 |     |     |     |     | 915 |     | |
| gtg | cat | gat | ggg | ggg | atg | ctt | atg | cta | cta | cca | ttc | cta | ctg | aaa | cag | 2960 |
| Val | His | Asp | Gly | Gly | Met | Leu | Met | Leu | Leu | Pro | Phe | Leu | Leu | Lys | Gln | |
|     |     |     | 920 |     |     |     | 925 |     |     |     |     | 930 |     |     |     | |
| cac | aag | gtg | tgg | cga | aag | tgc | agc | ata | cgg | atc | ttc | aca | gta | gcc | caa | 3008 |
| His | Lys | Val | Trp | Arg | Lys | Cys | Ser | Ile | Arg | Ile | Phe | Thr | Val | Ala | Gln | |
|     |     | 935 |     |     |     |     | 940 |     |     |     |     | 945 |     |     |     | |
| tta | gaa | gac | aac | agt | atc | caa | atg | aag | aag | gac | cta | gcc | acc | ttc | cta | 3056 |
| Leu | Glu | Asp | Asn | Ser | Ile | Gln | Met | Lys | Lys | Asp | Leu | Ala | Thr | Phe | Leu | |
|     | 950 |     |     |     |     | 955 |     |     |     |     | 960 |     |     |     |     | |
| tat | cac | tta | cgc | att | gag | gcg | gag | gta | gaa | gtg | gtg | gag | atg | cat | gac | 3104 |
| Tyr | His | Leu | Arg | Ile | Glu | Ala | Glu | Val | Glu | Val | Val | Glu | Met | His | Asp | |
| 965 |     |     |     | 970 |     |     |     |     | 975 |     |     |     |     | 980 |     | |
| agt | gat | ata | tca | gca | tat | act | tac | gag | cgc | act | ttg | atg | atg | gaa | caa | 3152 |
| Ser | Asp | Ile | Ser | Ala | Tyr | Thr | Tyr | Glu | Arg | Thr | Leu | Met | Met | Glu | Gln | |
|     |     |     | 985 |     |     |     | 990 |     |     |     |     | 995 |     |     |     | |

| | | | | | | | | | | | | | | | | |
|---|---|---|---|---|---|---|---|---|---|---|---|---|---|---|---|---|
| agg | tcc | cag | atg | ctt | cgg | cac | atg | cgg | cta | tcc | aaa | aca | gag | cga | gac | 3200 |
| Arg | Ser | Gln | Met | Leu | Arg | His | Met | Arg | Leu | Ser | Lys | Thr | Glu | Arg | Asp | |
| | | 1000 | | | | | 1005 | | | | | 1010 | | | | |
| aga | gag | gca | caa | ttg | gtg | aaa | gac | cga | aac | tca | atg | cta | cga | ttg | acc | 3248 |
| Arg | Glu | Ala | Gln | Leu | Val | Lys | Asp | Arg | Asn | Ser | Met | Leu | Arg | Leu | Thr | |
| | 1015 | | | | | 1020 | | | | | 1025 | | | | | |
| agc | att | ggc | tct | gat | gag | gac | gaa | gag | aca | gaa | acc | tat | cag | gag | aag | 3296 |
| Ser | Ile | Gly | Ser | Asp | Glu | Asp | Glu | Glu | Thr | Glu | Thr | Tyr | Gln | Glu | Lys | |
| | 1030 | | | | | 1035 | | | | | 1040 | | | | | |
| gtg | cac | atg | act | tgg | aca | aaa | gac | aag | tac | atg | gca | tcc | cgg | gga | caa | 3344 |
| Val | His | Met | Thr | Trp | Thr | Lys | Asp | Lys | Tyr | Met | Ala | Ser | Arg | Gly | Gln | |
| 1045 | | | | | 1050 | | | | | 1055 | | | | | 1060 | |
| aaa | gcg | aag | tca | atg | gaa | gga | ttc | cag | gac | ctg | ctt | aac | atg | cgt | ccg | 3392 |
| Lys | Ala | Lys | Ser | Met | Glu | Gly | Phe | Gln | Asp | Leu | Leu | Asn | Met | Arg | Pro | |
| | | 1065 | | | | | 1070 | | | | | 1075 | | | | |
| gac | cag | tcc | aat | gtg | agg | cgg | atg | cat | aca | gca | gtg | aaa | ctc | aac | gag | 3440 |
| Asp | Gln | Ser | Asn | Val | Arg | Arg | Met | His | Thr | Ala | Val | Lys | Leu | Asn | Glu | |
| | 1080 | | | | | 1085 | | | | | 1090 | | | | | |
| gtt | ata | gtt | aac | aag | tcc | cat | gaa | gca | aag | ctg | gtt | tta | ttg | aat | atg | 3488 |
| Val | Ile | Val | Asn | Lys | Ser | His | Glu | Ala | Lys | Leu | Val | Leu | Leu | Asn | Met | |
| | | 1095 | | | | | 1100 | | | | | 1105 | | | | |
| cca | ggg | cca | ccc | cga | aac | cct | gag | ggt | gat | gaa | aac | tac | atg | gag | ttc | 3536 |
| Pro | Gly | Pro | Pro | Arg | Asn | Pro | Glu | Gly | Asp | Glu | Asn | Tyr | Met | Glu | Phe | |
| 1110 | | | | | 1115 | | | | | 1120 | | | | | | |
| cta | gag | gtg | ctt | acc | gag | gga | cta | gag | cga | gtc | cta | ctt | gtc | cgg | ggt | 3584 |
| Leu | Glu | Val | Leu | Thr | Glu | Gly | Leu | Glu | Arg | Val | Leu | Leu | Val | Arg | Gly | |
| 1125 | | | | | 1130 | | | | | 1135 | | | | | 1140 | |
| ggt | ggc | agt | gaa | gtg | atc | acc | att | tat | tca | taacctactc | tgaatgaccg | | | | | 3634 |
| Gly | Gly | Ser | Glu | Val | Ile | Thr | Ile | Tyr | Ser | | | | | | | |
| | | | 1145 | | | | | 1150 | | | | | | | | |

| | |
|---|---|
| tgcttgacct gttttcttaa aaggcctacg tcctccatgg aagtgccagc tcattactac | 3694 |
| cactcccact caactagaag cctgtgttct gtacacatca tactgaactc ttgatgagct | 3754 |
| gagcctcaag tacctgtgta aaagagctcc catctgatct gcagtcatta cagaaaaagc | 3814 |
| aaatattccc tcaacatcag aacaatgctc aagtctttca agccactgtc tgagcagtca | 3874 |
| aaggcaaatt agaattaaca agctgagcca ataaatgaat tggtaaaagg gatgctagaa | 3934 |
| attcaactga agaaaaaaag caagtcaagt acgtattcag cattaaagat gaatctcaga | 3994 |
| agtcatggtt caatgttgac actgtgagga taacaactag agacagcttc atcttactaa | 4054 |
| agaatttatg gtcaagtata tttggaccta ttatcctcgg caagccaaga tgcaaacatt | 4114 |
| ttttagctat atttctttag tatacccact gctgtaattt tatattagga tactaacttg | 4174 |
| aaacatggct gcagcctcta cttcttcaaa acatcccc caaaatacca gatttaaata | 4234 |
| tccaaaaaaa aaaaaaaaaa aaaaaa | 4260 |

```
<210> SEQ ID NO 16
<211> LENGTH: 1150
<212> TYPE: PRT
<213> ORGANISM: Homo sapiens
<220> FEATURE:
<221> NAME/KEY: misc_feature
<222> LOCATION: (35)
<223> OTHER INFORMATION: Xaa=Leu or Ile
<220> FEATURE:
<221> NAME/KEY: misc_feature
<222> LOCATION: (346)
<223> OTHER INFORMATION: Xaa=Leu or Ile
<220> FEATURE:
<221> NAME/KEY: misc_feature
<222> LOCATION: (789)
<223> OTHER INFORMATION: Xaa=Leu or Ile
```

<400> SEQUENCE: 16

| | | | | | | | | | | | | | | |
|---|---|---|---|---|---|---|---|---|---|---|---|---|---|---|
|Met|His|Pro|Pro|Glu|Thr|Thr|Thr|Lys|Met|Ala|Ser|Val|Arg|Phe|Met
|1| | | |5| | | | |10| | | | |15|
|Val|Thr|Pro|Thr|Lys|Ile|Asp|Asp|Ile|Pro|Gly|Leu|Ser|Asp|Thr|Ser
| | | |20| | | | |25| | | | |30| |
|Pro|Asp|Xaa|Ser|Ser|Arg|Ser|Ser|Arg|Val|Arg|Phe|Ser|Ser|Arg
| | |35| | | | |40| | | | |45| | |
|Glu|Ser|Val|Pro|Glu|Thr|Ser|Arg|Ser|Glu|Pro|Met|Ser|Glu|Met|Ser
| |50| | | | |55| | | | |60| | | |
|Gly|Ala|Thr|Thr|Ser|Leu|Ala|Thr|Val|Ala|Leu|Asp|Pro|Pro|Ser|Asp
|65| | | | |70| | | | |75| | | | |80|
|Arg|Thr|Ser|His|Pro|Gln|Asp|Val|Ile|Glu|Asp|Leu|Ser|Gln|Asn|Ser
| | | | |85| | | | |90| | | | |95| |
|Ile|Thr|Gly|Glu|His|Ser|Gln|Leu|Leu|Asp|Asp|Gly|His|Lys|Lys|Ala
| | | |100| | | | |105| | | | |110| | |
|Arg|Asn|Ala|Tyr|Leu|Asn|Asn|Ser|Asn|Tyr|Glu|Glu|Gly|Asp|Glu|Tyr
| | | |115| | | | |120| | | | |125| | |
|Phe|Asp|Lys|Asn|Leu|Ala|Leu|Phe|Glu|Glu|Met|Asp|Thr|Arg|Pro
| |130| | | | |135| | | | |140| | | |
|Lys|Val|Ser|Ser|Leu|Leu|Asn|Arg|Met|Ala|Asn|Tyr|Thr|Asn|Leu|Thr
|145| | | | |150| | | | |155| | | | |160|
|Gln|Gly|Ala|Lys|Glu|His|Glu|Glu|Ala|Glu|Asn|Ile|Thr|Glu|Gly|Lys
| | | | |165| | | | |170| | | | |175| |
|Lys|Lys|Pro|Thr|Lys|Thr|Pro|Gln|Met|Gly|Thr|Phe|Met|Gly|Val|Tyr
| | | |180| | | | |185| | | | |190| | |
|Leu|Pro|Cys|Leu|Gln|Asn|Ile|Phe|Gly|Val|Ile|Leu|Phe|Leu|Arg|Leu
| | | |195| | | | |200| | | | |205| | |
|Thr|Trp|Val|Val|Gly|Thr|Ala|Gly|Val|Leu|Gln|Ala|Phe|Ala|Ile|Val
| | | |210| | | | |215| | | | |220| | |
|Leu|Ile|Cys|Cys|Cys|Cys|Thr|Met|Leu|Thr|Ala|Ile|Ser|Met|Ser|Ala
|225| | | | |230| | | | |235| | | | |240|
|Ile|Ala|Thr|Asn|Gly|Val|Val|Pro|Ala|Gly|Gly|Ser|Tyr|Phe|Met|Ile
| | | |245| | | | |250| | | | |255| | |
|Ser|Arg|Ala|Leu|Gly|Pro|Glu|Phe|Gly|Gly|Ala|Val|Gly|Leu|Cys|Phe
| | | |260| | | | |265| | | | |270| | |
|Tyr|Leu|Gly|Thr|Thr|Phe|Ala|Ala|Ala|Met|Tyr|Ile|Leu|Gly|Ala|Ile
| | | |275| | | | |280| | | | |285| | |
|Glu|Ile|Phe|Leu|Val|Tyr|Ile|Val|Pro|Arg|Ala|Ala|Ile|Phe|His|Ser
| |290| | | | |295| | | | |300| | | |
|Asp|Asp|Ala|Leu|Lys|Glu|Ser|Ala|Ala|Met|Leu|Asn|Asn|Met|Arg|Val
|305| | | | |310| | | | |315| | | | |320|
|Tyr|Gly|Thr|Ala|Phe|Leu|Val|Leu|Met|Val|Leu|Val|Val|Phe|Ile|Gly
| | | |325| | | | |330| | | | |335| | |
|Val|Arg|Tyr|Val|Asn|Lys|Phe|Ala|Ser|Xaa|Phe|Leu|Ala|Cys|Val|Ile
| | | |340| | | | |345| | | | |350| | |
|Val|Ser|Ile|Leu|Ala|Ile|Tyr|Ala|Gly|Ala|Ile|Lys|Ser|Ser|Phe|Ala
| | | |355| | | | |360| | | | |365| | |
|Pro|Pro|His|Phe|Pro|Val|Cys|Met|Leu|Gly|Asn|Arg|Thr|Leu|Ser|Ser
| | | |370| | | | |375| | | | |380| | |
|Arg|His|Ile|Asp|Val|Cys|Ser|Lys|Thr|Lys|Glu|Ile|Asn|Asn|Met|Thr
|385| | | | |390| | | | |395| | | | |400|
|Val|Pro|Ser|Lys|Leu|Trp|Gly|Phe|Phe|Cys|Asn|Ser|Ser|Gln|Phe|Phe
| | | |405| | | | |410| | | | |415| | |

```
Asn Ala Thr Cys Asp Glu Tyr Phe Val His Asn Asn Val Thr Ser Ile
            420                 425                 430

Gln Gly Ile Pro Gly Leu Ala Ser Gly Ile Ile Thr Glu Asn Leu Trp
        435                 440                 445

Ser Asn Tyr Leu Pro Lys Gly Glu Ile Ile Glu Lys Pro Ser Ala Lys
    450                 455                 460

Ser Ser Asp Val Leu Gly Ser Leu Asn His Glu Tyr Val Leu Val Asp
465                 470                 475                 480

Ile Thr Thr Ser Phe Thr Leu Val Gly Ile Phe Pro Ser Val
                485                 490                 495

Thr Gly Ile Met Ala Gly Ser Asn Arg Ser Gly Asp Leu Lys Asp Ala
            500                 505                 510

Gln Lys Ser Ile Pro Ile Gly Thr Ile Leu Ala Ile Leu Thr Thr Ser
        515                 520                 525

Phe Val Tyr Leu Ser Asn Val Val Leu Phe Gly Ala Cys Ile Glu Gly
    530                 535                 540

Val Val Leu Arg Asp Lys Phe Gly Asp Ala Val Lys Gly Asn Leu Val
545                 550                 555                 560

Val Gly Thr Leu Ser Trp Pro Ser Pro Trp Val Ile Val Ile Gly Ser
                565                 570                 575

Phe Phe Ser Thr Cys Gly Ala Gly Leu Gln Ser Leu Thr Gly Ala Pro
            580                 585                 590

Arg Leu Leu Gln Ala Ile Ala Lys Asp Asn Ile Ile Pro Phe Leu Arg
        595                 600                 605

Val Phe Gly His Ser Lys Ala Asn Gly Glu Pro Thr Trp Ala Leu Leu
    610                 615                 620

Leu Thr Ala Ala Ile Ala Glu Leu Gly Ile Leu Ile Ala Ser Leu Asp
625                 630                 635                 640

Leu Val Ala Pro Ile Leu Ser Met Phe Phe Leu Met Cys Tyr Leu Phe
                645                 650                 655

Val Asn Leu Ala Cys Ala Leu Gln Thr Leu Leu Arg Thr Pro Asn Trp
            660                 665                 670

Arg Pro Arg Phe Arg Tyr Tyr His Trp Ala Leu Ser Phe Met Gly Met
        675                 680                 685

Ser Ile Cys Leu Ala Leu Met Phe Ile Ser Ser Trp Tyr Tyr Ala Ile
    690                 695                 700

Val Ala Met Val Ile Ala Gly Met Ile Tyr Lys Tyr Ile Glu Tyr Gln
705                 710                 715                 720

Gly Ala Glu Lys Glu Trp Gly Asp Gly Ile Arg Gly Leu Ser Leu Ser
                725                 730                 735

Ala Ala Arg Phe Ala Leu Leu Arg Leu Glu Glu Gly Pro Pro His Thr
            740                 745                 750

Lys Asn Trp Arg Pro Gln Leu Leu Val Leu Leu Lys Leu Asp Glu Asp
        755                 760                 765

Leu His Val Lys His Pro Arg Leu Leu Thr Phe Ala Ser Gln Leu Lys
    770                 775                 780

Ala Gly Lys Gly Xaa Thr Ile Val Gly Ser Val Ile Val Gly Asn Phe
785                 790                 795                 800

Leu Glu Asn Tyr Gly Glu Ala Leu Ala Ala Glu Gln Thr Ile Lys His
                805                 810                 815

Leu Met Glu Ala Glu Lys Val Lys Gly Phe Cys Gln Leu Val Val Ala
            820                 825                 830
```

-continued

Ala Lys Leu Arg Glu Gly Ile Ser His Leu Ile Gln Ser Cys Gly Leu
            835                 840                 845
Gly Gly Met Lys His Asn Thr Val Val Met Gly Trp Pro Asn Gly Trp
        850                 855                 860
Arg Gln Ser Glu Asp Ala Arg Ala Trp Lys Thr Phe Ile Gly Thr Val
865                 870                 875                 880
Arg Val Thr Thr Ala Ala His Leu Ala Leu Leu Val Ala Lys Asn Ile
            885                 890                 895
Ser Phe Phe Pro Ser Asn Val Glu Gln Phe Ser Glu Gly Asn Ile Asp
            900                 905                 910
Val Trp Trp Ile Val His Asp Gly Gly Met Leu Met Leu Leu Pro Phe
            915                 920                 925
Leu Leu Lys Gln His Lys Val Trp Arg Lys Cys Ser Ile Arg Ile Phe
            930                 935                 940
Thr Val Ala Gln Leu Glu Asp Asn Ser Ile Gln Met Lys Lys Asp Leu
945                 950                 955                 960
Ala Thr Phe Leu Tyr His Leu Arg Ile Glu Ala Val Glu Val Val
            965                 970                 975
Glu Met His Asp Ser Asp Ile Ser Ala Tyr Thr Tyr Glu Arg Thr Leu
            980                 985                 990
Met Met Glu Gln Arg Ser Gln Met Leu Arg His Met Arg Leu Ser Lys
            995                 1000                1005
Thr Glu Arg Asp Arg Glu Ala Gln Leu Val Lys Asp Arg Asn Ser Met
        1010                1015                1020
Leu Arg Leu Thr Ser Ile Gly Ser Asp Glu Asp Glu Glu Thr Glu Thr
1025                1030                1035                1040
Tyr Gln Glu Lys Val His Met Thr Trp Thr Lys Asp Lys Tyr Met Ala
            1045                1050                1055
Ser Arg Gly Gln Lys Ala Lys Ser Met Glu Gly Phe Gln Asp Leu Leu
            1060                1065                1070
Asn Met Arg Pro Asp Gln Ser Asn Val Arg Arg Met His Thr Ala Val
        1075                1080                1085
Lys Leu Asn Glu Val Ile Val Asn Lys Ser His Glu Ala Lys Leu Val
            1090                1095                1100
Leu Leu Asn Met Pro Gly Pro Pro Arg Asn Pro Glu Gly Asp Glu Asn
1105                1110                1115                1120
Tyr Met Glu Phe Leu Glu Val Leu Thr Glu Gly Leu Glu Arg Val Leu
            1125                1130                1135
Leu Val Arg Gly Gly Gly Ser Glu Val Ile Thr Ile Tyr Ser
            1140                1145                1150

<210> SEQ ID NO 17
<211> LENGTH: 712
<212> TYPE: DNA
<213> ORGANISM: Homo sapiens
<220> FEATURE:
<221> NAME/KEY: misc_feature
<222> LOCATION: (74)
<223> OTHER INFORMATION: n=a, c, g, or t
<220> FEATURE:
<221> NAME/KEY: misc_feature
<222> LOCATION: (250)
<223> OTHER INFORMATION: n=a, c, g, or t

<400> SEQUENCE: 17
agacaggaat ccggttctgc ccctgcatcc tcctctgctt cacccttctg tcagtagtgt      60
gggttatttt ttcncgttat gcatgtgcac ctttcccacc agacccaagt ggattgtcga     120

```
catcaaaaac accgggtggc tttgcataca cctcccccca gccagacctg tggggtattc     180
acctgatacn caacaggtgg ccgggtgtac acctttttagc aatctgatcc acgctatagt    240
cgcctgataa aggtttgcct gcacgcactt ggcccaacta gaacccgtgg gacactcacc    300
agataaagga cttacctcga caggaaactg ggggctgagg ggagggaggc ttcatctgct    360
gccctgagac catggcactg agccttcagc cccggaccag agggggttagc taggtagctc    420 ttcattctga aggaaagaag tcacacaaga ttggcattgt tttgtctttt tgttttttgt    480
ttttttctct cttaaaaaat atattcacct attggtgatg cactttctag gacagtcggc    540
ttgaattctg agtagaagta ttcttagttg gggctttgtg tgtggtgtga atcaaggtta    600
ttgaaatgtg ttatttttca agttatcttt tgtattgcag tcaaaagtag ctagcgtaag    660
aggaagattt tgcgaggttc cccccacttt ttttgttctt aaaaagaaca aa            712

<210> SEQ ID NO 18
<211> LENGTH: 1014
<212> TYPE: DNA
<213> ORGANISM: mouse
<220> FEATURE:
<221> NAME/KEY: misc_feature
<222> LOCATION: (525)
<223> OTHER INFORMATION: n=a, c, g, or t

<400> SEQUENCE: 18
tagccgccgc ctccagctcc tttgccagga cgagacctct ggaggcagg aatccactct      60 gcttcggcat cctctcgtgg ctctcctctt tctccttcct gtagtgtggg ggtattttcc    120
cgttatgcat gcgcatctct cccaccagac ccaagtggat tatcgacctc aaaaacatcg    180
ggtggctcag cacacacctc ctcccagcca gacctgtggg gtattcacct gatacacaac    240
aggtggctgg tgcacacctt tgcgcaatct gatccacgct cttatacgcc tgataagggt    300
gggcctgcat gctccgtcct cagctagaac cgtgggacac tcggcagata aaggactaac    360
tacctcatcc ggaccctggg ggttgagcag agggaggcgt caccagctgc tgtgagatca    420
tggcacggag cccacagccc tggaccaggg agatagcta ggattctgaa agaaccaagt    480
tatacaggat tagcatcgtt ttgttcttat tttgttttct cgaanattat ttttcagtta    540
ctggtggggc actttataaa acagctggct tgaattctat acacggattc ttaattgggc    600 cttttgtgggc tgtaaatcag ggtaattgag ggttttttggt ttttttttccc cttctatttt    660 tgcaatcaga agtagctagt gtaggaggaa gagttttttgt gagcttttcc ttttttcttt    720
gtcaaaaagg aaaggggggg gaaaatgcat ccaccagaag ccaccaccaa gatgtcctca    780
gttcggttca tggtgacacc aactaagatt gatgacattc caggtttgtc agacaccagc    840
ccggacctca gctctcggtc tagttctcga gtaagattta gctcccgaga aagtgtgcca    900
gaaacaagcc gtagtgagcc tatgagcgaa ctgtctgggg ctactacttc tctgcaact    960 gttgccctag atccttccag tgaccggact tctaatcccc aggatgttac ggag           1014

<210> SEQ ID NO 19
<211> LENGTH: 744
<212> TYPE: DNA
<213> ORGANISM: mouse
<220> FEATURE:
<221> NAME/KEY: misc_feature
<222> LOCATION: (574)
<223> OTHER INFORMATION: n=a, c, g, or t
```

```
<400> SEQUENCE: 19
aagtagatgt ttcacctgaa ggaggagaga agcctttcac tgactcttgc aaggttttcc      60
catatgcttt gaacttaagc aacaatggaa accgtccttt tgttttctga gttgacatag     120
tgccagtctt cattaaagag ggtagtttgt gaaataaagt gttccctgat ctttctcgtg     180
tgaagtaaaa ggacagatga tgagtaaggt tgagatgatg gaacccagag aagtggcaat     240
aaattaaagg aaacaagtgg gagacacagg gtggacagct cttgatgagc tcacgggctt     300
tagctttctg ccgcctggag aaactgccca gacagttgga gttctacagg ttaataacaa     360
taagctgggg tggagtgctt aagcctttta agagaatgat aaacagggcg gaaggcgtgt     420
cttcaagcgt cccactccct tggggctatg gtcacgtggg ctcagtactt cccgattccc     480
agccactgtc tccctaggct gtgctctgag tgtggaggga gagaggcagg gacgcacggg     540
aaggaaattt aaacgctgaa agcaagggtc tgtntgtaag aacaatgccg cacttcactg     600
tgaccaaggt agaagaccca gaggaggggg cagctggccc cctctctcct gagcccagct     660
cagcagaagt aaaagcccgg attcaggatc cccaagaacc aggtaagtcc tgcgcttgta     720
gcgtcggggg acccacagac tagt                                            744

<210> SEQ ID NO 20
<211> LENGTH: 52
<212> TYPE: DNA
<213> ORGANISM: Homo sapiens

<400> SEQUENCE: 20
atgcccaaca acctgacgga ctgcgaggac ggcgatgggg gagccaaccc gg              52

<210> SEQ ID NO 21
<211> LENGTH: 95
<212> TYPE: DNA
<213> ORGANISM: Homo sapiens

<400> SEQUENCE: 21
gtgatggcaa ccccaaggaa agcagtccct tcatcaacag caccgacaca gagaagggaa      60
aggagtatga tggcaagaac atggccttgt ttgag                                 95

<210> SEQ ID NO 22
<211> LENGTH: 132
<212> TYPE: DNA
<213> ORGANISM: Homo sapiens

<400> SEQUENCE: 22
gaggagatgg acaccagccc tatggtgtcc tccttgctca gtggcctggc caactacacc      60
aacctgcccc agggaagtag ggagcatgaa gaggcagaaa acaatgaggg tggaaaaaag     120
aagccggtgc ag                                                         132

<210> SEQ ID NO 23
<211> LENGTH: 147
<212> TYPE: DNA
<213> ORGANISM: Homo sapiens

<400> SEQUENCE: 23
gccccacgca tgggcacctt catgggcgtg tacctgccgt gcctgcagaa catctttggc      60
gtcatcctct tcctgcggct cacctgggtg gtgggcattg caggcatcat ggagtccttc     120
tgcatggtgt tcatctgctg ctcctgt                                         147
```

```
<210> SEQ ID NO 24
<211> LENGTH: 55
<212> TYPE: DNA
<213> ORGANISM: Homo sapiens

<400> SEQUENCE: 24
acgatgctca cggccatctc catgagtgca attgcaacga atggtgttgt gcctg            55

<210> SEQ ID NO 25
<211> LENGTH: 131
<212> TYPE: DNA
<213> ORGANISM: Homo sapiens

<400> SEQUENCE: 25
ctggtggctc ctactacatg atttccaggt ctctgggccc agagtttggg ggtgccgtgg       60
gcctctgctt ctacctgggc actacctttg caggagccat gtacatcctg ggcaccatcg      120
aaatcctgct g                                                           131

<210> SEQ ID NO 26
<211> LENGTH: 242
<212> TYPE: DNA
<213> ORGANISM: Homo sapiens

<400> SEQUENCE: 26
gcttacctct tcccagccat ggccatcttc aaggcagaag atgccagtgg ggaggcagca       60
gccatgctga caacatgcg tgtttacggc acctgtgtgc tcacctgcat ggccactgtg      120
gtgtttgtgg gtgtcaagta tgtcaacaag tttgcccttg tcttcctggg ttgtgtcatc      180
ctctccatcc tggccatcta tgctggggtc atcaagtctg ccttcgaccc acccaacttc      240
cc                                                                     242

<210> SEQ ID NO 27
<211> LENGTH: 212
<212> TYPE: DNA
<213> ORGANISM: Homo sapiens

<400> SEQUENCE: 27
gatctgcctc ctgggtaacc gcacgctgtc tcgccatggc tttgatgtct gtgccaagct       60
ggcttgggaa ggaaatgaga cggtgaccac acggctatgg ggcctttct gctcctctcg      120 cttcctcaac gccacctgtg atgaatactt cacccgaaac aatgtcacag agatccaggg      180
catccctggt gctgccagtg gcctcatcaa ag                                    212

<210> SEQ ID NO 28
<211> LENGTH: 171
<212> TYPE: DNA
<213> ORGANISM: Homo sapiens

<400> SEQUENCE: 28
agaacctctg gagctcctac ctgaccaagg gcgtgattgt ggagaggagt gggatgacct       60
cggtgggcct ggccgatggc actcctatcg acatggacca cccttatgtc ttcagtgata     120
tgacctccta cttcaccctg ctggttggca tctacttccc ctcagtcaca g              171

<210> SEQ ID NO 29
<211> LENGTH: 99
<212> TYPE: DNA
<213> ORGANISM: Homo sapiens
```

```
<400> SEQUENCE: 29
ggatcatggc tggttctaac cgctctgggg acctgaggga tgcccagaag tcaatcccca        60
ctggcaccat cctggccatc gccaccacct ctgctgtct                               99

<210> SEQ ID NO 30
<211> LENGTH: 58
<212> TYPE: DNA
<213> ORGANISM: Homo sapiens

<400> SEQUENCE: 30
acatcagctc cgttgttctg tttggggcct gcattgaggg ggtcgtcctg cgggacaa         58

<210> SEQ ID NO 31
<211> LENGTH: 175
<212> TYPE: DNA
<213> ORGANISM: Homo sapiens

<400> SEQUENCE: 31
gtttggcgaa gctgtgaatg gcaacctcgt ggtgggcact ctggcctggc catctccatg        60
ggtaattgtc atcggatcct tcttctccac ctgtggggct gggctgcaga gcctcacggg       120
ggccccacgc tgctgcagg ccatctcgag ggatggcatt gtgcccttcc tgcag            175

<210> SEQ ID NO 32
<211> LENGTH: 119
<212> TYPE: DNA
<213> ORGANISM: Homo sapiens

<400> SEQUENCE: 32
gtctttggcc atggcaaggc caatggagag ccgacctggg ccctgctcct gactgcctgc        60
atctgcgaga ttggcatcct cattgcatcc ctcgacgagg tggcccccat cctctctat       119

<210> SEQ ID NO 33
<211> LENGTH: 99
<212> TYPE: DNA
<213> ORGANISM: Homo sapiens

<400> SEQUENCE: 33
gttcttcctg atgtgctaca tgtttgtgaa tctggcctgt gcagtgcaga cgctgctgag        60
gacacccaac tggaggccac gctttcgata ttaccactg                               99

<210> SEQ ID NO 34
<211> LENGTH: 120
<212> TYPE: DNA
<213> ORGANISM: Homo sapiens

<400> SEQUENCE: 34
gaccctctcc ttcctgggca tgagcctctg cctggccctc atgttcatct gctcctggta        60
ttatgcactg gtagccatgc tcattgctgg actcatctac aagtacattg agtaccgtgg      120

<210> SEQ ID NO 35
<211> LENGTH: 105
<212> TYPE: DNA
<213> ORGANISM: Homo sapiens

<400> SEQUENCE: 35
ggcagagaag gagtgggggcg atgggatacg aggtctgtct ctcagtgcgg ctcgctatgc       60
cctcttacgc ctggaggaag ggcccccaca caccaagaac tggag                      105
```

<210> SEQ ID NO 36
<211> LENGTH: 169
<212> TYPE: DNA
<213> ORGANISM: Homo sapiens

<400> SEQUENCE: 36
gccacagctg ctggtgctgg tgcgtgtgga ccaagaccag aatgtggtgc accccagct       60 gctctcactg acctcccagc tgaaggcagg gaagggcctg accatcgtgg gctctgtcct      120
tgagggcacc tttctggaaa atcatccaca ggcccagcgg gcagaagag                  169

<210> SEQ ID NO 37
<211> LENGTH: 196
<212> TYPE: DNA
<213> ORGANISM: Homo sapiens

<400> SEQUENCE: 37
tctatcaggc gcctgatgga ggcagagaag gtgaagggct tctgccaggt ggtgatctcc      60
tccaacttgc gtgatggcgt gtcccatctg atccagtccg ggggcctcgg ggggctgcag      120
cacaacactg tgcttgttgg ctggccccgc aactggcgcc agaaggaaga tcatcagacg      180
tggaggaact tcattg                                                      196

<210> SEQ ID NO 38
<211> LENGTH: 170
<212> TYPE: DNA
<213> ORGANISM: Homo sapiens

<400> SEQUENCE: 38
agctggtccg ggaaaccaca gctggccact tagccctgct ggtcaccaag aacgtttcca      60
tgtttcctgg gaaccctgag cgcttctctg agggcagcat cgacgtttgg tggattgtgc      120
acgatggagg catgctcatg ctgctgccct tcctgctgcg gcaccacaag                 170

<210> SEQ ID NO 39
<211> LENGTH: 132
<212> TYPE: DNA
<213> ORGANISM: Homo sapiens

<400> SEQUENCE: 39
gtctggcgga agtgcaagat gcgtatcttc actgtggccc agatggatga caatagcatc      60
cagatgaaga aggatctgac cacatttctg tatcatttac gcatcactgc ggaggtcgag      120
gtggtggaga tg                                                          132

<210> SEQ ID NO 40
<211> LENGTH: 231
<212> TYPE: DNA
<213> ORGANISM: Homo sapiens

<400> SEQUENCE: 40
catgagagcg acatctcagc ttacacctat gagaagacgt tggtgatgga gcagcgttcc      60
cagatcctca acagatgca tttaaccaag aatgagcggg agcgggagat ccagagtatc      120
acagatgagt cacgaggctc aatccggaga agaatccag ccaacacgcg gctccgcctg       180
aacgtcccag aagagacggc tggtgacagt gaagagaagc cagaggagga g               231

<210> SEQ ID NO 41
<211> LENGTH: 215
<212> TYPE: DNA
<213> ORGANISM: Homo sapiens

```
<400> SEQUENCE: 41
gtgcagctga tccacgatca gagtgctccc agctgcccca gcagctcccc gtccccaggg    60
gaggagcctg aggggaagg ggagacagat ccggagaagg tgcatctcac ctggaccaag    120
gacaagtcgg tggcagagaa gaataagggc cccagtcctg tctcctctga gggcatcaag    180
gacttcttca gcatgaagcc ggagtgggag aactt                              215

<210> SEQ ID NO 42
<211> LENGTH: 134
<212> TYPE: DNA
<213> ORGANISM: Homo sapiens

<400> SEQUENCE: 42
gaaccagtcc aacgtgcggc gcatgcacac ggccgtgcgg ctgaacgagg tcatcgtgaa    60
gaaatcccgg gacgccaagc ttgttttgct caacatgcct gggcctcccc gcaaccgcaa    120
tggtgatgaa aact                                                     134

<210> SEQ ID NO 43
<211> LENGTH: 92
<212> TYPE: DNA
<213> ORGANISM: Homo sapiens

<400> SEQUENCE: 43
acatggagtt tctcgaggtc ctcacagagc acctggaccg ggtgatgctg gtccgcggcg    60
gcggccgcga ggtcatcacc atctactcct ga                                 92

<210> SEQ ID NO 44
<211> LENGTH: 290
<212> TYPE: DNA
<213> ORGANISM: Homo sapiens

<400> SEQUENCE: 44
tggctacacc actgtatgcc caggtggttg acaacaact gattggttcc agatccctga    60
cccctctccc ttctcaggtg atggcaaccc caaggaaagc agtcccttca tcaacagcac    120
cgacacagag aagggaaagg agtatgatgg caagaacatg gccttgtttg aggtgggctg    180
ctatggctgt tgggcccca cctacaattc attatcctga ttcatcagct gctctctccc    240
tccctcccta tagagcaata ccctcgtctc caccccctccc ttgagtctac               290

<210> SEQ ID NO 45
<211> LENGTH: 259
<212> TYPE: DNA
<213> ORGANISM: Homo sapiens

<400> SEQUENCE: 45
ccccatctct tcctctgccc ttcgccaccc agctcactcc acttgctccc ccagcctcct    60
agcactgaca ccctccctcc ataggaggag atggacacca gccctatggt gtcctccttg    120
ctcagtggcc tggccaacta caccaacctg ccccagggaa gtaggagca tgaagaggca    180 gaaaacaatg agggtggaaa aaagaagccg gtgcaggtga ggacctcggg ggatgagaaa    240
tggaagaaaa gggacggat                                                259

<210> SEQ ID NO 46
<211> LENGTH: 315
<212> TYPE: DNA
<213> ORGANISM: Homo sapiens
```

```
<220> FEATURE:
<221> NAME/KEY: misc_feature
<222> LOCATION: (294)
<223> OTHER INFORMATION: n=a, c, g, or t

<400> SEQUENCE: 46
gtgggggcag agaaacatgg aggaggagca cacctgggt gttcgtaatg atgaggactg      60
cagagactga tgctggcctc cctggcaggc cccacgcatg ggcaccttca tgggcgtgta    120
cctgccgtgc ctgcagaaca tctttggcgt catcctcttc ctgcggctca cctgggtggt    180
gggcattgca ggcatcatgg agtccttctg catggtgttc atctgctgct cctgtgtgag    240
tgacacccct cccctcacca cccccctgaca gctggggctt ggcagaggcc tggngggtgg    300
gaggtgggag gatgg                                                       315

<210> SEQ ID NO 47
<211> LENGTH: 249
<212> TYPE: DNA
<213> ORGANISM: Homo sapiens

<400> SEQUENCE: 47
tttggctggt gtttatgggg tataaggctt ggcccccacc caggccactg cggcccctac     60
cccagccacc gctctgatga tctctttcct cacagacgat gctcacgcc atctccatga    120 gtgcaattgc aacgaatggt gttgtgcctg gtaggtgact ggggctttgt ggggagggag    180
gatggctggg tggaaggagg gatagtgccc tgggctttgg gggacatcaa ggcccaagag    240
agataatat                                                             249

<210> SEQ ID NO 48
<211> LENGTH: 305
<212> TYPE: DNA
<213> ORGANISM: Homo sapiens

<400> SEQUENCE: 48
gcccataagc ctgtgaggcc tggagcaacc cccttctgcc tctgtcactg aacacccctc     60
accccttacg gcagcccagt gcccccgacc ctctcgctga taccagattc tccctgcagc    120
tggtggctcc tactacatga tttccaggtc tctgggccca gagtttgggg gtgccgtggg    180
cctctgcttc tacctgggca ctacctttgc aggagccatg tacatcctgg gcaccatcga    240
aatcctgctg gtaagagagg ctgaggagga ggtgtggaac cccaggttgt cagtcagtta    300
atcag                                                                 305

<210> SEQ ID NO 49
<211> LENGTH: 503
<212> TYPE: DNA
<213> ORGANISM: Homo sapiens

<400> SEQUENCE: 49
tttccagtct ggtaccactg tgactgtgct gtgatgagca tcttttttcc taaagcgctg     60
catgtagtgc aaagggctgc tgacttaggt atctgttctt cctgcccctt tcccacaggc    120
ttacctcttc ccagccatgg ccatcttcaa ggcagaagat gccagtgggg aggcagcagc    180
catgctgaac aacatgcgtg tttacggcac ctgtgtgctc acctgcatgg ccactgtggt    240
gtttgtgggt gtcaagtatg tcaacaagtt tgcccttgtc ttcctgggtt gtgtcatcct    300
ctccatcctg gccatctatg ctggggtcat caagtctgcc ttcgacccac ccaacttccc    360
gtgagtgcaa ggaatcgtcc tcctacctcc ctggccctgt ttcagagtct ctgccaaact    420
```

```
cccctccct gccctcaga atctcagagt ggtgtgggtt gggagtagct tcccttggga      480
gggaaaatct ctcttagttt ggg                                           503
```

<210> SEQ ID NO 50
<211> LENGTH: 387
<212> TYPE: DNA
<213> ORGANISM: Homo sapiens

<400> SEQUENCE: 50

```
ggggttgatc ttgaccctga cttttttgccc cctcccacct cctggtccca gagctctggt   60 cccccttatgg ctggcctccc cctgagcatt ctgtctcccc acagagaacc tctggagctc  120
ctacctgacc aagggcgtga ttgtggagag gagtgggatg acctcggtgg cctggccga   180 tggcactcct atcgacatgg accaccctta tgtcttcagt gatatgacct cctacttcac  240
cctgctggtt ggcatctact tcccctcagt cacaggtgaa ggggagctca gagagggaag  300
actctgcctg tgagtggatg gggaagagag agtcgatgat gatgttggga atttcttagt  360
ccaaaaaccc catcatgaaa gcaaccg                                       387
```

<210> SEQ ID NO 51
<211> LENGTH: 313
<212> TYPE: DNA
<213> ORGANISM: Homo sapiens

<400> SEQUENCE: 51

```
atgttaggac tagatcccag actcactgac cctgagggtg gtgcccttt ttctcatctg    60 tctggtctcc tgtggccctg gcttgagtcc tagctgcact tctgttttgc agggatcatg  120
gctggttcta accgctctgg ggacctgagg gatgcccaga agtcaatccc cactggcacc  180
atcctggcca tcgccaccac ctctgctgtc tgtatcctgc acagctgtgc tgggaccacc  240
ctcgggggag ggcaagaggg agggcagctg aacttgctgc cttacctgct ggtgcaggaa  300
gggtggggag ggg                                                      313
```

<210> SEQ ID NO 52
<211> LENGTH: 132
<212> TYPE: DNA
<213> ORGANISM: Homo sapiens

<400> SEQUENCE: 52

```
acatcagctc cgttgttctg tttggggcct gcattgaggg ggtcgtcctg cgggacaagt   60
aagataattg gggttgatcc tattctgggg gagggtggg tatagaaggc tgagttctgg   120
gaaacagacc ca                                                       132
```

<210> SEQ ID NO 53
<211> LENGTH: 365
<212> TYPE: DNA
<213> ORGANISM: Homo sapiens

<400> SEQUENCE: 53

```
agtcctgtgg caggcacaca gttggttctg tagttggtat ggagacctgc cctggaaatc    60
caggcagcac tgctcacctg gcatctcctg tccacatcat tccaggtttg gcgaagctgt  120
gaatggcaac ctcgtggtgg gcactctggc ctggccatct ccatgggtaa ttgtcatcgg  180
atccttcttc tccacctgtg gggctgggct gcagagcctc acgggggccc cacgcctgct  240
gcaggccatc tcgagggatg gcattgtgcc cttcctgcag gtcagtgtgg gagaagaaca  300
```

| | |
|---|---|
| gcccaccctc agtagaccag ccaggcccct gcccagagag accacacagt gacccagggc | 360 |
| cataa | 365 |

<210> SEQ ID NO 54
<211> LENGTH: 209
<212> TYPE: DNA
<213> ORGANISM: Homo sapiens

<400> SEQUENCE: 54

| | |
|---|---|
| ctgcctctac tccactggtt cccgaggcta ggggagaggg ctgagaaatc ccttgaggtc | 60 |
| tcagtcccat gatgattgct ctttccccag gtctttggcc atggcaaggc caatggagag | 120 |
| ccgacctggg ccctgctcct gactgcctgc atctgcgaga ttggcatcct cattgcatcc | 180 |
| ctcgacgagg tggcccccat cctctctat | 209 |

<210> SEQ ID NO 55
<211> LENGTH: 209
<212> TYPE: DNA
<213> ORGANISM: Homo sapiens

<400> SEQUENCE: 55

| | |
|---|---|
| gttcttcctg atgtgctaca tgtttgtgaa tctggcctgt gcagtgcaga cgctgctgag | 60 |
| gacacccaac tggaggccac gctttcgata ttaccactgg tgggtgctct gtccccacac | 120 |
| ttccactgag ccacttgctc acctccacgc caatcctcac cttactccag tccatcccct | 180 |
| ctgggtctaa ggaccccaaa cctgaagag | 209 |

<210> SEQ ID NO 56
<211> LENGTH: 336
<212> TYPE: DNA
<213> ORGANISM: Homo sapiens

<400> SEQUENCE: 56

| | |
|---|---|
| gaggagagat ggctagatga cctggtggtg ggtgtatggt gtgtggatgg ttggttacat | 60 |
| ggtatatgga ttatgtgact ctgcacactc ttcaggccac agctgctggt gctggtgcgt | 120 |
| gtggaccaag accagaatgt ggtgcacccc cagctgctct cactgacctc ccagctgaag | 180 |
| gcagggaagg gcctgaccat cgtgggctct gtccttgagg gcacctttct ggaaaatcat | 240 |
| ccacaggccc agcgggcaga agaggtgagc agaggccctg gttgggcttg ggaaaaggtc | 300 |
| aggacactta ggaagacagt ctctatcctt ttgtac | 336 |

<210> SEQ ID NO 57
<211> LENGTH: 272
<212> TYPE: DNA
<213> ORGANISM: Homo sapiens

<400> SEQUENCE: 57

| | |
|---|---|
| cagggcaggc ctgaggctgg tgccttgtct tttccccctc ccctagtcta tcaggcgcct | 60 |
| gatggaggca gagaaggtga agggcttctg ccaggtggtg atctcctcca acttgcgtga | 120 |
| tggcgtgtcc catctgatcc agtccggggg cctcggggg ctgcagcaca acactgtgct | 180 |
| tgttggctgg ccccgcaact ggcgccagaa ggaagatcat cagacgtgga ggaacttcat | 240 |
| tggtaacgct attgggggct ggggacagaa ga | 272 |

<210> SEQ ID NO 58
<211> LENGTH: 328
<212> TYPE: DNA
<213> ORGANISM: Homo sapiens

<400> SEQUENCE: 58

```
tgttgggaga accagagtca ctgtttcccc ctctggccct ctccttggcc tccctcagag      60
ctggtccggg aaaccacagc tggccactta gccctgctgg tcaccaagaa cgtttccatg     120
tttcctggga accctgagcg cttctctgag ggcagcatcg acgtttggtg gattgtgcac     180
gatggaggca tgctcatgct gctgcccttc ctgctgcggc accacaaggt gagttgtgtg     240
cgtgagtgta tgcacgtgtg agtgtgtgta tgcatgtatg catttgtgtg catatgtgca     300
caactgcagg tcagactcag gggctctg                                       328
```

<210> SEQ ID NO 59
<211> LENGTH: 303
<212> TYPE: DNA
<213> ORGANISM: Homo sapiens

<400> SEQUENCE: 59

```
agggcctggc cctggatctc ctcatcacat ctgggctgga cctttctgaa tccccttcat      60
cgcctgcagg tctggcggaa gtgcaagatg cgtatcttca ctgtggccca gatggatgac    120
aatagcatcc agatgaagaa ggatctgacc acatttctgt atcatttacg catcactgcg    180
gaggtcgagg tggtggagat ggtgagtccc caggagacac cgctggggtt ccacctggcc    240
ctctttcctc ttggccccag caccaagtag ggcaactcta acacccatca gcttatgatg    300
cta                                                                  303
```

<210> SEQ ID NO 60
<211> LENGTH: 295
<212> TYPE: DNA
<213> ORGANISM: Homo sapiens

<400> SEQUENCE: 60

```
catgagagcg acatctcagc ttacacctat gagaagacgt tggtgatgga gcagcgttcc      60
cagatcctca aacagatgca tttaaccaag aatgagcggg agcgggagat ccagagtatc    120
acagatgagt cacgaggctc aatccggaga agaatccag ccaacacgcg gctccgcctg     180
aacgtcccag aagagacggc tggtgacagt gaagagaagc cagaggagga ggtgtgcagc    240
ttgggtggtt tggccccaac cagtgggagc agagcccttg gcctccaaag gactc        295
```

<210> SEQ ID NO 61
<211> LENGTH: 400
<212> TYPE: DNA
<213> ORGANISM: Homo sapiens

<400> SEQUENCE: 61

```
ggctttgaac gtcccagaag agacggctgg tgacagtgaa gagaagccag aggaggaggt      60
gcagctgatc cacgatcaga gtgctcccag ctgccccagc agctcccccgt ccccagggga   120
ggagcctgag ggggaagggg agacagatcc ggagaaggtg catctcacct ggaccaagga   180
caagtcggtg gcagagaaga ataagggccc cagtcctgtc tcctctgagg gcatcaagga   240
cttcttcagc atgaagccgg agtgggagaa cttgtaagtg cttcagcatt ttttcattct   300
ctctcctagg atggccaggg tccctaccct cctcactctg ttgtgaaccc ctaattggtg   360
ccacgacctc tgggatctct gaatagccta gcctggagat                         400
```

<210> SEQ ID NO 62
<211> LENGTH: 346
<212> TYPE: DNA
<213> ORGANISM: Homo sapiens

```
<400> SEQUENCE: 62
tgcaagaacc agtccccagc agcccagttc gggctggaag ggcgactggc tccaatcttc      60
tctacccccc cggctcacgc ggtctccact cctccttcct gccgcaggaa ccagtccaac     120
gtgcggcgca tgcacacggc cgtgcggctg aacgaggtca tcgtgaagaa atcccgggac     180
gccaagcttg ttttgctcaa catgcctggg cctccccgca accgcaatgg tgatgaaaac     240
tgtatcctgg aattaaaatt gggggaaaga gggaggtgga cgtcagggaa tctgggtcct     300
gtccctggga tggaagagct gagctgttcc tgcctccgga tcagca                    346

<210> SEQ ID NO 63
<211> LENGTH: 2733
<212> TYPE: DNA
<213> ORGANISM: Homo sapiens

<400> SEQUENCE: 63
gggacacggg cgcgagaggt ccctggcag ccgagcgcga ccccaatttc gtcgggaggg       60
aaggagaccg ggtctttctc cttgaccggc tctcagacat ggagtttctc gaggtcctca     120
cagagcacct ggaccgggtg atgctggtcc gcggcggcgg ccgcgaggtc atcaccatct     180
actcctgaga accaggtcct gccacccggg cccgagcgcg cccggcccgc ggctccggag     240
ccctcgccgc gcccccgcc gctgtcaccg tttacataca gaccctgtgc ccgtgtcctg      300
gccccttacc ccgctgcctg aagcccggag gccacgcctg ttgggctga ttcggagagg      360 gcgccccgcc gcgcagagac cagagctcct cagtgccagt ttggcccctg ggtcttcgct     420 gcccttttc taagcccggc ctcgtctcgc cggaggagac gctgcaataa aggttgggag      480
aaggcgcgga aaggagagga gctggggcct tggggacccc caggtagtcc atgcggccca     540
ttcctcccct tcccactccc gccgcggtcc tcgctctgcg ctcctccggc gctgctccct     600
ggctcccggc ggcccggagg cccgcggggt gggaaggccg cgcttgccgt ctccgccgcc     660
ccttctcgcc gagccgtggg gcgcgggcgg ccgagcctat acatagtgta caggagacat     720
cgcgtgtatt tttaacgtcc ccatatttat gtgactagaa gcgcaacaga cttctcgcca     780
tagtcgagct ctcccgctgg gggcactgcg gggaggcgag gcctcgggaa gctgaatttt     840
ccttgacgtc caagagtttg agagcgaaag tgctttaggc ccaggcgggg gtcgtggcct     900
cgttccctcg acacctccgt cctgctctcg cctcttcgcc ctttccgcgc gcccttggct     960
tcccaccctc ctctccagtc cttttccgag atgaggtgag acaagggtcc aacttttcct    1020
ggattcgcct cccagcggac gtgagcttcc actgcggctg cagagacgcg agcaacctct    1080
tctcatcggc tcttatgcaa gttggggcca ggataggga gggtgctcc tcaagaggaa      1140 gaaaccgaga ggcccgcgcc ccaccgagga agccccgccc cggtgccttc gctggggagc    1200
aggcgtctct cctcagtcgg cttgtcgcct gctccccgta tcccatggct cctcgccaaa    1260
gactgaaatt gtggagctgg agggcgcccc ctccccggag tttcctccct gggacaagtg    1320
agggaggagg gggccgattc tggtttaggg gccggaccca ctgagaggcc ccagagccgc    1380
ccgtgatgtt cctcccccgt ccccatctgg cagctcctgt ctcgcctgag ggacccagcc    1440
gccttctccg tgctctgggg ccgggcctcg ctgcttagca gcggcctcta gctccgtctc    1500
ccggggacct gggcctgagg gagggctgga gtcagcacgc gctttgtcct tagcgcctgt    1560
ctgctctcct ctaactagga cccagggcct ttggcttccc cagctcatcc ttggcccttc    1620
cgctccacca gcctggtctg aggcgtgctc tgtccttaga gaaggcgcgg tggccgggtt    1680
cccttcccct agggcacatt actaaggggg tcaggcactg catgctcgtt ccagcaccat    1740
```

-continued

```
ctgggactgg gtacagtacc tccagcccca gggccctgac ctgcgcacct agcttgacat    1800
ctcacgcacc tcccagagct ggcgccactg agtaatccgg acctcaccac ctcttttcct    1860
ttgagcccaa ggcagagcta gagctggagc tggcgccacc cagacagcgt caggtgtggc    1920
tggggtaggt ttggaggtct gccagttacg ccaagtcccc tctgagattc gatcagggga    1980
ctggatagat tctttcaggt actcaatcag gaagctggag gtgttagaca ccagcccccct   2040 gcatccttca gtagacctcc ctctgaacac cacagccagt cctgccttc tgggggcctg     2100 aatattccag agctgatgtg atgggctgtg cagaaggggg ctgtatcaac atcaattagg    2160
gaaccaaagt tgcactatct gggcccagat tgtctggttg caagagcaa agtttccgtt     2220 gatgaaacag acatcccaca acaaaaaccc aagttttctg tgctacatgt gcaatatttg    2280
ttatgaatgt tatcacaagt cattcatcaa gttatcttta taatcactgt agttagatgt    2340
ttcatgtcca ttcaagtgac ttttattctg agtgcaatat ttcaatagcc ttgtagtgat    2400
aactagtgtt gcttttgttt agatgatcta tgtgcagggc aatgcaatga agttgaaacc    2460
ccttggtaat aggagaggtt gcaaaccaaa tcaagagtat ttattactat tactgctatt    2520
attattaggc ctgcctttaa ttttcagtgt aagtgttcag tatgccgcat cctgcctcag    2580
tattgatctt gtgttctttg tgccaatatg aaaaggagag ggttggttct ttcctttatt    2640
gttgaatgct cccatttaat gctttatggc ttttactgta ttacttttttt agactcccgt    2700 ctgcacaaaa tgcaataaaa ataattttat taa                                 2733
```

<210> SEQ ID NO 64
<211> LENGTH: 304
<212> TYPE: DNA
<213> ORGANISM: Homo sapiens

<400> SEQUENCE: 64

```
cctccgtgca agatctgtag ttggccttgc tgtgcttgct tttagttcct tctccagctg     60
actgtgagtt gttttttccct caactaggag atggaaatcc aagagaaaac agcccattcc   120
tcaacaatgt cgaggtggaa caagagagct tctttgaagg gaagaacatg gcacttttcg   180
aggtaacttt acttttttaga agaagaaggt gccaggccg ttgctttgat gtggaaaagt    240
aaaggagccc ctgggggccc ccaggccggg gcctcccaca ggactggaca ccacgtggaa   300
ggaa                                                                304
```

<210> SEQ ID NO 65
<211> LENGTH: 268
<212> TYPE: DNA
<213> ORGANISM: Homo sapiens

<400> SEQUENCE: 65

```
ggtcgggggg cccacggcga ggtgcgggcc gcctgtggcc atgtccacgc cgcgcaggag    60
gagatggaca gtaaccccat ggtgtcctcg ctgctcaaca agctggccaa ctacaccaac   120
ctgagccagg gcgtggtgga gcacgaggag gacgaggaga gccggcggcg ggaggccaag   180
gttctgccac cctgcccgtg cccgcccagt ccccgcccag tccccgcccc gtgtgtcccg   240
gcagggttag atcacgccgg caaggcag                                       268
```

<210> SEQ ID NO 66
<211> LENGTH: 180
<212> TYPE: DNA
<213> ORGANISM: Homo sapiens

```
<400> SEQUENCE: 66
tgggagtgtt gcgatgccgg cagagctgtt ggaaaactct cctcagatgg ctgcctgtct    60
ttttgcagac aatgctgacc gccatttcca tgagtgcgat cgctaccaac ggtgtggtcc   120
caggtaaggg gtgcccgcca gccgcggccc tgagtcctgt tagaggagtc tgtgttttgc   180

<210> SEQ ID NO 67
<211> LENGTH: 272
<212> TYPE: DNA
<213> ORGANISM: Homo sapiens

<400> SEQUENCE: 67
aatggcagcg cagaccgcac ctcgggtccg agtccaagtg cgccctgac ccgcggctgc     60 cgcctttgtc tccgcagctg gcgggtccta ctacatgata tcgcgctcgc tgggacccga   120
gtttggaggc gctgtcggcc tctgcttcta cctgggcacg acgtttgcag ggccatgta    180 tattttgggg accatcgaga ttttcctggt aagtgtgctg ctttggaagg gttcccaccc   240
cacagtctgt ggcaggatgc caaggggccc tg                                 272

<210> SEQ ID NO 68
<211> LENGTH: 359
<212> TYPE: DNA
<213> ORGANISM: Homo sapiens

<400> SEQUENCE: 68
ttgcgggagg gacgggcact ggggagttgt gtccggggac ggcctcccga cctgccttgt    60
tcccacagac gtacatctcc ccgggtgcgg ccatcttcca ggcggaggct gcaggtggcg   120
aggcggccgc catgctgcac aacatgcgtg tgtacggcac gtgcacgctc gtgctcatgg   180
ccctggtggt cttcgtgggc gtcaagtatg tcaacaagct ggcgctggtc ttcctggcct   240
gcgtcgtgct gtccatcctg gccatctatg ccggcgtcat caagtctgcc ttcgaccccc   300
cggacatccc gtgagtctcg gggcctctga gccgagggtg ggtgtggggc tggggccag    359

<210> SEQ ID NO 69
<211> LENGTH: 378
<212> TYPE: DNA
<213> ORGANISM: Homo sapiens

<400> SEQUENCE: 69
atgggtgccc agttggggag ctgggtgggg cagtaaaagc cacttcggtg gcagcacacg    60
tgccgtgcct cccgtcccg cccagggtct gcctcctggg gaaccgcacg ctgtcacggc    120
gcagcttcga tgcctgcgtc aaggcctacg gcatccacaa caactcagcc acctccgcgc   180 tctgggggcct cttctgcaac ggctcccagc ccagcgccct ctgtgacgag tacttcatcc   240
agaacaacgt caccgaaatc cagggcatcc cgggcgcggc cagtggtgtc ttcctgggtg   300
aggctcacag ggctgcagct ggagctgggg ggtggcgggg gcagcaggcg ctggccctgg   360
tggctgctct cgccttag                                                 378

<210> SEQ ID NO 70
<211> LENGTH: 320
<212> TYPE: DNA
<213> ORGANISM: Homo sapiens

<400> SEQUENCE: 70
gagtgggcgg cccatggcg ggggcactgc acagaaggtg ccagaaaccc atgggatctt     60
ccttgcccgg cagagaacct gtggagtacg tacgcgcacg cggggggcgtt tgtggagaag   120
```

```
aaaggtgtgc cctcggtgcc cgtggcagag gagagccgtg ccagcacact gccctacgtg    180
ctcaccgaca tcgcggcctc cttcaccctg ctggttggca tctacttccc ttccgtgacc    240
ggtgagcccg ctgctccagg cttccccttc tctttctttc tctccctctc ttttttgagg    300
caaggtcttg ctctgtcacc                                                320
```

<210> SEQ ID NO 71
<211> LENGTH: 302
<212> TYPE: DNA
<213> ORGANISM: Homo sapiens

<400> SEQUENCE: 71

```
ggggtctccc cagagaccgc ctttccagct ttctgggcag gggctgccat cacatggcac     60
tgactcctca gatgggtctt tgcagcattt tcatgttcac aggtatcatg gcgggttcaa    120
accggtccgg ggacctcaag gatgcacaga agtccatccc cacggggacc atcctggcca    180
tagtgacgac gtctttcatc tgtatccttg gaggggtgca ggcgagggtt ccagcctctg    240
cctgggggga ggcccccatg ccctccccgg ctcagcatca taccctcggc caccagcatg    300
tg                                                                   302
```

<210> SEQ ID NO 72
<211> LENGTH: 304
<212> TYPE: DNA
<213> ORGANISM: Homo sapiens

<400> SEQUENCE: 72

```
tctgactcag gctcacttgc tgaaagccgc ccgcccgcct gcccgcctgc ctgcaggttc     60
ggggaggccc tgcaggggaa cctggtcatc ggcatgctgg cctggccctc cccctgggtc    120
atcgtcatcg gctccttctt ctccacctgc ggtgccggcc tgcagaccct cacgggggca    180
ccgcgcctac tgcaggccat tgcccgtgac ggcatcgtcc ccttcctgca ggtgagtccc    240
gcaccctcgt acgggggggac cctggaaggt cagggtcggg ggctctcctc ccctgtttta    300
tcct                                                                 304
```

<210> SEQ ID NO 73
<211> LENGTH: 263
<212> TYPE: DNA
<213> ORGANISM: Homo sapiens

<400> SEQUENCE: 73

```
tgaccagcct gcagcttctc tcctaaaagg gtggtgtcat ctgccccatc ttcctgccct     60
tctccctgca ggtgtttggc cacgggaagg ccaacgggga gcccacgtgg gcgctgctgc    120
tgacagtcct catctgcgag actggcatcc tcatcgcctc tctggacagc gtggccccga    180
tcctctccat gtgagcccccc acaggacggg gacctgggga tgggtgtatg ggcctggagc    240
gtggggcagt gtggatggga ggt                                            263
```

<210> SEQ ID NO 74
<211> LENGTH: 249
<212> TYPE: DNA
<213> ORGANISM: Homo sapiens

<400> SEQUENCE: 74

```
actgggggct aggggggccc agtgggcccg tatcagtggc cggccgtccc tgcaggttct     60
tcctcatgtg ctacctgttc gtgaacctgg cctgcgccgt gcagaccctg ctacgtaccc    120
ccaactggcg tccacgcttc aagttctacc actggtgagg ctactcagca cgggcgtgag    180
```

```
gagccccaca ggctgggaca ctgggtgcct ctgccactgg tgaggccgct cagcacaggc    240
gtcaggagc                                                            249

<210> SEQ ID NO 75
<211> LENGTH: 264
<212> TYPE: DNA
<213> ORGANISM: Homo sapiens

<400> SEQUENCE: 75
gtgggggctt gcatggcgtt gggccgcccc gagccacttg ccccgccccc aggaccctgt    60
cctttctggg tatgagcctg tgcctggcgc tgatgttcat ctgctcctgg tactacgcgc    120
tgtccgccat gctcatcgct ggctgcatct acaagtacat cgagtaccgc gggtaagcgc    180
tgtcagcccc ccttacagac ccggcgcacg ggagggcggg cccctctcat gctatgcctg    240
gggcagctcc ctggaggggc ctcc                                          264

<210> SEQ ID NO 76
<211> LENGTH: 290
<212> TYPE: DNA
<213> ORGANISM: Homo sapiens

<400> SEQUENCE: 76
tgccccaact cacctgcccc cagaagtccc ctttcccagg tgggagagga gcctccaggt    60
acgcggctgg acaaacccg acttcctttc ccacagggcc gagaaggagt ggggcgatgg    120
catccgtggc ctatccctga cgccgcccg ctacgccctg ctgcgcgtgg agcacggtcc    180
cccccacacc aagaactgga ggtgagcacc gcccatgccc cgtggtcctc agacgcacag    240
aagagctgtt tctgaggtcg gcctttgagt ggggacccttt gagtctcagg              290

<210> SEQ ID NO 77
<211> LENGTH: 400
<212> TYPE: DNA
<213> ORGANISM: Homo sapiens

<400> SEQUENCE: 77
gcctgtcatg tatctcccgt cccacctgtg tcgtgtgccc cgcccgtccc atctgccctg    60
cctgttgatg ggccgtgccc tggtaagcgt tgccgtggta acagccgccc cacccctggct  120 gcaggcccca ggtgctggtg atgctgaacc tggacgcgga gcaggccgtg aagcaccccc    180
gcctgctgtc cttcacgtcg cagctgaagg ccggcaaggg cctgaccatc gtgggctcgg    240
tgctggaggg gacgtacctg gacaagcaca tggaggctca gcgggccgag gaggtgggcc    300
gggcggggtc tggggggcca ggcctcttc ccaccccagc tgcacaggaa acatgccctg    360
gcatgtcctc atcgcagcgt gtcaacacgg tgctgtgcgt                         400

<210> SEQ ID NO 78
<211> LENGTH: 372
<212> TYPE: DNA
<213> ORGANISM: Homo sapiens

<400> SEQUENCE: 78
ggtgccctgg ccaccgtggg tggtgggcgt gggtctgtgc accccattcc tgctgtagca    60
ccaacctgtc ctgtctcccg cagaacatac ggtccctaat gagcacagag aagaccaagg    120
gcttctgcca gctggtggtc tcgtccagcc tgcgggatgg catgtcccac ctgatccagt    180
cggccggcct gggcggcctg aagcacaaca cggtgctcat ggcctggccc gcatcctgga    240
agcaggagga caacccctttc tcctggaaga actttgtagg taggcatggc tggcggccct    300
```

```
tcggcatccc ctcaccgtcc cctctgtgtc ctctcagtgt cccctcgctg tcccctcgct    360
gtcccctcac tg                                                        372
```

<210> SEQ ID NO 79
<211> LENGTH: 321
<212> TYPE: DNA
<213> ORGANISM: Homo sapiens

<400> SEQUENCE: 79

```
gcactggctg tgagtccccg gggaggcccc ttccgcaccc tggcctcaga tgacctgcgg    60
acggccgcct ctctccgcag acaccgtccg cgacaccacc gccgcgcacc aggtctctgct  120 ggtggccaag aacgtcgact cgtttccgca aaaccaggag cgcttcggcg ggggccacat   180
cgacgtgtgg tggatcgtgc acgacggcgg catgctcatg ctgctgccct tcctgctgcg   240
ccagcacaag gtggggcgtg cgacggggac acgccagccg gagcacggcc accccacgtg   300
ctgcgggccg ggacgggctc c                                             321
```

<210> SEQ ID NO 80
<211> LENGTH: 262
<212> TYPE: DNA
<213> ORGANISM: Homo sapiens

<400> SEQUENCE: 80

```
ggtaccaggc tggtgttgga gccatccgtg gttctgtgca caccgggctt actacgtgct    60
tgggaacttt ctaggttgaa aacgacatat ctgctttcac ctacgagagg acactaatga   120
tggagcagag gtcgcagatg ctgaagcaga tgcagctgtc caagaacgag caggagcgag   180
aggtacgtgg gggccgtggc cacagacacc aggctttctg agaagtatag ccgacttcgc   240
tgagtctttt ctgggaccct cc                                            262
```

<210> SEQ ID NO 81
<211> LENGTH: 318
<212> TYPE: DNA
<213> ORGANISM: Homo sapiens

<400> SEQUENCE: 81

```
cctccggcct ggcatcccgg gtcgctctcg cccagaggag ttttgagacc ggctggtctc    60
accgagtccc gggcccgcca ggcccagctg atccacgaca ggaacaccgc gtcccacacc   120
gcggcggcag ccaggaccca agcgccgcct acgccagaca aggtgcagat gacctggacc   180
agggagaagc tgatcgctga aagtacagg agcagagaca ccagcctatc cggtttcaaa    240
gacctcttca gcatgaagcc gtgagtgtcc gtgcgtgtgg cctgggggga acagatcctg   300
gcagtgctgg cccggcag                                                 318
```

<210> SEQ ID NO 82
<211> LENGTH: 299
<212> TYPE: DNA
<213> ORGANISM: Homo sapiens

<400> SEQUENCE: 82

```
atcagggctc agctcagcct cgtgtccgga gcgtggggtg cacccgccgc ccgctgaccg    60
tgcccacctc ccctgcaggg accagtccaa cgtcaggcgg atgcacacgg ctgtgaagct   120
caatggcgtc gtcctcaaca gtcccagga tgcgcagctg gtcctgctca acatgccagg    180
tcctcccaaa aaccgcagg gagacgagaa ctgtatccct tcttgcagtg tgcctgctga    240
gcgtgcgggc accccctggt ggcttctcgc taagacctgg gtttgtgggt gctgggagt    299
```

-continued

<210> SEQ ID NO 83
<211> LENGTH: 2168
<212> TYPE: DNA
<213> ORGANISM: Homo sapiens

<400> SEQUENCE: 83

| | | | | | |
|---|---|---|---|---|---|
| ctaaccagga | gaggataaac | ctcactccta | tcacgatttc | agctacacac | gctcaggtaa | 60 |
| gatcagctgt | ggccttaact | ctgttgacca | cagacatgga | gtttcttgaa | gtcctgaccg | 120 |
| agggggctgaa | cagagtcctc | ctggtcaggg | gtggcggccg | ggaggtgatc | accatctact | 180 |
| cctaatgccc | aacagcatca | cggcactctg | gacaggcac | ggaggacggc | gtgggcagcc | 240 |
| tgggcctggg | cttggcccag | ggaaccagac | ggcagacaca | cctgtccccc | agtgatgcca | 300 |
| cccaagctgc | ccatgggct | tcctacgaa | gtttctaggc | ccgtcaccta | gggctctcct | 360 |
| gttcagcctt | aacaggctca | gcaaatcagg | gcgtggctgg | acgatttcct | tgcatctgag | 420 |
| ggcagacgct | gctaccggag | tgacctggac | gtggccagat | cttctcgcag | gtcacaagaa | 480 |
| gccagtgagc | ccttgccttg | gtttctggaa | gttcttttcc | ttggctggat | tacccagtg | 540 |
| gttaggttgc | atttctaccc | catccagaac | attcttggaa | gagcacccgg | agctgaagct | 600 |
| gtccctgatg | atgaaggtga | aacgtcagcc | ctggccatgg | ctccgctcag | gccccggtc | 660 |
| acctccgagt | cactctgttc | cttgactgtc | tttgtgtttc | tgtacctcaa | ggcactgaag | 720 |
| ctggaggact | ctgtccatgc | ccgtgtcacc | ctcgtgtggg | agcctctggg | ctcggcaggt | 780 |
| ccacatttca | tgagctgagg | cgtgggccag | ggccatctgg | aaagggaact | cggcttttcc | 840 |
| agaacgtggt | ggatcatctg | tcgggtgtgt | ggtgaacacg | ttcagttcat | cagggcctac | 900 |
| gctccgggaa | ggggccccca | gctgtggctc | tgccatgccg | ggctgtgttt | gcagctgtcc | 960 |
| gagtctccat | ccacctttag | aaaaccagtc | acttcttttc | ataagcactg | acagggccca | 1020 |
| gcccacagcc | acaggtgcga | tcagtgcctc | acgcaggcaa | atgcactgaa | acccaggggc | 1080 |
| acacgcgcgc | agagtgaaca | gtgagttccc | ccgacagccc | acgacagcca | ggactgccct | 1140 |
| ccccaccccca | ccccaccccca | ggagcacggc | acacagttca | gcctctgagc | tggctcacac | 1200 |
| gtgccatccc | caccccggtg | ctccagggaa | ggaggacacg | gacccgacgt | gggaggtcct | 1260 |
| caggcagcag | tggcgcctgg | tgtcaggtct | gtctggctga | gtcccgggcg | tcccctgcca | 1320 |
| tggcctgtgc | cttgcatgga | ggcggcggtg | gcactgaaga | gatagctttc | aagggcccaa | 1380 |
| cactttgcac | ttcggctggc | tgtgagtttc | tgctttgtag | gttgtggtca | catttgcagg | 1440 |
| ctgcgggcag | tggcaccgac | ttgggcctcc | ctttctatgt | ggcatattta | tttatttaaa | 1500 |
| cacccccaggg | agttacgtgg | taacaaggtt | gtccataaag | aggttgcttc | tatatactag | 1560 |
| aggccccaga | tggcaggcct | tgggctacgt | ctggcttgca | tggtctccca | agggaatcaa | 1620 |
| ccccatcaac | aaagttcaaa | tcggggcaga | ggctgcactt | gtgcccccag | atgtttctga | 1680 |
| ggagccagat | tagggctggc | attgctgtag | agtgacggc | gctgcccaga | gcgtgtccca | 1740 |
| gacatcacag | cggggctcag | cagttcccac | agcctctgcc | tgccttggct | aagcatgagt | 1800 |
| taagcagcaa | aacgctcctc | catgtctgga | tggggccggc | aggtcctgtg | tcccctgcac | 1860 |
| ctggaggaga | gcaggctaga | ggcacagcgg | ccacatggtg | ctggctctga | acgttggttg | 1920 |
| gtggctggaa | aacagccctg | cttctgaggg | ccgtcagtt | ctgcacacga | aaccacctcc | 1980 |
| tgagggctca | gctctgcccc | cgccctgggc | tgcagcctct | gcacgcaagc | accaggcatc | 2040 |
| cttttgtgttg | tcaactccgt | gtaaccagta | actacagcca | tttacaattg | actccgtttc | 2100 |

| | |
|---|---|
| cttttgtagg tttccctgtc tgtctgtgtt agtagaaaaa taaaatccta tgaaatctga | 2160 |
| aaaaaaaa | 2168 |

<210> SEQ ID NO 84
<211> LENGTH: 489
<212> TYPE: DNA
<213> ORGANISM: Homo sapiens

<400> SEQUENCE: 84

| | |
|---|---|
| tgagtagaag tattcttagt tggggctttt tgtgtggtgt gaatcaaggt tattgaaatg | 60 |
| tgttattttt caagttatct tttgtattgc agtcaaaagt agctagcgta agaggaagat | 120 |
| tttgcgaggt tcccccccact ttttttgttc ttaaaaagaa caaatgcat cctccagaaa | 180 |
| ccaccaccaa gatggcttca gttcggttca tggtgacacc gacaaagatc gatgacattc | 240 |
| caggtttgtc agacaccagt ccggacctca gctctcgatc tagttcccga gtaagattta | 300 |
| gctcccggga aagcgtgcct gaaacaagcc ggagtgagcc tatgagtgag atgtctgggg | 360 |
| ccaccacttc gctggcaact gttgcactgg atccacccag tgaccggact tctcaccccc | 420 |
| aggatgtcat cgagggtaag tagaaacaca gaccgcagca tactttcatt actgggttct | 480 |
| ttatccaag | 489 |

<210> SEQ ID NO 85
<211> LENGTH: 291
<212> TYPE: DNA
<213> ORGANISM: Homo sapiens

<400> SEQUENCE: 85

| | |
|---|---|
| ctggaaggaa gtttaaatac agaaagagca aagtattatc taactataac aatgccacat | 60 |
| tttactgtga ctaaggtaga ggacccagag gaggggggcag cggcttcgat ctctcaagag | 120 |
| cctagtttag cagacataaa agcccggatt caggattcag atgaaccagg tgagtacgca | 180 |
| acttgggagc ttttggaacc tataaaatgt ttcatgaaag aagtaactag gatatcaaaa | 240 |
| ttcaaaatgc cttctttagg acagagaaaa gtgttgtggt tgaggtgttt t | 291 |

<210> SEQ ID NO 86
<211> LENGTH: 299
<212> TYPE: DNA
<213> ORGANISM: Homo sapiens

<400> SEQUENCE: 86

| | |
|---|---|
| ttaaatttt ttgcttattt ccttggttga cttttgttgc tgattttaaa gaaattattt | 60 |
| gttttgatca ttcattttt tcttttcttt tcaattgttt gttttcaga cctgagtcag | 120 |
| aactccatca caggggaaca cagccaactg ttaggtatag tattactgtg gggattgact | 180 |
| ttatccaaag tcacccttaa ctcatttatc ctaacagaca ttactcccctt ctctgattct | 240 |
| attttctatc ccctccttt ctacttccca cccaacaact ttttcctgc tgtttctat | 299 |

<210> SEQ ID NO 87
<211> LENGTH: 366
<212> TYPE: DNA
<213> ORGANISM: Homo sapiens

<400> SEQUENCE: 87

| | |
|---|---|
| agattaaatt tgaatatgaa aatgggttat attaataccg aagcaacctg cacttatctg | 60 |
| gtgctgatgt ttcttcgtca gaaccagtg agaaactaac ttggtctact ttttttttttc | 120 |
| cagacgacgg acataagaaa gctcgaaatg cttatctcaa taattccaat tatgaagaag | 180 |

```
gagatgaata ttttgataaa aatttggcac tctttgaggt catattttgg agaaaactat    240
ggactcgagc actttaggaa cagagatctc atgatagcca tattttaccc catttggttt    300 aaaaattta caagctggat aatttaatgt taaagaaaa tattgtaact tgttattata    360
gtaaat                                                                366

<210> SEQ ID NO 88
<211> LENGTH: 342
<212> TYPE: DNA
<213> ORGANISM: Homo sapiens

<400> SEQUENCE: 88
agcaagatta ttttgatact tatgttcagt gttctttgta gctcatttct tccatgtcac     60
tggctttata ggaagaaatg gacaccagac cgaaggtgtc ttccctcctc aaccgcatgg    120
ccaattacac taatctgact caaggagcaa aggaacatga agaggcagaa acatcactg    180 aaggaaaaa gaagcccacc aaggtgaggc ctcagaataa caaggaatac atagaaagag    240
ccctgtatat aagaaagaag gaaataccta aggcaccatt ctgtgttcag cagctattta    300
ttaaatgctt gagaggtgcc tggaactgtt ctgggcacca gc                      342

<210> SEQ ID NO 89
<211> LENGTH: 238
<212> TYPE: DNA
<213> ORGANISM: Homo sapiens

<400> SEQUENCE: 89
gctccctctg ggtgtggggt acgagcccct gggacacgct atgctctgtc gcaggctccg     60
cgcatgggca ccttcatcgg cgtctacctg ccgtgcctgc agaacatcct gggcgtcatc    120
ctcttcctgc gcctgacgtg gatcgtgggg gtggctggtg tcctggagtc cttcctcatc    180
gtggccatgt gctgcacatg tgtgtgagtc tcccccggcc aggtgtggct gtgccttc      238

<210> SEQ ID NO 90
<211> LENGTH: 167
<212> TYPE: DNA
<213> ORGANISM: Homo sapiens

<400> SEQUENCE: 90
tatagaaatg tcatctttac acagtaacaa tcctctcctt tccttttctc tgcagacaat     60
gttgactgct atctccatga gtgccattgc cactaatgga gtggtgccag gttagtaggt    120
caaggttgta tttcaagatt tatcagtgtt gactctgtgt ttatgct                 167

<210> SEQ ID NO 91
<211> LENGTH: 359
<212> TYPE: DNA
<213> ORGANISM: Homo sapiens

<400> SEQUENCE: 91
catttaacct ttatgtatat attttttctt atttctgttt tattcatatt cctcttgcta     60
atacacactc tttcttctat tcaccttctg ttttgtcttt tagctggggg ctcatacttt    120
atgatttccc gggcactggg cccagagttt ggtggggctg ttggcctctg cttttatctt    180
ggtaccacat ttgcagcagc catgtacatc cttggtgcca ttgaaatctt tctggtaagt    240
aatgacttca ttgtggtcta taatatagaa gaaattgaa tttaggttta ttcttttgcta    300 tgaaagcttc tgagagatca gctgtgggaa taaatcaggt gattgactgc caacgtcag    359
```

<210> SEQ ID NO 92
<211> LENGTH: 402
<212> TYPE: DNA
<213> ORGANISM: Homo sapiens

<400> SEQUENCE: 92

| | | |
|---|---|---|
| ttcttttgtg aaagtaaatg caaacgaata cagccttttt acttaattat tttgaaataa | 60 |
| cctaattttc tcctttattt ttacctaaca ggtctatatc gtccccgag ctgccatctt | 120 |
| tcacagtgat gacgcactca aggaatcagc agccatgcta ataacatgc gtgtctacgg | 180 |
| cacagctttc ttggtcctta tggtattagt ggtatttatc ggcgtacgct atgtgaacaa | 240 |
| gtttgcctca cttttcctgg cctgtgtcat tgtgtccatc ttggccatct atgctggagc | 300 |
| catcaagtct tcttttgctc ctccacactt cccgtacgtg tctgtctctc tgcctagcca | 360 |
| tccttattgg gtagtaattg aaaatatctg gtggtgtgat aa | 402 |

<210> SEQ ID NO 93
<211> LENGTH: 363
<212> TYPE: DNA
<213> ORGANISM: Homo sapiens

<400> SEQUENCE: 93

| | | |
|---|---|---|
| tactaacctg tttccttttt ttttaatgta cttttttcc ttacttgatc tttctcccta | 60 |
| tttcttttca cttagggtct gcatgctggg taaccgcact ctttcatcaa gacacattga | 120 |
| cgtttgctct aagaccaagg aaattaacaa catgacagtc ccatcaaagt tatgggatt | 180 |
| cttctgtaac tcgagtcaat ttttcaatgc cacctgtgat gaatactttg ttcacaataa | 240 |
| cgtcacttca atccagggca ttcctggatt ggctagtggt ataattacag gtaagttagg | 300 |
| gagttattgg acaagttttt tcctattttc tggggaaaat aggccttgtc atcttagatt | 360 |
| cct | 363 |

<210> SEQ ID NO 94
<211> LENGTH: 291
<212> TYPE: DNA
<213> ORGANISM: Homo sapiens

<400> SEQUENCE: 94

| | | |
|---|---|---|
| tagaaaatta attatctttt ttttttttcat actgctgctg cttaaattcc cattttccc | 60 |
| actgcagaga atctttggag taattaccta cccaagggag agatcatcga aaagccttca | 120 |
| gccaaatctt ctgatgtctt aggcagctta aaccatgaat atgttcttgt tgacatcacc | 180 |
| acctccttca cgcttctggt gggaatcttc tttccctctg ttacaggtaa acacataggc | 240 |
| tgttgtatat tttagaagct gtcagaccca tggagtgatt tttctcagga g | 291 |

<210> SEQ ID NO 95
<211> LENGTH: 250
<212> TYPE: DNA
<213> ORGANISM: Homo sapiens

<400> SEQUENCE: 95

| | | |
|---|---|---|
| agatttgctt ctactctttg ctatcagtat caatatcaaa gtgtccaaga agttaacttg | 60 |
| gtttttccc ccttatctct aaaggtatca tggctggatc aaacagatct ggagatctga | 120 |
| aagatgctca gaagtctatt ccgattggta ctatccttgc catcctgacc acctcctttg | 180 |
| tttgtatcct ttttatggat ccagtctgag tcttagtcat aggagcatcc agtagaacta | 240 |
| agatgatcag | 250 |

<210> SEQ ID NO 96
<211> LENGTH: 205
<212> TYPE: DNA
<213> ORGANISM: Homo sapiens

<400> SEQUENCE: 96

```
agaaagtgtc tactgagtgt ctactttctg tctcatgtta gagggtaaac aacagtttcc     60
ttgactcctc aatatggtag atttaagcaa tgttgtcctt tttggtgcat gtattgaagg    120
ggttgttctc agagacaagt gagtaatgaa tttctttgta acaattatgt gtgtgtctgc    180
catgacttct gatcattcca catag                                         205
```

<210> SEQ ID NO 97
<211> LENGTH: 449
<212> TYPE: DNA
<213> ORGANISM: Homo sapiens

<400> SEQUENCE: 97

```
agcctggtgg aggtttcaag ccaacgggga ctggaggccg ggcctcagct ttccaaggag     60
tcgcccccac tgcactgggc ccctcgctct ggtgggaga agacattttg tctgactcag    120
gctcacttgc tgaaagccgc ccgcccgcct gcccgcctgc ctgcaggttc ggggaggccc    180
tgcaggggaa cctggtcatc ggcatgctgg cctggccctc ccctgggtc atcgtcatcg     240
gctccttctt ctccacctgc ggtgccggcc tgcagaccct cacgggggca ccgcgcctac    300
tgcaggccat tgcccgtgac ggcatcgtcc ccttcctgca ggtgagtccc gcaccctcgt    360
acggggggac cctggaaggt cagggtcggg ggctctcctc ccctgtttta tcctcacagc    420
agccgtgtgt gggacgcatg cccgcggct                                    449
```

<210> SEQ ID NO 98
<211> LENGTH: 304
<212> TYPE: DNA
<213> ORGANISM: Homo sapiens

<400> SEQUENCE: 98

```
tatctctagt ctttcagtct aaagttattt cctagattaa atttcccact cctatttctt     60
tcccaggttc ggtgatgctg tgaaaggtaa tttggtggta ggcaccttat cttggccatc    120
cccatgggtg attgttattg ctccttctt ttcaacatgt ggggctggac ttcagagcct    180
cacaggtgca ccgaggctgc tacaagctat tgccaaggat aacatcatac cgtttctgag    240
ggtgagtgac ctttattat gccctcttct ttttttccca gctttaatga gaaacagtgt    300
ggtc                                                               304
```

<210> SEQ ID NO 99
<211> LENGTH: 249
<212> TYPE: DNA
<213> ORGANISM: Homo sapiens

<400> SEQUENCE: 99

```
gctagagaaa tcagagagca atgactcagt actcctgtgc ctgatatttc ccttctgtgt     60
acaggttttt ggccacagca aagccaatgg ggaacctacc tgggctttac ttctaactgc    120
tgccattgca gagcttggaa tactcattgc ctccctggat cttgtggccc caattctttc    180
catgtaagag ccagtgattc tcttcagtta ttcttgctta aatgataaat aatacatgtt    240
tatttccat                                                          249
```

```
<210> SEQ ID NO 100
<211> LENGTH: 255
<212> TYPE: DNA
<213> ORGANISM: Homo sapiens

<400> SEQUENCE: 100
cttcaataca gcaaaggtat tcagttactt aaccttcaaa gaatcatctt ccagtaataa      60
tcattcctct tactctttat tcttcaggtt ttttctcatg tgttacctct ttgtaaactt     120
ggcatgtgcc ttgcaaacat tacttcgaac acccaactgg agaccccgat tccgctacta     180
ccattggtaa gtctgcttct tttattcttt ttactcacgt ttggagagaa cccatctttg     240
aactagaaaa ctagg                                                     255

<210> SEQ ID NO 101
<211> LENGTH: 251
<212> TYPE: DNA
<213> ORGANISM: Homo sapiens

<400> SEQUENCE: 101
gagaagcacc tttgacatag gcttcttttt cagctacttt aaaagatact tttttgtttt      60
taattttcta gggcccttc tttcatggga atgagtatct gtctggctct gatgttcatt     120
tcttcctggt attatgccat tgtagccatg gtaatagctg gtatgatcta caagtacatt     180
gaataccaag ggtgagtgtg gatttaatct tgatcactgc taaaagtagc aagactagct     240
agtttggtta g                                                         251

<210> SEQ ID NO 102
<211> LENGTH: 313
<212> TYPE: DNA
<213> ORGANISM: Homo sapiens

<400> SEQUENCE: 102
accttgcaca tgtgtgattt ttagattcag aaaaaaactt tattttttaa aattatactt      60
actatagttt aaatttgtct ctgctctttt cttttctca cagagctgag aaagaatggg     120
gtgatggtat ccgtgggctg tccctcagtg cagcccggtt tgctttgctt cgattggagg     180
aaggacctcc acacactaaa aactggaggt aaagaaatca acactagcag tatttggcac     240
atggttaaca cacaacaaat atgtgttttg ttgattttag gataaggaaa ccatatgtgg     300
ctcaaggaat tgg                                                       313

<210> SEQ ID NO 103
<211> LENGTH: 305
<212> TYPE: DNA
<213> ORGANISM: Homo sapiens

<400> SEQUENCE: 103
ggtggagtct gtcattctgt tccccaaacc caaaatgttt tctcctcccc tccaaccccc      60
accaacctct tcacaggcct cagttgcttg tattactgaa actagatgaa gacttacatg     120
tcaagcatcc tcgcctcctc acctttgcct cacagctcaa agcaggaaaa ggtctcacta     180
ttgtgggctc tgtcatcgtg gggaacttcc tagagaacta cggtgaagct ttagctgctg     240
agcaggtaag agtcaggctt ttgaggtatt ggaactcagt ttacagcttt gtgatgttaa     300
gtagt                                                                305
```

<210> SEQ ID NO 104
<211> LENGTH: 323
<212> TYPE: DNA
<213> ORGANISM: Homo sapiens

<400> SEQUENCE: 104

| | | |
|---|---|---|
| acaatgggtt aaaatgtcca gagtgaacca gttcagtgtt gcggtcctgt gtctctttca | 60 |
| gaccataaag cacctaatgg aggcagagaa ggtaaaagga ttctgccagc tggtggtggc | 120 |
| cgccaagctg agagagggca tttcccacct catccagtca tgtggccttg ggggcatgaa | 180 |
| gcacaacacg gtggtgatgg gctggcctaa tggctggcgt caaagcgaag atgcccgcgc | 240 |
| ttggaagact tttattggta ctaaccattt ctcatacaaa cctaaaggcc caagtcgagg | 300 |
| gtatatagtt aatgtctgtc acc | 323 |

<210> SEQ ID NO 105
<211> LENGTH: 312
<212> TYPE: DNA
<213> ORGANISM: Homo sapiens

<400> SEQUENCE: 105

| | | |
|---|---|---|
| gagcatttcc ttgctttcct gacatgctag gaagcaaggc aagcctaagg attcttctct | 60 |
| gcttattctt ttttctccct aggcacagtt cgagtgacaa ctgctgccca tcttgcactg | 120 |
| ctggtggcta aaaacatctc cttctttccc agcaatgtgg agcaattttc tgagggcaac | 180 |
| attgatgtgt ggtggattgt gcatgatggg gggatgctta tgctactacc attcctactg | 240 |
| aaacagcaca aggtatttta taccaacttttt tttttacaaa agtctttctc ccttctgtcc | 300 |
| tggttcacag ga | 312 |

<210> SEQ ID NO 106
<211> LENGTH: 335
<212> TYPE: DNA
<213> ORGANISM: Homo sapiens

<400> SEQUENCE: 106

| | | |
|---|---|---|
| acatatagca aggttcttct agaccacaat gtctaatgtc ttaggaaata accttttttg | 60 |
| cctccttgct ctaattttc acatgtgtat gtcactctct caggtgtggc gaaagtgcag | 120 |
| catacggatc ttcacagtag cccaattaga agacaacagt atccaaatga agaaggacct | 180 |
| agccaccttc ctatatcact tacgcattga ggcggaggta gaagtggtgg agatggtgag | 240 |
| aaagctgagt ttgagataca agaggttcat tcccccattc ctctccctgt cttccttgaa | 300 |
| tcttttctgg tttgggaaat ttttcagatc taaat | 335 |

<210> SEQ ID NO 107
<211> LENGTH: 235
<212> TYPE: DNA
<213> ORGANISM: Homo sapiens

<400> SEQUENCE: 107

| | | |
|---|---|---|
| ggttcatcct tctttctcct ttgtgctttt tgcccctttt atgtgatgtc tatggcagca | 60 |
| tgacagtgat atatcagcat atacttacga gcgcactttg atgatggaac aaaggtccca | 120 |
| gatgcttcgg cacatgcggc tatccaaaac agagcgagac agagaggtga gacattactg | 180 |
| catcaatcca atccgtgctc tctaaagtct gtcactgaaa gggatgatac tgggc | 235 |

<210> SEQ ID NO 108
<211> LENGTH: 335
<212> TYPE: DNA
<213> ORGANISM: Homo sapiens

<400> SEQUENCE: 108

```
cccattactg cttcaaaata accaaagatg aagcataaga gaaaatttgg tagaataact      60
tgtgttggac cttcttcctc aggcacaatt ggtgaaagac cgaaactcaa tgctacgatt    120
gaccagcatt ggctctgatg aggacgaaga gacagaaacc tatcaggaga aggtgcacat    180
gacttggaca aaagacaagt acatggcatc ccggggacaa aaagcgaagt caatggaagg    240
attccaggac ctgcttaaca tgcgtccgta agttttccca ctcccaagtt tatcataaaa    300
ttacctaatc agtggcacaa atgtgacttt gcctg                               335
```

<210> SEQ ID NO 109
<211> LENGTH: 274
<212> TYPE: DNA
<213> ORGANISM: Homo sapiens

<400> SEQUENCE: 109

```
ggatctcaag ttttaacgt tgactttatg gctagttgtc ttttaccttt aacgaacctt      60
tatttcttcc ccactcaggg accagtccaa tgtgaggcgg atgcatacag cagtgaaact    120
caacgaggtt atagttaaca gtcccatga agcaaagctg gttttattga atatgccagg     180
gccaccccga aaccctgagg gtgatgaaaa ctgtatcctt ccaagagtg gggcttccag     240
tagggaaaat ctcctaacc tctttctgag ataa                                 274
```

<210> SEQ ID NO 110
<211> LENGTH: 807
<212> TYPE: DNA
<213> ORGANISM: Homo sapiens

<400> SEQUENCE: 110

```
cctcagatta tgatgatgcc aggttttaag tttgtgctct tcttttgcct gtctccttga      60
caagttttga agacatggag ttcctagagg tgcttaccga gggactagag cgagtcctac    120
ttgtccgggg tggtggcagt gaagtgatca ccatttattc ataacctact ctgaatgacc    180
gtgcttgacc tgttttctta aaaggcctac gtcctccatg gaagtgccag ctcattacta    240
ccactcccac tcaactagaa gcctgtgttc tgtacacatc atactgaact cttgatgagc    300
tgagcctcaa gtacctgtgt aaaagagctc ccatctgatc tgcagtcatt acagaaaaag    360
caaatattcc ctcaacatca gaacaatgct caagtctttc aagccactgt ctgagcagtc    420
aaaggcaaat tagaattaac aagctgagcc aataaatgaa ttggtaaaag ggatgctaga    480
aattcaactg aagaaaaaaa gcaagtcaag tacgtattca gcattaaaga tgaatctcag    540
aagtcatggt tcaatgttga cactgtgagg ataacaacta gagacagctt catcttacta    600
aagaatttat ggtcaagtat atttggacct attatcctcg gcaagccaag atgcaaacat    660
ttttagcta tatttctta gtatacccac tgctgtaatt ttatattagg atactaactt     720
gaaacatggc tgcagcctct acttcttcaa aaacatcccc ccaaaatacc agatttaaat    780
atccaaaaaa aaaaaaaaaa aaaaaaa                                         807
```

<210> SEQ ID NO 111
<211> LENGTH: 3422
<212> TYPE: DNA
<213> ORGANISM: Homo sapiens

```
<220> FEATURE:
<221> NAME/KEY:
<222> LOCATION:
<223> OTHER INFORMATION: n=a, c, g, or t

<400> SEQUENCE: 111
ntncntangt ctctccaggt cgacggtatc anaagcttga tatcgaattc ctgcagcccg        60
ggggatcctg accggaaagg gagttgcgcc ggggaagaca agtacacagg cctccacnga       120
ccgccggctg ggttcagcca ggaacagtgt ggctggacag acggctgctg gggaagggac       180
gatggncatc tcttgatgag ccaggtggna caggatggct ggaacctgag ggggcctgat       240
tcggaatcag tctgagtcag ctcacgtgca gagacagaca tggggagaaa aggcgacngt       300
gggagggaca gtgacaaggg tggtctccca ggtggncagt gactggggc tagggggcc        360
cagtgggccc gtatcagtgg ccggccgtcc ctgcaggttc ttcctcatgt gctacctgtt       420
cgtgaacctg gcctgcgccg tgcagaccct gctacgtacc cccaactggc gtccacgctt       480
caagttctac cactggtgag gctactcagc acgggcgtga ggagcccac aggctgggac        540
actgggtgcc tctgccactg gtgaggccgt cagcacagg cgtcaggagc ccacaggct         600
gggacactgg gtgcctctgc aaggccagct gctctgggcc tgaagacccc agcgcgtcct       660
tgactgttcc tttgcggagt aagccctgc gcagctgatg agactgcacc tgaggaaggc        720
ctctggttac gaggatgccc aggtgtctgc atgtgccttg tacctcccgt ggtcagccca       780
gccttccagg cttggggcgt agcccatcag ggctgtgggt cttcttaact cccctcccag       840
gaataagccc tgggtggacg cttnagcccc ttgttgcatg cacaagccaa gtgctgtgtg       900
cacgctggga actggagcta tgtactgggn tttggagtga cagcttccac aagggcccaa       960
ggaccacgta cccttaaag gtgggtgagt acaagccatg gncgtnaggc gtcagtgact       1020
ggtttnctag tggtnacaga nagtttactg anggaagggc aatgtccntg tggtggtggc      1080
tnaggtgtgg gggcttgcat ggcgttgggc cgccccgagc cacttgcccc gcccccagga      1140
ccctgtcctt tctgggtatg agcctgtgcc tggcgctgat gttcatctgc tcctggtact      1200
acgcgctgtc cgccatgctc atcgctggct gcatctacaa gtacatcgag taccgcgggt      1260
aagcgctgtc agccccctt acagacccgg cgcacgggag ggcgggcccc tctcatgcta      1320
tgcctggggc agctccctgg aggggcctcc ctggggcttg agcgtcgtgt gccctcacag      1380
gggcagctgg gagcacgtcc aggtgggctg tgttgtgaaa gctgggtttt ccctcccact      1440
tccagccagg ccgaggtgcc tgcacttgtg gacagggtct ccagcctgga gctctgtctc      1500
gtgccgtcct cagcaggcgg tgagcccacg gctgactatt cctgctacgt gtctcgcgag      1560
gtgtccccag gttgtgtctg tactcactcg gcagccacag gcgtccttcc cgtgcccag       1620
cacccaccct ccctccacct gcacccgcct cgtgcccggg gtccagccac ttccctgtca      1680
tgggcctcct gccccgtc ctgtgaggaa ggcacctcac gcatgctgga cgtagacctc        1740
gttccctcca cagccacagc accctctgac ccggtggctc ctaggacggg ctccntttag      1800
ggcaagggtg ggcatggagg cctccctcct catccaggga cttttcctgg gggtcctgtt      1860
tgccccaact cacctgcccc cagaagtccc ctttcccagg tggagagga gcctccaggt       1920
acgcggctgg acaaaccccg acttcctttc ccacagggcc gagaaggagt ggggcgatgg      1980
catccgtggc ctatccctga acgccgcccg ctacgccctg ctgcgcgtgg agcacggtcc      2040
cccccacacc aagaactgga ggtgagcacc gcccatgccc cgtggtcctc agacgcacag      2100
aagagctgtt tctgaggtcg gcctttgagt ggggacctt gagtctcagg ggcctctcac       2160
```

```
cttcagccgc tcaggcaagg tctggggtgt gaacactgcc tggtgcagag cggatggcgc    2220
agctgggggc cggggtgtc cctgctgcag ggtgggggtg tggggagccg ccccctctgc    2280
cagcacagcc ctgggcttgg ggtgggagag ggtggctcct gctgaagcaa aggccatctt    2340
tgggaagcct ctgcccctca gggcctcggc ggggcctca ggcgtgtgcc ccgggccatt     2400
gtcccctcag gggnnttggc gggggcctng gtgtgcccc gggccattgt ccctcaggg     2460 cctcggtggg ggcttcaggt gtgtgtcctg gccattgtc tcacctgtct agcatgtcac    2520
ctgtccacct gtctaaccta cctgttctcc tgtcctgcct ggctagtgcc cacctgtcat    2580
cggccctgcc tgtcccacct ggcttctgtg gcctgtctca cctgtcacct gttcaactta    2640
ccccacgtgt gtcacgtttc cccatcccat ctgtcacctg ccccttttgt ccctgtccc    2700 gcctgtcatg tatctcccgt cccacctgtg tcgtgtgccc cgcccgtccc atctgccctg    2760
cctgttgatg ggccgtgccc tggtaagcgt tgccgtggta acagccgccc caccctggct    2820
gcaggcccca ggtgctggtg atgctgaacc tggacgcgga cgaggccgtg aagcaccccc    2880
gcctgctgtc cttcacgtcg cagctgaagg ccggcaaggg cctgaccatc gtgggctcgg    2940
tgctggaggg gacgtacctg gacaagcaca tggaggctca gcgggccgag gaggtggggcc   3000 gggcggggtc tgggggggcca ggcctctttc ccaccccagc tgcacaggaa acatgccctg    3060
gcatgtcctc atcgcagcgt gtcaacacgg tgctgtgcgt ggcgctgctg tgttttagcc    3120
gtggcggtgg ctttgagctc agagcagcgc gctaaggcct gggagcacca gccgcacccc    3180
gggaagcttg ggaggtgtga gggccattag ctttccaagg gcgaaccctg ggaccgcctc    3240
ctcccgccat gggtgagccc cgtccagagc cgtaatcatg gttctgctgc aagctcagtc    3300
tcccgctgtt caggctcact gggggctgca taagtgtgat gcccgtgtgc tgggggctca    3360
ctgggggctg cataagtgtg atgcccgtgt gctgggggct cactgggggc tgcataagtg    3420
tg                                                                    3422
```

<210> SEQ ID NO 112
<211> LENGTH: 2290
<212> TYPE: DNA
<213> ORGANISM: Xenopus laevis
<220> FEATURE:
<221> NAME/KEY:
<222> LOCATION:
<223> OTHER INFORMATION: n=a, c, g, or t

<400> SEQUENCE: 112

```
cggcacgagg gcacagtact tctgggagac tacctagaca gccatgcaga gtcacaggca     60
gcagagcagg cactgaaaca cttaatggaa caagaaaaag taaaaggctt ttgccaagtg    120
gttgtggctc agaagttgaa agagggcctt tcacatctta tacagtcctg tggtcttgga    180
ggaatgaggc ataacactgt aatcatgagc tggccaagta gctggagaca gagtgatgac    240
tcacgggctt ggaaatcctt cattactacc attcgtgtga ccacagctgc acgccaagca    300
cttctggtag caaagaatgt atcctttttc cctggctccc gtgaaacatt agcagaaggg    360
cacattgatg tttggtggat agtacatgat ggggcatgc ttatgcttct gcccttcctt     420
ctaaaacaac acaaggtgtg gaggaagtgt aagatgcgta ttttcactgt ggctcagatg    480
gaagacaaca gtattcaaat gaaaaaggac ttggctacct tctttatca tttacgtatc     540 gctgctgatg tggaagtagt ggagatgcat gacagtgata tatctgcata cacatatgaa    600
cgcacactca tgatggagca gagatcacaa atgctgagac aaatgcgtct ttctaaaaca    660
gatcgggagc gagaggctca gttggtgaag gacaggaatt caatcctgcg tttaaccagt    720
```

-continued

```
gtgggctctg atgatgatga agatacagag gctgccccag agagagtaca tatgacttgg    780
accagggaca agcaccatgc agtccgtgtt gcccaaagca aaccaatgcc gagctgtcag    840
gacctcctca acatacgacc ggaccagtca aatgttcggc gtatgcacac agctgtgaaa    900
cttaatgaag tcattgtgaa taaatcccat gatgccaaac tggttttgct caacatgcca    960 ggacccctc gtaaccctca gggtgatgaa attatatgg agtttctaga ggttctgaca     1020
gagggcttgg agcgtgtgct ggtagtgaga ggaggtggaa cagaggtgat caccatttac   1080
tcgtaggcac gcatagagtg cattactcag gttgggggtt gtggaaacca atctgagaga   1140
gagtggagag atggaacttt tgttaatgcc aaattaatcc actcccttga acggaaaatg   1200
ctgaaaattc tcagaagtgt tggcattaaa gatcttttcc cataaattgt agttctcaaa   1260
aagggagtca ccaaaatacc ctgtttaatg ccaagggga gtgccatgaa tgcatttatt    1320
gtccaaagaa tcacaatcac ctctgactgg aaaaagactg aataagacat catgctgtga   1380
caatgtacat ctctatgcag cagtgctcct gccttttcaa taatgcttaa tgttctactc   1440
agctgaagat atccagatta tttaagacgt atctttggac aaactaatta ttcttaatta   1500
ataatataca aaattactgt atgcaaatag ctcagttttc atgaatgggt tcagagaact   1560
agccattgtt aagtcactga cccctactaa cttaagcaaa ttcacaagtt tgtgcatatt   1620
gttaagactc agctttatca gatcagactc ctgtctcctt ataacccact gaacaccaaa   1680
tagaacttct cttgttggcc acaaaaacct tgggtgttct aatgtattac attcctgtga   1740
aagtgaagcc tccttccttt ttttttttcat gcatgctgtc ctgattagaa ctgtgcatct   1800
ggcaattctt cagacangca ttgctggttg agactactag cccaaaagtc ttctcttagg   1860
ccagagaaat gtactttgtg gactcatgaa ctaaacatga gtagcagtac cttgattcat   1920
tgcagtttta tatccggaag ggatgggaac ccccactagt tttatttaaa tttgcactac   1980
gttttttttt ttaatacgac atgcaaattg agcaggtttt aatttattgt tcagtgcatc   2040
atgctatgtg tttgttcatt ctatgactgc tgtctctatt tctttgttgt attgctggat   2100
agagtagata ccnaaagtat tgaaactagc aatagctgca ttatagagaa gctgccttgt   2160
ntagcctgtt ttatggctgg caataaaagc ctttatgtct atgtcccctg tttgttgtgg   2220
aggatgggtt caaaactaca gaagaacaaa taaagtttta aagaaaaaa aaaaaaaaa     2280 aaaaaaaaaa                                                          2290
```

<210> SEQ ID NO 113
<211> LENGTH: 361
<212> TYPE: PRT
<213> ORGANISM: Xenopus laevis

<400> SEQUENCE: 113

```
Arg His Glu Gly Thr Val Leu Leu Gly Asp Tyr Leu Asp Ser His Ala
  1               5                  10                  15

Glu Ser Gln Ala Ala Glu Gln Ala Leu Lys His Leu Met Glu Gln Glu
             20                  25                  30

Lys Val Lys Gly Phe Cys Gln Val Val Ala Gln Lys Leu Lys Glu
         35                  40                  45

Gly Leu Ser His Leu Ile Gln Ser Cys Gly Leu Gly Gly Met Arg His
     50                  55                  60

Asn Thr Val Ile Met Ser Trp Pro Ser Trp Arg Gln Ser Asp Asp
 65                  70                  75                  80

Ser Arg Ala Trp Lys Ser Phe Ile Thr Thr Ile Arg Val Thr Thr Ala
             85                  90                  95
```

-continued

```
Ala Arg Gln Ala Leu Leu Val Ala Lys Asn Val Ser Phe Phe Pro Gly
        100                 105                 110
Ser Arg Glu Thr Leu Ala Glu Gly His Ile Asp Val Trp Trp Ile Val
    115                 120                 125
His Asp Gly Gly Met Leu Met Leu Leu Pro Phe Leu Leu Lys Gln His
130                 135                 140
Lys Val Trp Arg Lys Cys Lys Met Arg Ile Phe Thr Val Ala Gln Met
145                 150                 155                 160
Glu Asp Asn Ser Ile Gln Met Lys Lys Asp Leu Ala Thr Phe Leu Tyr
                165                 170                 175
His Leu Arg Ile Ala Ala Asp Val Glu Val Val Glu Met His Asp Ser
            180                 185                 190
Asp Ile Ser Ala Tyr Thr Tyr Glu Arg Thr Leu Met Met Glu Gln Arg
        195                 200                 205
Ser Gln Met Leu Arg Gln Met Arg Leu Ser Lys Thr Asp Arg Glu Arg
    210                 215                 220
Glu Ala Gln Leu Val Lys Asp Arg Asn Ser Ile Leu Arg Leu Thr Ser
225                 230                 235                 240
Val Gly Ser Asp Asp Asp Glu Asp Thr Glu Ala Ala Pro Glu Arg Val
                245                 250                 255
His Met Thr Trp Thr Arg Asp Lys His His Ala Val Arg Val Ala Gln
            260                 265                 270
Ser Lys Pro Met Pro Ser Cys Gln Asp Leu Leu Asn Ile Arg Pro Asp
        275                 280                 285
Gln Ser Asn Val Arg Arg Met His Thr Ala Val Lys Leu Asn Glu Val
    290                 295                 300
Ile Val Asn Lys Ser His Asp Ala Lys Leu Val Leu Leu Asn Met Pro
305                 310                 315                 320
Gly Pro Pro Arg Asn Pro Gln Gly Asp Glu Asn Tyr Met Glu Phe Leu
                325                 330                 335
Glu Val Leu Thr Glu Gly Leu Glu Arg Val Leu Val Val Arg Gly Gly
            340                 345                 350
Gly Thr Glu Val Ile Thr Ile Tyr Ser
        355                 360
```

<210> SEQ ID NO 114
<211> LENGTH: 23
<212> TYPE: DNA
<213> ORGANISM: Homo sapiens

<400> SEQUENCE: 114 cagtccctcgttctaagacttcc                          23

<210> SEQ ID NO 115
<211> LENGTH: 23
<212> TYPE: DNA
<213> ORGANISM: Homo sapiens

<400> SEQUENCE: 115 gtgtcttaaggagacaccacagc                          23

<210> SEQ ID NO 116
<211> LENGTH: 19
<212> TYPE: PRT
<213> ORGANISM: mouse

```
<400> SEQUENCE: 116

Lys Lys Ala Arg Asn Ala Tyr Leu Asn Asn Ser Asn Tyr Glu Glu Gly
 1               5                   10                  15

Asp Glu Tyr

<210> SEQ ID NO 117
<211> LENGTH: 18
<212> TYPE: PRT
<213> ORGANISM: mouse

<400> SEQUENCE: 117

Ala Glu Arg Thr Glu Glu Pro Glu Ser Pro Glu Ser Val Asp Gln Thr
 1               5                   10                  15

Ser Pro

<210> SEQ ID NO 118
<211> LENGTH: 84
<212> TYPE: DNA
<213> ORGANISM: homo sapiens

<400> SEQUENCE: 118
gtgtgtgtgt gtgtgtgtgt gtgtgtgtgt gtgtgtgcgc gcgcgcgcgc atgtgtgtgt      60
gcgtgtgtgt gtgtgtgtgt gtgt                                             84

<210> SEQ ID NO 119
<211> LENGTH: 74
<212> TYPE: DNA
<213> ORGANISM: homo sapiens

<400> SEQUENCE: 119
gtgtgtgtgt gtgtgtgtgt gtgtgtgtgt gtgcgcgcgc gcatgtgtgt gtgtgcgtgt      60
gtgtgtgtgt gtgt                                                        74

<210> SEQ ID NO 120
<211> LENGTH: 94
<212> TYPE: DNA
<213> ORGANISM: homo sapiens

<400> SEQUENCE: 120
gtgtgtgtgt gtgtgtgtgt gtgtgtgtgt gtgtgtgcgc gcgcatatgt gtgtgtgcgc      60
gtgtgtgtgt gcgtgtgtgt gtgtgtgtgt gtgt                                  94

<210> SEQ ID NO 121
<211> LENGTH: 92
<212> TYPE: DNA
<213> ORGANISM: homo sapiens

<400> SEQUENCE: 121
gtgtgtgtgt gtgtgtgtgt gtgtgtgtgt gtgcgcgcgc gcgcatgtgt gtgtgcgcgt      60
gtgtgtgtgc gtgtgtgtgt gtgtgtgtgt gt                                    92

<210> SEQ ID NO 122
<211> LENGTH: 72
<212> TYPE: DNA
<213> ORGANISM: homo sapiens

<400> SEQUENCE: 122
gtgtgtgtgt gtgtgtgtgt gtgtgtgtgc gcgcgcgcat gtgtgtgtgc gtgtgtgtgt      60
gtgtgtgtgt gt                                                          72
```

<210> SEQ ID NO 123
<211> LENGTH: 86
<212> TYPE: DNA
<213> ORGANISM: homo sapiens

<400> SEQUENCE: 123
gtgtgtgtgt gtgtgtgtgt gtgtgtgtgt gtgtgtgtgc gcgcgcgcgc atatgtgtgt        60
gtgcgcgtgt gtgtgtgtgt gtgtgt                                             86

<210> SEQ ID NO 124
<211> LENGTH: 80
<212> TYPE: DNA
<213> ORGANISM: homo sapiens

<400> SEQUENCE: 124
gtgtgtgtgt gtgtgtgtgt gtgtgtgtgt gtgtgcgcgc gcgcgcgcat atgtgtgcgc        60
gtgtgtgtgt gtgtgtgtgt                                                    80

<210> SEQ ID NO 125
<211> LENGTH: 80
<212> TYPE: DNA
<213> ORGANISM: homo sapiens

<400> SEQUENCE: 125
gtgtgtgtgt gtgtgtgtgt gtgtgtgtgt gtgtgcgcgc gcgcgcatat gtgtgtgtgc        60
gtgtgtgtgt gtgtgtgtgt                                                    80

<210> SEQ ID NO 126
<211> LENGTH: 78
<212> TYPE: DNA
<213> ORGANISM: homo sapiens

<400> SEQUENCE: 126
gtgtgtgtgt gtgtgtgtgt gtgtgtgtgt gtgcgcgcgc gcgcatatgt gtgtgcgcgt        60
gtgtgtgtgt gtgtgtgt                                                      78

<210> SEQ ID NO 127
<211> LENGTH: 76
<212> TYPE: DNA
<213> ORGANISM: homo sapiens

<400> SEQUENCE: 127
gtgtgtgtgt gtgtgtgtgt gtgtgtgtgt gcgcgcgcgc gcatgtgtgt gtgcgtgtgt        60
gtgtgtgtgt gtgtgt                                                        76

<210> SEQ ID NO 128
<211> LENGTH: 78
<212> TYPE: DNA
<213> ORGANISM: homo sapiens

<400> SEQUENCE: 128
gtgtgtgtgt gtgtgtgtgt gtgtgtgtgt gtgcgcgcgc gcgtatgtgt gtgtgcgtgt        60
gtgtgtgtgt gtgtgtgt                                                      78

<210> SEQ ID NO 129
<211> LENGTH: 76
<212> TYPE: DNA
<213> ORGANISM: homo sapiens

<400> SEQUENCE: 129

```
gtgtgtgtgt gtgtgtgtgt gtgtgtgtgt gtgcgcgcgc gtatgtgtgt gtgtgcgtgt      60
gtgtgtgtgt gtgtgt                                                       76
```

<210> SEQ ID NO 130
<211> LENGTH: 21
<212> TYPE: DNA
<213> ORGANISM: mouse

<400> SEQUENCE: 130

```
tccagaaccg tggacagcgc c                                                 21
```

<210> SEQ ID NO 131
<211> LENGTH: 1530
<212> TYPE: DNA
<213> ORGANISM: mouse
<220> FEATURE:
<221> NAME/KEY:
<222> LOCATION:
<223> OTHER INFORMATION: n=a,c, g, or t; sequence "nnnnn" comprises an
      undetermined number of nucleotides

<400> SEQUENCE: 131

```
gaattctgct actcattggc tttgtgtgcc taggcagtac tttctctct tgggagttca       60
gttttttgt ttttgttttt tcatttacg aaatgaaagc tatacgttag ataagatgaa       120
cagttctgtc cagcaattct ccagggattt ttgaggactc aagctgggaa ccagggtgac     180
tgtatagcta tttcctcttt ccattgctag tatgtttaga tctagatgca aagggtctaa     240
acctcaaatg tcactttctg aagcatctcc accattggcc caagtctggc ttcggggtcc     300
agggtaatca agctcctggg ggggtgctgg tttcagaaga ggaggacagg agagcatgtc     360
cggcctggaa gcctcagaaa gcaatcctgg attagaggat tagacattcc cgccccagga    420
gaaaatctgg tccccaaccg aggtggcctc attctcccct tccccactca cctggccagc   480
ttggggccag cataccctcc ctagaggctg caccatctcg ggtgggaagg aagtgctaca    540
ggaccccagt gctccctgtt cctcgctgca tttcatccat agatcattcc acaggagaaa    600
tccccttgtc tgtggtgtgg actccagggt cttgtnnnnn gggccccgcc tgcgccagag   660
tggggggggc tgcgtctgct ctagggaagc gagggccgcg tccccgcag catcccctcc     720
ataccacccg cgcaagcccc cagttttccc gtgagggggc caccggagct ctctgcccgc  780
ctctctgccc ttccctccct ccctccggtc ccccccctcca agaaaaaccc gccagtggct   840
cacgcctcct gcataacggt atgaggtgag cagcgcccgc tactgagagg gggcgcgcgc     900
gggtgtgagc gtgtgtccgt gtgcgagtgt gtgtgcgccg ggcggcggg cactgcagct    960
tcttcctccg tggagcggag agcaagcgag agagctcgag caagcgagcg agcggagaag  1020
gcgggcagag gggcgcgggc gaagcggcgc agccatcccg agcccggcgc cgcgcagcca   1080
ccangctcaa caacctgacg gactgcgagg acggcgatgg gggagccaac cccggtaagc    1140
agtggtccgg gggcggcggg ggaggggta gcgaggagga aggaggagaa ggaggagaag      1200
gagaaggagg agggcagctt cggagtgggg ggcagagccg gggccgcctc ctgcagagga    1260
acagcctggg gctgaccggg gcggcggatg cctggaggct gcaggaggc tagctccatt    1320
ggaatgcgct aggcgctgtc cacggttctg gaatgcgccg cgctcccgag gcagattcgg   1380
aactgggggt tggaatgatc cacggcctgg gggcagactt ggattagcta aaccggagag   1440
```

```
gccgtgggaa ggggatgaaa tagctagaac agggctgacg tgctgttcga cgtgcaggag    1500
ggaggctcct ttccggagtt gggaccccac                                    1530
```